US008415136B1

(12) United States Patent
Gardner et al.

(10) Patent No.: US 8,415,136 B1
(45) Date of Patent: Apr. 9, 2013

(54) PRODUCTION OF ACETYL-COENZYME A DERIVED ISOPRENOIDS

(71) Applicant: Amyris, Inc., Emeryville, CA (US)

(72) Inventors: Timothy Stevens Gardner, Emeryville, CA (US); Kristy Michelle Hawkins, Emeryville, CA (US); Adam Leon Meadows, Emeryville, CA (US); Annie Ening Tsong, Emeryville, CA (US); Yoseph Tsegaye, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 13/673,819

(22) Filed: Nov. 9, 2012

Related U.S. Application Data

(60) Provisional application No. 61/557,893, filed on Nov. 9, 2011.

(51) Int. Cl.
*C12N 1/19* (2006.01)
*C12P 1/00* (2006.01)

(52) U.S. Cl. ...................................... 435/254.2; 435/41

(58) Field of Classification Search ........................ None
See application file for complete search history.

(56) References Cited

U.S. PATENT DOCUMENTS

| | | | | |
|---|---|---|---|---|
| 7,253,001 | B2 | 8/2007 | Wahlbom et al. | |
| 7,659,097 | B2 | 2/2010 | Renninger et al. | |
| 7,785,858 | B2 | 8/2010 | Kozlov et al. | |
| 8,012,722 | B2 | 9/2011 | Chinen et al. | |
| 2010/0248233 | A1 | 9/2010 | Müller et al. | |
| 2011/0275130 | A1* | 11/2011 | Pronk et al. | 435/165 |
| 2011/0287476 | A1 | 11/2011 | Renninger et al. | |

FOREIGN PATENT DOCUMENTS

WO WO 2011/159853 A1 12/2011

OTHER PUBLICATIONS

Chinen, et al., Innovative metabolic pathway design for efficient L-glutamate production by suppressing $CO_2$ emission. *J Biosci Bioeng*. (2007) 103(3):262-269.

Hedl, et al., Class II 3-hydroxy-3-methylglutaryl coenzyme A reductases. *J Bacteriol*. (2004) 186(7):1927-1932.

Lan, et al., ATP drives direct photosynthetic production of 1-butanol in cyanobacteria. *Proc Natl Acad Sci USA*. (2012) 109(16):6018-6023.

Matsumoto, et al., A new pathway for poly(3-hydroxybutyrate) production in *Escherichia coli* and *Corynebacterium glutamicum* by functional expression of a new acetoacetyl-coenzyme A synthase. *Biosci Biotechnol Biochem*. (2011) 75(2):364-366.

Okamura, et al., Unprecedented acetoacetyl-coenzyme A synthesizing enzyme of the thiolase superfamily involved in the mevalonate pathway. *Proc Natl Acad Sci USA*. (2010) 107(25):11265-11270.

Sonderegger, et al., Metabolic engineering of a phosphoketolase pathway for pentose catabolism in *Saccharomyces cerevisiae*. *Appl Environ Microbiol*. (2004) 70(5):2892-2897.

* cited by examiner

*Primary Examiner* — Suzanne M Noakes
*Assistant Examiner* — Jae W Lee
(74) *Attorney, Agent, or Firm* — Squire Sanders (US) LLP

(57) ABSTRACT

Provided herein are compositions and methods for the heterologous production of acetyl-CoA-derived isoprenoids in a host cell. In some embodiments, the host cell is genetically modified to comprise a heterologous nucleotide sequence encoding an acetaldehyde dehydrogenase, acetylating (ADA, E.C. 1.2.1.10) and an MEV pathway comprising an NADH-using HMG-CoA reductase. In some embodiments, the host cell is genetically modified to comprise a heterologous nucleotide sequence encoding an ADA and an MEV pathway comprising an acetoacetyl-CoA synthase. In some embodiments, the genetically modified host cell further comprises one or more heterologous nucleotide sequences encoding a phosphoketolase and a phosphotransacetylase. In some embodiments, the genetically modified host cell further comprises a functional disruption of the native PDH-bypass. The compositions and methods described herein provide an energy-efficient yet redox balanced route for the heterologous production of acetyl-CoA-derived isoprenoids.

26 Claims, 14 Drawing Sheets

Figure 1:
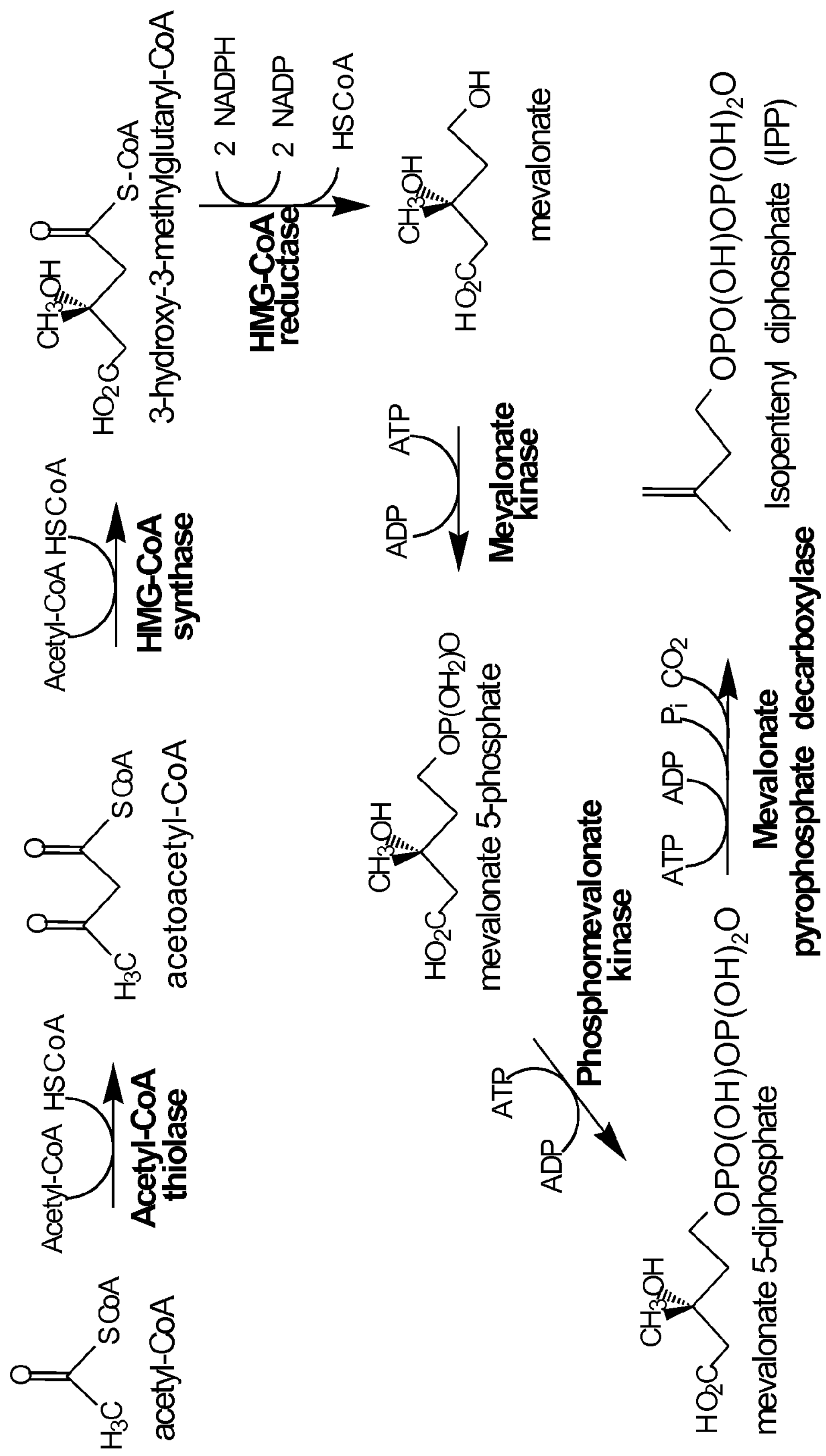

| Pathway | Carbon in | Carbon out | ATP | NADH | NADPH |
|---|---|---|---|---|---|
| Glycolysis | 4.8 Glucose | 9.6 Pyruvate | +9.6 | +9.6 | 0 |
| PDH bypass | 9 Pyruvate | 9 Acetyl-CoA | -18 | 0 | +9 |
| TCA | 0.6 Pyruvate | - | +0.6 | +3 | 0 |
| Isoprenoid | 9 Acetyl-CoA | 1 Farnesene | -9 | 0 | -6 |
| Respiration | - | - | +16.8 | -12.6 | -3 |
| Overall | 4.8 Glucose | 1 Farnesene | 0 | 0 | 0 |

| Pathway | Carbon in | Carbon out | ATP | NADH | NADPH |
|---|---|---|---|---|---|
| Glycolysis | 4.5 Glucose | 9 Pyruvate | +9 | +9 | 0 |
| PDH bypass | 9 Pyruvate | 9 Acetyl-CoA | 0 | +9 | 0 |
| TCA | - | - | 0 | 0 | 0 |
| Isoprenoid | 9 Acetyl-CoA | 1 Farnesene | -9 | -6 | 0 |
| Respiration | - | - | +13.5 | -12.6 | 0 |
| Overall | 4.5 Glucose | 1 Farnesene | + 14.1 | 0 | 0 |

| Pathway | Carbon in | Carbon out | ATP | NADH | NADPH |
| --- | --- | --- | --- | --- | --- |
| Glycolysis | 4.5 Glucose | 9 Pyruvate | +9 | +9 | 0 |
| PDH bypass | 9 Pyruvate | 9 Acetyl-CoA | 0 | +9 | 0 |
| TCA | - | - | 0 | 0 | 0 |
| Isoprenoid | 9 Acetyl-CoA | 1 Farnesene | -12 | -6 | 0 |
| Respiration | - | - | +13.5 | -12.6 | 0 |
| Overall | 4.5 Glucose | 1 Farnesene | + 11.1 | 0 | 0 |

| Pathway | Carbon in | Carbon out | ATP | NADH | NADPH |
|---|---|---|---|---|---|
| Glycolysis | 3.8 Glucose | 4.9 Pyruvate | +4.9 | +4.9 | 0 |
| PDH bypass | 4.9 Pyruvate | 4.9 Acetyl-CoA | 0 | +4.9 | 0 |
| PK/PTA | 1.6 F6P | 4.9 Acetyl-CoA | 0 | 0 | 0 |
| Isoprenoid | 9 Acetyl-CoA | 1 Farnesene | -9 | -6 | 0 |
| Respiration | - | - | +4.2 | -3.8 | 0 |
| Overall | 3.8 Glucose | 1 Farnesene | 0 | 0 | 0 |

Max Stoichiometric Yield = 29.8 wt%

A

| Parental Strain #: | Y12869 | Y12869 |
|---|---|---|
| Transformed with: | ms63909, ms64472 | ms63907, ms64472 |
| ACS1,ACS2,ALD6 status: | --- | --- |
| heterologous ADA: | + | + |
| HMGr cofactor specificity: | NADPH | NADH |

B

| Parental Strain #: | Y968 | Y968 |
|---|---|---|
| Transformed with: | ms63909, ms64472 | ms63907, ms64472 |
| ACS1,ACS2,ALD6 status: | + | + |
| heterologous ADA: | - | - |
| HMGr cofactor specificity: | NADPH | NADH |

| Parental Strain #: | Y968 | Y12869 | Y968 | Y12869 |
|---|---|---|---|---|
| Transformed with: | ms63909 | ms63909 | ms63908 | ms63908 |
| ACS1,ACS2,ALD6 status: | + | --- | + | --- |
| heterologous ADA: | - | + | - | + |
| Acetyl-CoA to acetoacetyl-CoA via: | ERG10 | ERG10 | nphT7 | nphT7 |

PRODUCTION OF ACETYL-COENZYME A DERIVED ISOPRENOIDS

This application claims benefit of priority of U.S. Provisional Application No. 61/557,893, filed on Nov. 9, 2011, the contents of which are hereby incorporated by reference in their entirety.

1. FIELD OF THE INVENTION

The present disclosure relates to compositions and methods for producing acetyl-CoA derived isoprenoids in engineered host cells.

2. BACKGROUND

Acetyl coenzyme A (acetyl-CoA) is a key intermediate in the synthesis of essential biological compounds, including polyketides, fatty acids, isoprenoids, phenolics, alkaloids, vitamins, and amino acids. Among the metabolites derived from acetyl-CoA are primary and secondary metabolites, including compounds of industrial utility. Isoprenoids, for example, are used in pharmaceutical products and as biofuels, food additives, and other specialty chemicals. An isoprenoid product is typically composed of repeating five carbon isopentenyl diphosphate (IPP) units, although irregular isoprenoids and polyterpenes have been reported. In nature, isoprenoids are synthesized by consecutive condensations of their precursor IPP and its isomer dimethylallyl pyrophosphate (DMAPP). Two pathways for these precursors are known. Prokaryotes, with some exceptions, typically employ the deoxyxylulose-5-phosphate (DXP) pathway to convert pyruvate and glyceraldehyde 3-phosphate (G3P) to IPP and DMAPP. Eukaryotes, with the exception of plants, generally use the mevalonate-dependent (MEV) pathway to convert acetyl-CoA to IPP, which is subsequently isomerized to DMAPP.

The unicellular fungus *Saccharomyces cerevisiae* and its close relatives use two endogenous pathways to generate acetyl-CoA. One pathway takes place in the mitochondrial matrix, where the PDH complex catalyzes the oxidative decarboxylation of pyruvate, generated from glucose via glycolysis, to acetyl CoA. The PDH complex consists of 60 polypeptide chains –24 chains of the lipoamide reductase-transacetylase, 12 chains of dihydrolipyl dehydrogenase, and 24 chains of pyruvate decarboxylase. This massive complex converts pyruvate to acetyl-CoA, generating NADH as a byproduct. The resulting acetyl-CoA can then be completely oxidized to $CO_2$ and $H_2O$ via the citric acid cycle for energy generation, or be used for biosynthetic reactions that are performed in the mitochondria.

The acetyl-CoA generated in the mitochondria is unable to cross the mitochondrial membrane into the cytosol. Thus, to generate cytosolic acetyl-CoA, which is needed for the biosynthesis of important primary and secondary metabolites, *S. cerevisiae* uses an independent mechanism located in the cytosol known as the "PDH-bypass." This multi-step pathway catalyzes: (1) the decarboxylation of pyruvate into acetaldehyde by pyruvate decarboxylase (PDC, EC 4.1.1.1); (2) the conversion of acetaldehyde into acetate by acetaldehyde dehydrogenase (ACDH, EC 1.2.1.5 and EC 1.2.1.4), which reduced one $NADP^+$ to one NADPH; and (3) the synthesis of acetyl-CoA from acetate and CoA by acetyl-CoA synthetase (ACS, EC 6.2.1.1), which hydrolyzes 1 ATP to 1 AMP, the energetic equivalent of hydrolyzing 2 ATP to 2 ADP.

Since nature provides only low yield sources for the extraction of many acetyl-CoA derived biomolecules, fermentative production using genetically modified microorganisms has become a promising alternative for their production. However, utilization of the native acetyl-CoA pathway for production of the acetyl-CoA intermediate has certain limitations. For example, isoprenoid production via the native MEV pathway requires three acetyl-CoA molecules and the oxidation of two NADPH for each molecule of mevalonate generated, as shown in FIG. 1. While the PDH-bypass generates one NADPH per acetyl-CoA produced, two ATP equivalents are expended in the process. Thus, while the generation of NADPH is beneficial with regard to the cofactor requirements of the native MEV pathway, the expenditure of six ATP equivalents per mevalonate generated results in an energetically inefficient reaction, as more carbon source must be diverted to ATP synthesis, e.g., via the TCA cycle and oxidative phosphorylation, at the expense of product yield.

Thus, one of the challenges in designing a production host that efficiently produces acetyl-CoA derived compounds is to optimize acetyl-CoA production such that the ATP requirements are minimized, while also meeting the co-factor and requirements of the biosynthetic pathway. The compositions and methods provided herein address this need and provide related advantages as well.

3. SUMMARY OF THE INVENTION

The compositions and methods described herein provide for the energetically efficient and co-factor balanced production of acetyl-CoA derived isoprenoids. By utilizing a heterologous acylating acetaldehyde dehydrogenase (alternately referred to as "acetylaldehyde dehydrogenase, acetylating," "acetylaldehyde dehydrogenase, acylating," or "ADA" (EC 1.2.1.10)) as an alternative to the PDH-bypass for cytosolic production of acetyl-CoA, two equivalents of ATP are saved per molecule of acetyl-CoA produced. ADA converts acetaldehyde directly to acetyl-CoA without expenditure of ATP, and reduces one $NAD^+$ to one NADH in the process.

While the ATP savings gained from replacement of the PDH-bypass with ADA can be utilized towards higher product yields, there are potential shortcomings associated with the use of ADA in combination with the native mevalonate pathway. First, inactivation of the native PDH-bypass removes one source of NADPH, while the reaction catalyzed by ADA produces NADH. Thus, the replacement of the PDH-bypass with ADA, without further pathway modification, introduces a redox imbalance in isoprenoid synthesis, which consumes NADPH.

Secondly, ADA catalyzes the following reversible reaction:

$$\text{Acetaldehyde}+\text{NAD}^+ + \text{Coenzyme A} \leftrightharpoons \text{Acetyl-CoA} + \text{NADH} + \text{H}^+$$

The native PDH-bypass reaction for forming acetyl-CoA is thermodynamically favorable because the reaction is coupled to the hydrolysis of ATP to AMP. In contrast, the ADA reaction is not coupled to ATP, and is much closer to equilibrium than the native PDH-bypass reactions for forming Acetyl-CoA. Thus, the reaction catalyzed by ADA has a lower a thermodynamic driving force behind the conversion of acetaldehyde to acetyl-CoA, and without further pathway modification, the theoretical energy gains of ADA may not be realized.

The compositions and methods described herein address these shortcomings. In some embodiments, to address the redox imbalance introduced by replacement of the PDH-bypass with ADA, the genetically modified host cells further utilize an NADH-using enzyme in the isoprenoid pathway to consume ADA-generated NADH. Thus, the pool of NADH generated by the ADA-mediated conversion of acetaldehyde to acetyl-CoA can be utilized directly towards isoprenoid synthesis. In some embodiments, the NADH-using enzyme is an enzyme that is non-native to the isoprenoid pathway. For example, the NADH-using enzyme can replace an NADPH-using enzyme that is native to the isoprenoid pathway. In particular embodiments, the NADH-using enzyme is an NADH-using 3-hydroxy-3-methylglutaryl-CoA reductase (HMG-CoA reductase) that converts HMG-CoA to mevalonate.

Figure 5:
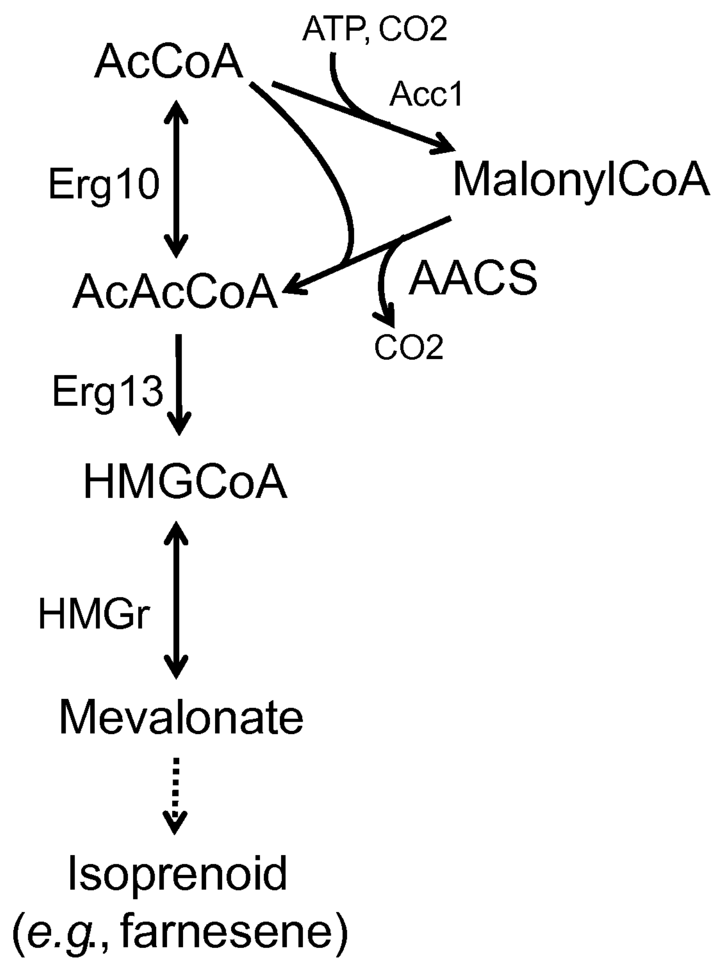

In some embodiments, to address the lower thermodynamic driving force behind the ADA reaction, the genetically modified host cells further utilize, as a first step in the mevalonate pathway, a thermodynamically favorable reaction immediately downstream of acetyl-CoA to provide a pull on the ADA reaction. In some embodiments, the formation of acetoacetyl-CoA from acetyl-CoA is catalyzed by an acetoacetyl-CoA synthase (AACS; alternately referred to as an acetyl-CoA:malonyl-CoA acyltransferase). The reaction catalyzed by AACS is thermodynamically more favorable than the reaction catalyzed by the acetyl-CoA thiolase of the native mevalonate pathway, due to the hydrolysis of 1 ATP resulting from the generation of malonyl-CoA by acetyl-CoA carboxylase (FIG. 5). Thus, AACS provides a stronger pull on acetyl-CoA to drive the ADA reaction forward.

Figure 2:
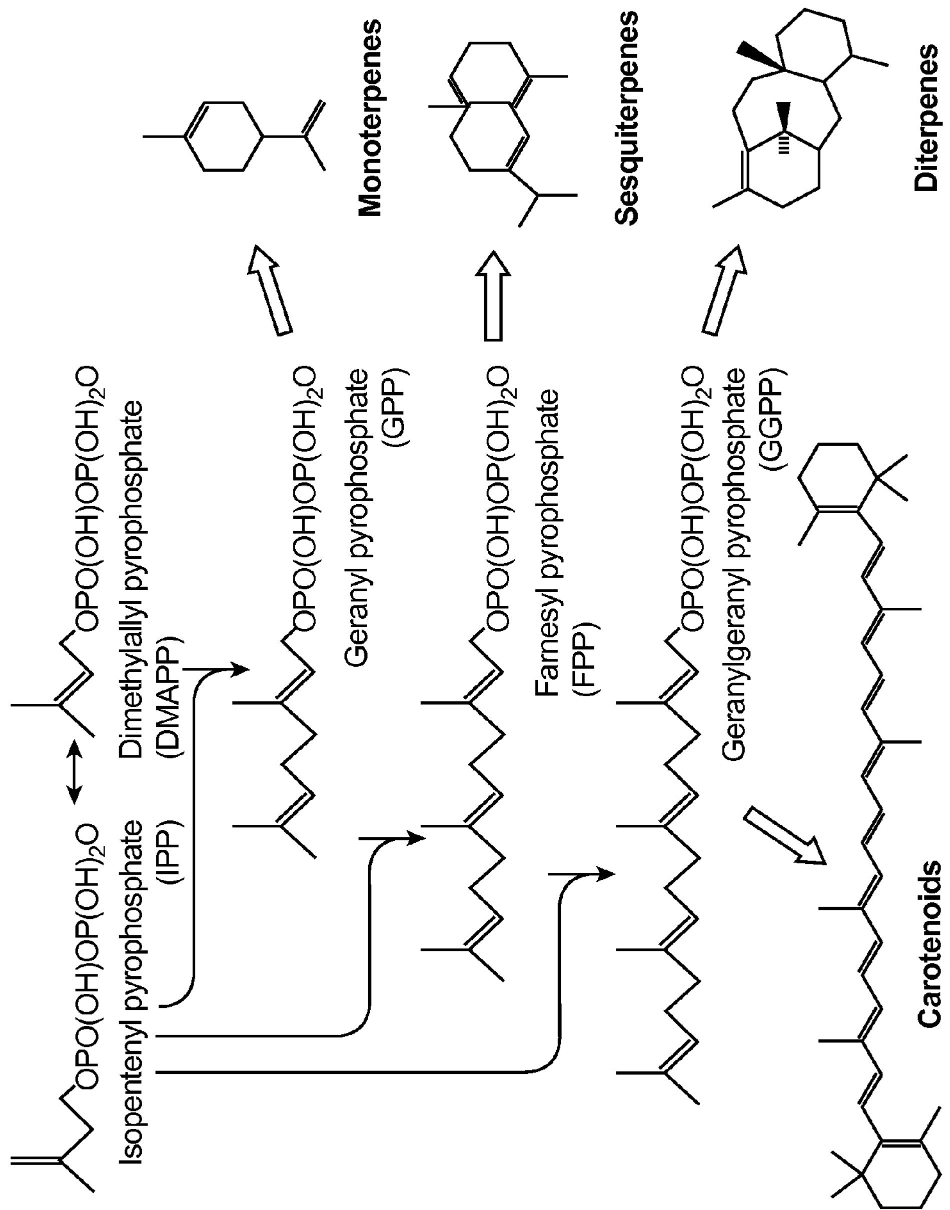
Figure 3:
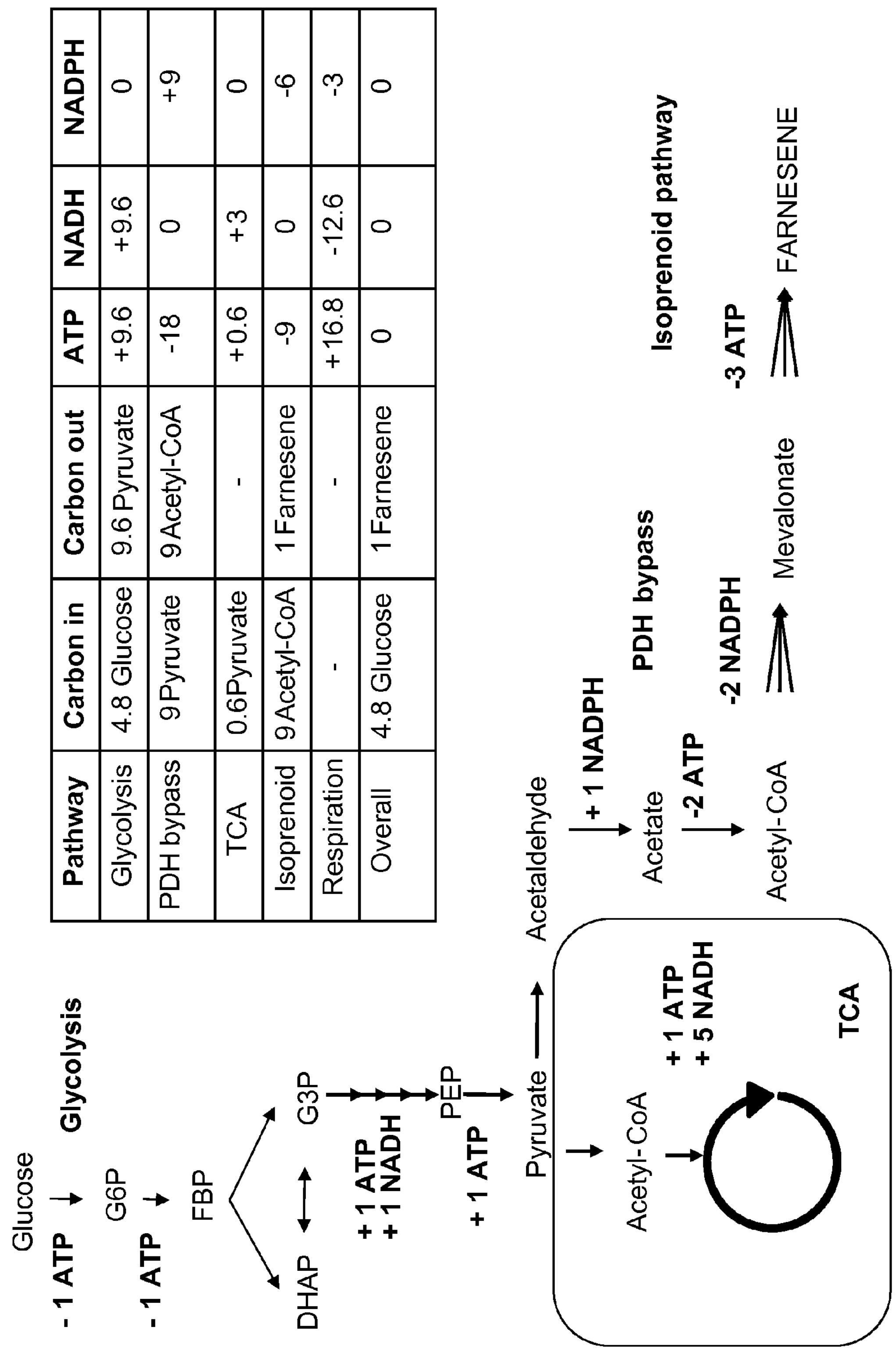
Figure 4:
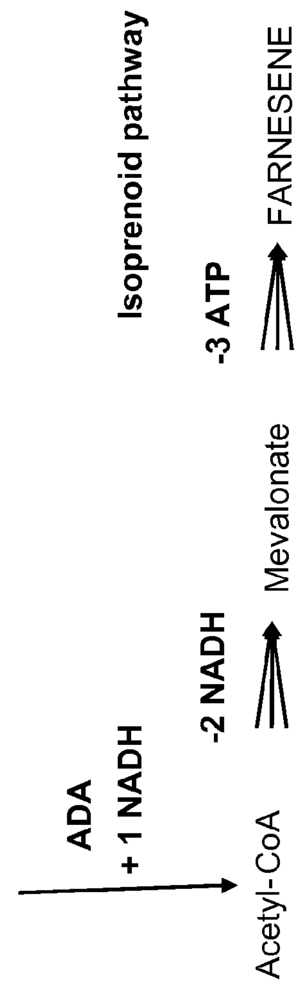
Figure 4:
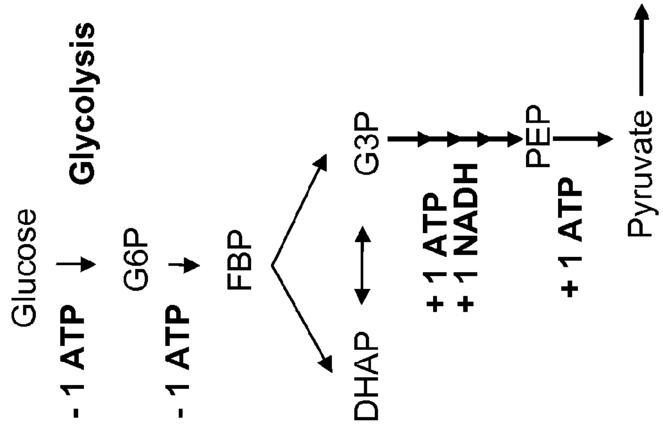

The advantages of utilizing a heterologous ADA in combination with these modifications are exemplified by the improved theoretical yield of the sesquiterpene farnesene in host cells comprising a MEV pathway. Isoprenoid production via the native mevalonate pathway is illustrated in FIG. 1 and FIG. 2. As indicated in FIG. 3, when cytosolic acetyl-CoA is synthesized from glucose using only the chemical reactions which occur in the native yeast metabolic network, the maximum possible stoichiometric yield for conversion of glucose to farnesene via the mevalonate pathway is 23.6 wt %, with 4.77 molecules of glucose being required for the synthesis of each molecule of farnesene. 27 ATP are required per molecule of farnesene, 18 of which are consumed in the synthesis of cytosolic acetyl-CoA from acetaldehyde via the PDH-bypass. However, by including the reactions catalyzed by ADA and NADH-using HMG-CoA reductase into the metabolic network for mevalonate production, as illustrated in FIG. 4, the maximum theoretical stoichiometric yield is improved to 25.2 wt %. In particular, ADA converts acetaldehyde to acetyl-CoA without any ATP input; this reduces the ATP equivalents required for farnesene synthesis to 9, resulting in a savings of 18 ATP equivalents per molecule of farnesene produced (2 ATP equivalents per acetyl-CoA×9 acetyl-CoAs per 1 farnesene). This savings in ATP usage during acetyl-CoA production eliminates the cell's need for oxygen to run the TCA cycle for farnesene production. The oxygen requirement for conversion of glucose to farnesene decreases from 7.8 molecules of $O_2$ per glucose consumed to 6, thereby reducing a major production cost of providing oxygen to fermenters at scale. In addition, redox imbalance is alleviated by co-introduction of an NADH-using HMG-CoA reductase, which consumes NADH generated by ADA.

Figure 6:
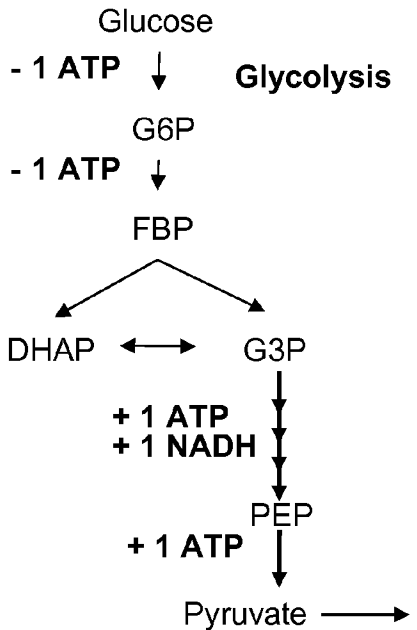
Figure 6:
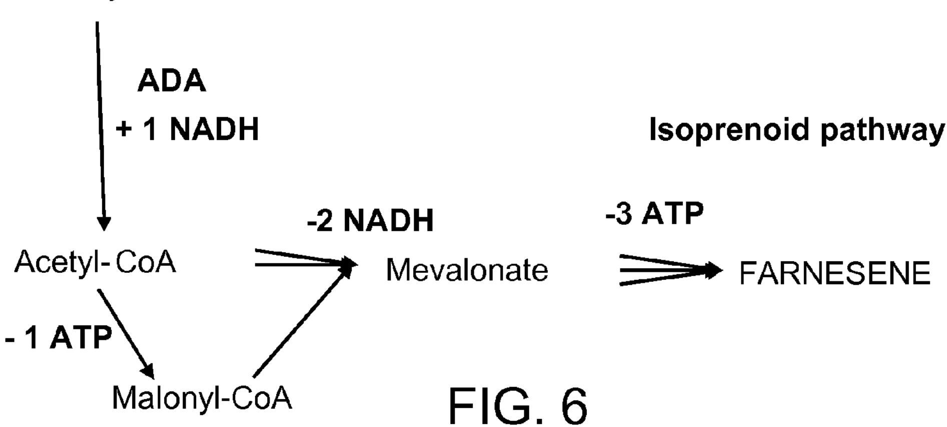

As indicated in FIG. 4, there remains a stoichiometric excess of ATP in a strain that comprises both an ADA and an NADH-using HMG-CoA reductase, which can be used by the cell for maintenance and growth. Alternatively, some of this excess ATP can be utilized towards improving the kinetics of acetoacetyl-CoA production, by introducing an acetoacetyl-CoA synthase (AACS). As illustrated in FIG. 5, AACS is an enzyme which synthesizes acetoacteyl-CoA from malonyl-CoA and acetyl-CoA. Malonyl-CoA synthesis requires an energetic input of 1 ATP per molecule of acetyl-CoA converted (catalyzed by acetyl-CoA carboxylase, thereby improving the thermodynamic driving force of acetoacetyl-CoA synthesis from acetyl-CoA. Importantly, this does not affect the maximum stoichiometric yield of farnesene from sugar or the oxygen demand of the pathway, as there is still excess ATP available in this strain design, as illustrated in FIG. 6.

Figure 7:
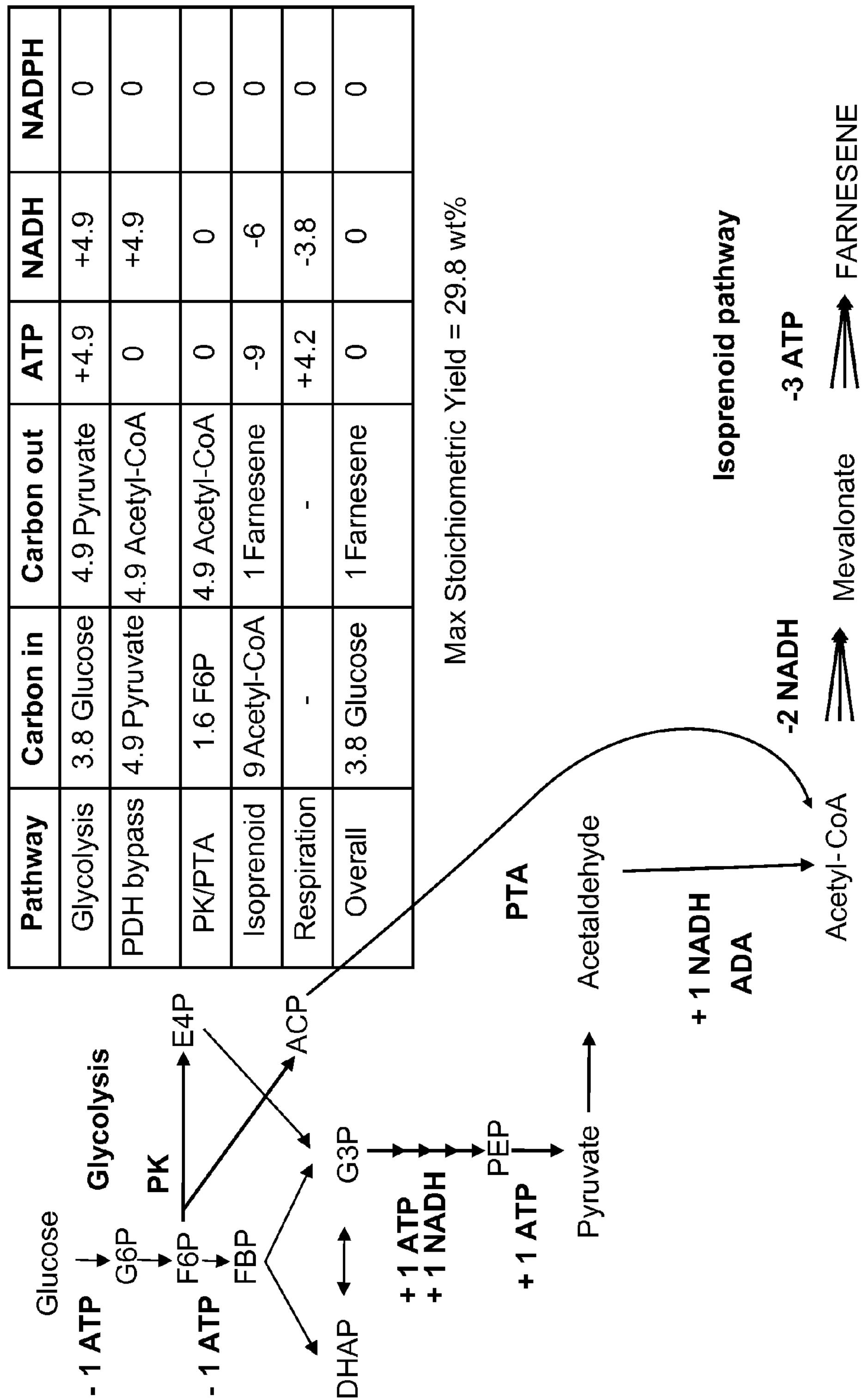
Figure 13:
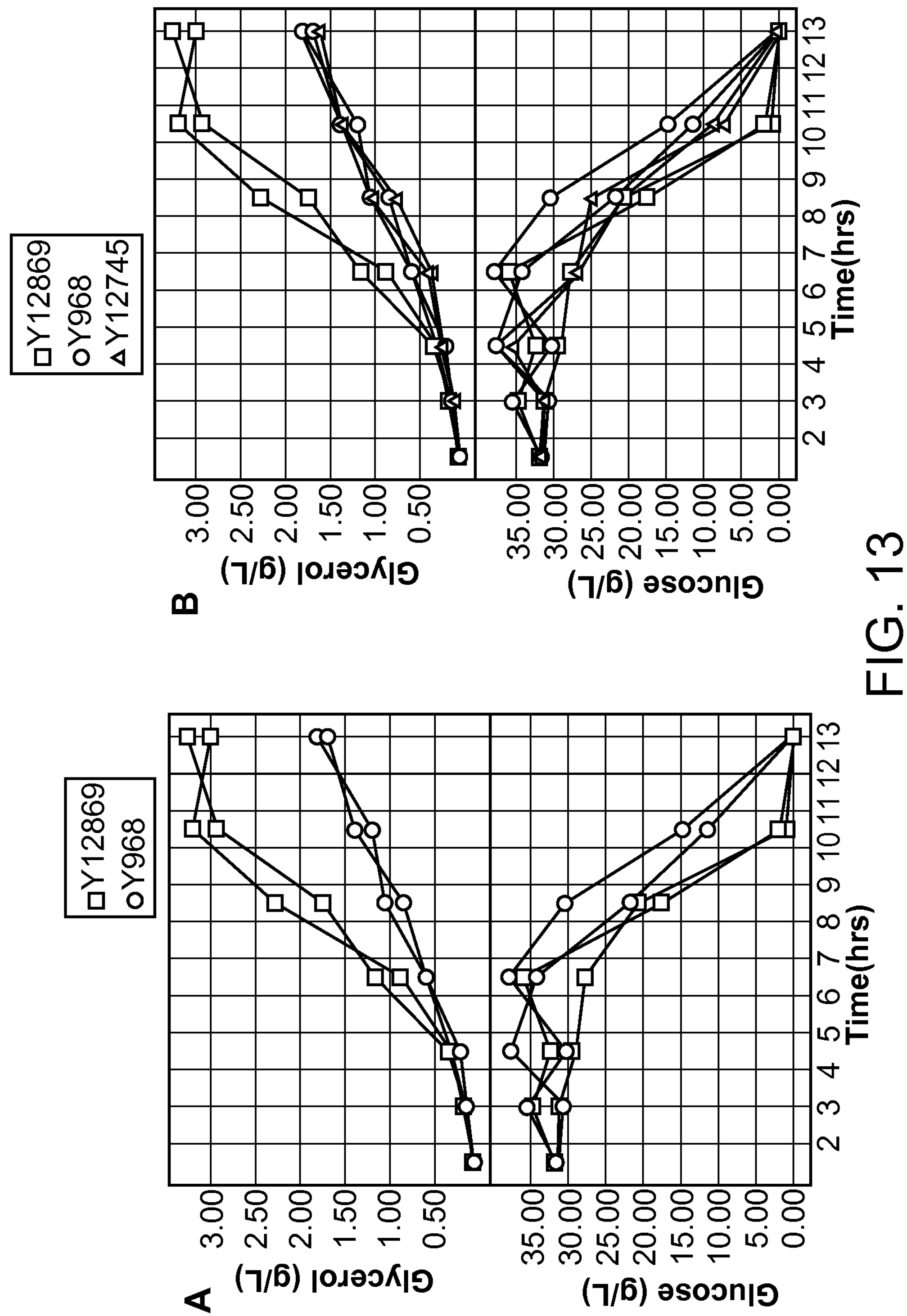

As shown in FIG. 7, additional efficiencies can be gained via the introduction of phosphoketolase (PK) and phosphotransacetylase (PTA) enzymes. PK and PTA catalyze the reactions to convert fructose-6-phosphate (F6P) or xylulose-5-phosphate (X5P) to acetyl-CoA. With these metabolic pathways available, at optimality, the reaction network is able to reach 29.8 wt % mass yield or greater, a significant increase in maximum theoretical yield. This solution involves diverting carbon away from lower glycolysis (G3P→pyruvate), which results in less ATP and NADH generation, both of which are already in excess in a network comprising the ADA and NADH-using HMG-CoA reductase modifications. One benefit of reducing flux through lower glycolysis is that less $CO_2$ is produced in converting pyruvate into acetaldehyde, and thus more carbon can be captured in the end product, thereby increasing the maximum theoretical yield of the network. A second benefit is that less NADH is produced, and therefore significantly less oxygen is needed to reoxidize it. In particular, the oxygen demand at optimality is only 1.84 molecules of $O_2$ per glucose consumed. The redox impact of the addition of PK and PTA to an ADA background is visible even at low yields in the microscale, as illustrated in FIG. 13, where glycerol production returns to wild-type levels.

Thus, provided herein are genetically modified host cells and methods of their use for the production of acetyl-CoA-derived isoprenoids. In one aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate; and (b) a heterologous nucleic acid encoding an acylating acetylaldehyde dehydrogenase.

In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an acetyl-CoA:malonyl-CoA acyltransferase (i.e., an acetoacetyl-CoA synthase (AACS)).

In some embodiments, the one or more enzymes of the MEV pathway comprise an NADH-using enzyme that converts HMG-CoA to mevalonate. In some embodiments, the one or more enzymes of the MEV pathway comprise an NADH-using HMG-CoA reductase.

In some embodiments, the genetically modified host cell further comprises a heterologous nucleic acid encoding a phosphoketolase. In some embodiments, the genetically modified host cell further comprises a heterologous nucleic acid encoding a phosphotransacetylase.

In some embodiments, the amino acid sequence of the ADA is at least 80% identical to SEQ ID NO:2. In some embodiments, the amino acid sequence of the acetyl-CoA:malonyl-CoA acyltransferase is at least 80% identical to SEQ ID NO:16. In some embodiments, the amino acid sequence of the NADH-using HMG-CoA reductase is at least 80% identical to SEQ ID NO:20. In some embodiments, the amino acid sequence of the phosphoketolase is at least 80% identical to SEQ ID NO:12. In some embodiments, the amino acid sequence of the phosphotransacetylase is at least 80% identical to SEQ ID NO:14.

In some embodiments, the genetically modified host cell further comprises a functional disruption of one or more enzymes of the native pyruvate dehydrogenase (PDH)-bypass. In some embodiments, the one or more enzymes of the PDH-bypass are selected from acetyl-CoA synthetase 1 (ACS1), acetyl-CoA synthetase 2 (ACS2), and aldehyde dehydrogenase 6 (ALD6). In some embodiments, ACS1 is functionally disrupted. In some embodiments, ACS2 is functionally disrupted. In some embodiments, ALD6 is functionally disrupted. In some embodiments, ACS1 and ACS2 are functionally disrupted. In some embodiments, ACS1, ACS2 and ALD6 are functionally disrupted.

In some embodiments, the genetically modified host cell further comprises a functional disruption of one or more enzymes having alcohol dehydrogenase (ADH) activity. In some embodiments, the one or more enzymes having ADH activity are selected from alcohol dehydrogenase 1 (ADH1), alcohol dehydrogenase 3 (ADH3), alcohol dehydrogenase 4 (ADH4), and alcohol dehydrogenase 5 (ADH5).

In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate. In some embodiments, the one or more enzymes of the MEV pathway are selected from HMG-CoA synthase, mevalonate kinase, phosphomevalonate kinase and mevalonate pyrophosphate decarboxylase.

In some embodiments, the host cell comprises a plurality of heterologous nucleic acids encoding all of the enzymes of the MEV pathway. In some embodiments, the one or more heterologous nucleic acids encoding one or more enzymes of the MEV pathway are under control of a single transcriptional regulator. In some embodiments, the one or more heterologous nucleic acids encoding one or more enzymes of the MEV pathway are under control of multiple heterologous transcriptional regulators.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound. In some embodiments, the enzyme that can modify IPP or a polyprenyl to form an isoprenoid compound is selected from the group consisting of carene synthase, geraniol synthase, linalool synthase, limonene synthase, myrcene synthase, ocimene synthase, α-pinene synthase, β-pinene synthase, γ-terpinene synthase, terpinolene synthase, amorphadiene synthase, α-farnesene synthase, β-farnesene synthase, farnesol synthase, nerolidol synthase, patchouliol synthase, nootkatone synthase, and abietadiene synthase. In some embodiments, the isoprenoid is selected from the group consisting of a hemiterpene, monoterpene, diterpene, triterpene, tetraterpene, sesquiterpene, and polyterpene. In some embodiments, the isoprenoid is a $C_5$-$C_{20}$ isoprenoid. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

In some embodiments, the genetically modified host cell is a yeast cell. In some embodiments, the yeast is *Saccharomyces cerevisiae.*

In another aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate; (b) a heterologous nucleic acid encoding an acetylaldehyde dehydrogenase, acetylating (ADA); (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); (d) a heterologous nucleic acid encoding a phosphoketolase (PK); and (e) a heterologous nucleic acid encoding a phosphoketolase (PTA).

In another aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate, wherein the one or more enzymes comprise a NADH-using HMG-CoA reductase; (b) a heterologous nucleic acid encoding an acetylaldehyde dehydrogenase, acetylating (ADA); and (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6).

In another aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate, wherein the one or more enzymes comprise a NADH-using HMG-CoA reductase; (b) a heterologous nucleic acid encoding an acetylaldehyde dehydrogenase, acetylating (ADA); (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); (d) a heterologous nucleic acid encoding a phosphoketolase (PK); and (e) a heterologous nucleic acid encoding a phosphoketolase (PTA).

In another aspect, provided herein is genetically modified host cell capable of producing an isoprenoid, the cell comprising: (a) one or more heterologous nucleic acids encoding one or more enzymes of a mevalonate (MEV) pathway for making isopentenyl pyrophosphate, wherein the one or more enzymes comprise an acetyl-CoA:malonyl-CoA acyltransferase; (b) a heterologous nucleic acid encoding acetylaldehyde dehydrogenase, acetylating (ADA); and (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6).

In another aspect, provided herein is a genetically modified host cell capable of producing an isoprenoid, the cell comprising: (a) one or more heterologous nucleic acids encoding a plurality of enzymes of a mevalonate (MEV) pathway for making isopentenyl pyrophosphate, wherein the plurality of enzymes comprise an acetyl-CoA:malonyl-CoA acyltransferase and an NADH-using HMG-CoA reductase; (b) a heterologous nucleic acid encoding an acetylaldehyde dehydrogenase, acetylating (ADA); (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); (d) a heterologous nucleic acid encoding a phosphoketolase (PK); and (e) a heterologous nucleic acid encoding a phosphoketolase (PTA).

In another aspect, provided herein is a method for producing an isoprenoid, the method comprising: (a) culturing a population of genetically modified yeast cells described herein in a medium with a carbon source under conditions suitable for making said isoprenoid compound; and (b) recovering said isoprenoid compound from the medium.

4. BRIEF DESCRIPTION OF THE FIGURES

FIG. 1 provides a schematic representation of the mevalonate ("MEV") pathway for the production of isopentenyl diphosphate ("IPP").

FIG. 2 provides a schematic representation of the conversion of IPP and dimethylallyl pyrophosphate ("DMAPP") to geranyl pyrophosphate ("GPP"), farnesyl pyrophosphate ("FPP"), and geranylgeranyl pyrophosphate ("GGPP").

FIG. 3 provides a schematic representation of the optimal flow of carbon and the metabolic requirements and yields in the conversion of glucose to farnesene via the mevalonate pathway, wherein cytosolic acetyl-CoA is generated via the "wild-type" PDH-bypass.

FIG. 4 provides a schematic representation of the optimal flow of carbon and the metabolic requirements and yields in the conversion of glucose to farnesene via the mevalonate pathway, wherein cytosolic acetyl-CoA is generated via ADA, and the mevalonate pathway comprises an NADH-using HMGr instead of an NADPH-using HMGr.

FIG. 5 provides a schematic representation of farnesene production from acetyl-CoA, wherein acetoacteyl-CoA (AcAcCoA) is synthesized from malonyl-CoA and acetyl-CoA (AcCoA) by acetoacetyl-CoA synthase (AACS). Malonyl-CoA synthesis requires an energetic input of 1 ATP per molecule of acetyl-CoA converted (catalyzed by acetyl-CoA carboxylase (ACC1)).

FIG. 6 provides a schematic representation of the optimal flow of carbon and the metabolic requirements and yields in the conversion of glucose to farnesene via the mevalonate pathway, wherein cytosolic acetyl-CoA is generated via ADA, the mevalonate pathway comprises an NADH-using HMGr instead of an NADPH-using HMGr, and acetoacteyl-CoA is synthesized from malonyl-CoA and acetyl-CoA by acetoacetyl-CoA synthase.

FIG. 7 provides a schematic representation of the optimal flow of carbon and the metabolic requirements and yields in the conversion of glucose to farnesene via the mevalonate pathway, wherein cytosolic acetyl-CoA is generated via ADA, the mevalonate pathway comprises an NADH-using HMGr instead of an NADPH-using HMGr, and phosphoketolase (PK) and phosphotransacetylase (PTA) catalyze the reactions to convert fructose-6-phosphate (F6P) to acetyl-CoA.

Figure 8:
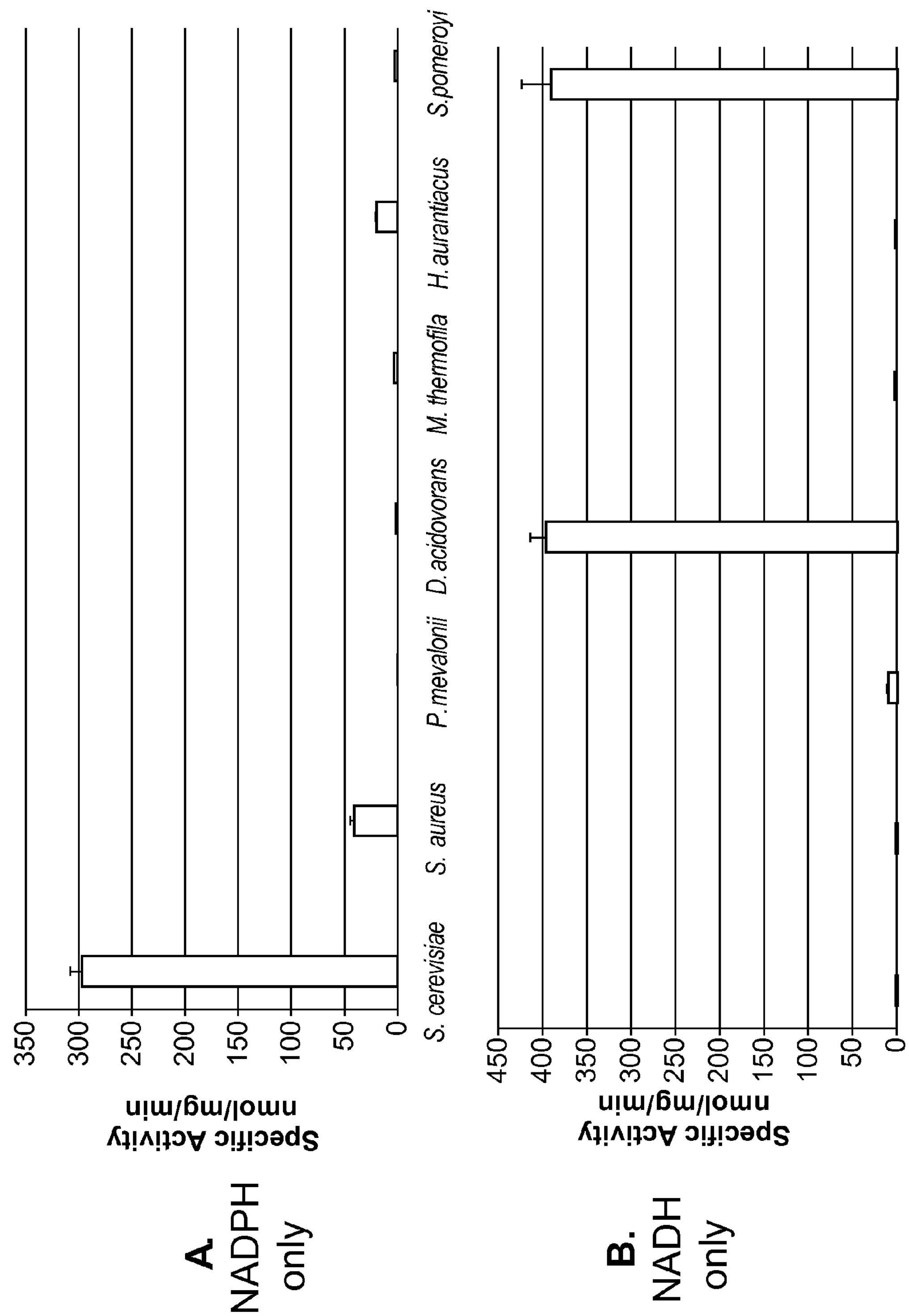

FIG. 8 provides the NADPH-specific or NADH-specific activities (measured as nmol/mg/min) of hydroxymethylglutaryl-CoA reductases from *Sacchormyces cerevisiae* (Sc. tHMG-CoA reductase), *Pseudomonas mevalonii* (Pm.), *Delftia acidovorans* (Da.) and *Silicibacter pomeroyi* (Sp.).

Figure 9:
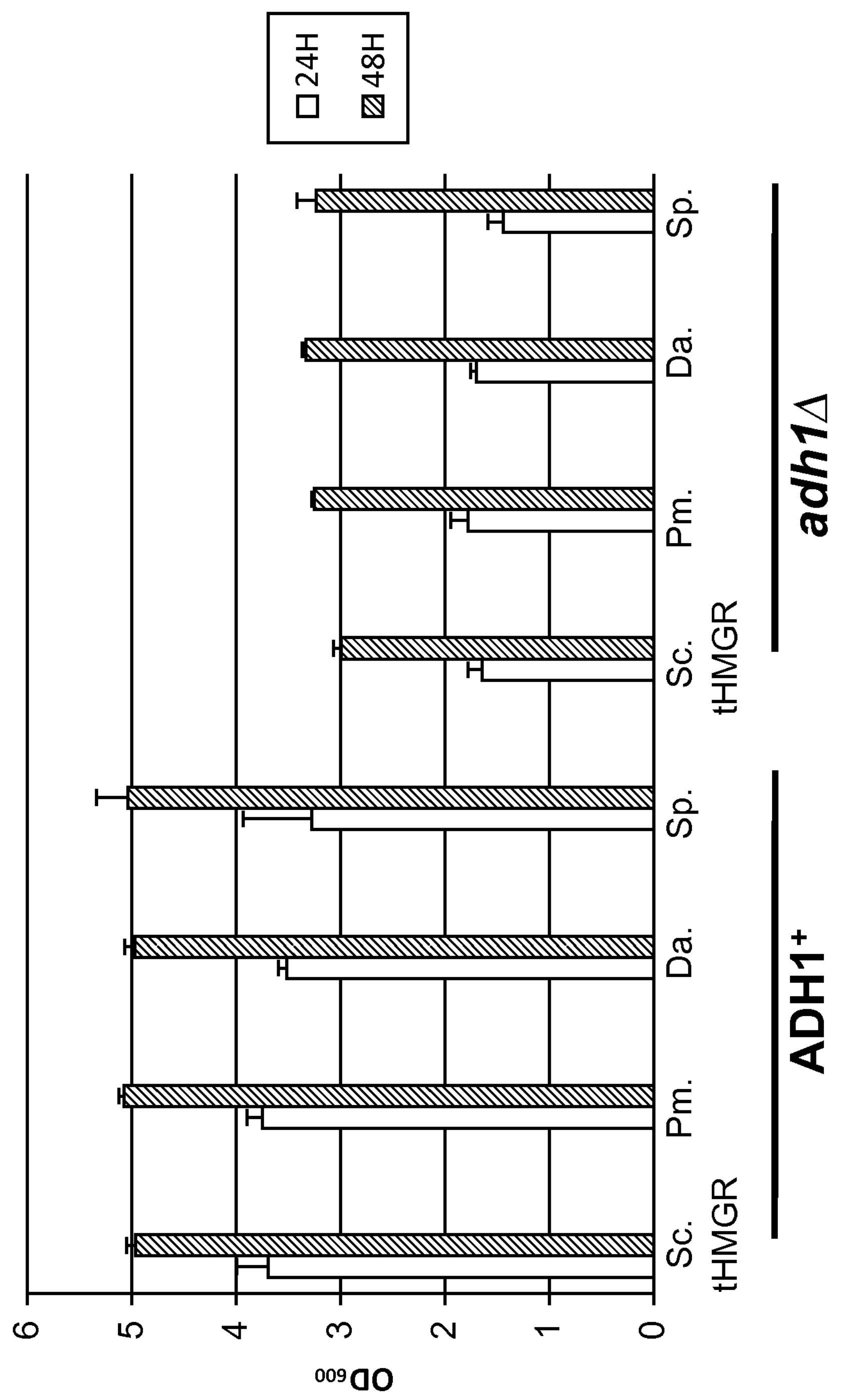

FIG. 9 provides cell densities (measured as $OD_{600}$) after 24 and 48 hours for *S. cerevisiae* (Sc.) strains comprising a heterologous MevT pathway comprising an NADPH-using HMG-CoA reductase (Sc. tHMG-CoA reductase) or an NADH-using HMG-CoA reductase (Pm.—*Pseudomonas mevalonii*; Da.—*Delftia acidovorans*; Sp.—*Silicibacter pomeroyi*) in a wild-type ADH1, and an ADH1 knockout (adh1Δ) background, respectively.

Figure 10:
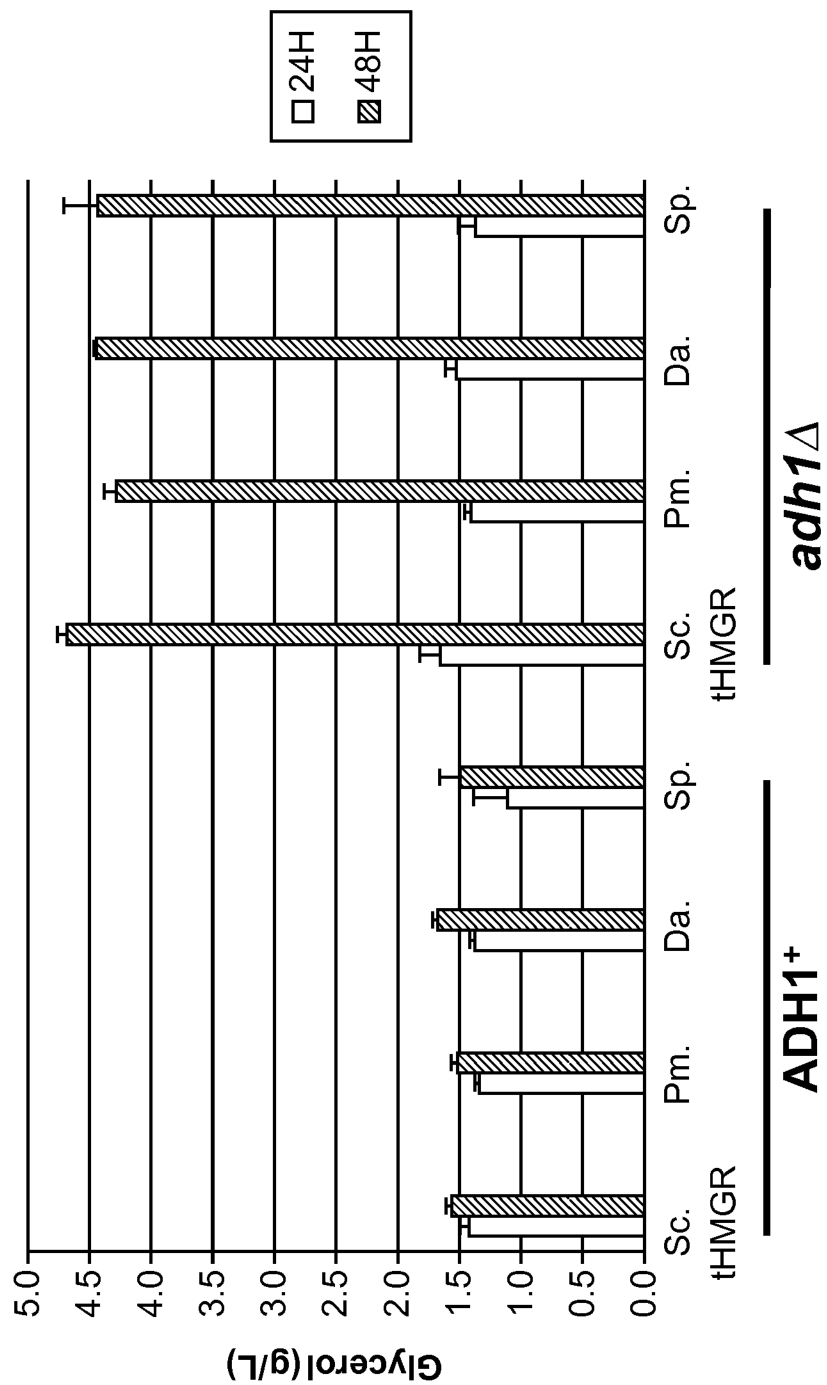

FIG. 10 provides glycerol production (measured as g/L) after 24 and 48 hours for *S. cerevisiae* (Sc.) strains a heterologous MevT pathway comprising an NADPH-using HMG-CoA reductase (Sc. tHMG-CoA reductase) or an NADH-using HMG-CoA reductase (Pm.—*Pseudomonas mevalonii*; Da.—*Delftia acidovorans*; Sp.—*Silicibacter pomeroyi*) in both a wild-type ADH1 and ADH1 knockout background.

Figure 11:
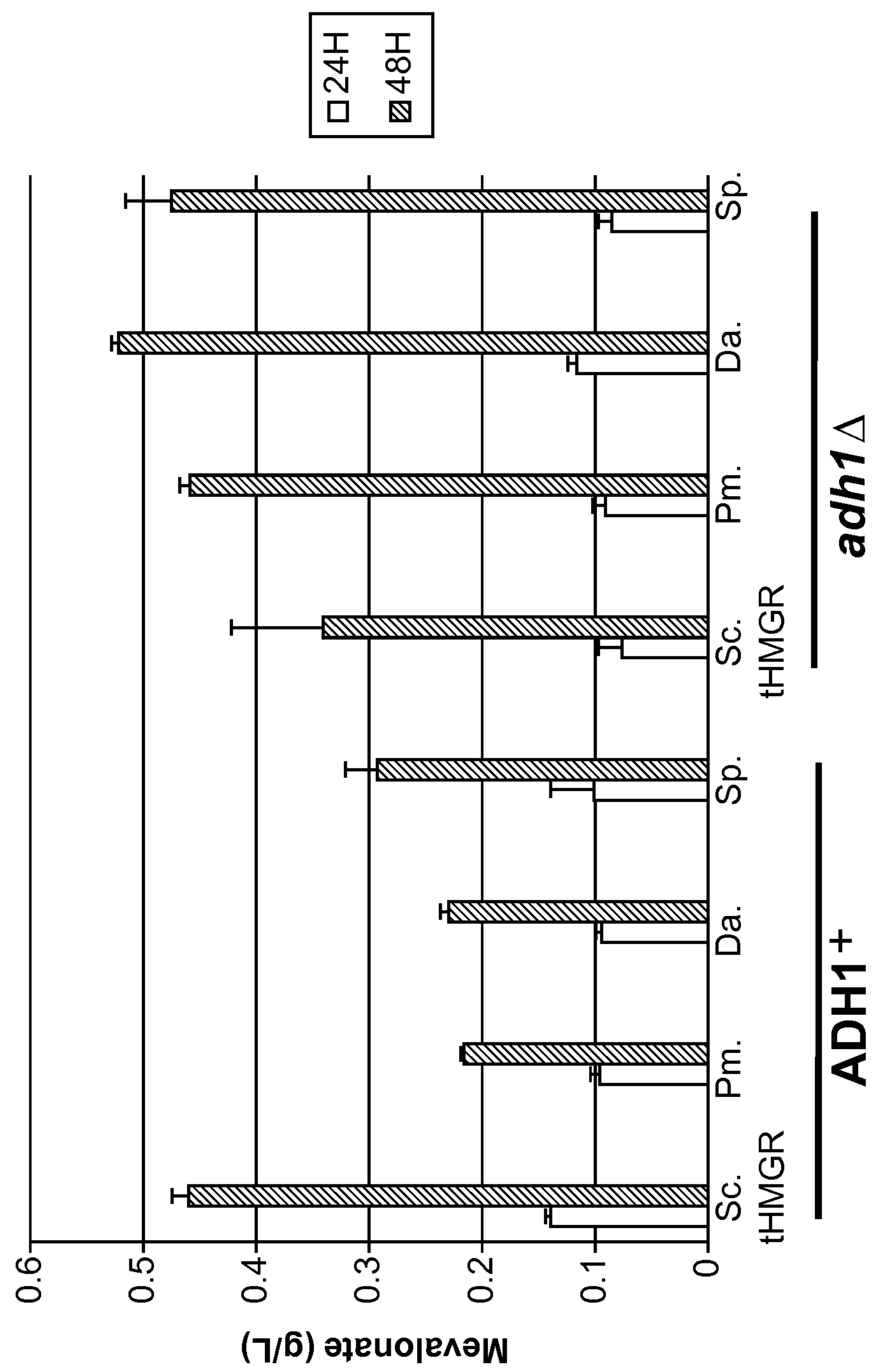

FIG. 11 provides mevlonate production (measured as g/L) after 24 and 48 hours for *S. cerevisiae* (Sc.) strains comprising an NADPH-using HMG-CoA reductase (Sc. tHMG-CoA reductase) or an NADH-using HMG-CoA reductase (Pm.—*Pseudomonas mevalonii*; Da.—*Delftia acidovorans*; Sp.—*Silicibacter pomeroyi*) in both a wild-type ADH1 and ADH1 knockout (adh1Δ) background.

Figure 12:
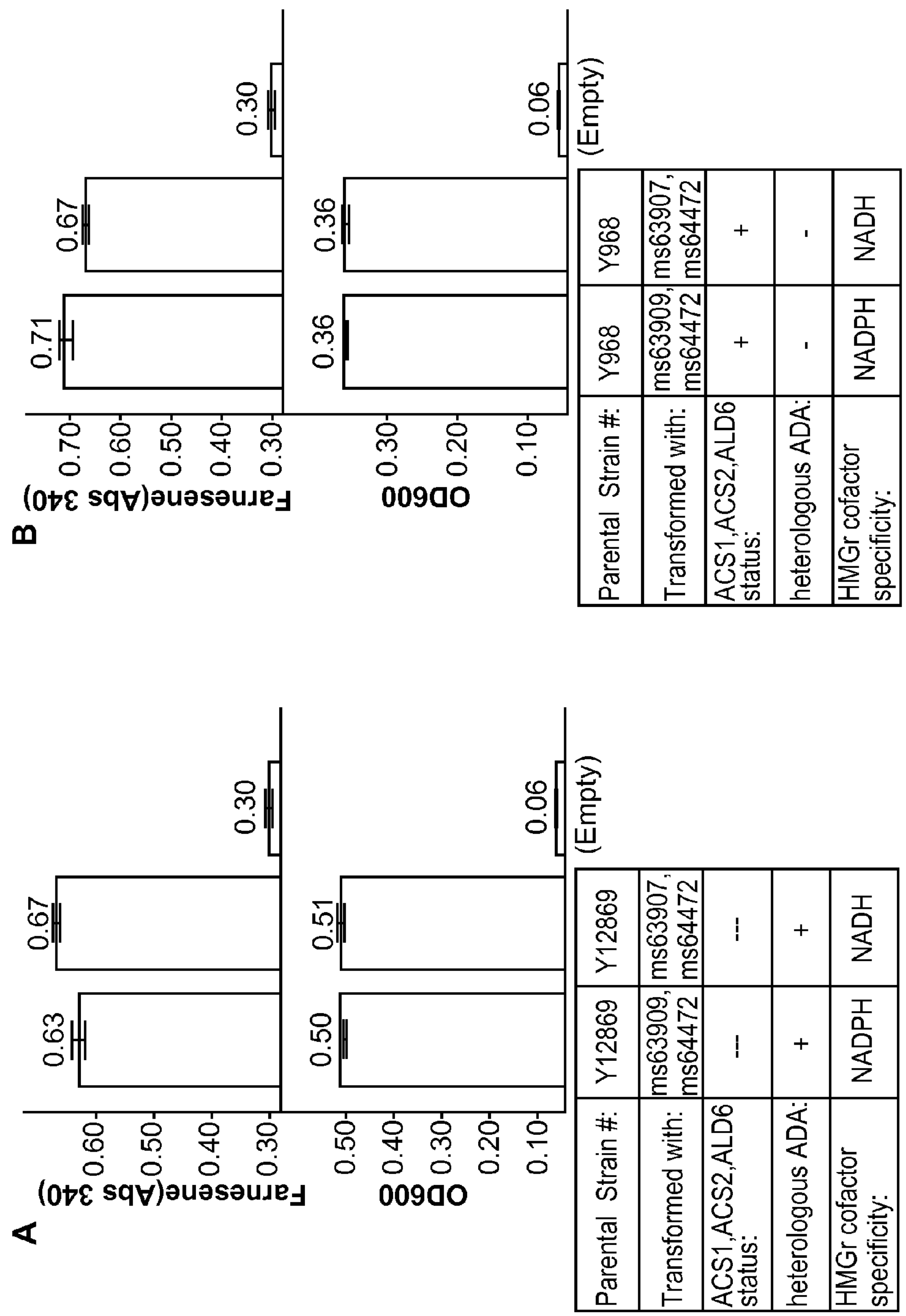

FIG. 12 provides farnesene production and cell densities of *S. cerevisiae* strains comprising: (A) heterologously expressed ADA (Dz.eutE) coupled with acs1Δ acs2Δ ald6Δ and an MEV pathway comprising either an NADPH-using HMG-CoA reductase or an NADH-using HMG-CoA reductase; (B) an intact (wild-type) PDH-bypass and an MEV pathway comprising either an NADPH-using HMG-CoA reductase or an NADH-using HMG-CoA reductase. Columns indicated as "Empty" represent wells with media only (no cells).

FIG. 13 provides glycerol production (top panels) and glucose consumption (lower panels) by: (A) a wild-type strain (Y968); a strain heterologously expressing ADA (Dz.eutE) (Y12869); and (B) a strain heterologously expressing ADA (Dz.eutE), phosphoketolase (PK) and phosphotransacetylase (PTA) (Y12745).

Figure 14:
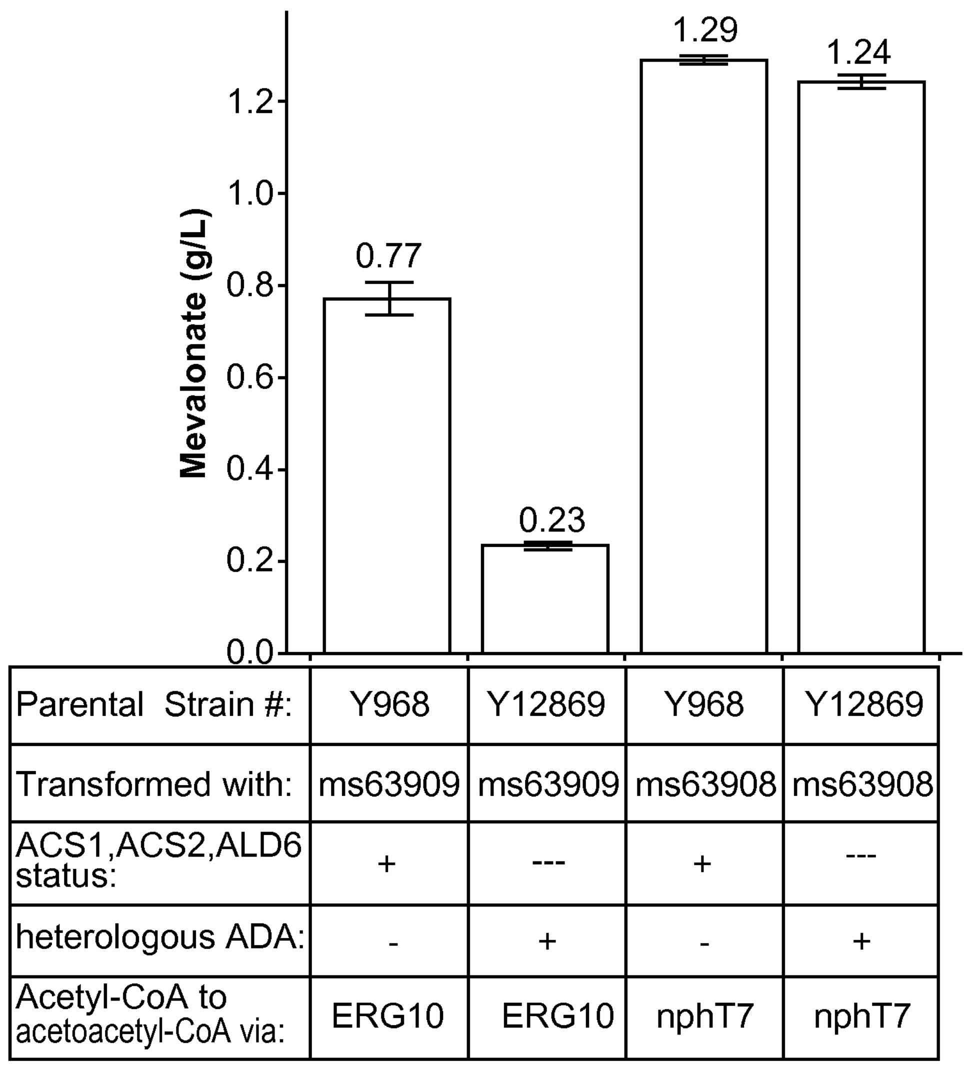

FIG. 14 provides mevalonate production by *S. cerevisiae* strains comprising either an intact (wild-type) PDH-bypass or heterologously expressed ADA (Dz.eutE) coupled with acs1Δ acs2 Δ ald6Δ; and an MEV pathway comprising either ERG10 (acetyl-CoA thiolase) or nphT7 (acetoacetyl-CoA synthase).

5. DETAILED DESCRIPTION OF THE EMBODIMENTS

5.1 Terminology

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

On the other hand, the term "native" or "endogenous" as used herein with reference to molecules, and in particular enzymes and nucleic acids, indicates molecules that are expressed in the organism in which they originated or are found in nature, independently of the level of expression that can be lower, equal, or higher than the level of expression of the molecule in the native microorganism. It is understood that expression of native enzymes or polynucleotides may be modified in recombinant microorganisms.

As used herein, to "functionally disrupt" or a "functional disruption" e.g., of a target gene, for example, one or more genes of the PDH-bypass, means that the target gene is altered in such a way as to decrease in the host cell the activity of the protein encoded by the target gene. Similarly, to "functionally disrupt" or a "functional disruption" e.g., of a target protein, for example, one or more enzymes of the PDH-bypass, means that the target protein is altered in such a way as to decrease in the host cell the activity of the protein. In some embodiments, the activity of the target protein encoded by the target gene is eliminated in the host cell. In other embodiments, the activity of the target protein encoded by the target gene is decreased in the host cell. Functional disruption of the target gene may be achieved by deleting all or a part of the gene so that gene expression is eliminated or reduced, or so that the activity of the gene product is eliminated or reduced. Functional disruption of the target gene may also be achieved by mutating a regulatory element of the gene, e.g., the promoter of the gene so that expression is eliminated or reduced, or by mutating the coding sequence of the gene so that the activity of the gene product is eliminated or reduced. In some embodiments, functional disruption of the target gene results in the removal of the complete open reading frame of the target gene.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an ADA, heterologous expression of an NADH-using HMG-CoA reductase, heterologous expression of an AACS, heterologous expression of a phosphoketolase, heterologous expression of a phosphotrancacetylase, and heterologous expression of one or more enzymes of the mevalonate pathway.

As used herein, the term "production" generally refers to an amount of an isoprenoid produced by a genetically modified host cell provided herein. In some embodiments, production is expressed as a yield of isoprenoid by the host cell. In other embodiments, production is expressed as a productivity of the host cell in producing the isoprenoid.

As used herein, the term "productivity" refers to production of an isoprenoid by a host cell, expressed as the amount of isoprenoid produced (by weight) per amount of fermentation broth in which the host cell is cultured (by volume) over time (per hour).

As used herein, the term "yield" refers to production of an isoprenoid by a host cell, expressed as the amount of isoprenoid produced per amount of carbon source consumed by the host cell, by weight.

5.2 Genetically Modified Microbes Producing Acetyl-CoA Derived Isoprenoids

5.2.1 Host Cells

Host cells useful compositions and methods provided herein include archae, prokaryotic, or eukaryotic cells.

Suitable prokaryotic hosts include, but are not limited, to any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans*, or *Hansenula polymorpha* (now known as *Pichia angusta*). In some embodiments, the host microbe is a strain of the genus *Candida*, such as *Candida lipolytica, Candida guilliermondii, Candida krusei, Candida pseudotropicalis*, or *Candida utilis*.

In a particular embodiment, the host microbe is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

5.2.2 Heterologous ADA for Acetyl-CoA Production

In one aspect, provided herein is a genetically modified host cell capable of producing an acetyl-CoA derived isoprenoid, the cell comprising one or more heterologous nucleotide sequences encoding acylating acetaldehyde dehydrogenase (alternately referred to as "acetylaldehyde dehydrogenase, acetylating," "acetylaldehyde dehydrogenase, acylating," or ADA (EC 1.2.1.10)).

Proteins capable of catalyzing this reaction that are useful for the compositions and methods provided herein include the following four types of proteins:

(1) Bifunctional proteins that catalyze the reversible conversion of acetyl-CoA to acetaldehyde, and the subsequent reversible conversion of acetaldehyde to ethanol. An example of this type of protein is the AdhE protein in *E. coli* (Gen Bank No: NP_415757). AdhE appears to be the evolutionary product of a gene fusion. The $NH_2$-terminal region of the AdhE protein is highly homologous to aldehyde:$NAD^+$ oxidoreductases, whereas the COOH-terminal region is homologous to a family of $Fe^{2+}$-dependent ethanol:$NAD^+$ oxidoreductases (Membrillo-Hernandez et al., (2000) *J. Biol. Chem.* 275: 33869-33875). The *E. coli* AdhE is subject to metal-catalyzed oxidation and therefore oxygen-sensitive (Tamarit et al. (1998) *J. Biol. Chem.* 273:3027-32).

(2) Proteins that catalyze the reversible conversion of acetyl-CoA to acetaldehyde in strictly or facultative anaerobic microbes but do not possess alcohol dehydrogenase activity. An example of this type of protein has been reported in *Clostridium kluyveri* (Smith et al. (1980) *Arch. Biochem. Biophys.* 203: 663-675). An ADA has been annotated in the genome of *Clostridium kluyveri* DSM 555 (accession no: EDK33116). A homologous protein AcdH is identified in the genome of *Lactobacillus plantarum* (accession no: NP_784141). Another example of this type of protein is the ald gene product in *Clostridium beijerinckii* NRRL B593 (Toth et al. (1999) *Appl. Environ. Microbiol.* 65: 4973-4980, accession no: AAD31841).

(3) Proteins that are involved in ethanolamine catabolism. Ethanolamine can be utilized both as carbon and nitrogen source by many enterobacteria (Stojiljkovic et al. (1995) *J. Bacteriol.* 177: 1357-1366). Ethanolamine is first converted by ethanolamine ammonia lyase to ammonia and acetaldehyde, subsequently, acetaldehyde is converted by ADA to acetyl-CoA. An example of this type of ADA is the EutE protein in *Salmonella typhimurium* (Stojiljkovic et al. (1995) *J. Bacteriol.* 177: 1357-1366, accession no: AAL21357; see also U18560.1). *E. coli* is also able to utilize ethanolamine (Scarlett et al. (1976) *J. Gen. Microbiol.* 95:173-176) and has an EutE protein (accession no: AAG57564; see also EU897722.1) which is homologous to the EutE protein in *S. typhimurium.*

(4) Proteins that are part of a bifunctional aldolase-dehydrogenase complex involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) *Biodegradation* 5, 219-236). 4-Hydroxy-2-ketovalerate is first converted by 4-hydroxy-2-ketovalerate aldolase to pyruvate and acetaldehyde, subsequently acetaldehyde is converted by ADA to acetyl-CoA. An example of this type of ADA is the DmpF protein in *Pseudomonas* sp CF600 (accession no: CAA43226) (Shingler et al. (1992) *J. Bacteriol.* 174:71 1-24). *E. coli* has a homologous MphF protein (Ferrandez et al. (1997) *J. Bacteriol.* 179: 2573-2581, accession no: NP_414885) to the DmpF protein in *Pseudomonas* sp. CF600.

In some embodiments, an ADA (or nucleic acid sequence encoding such activity) useful for the compositions and methods described herein is selected from the group consisting of *Escherichia coli* adhE, *Entamoeba histolytica* adh2, *Staphylococcus aureus* adhE, *Piromyces* sp.E2 adhE, *Clostridium kluyveri* (EDK33116), *Lactobacillus plantarum* acdH, and *Pseudomonas putida* (YP 001268189), as described in International Publication No. WO 2009/013159, the contents of which are incorporated by reference in their entirety. In some embodiments, the ADA is selected from the group consisting of *Clostridium botulinum* eutE (FR745875.1), *Desulfotalea psychrophila* eutE (CR522870.1), *Acinetobacter* sp. HBS-2 eutE (ABQ44511.2), *Caldithrix abyssi* eutE (ZP_09549576), and *Halorubrum lacusprofundi* ATCC 49239 (YP_002565337.1).

In particular embodiments, the ADA useful for the compositions and methods provided herein is eutE from *Dickeya zeae*. A representative eutE nucleotide sequence of *Dickeya zeae* includes accession number NC_012912.1:1110476 . . . 1111855 and SEQ ID NO: 1 as provided herein. A representative eutE protein sequence of *Dickeya zeae* includes accession number YP_003003316, and SEQ ID NO: 2 as provided herein.

ADAs also useful in the compositions and methods provided herein include those molecules which are said to be "derivatives" of any of the ADAs described herein. Such a "derivative" has the following characteristics: (1) it shares substantial homology with any of the ADAs described herein; and (2) is capable of catalyzing the conversion of acetaldehyde to acetyl-CoA. A derivative of an ADA is said to share "substantial homology" with ADA if the amino acid sequences of the derivative is at least 80%, at least 85% and more preferably at least 90%, and most preferably at least 95%, the same as that of any of the ADAs described herein.

5.2.2.1 Methods for Identifying Functional ADAs

In another aspect, provided herein is a screening method for ADAs with elevated in vivo performance. In this screening method, ADAs with elevated in vivo performance are identified by their ability to rescue engineered host cells from cell death. The engineered host cells comprise a heterologous pathway for the production of a cytosolic acetyl-CoA derived secondary metabolite, e.g., an isoprenoid. In some embodiments, the engineered host cells further comprise a functionally disrupted PDH-bypass pathway, and a weakly active ADA, wherein the combined activities of the functionally disrupted PDH-bypass pathway and the weakly active ADA do not produce enough cytosolic acetyl-CoA to meet the requirements for production of both: (1) the cytosolic acetyl-CoA derived secondary metabolite; and (2) the cytosolic acetyl-CoA derived primary metabolites required for cell survival, health, and/or growth. For survival, health, and/or growth, the host cell thus requires an active ADA that enables production of an elevated pool of cytosolic acetyl-CoA.

In some embodiments, the method of screening for ADAs with elevated in vivo performance comprises: (a) expressing a control ADA in a host cell having a functionally disrupted PDH-bypass pathway to produce an elevated level of a cytosolic acetyl-CoA derived secondary metabolite, wherein production of the elevated level of the cytosolic acetyl-CoA derived secondary metabolite reduces the viability of the host cell compared to a parent cell not producing the elevated level of the cytosolic acetyl-CoA derived secondary metabolite; and (b) expressing in the host cell a test ADA instead of the control ADA; whereby an increase in viability of the host cell expressing the test ADA compared to the host cell expressing the control ADA identifies the test ADA as having improved in vivo performance compared to the control ADA.

In some embodiments, production of the elevated level of a cytosolic acetyl-CoA derived secondary metabolite in the host cell is inducible. Induction may occur in response to an inducing agent (e.g., galcatose) or specific growth condition (e.g., growth temperature). When grown in the absence of the inducing agent, the ADA activity of the host cell is sufficient to enable production of the cytosolic acetyl-CoA required by the host cell for survival. However, when grown in the presence of the inducing agent, the ADA activity of the host cell is not sufficient to enable production of both the cytosolic acetyl-CoA required by the host cell for survival and the elevated level of the cytosolic acetyl-CoA derived secondary metabolite. In the latter case, the host cell thus requires for survival a more active ADA that enables production of an elevated pool of cytosolic acetyl-CoA. The production of the cytosolic acetyl-CoA derived secondary metabolite in the host cell may range from about 10% to at least about 1,000-fold, or more, higher than the production of the cytosolic acetyl-CoA derived secondary metabolite in the parent cell.

The reduced viability of the host cell expressing the control ADA compared to the parent cell may range from decreased cell growth to lethality. Thus, in some embodiments, the host cell expressing the control ADA produces a reduced number of progeny cells in a liquid culture or on an agar plate compared to the parent cell. In other embodiments, the host cell expressing the control ADA produces no progeny cells in a liquid culture or on an agar plate compared to the parent cell. Accordingly, the increase in viability of the host cell expressing the test ADA instead of the control ADA may be apparent in liquid culture by a higher number of progeny cells, or on an agar plate by a larger colony size, compared to the number of progeny cells or colony size produced by the host cell expressing the control ADA.

Production of the elevated level of the cytosolic acetyl-CoA derived secondary metabolite in the host cell may be effected by modifying the expression and/or activity of an enzyme involved in the production of the cytosolic acetyl-CoA derived secondary metabolite or its precursors in the host cell. In some such embodiments, the expression and/or activity of an enzyme of the MEV or DXP pathway is modified. In some such embodiments, the expression and/or activity of a HMG-CoA reductase and/or a mevalonate kinase is modified.

The control ADA and test ADA may be naturally occurring ADAs or non-naturally occurring ADAs. In some embodiments, the test ADA is a variant of the control ADA that differs from the control ADA by one or more amino acid substitutions, deletions, and/or additions. In some embodiments, the test ADA comprises identical amino acids as the control ADA but the codons encoding these amino acids differ between the test ADA and the control ADA. In some such embodiments, the codons are optimized for usage in the host cell. In some embodiments, the control ADA and/or test ADA is fused to a pyruvate decarboxylase. In some embodiments, expression of the test ADA is under regulatory control of a strong promoter. In some embodiments, expression of the test ADA is under regulatory control of a medium strength promoter. In some embodiments, expression of the test ADA is under regulatory control of a weak promoter.

The increase in viability of the host cell in the presence of the test ADA may be effected by a test ADA that is more active than the control ADA or by a test ADA that is similarly or less active than the control ADA but that is expressed at a higher level. Identification of test ADAs with increased activity can be accomplished by expressing the control ADA and the test ADA at similar levels in the host cell. This can be accomplished, for example, by placing the nucleotide sequences encoding the control ADA and test ADA in the host cell under the control of the same regulatory elements. In other embodiments in which the method is used, for example, to identify regulatory elements (e.g., promoters) that provide a desired expression level, the test ADA differs from the control ADA not in nucleotide or amino acid sequence but in expression level. In such embodiments, different regulatory elements can be used for the expression of the control ADA and the test ADA, and comparison of host cell viabilities provides information not about the activity of the test ADA but about the strength of the regulatory elements driving the expression of the test ADA.

To prevent a competitive growth situation in which fast growing false positive host cells comprising a growth promoting mutation rather than an improved ADA variant take over a host cell culture, one embodiment of the screening method involves an agar-plate based selection system. In this embodiment, the host cell is plated on an agar plate, and a host cell comprising a test ADA variant with improved in vivo performance is identified by colony growth.

A substantial advantage of the presently disclosed screening method is its simplicity and capacity for high-throughput implementation. ADA variants are identified simply based on cell viability, making other costly and time consuming screening methods virtually unnecessary. Thus, in one embodiment, the method is used to screen a collection of ADA variants (e.g., a library of mutant ADAs) for ADA variants with improved in vivo performance. In such an embodiment, not a single test ADA is expressed in a host cell but a collection of test ADAs are expressed in a collection of host cells. The host cells can then be grown on agar plates, and host cells expressing ADA variants with improved in vivo performance can be identified based on colony growth. In some embodiments, the collection of ADA variants comprises from 2 to 5, from 5 to 10, from 10 to 50, from 50 to 100, from 100 to 500, from 500 to 1,000, from 1,000 to 10,000, from 10,000 to 100,000, from 100,000 to 1,000,000, and more, ADA variants.

Another major advantage of the presently disclosed screening method is its continued capacity to select for better and better ADA variants in an iterative fashion, wherein a test ADA identified in an iteration is used as the control ADA in a subsequent iteration. Such an embodiment requires, however, that at each iteration the production of the cytosolic acetyl-CoA derived secondary metabolite in the host cell is checked and potentially increased (e.g., by increasing or decreasing expression levels of enzymes, adding or subtracting enzymes, increasing or decreasing copy numbers of genes, replacing promoters controlling expression of enzymes, or altering enzymes by genetic mutation) to a level that causes reduced viability when the host cell expresses the new control ADA (i.e., the test ADA of the previous iteration). Alternatively, or in addition, at each iteration, the expression of the control ADA can be reduced (e.g., by decreasing expression of or by using weaker promoters or by reducing the stability of the control ADA transcript or polypeptide) to provide reduced control ADA activity. In the next iteration, a test ADA can then be identified that has yet increased in vivo performance compared to the test ADA of the previous iteration.

Another major advantage of the presently disclosed screening method is that selection for improved ADAs occurs in vivo rather than in vitro. As a result, improvements of multiple enzyme properties that enhance the in vivo performance of the ADA variant can be obtained.

Enzymes developed using the presently disclosed screening method can be subjected to additional means of optional screening including but not limited to a fluorescent screen and/or a direct quantitation of the cytosolic acetyl-CoA derived secondary metabolite by gas chromatography. More specifically, this includes a Nile Red-based high throughput fluorescent assay for measuring production of a sesquiterpene such as farnesene, and a gas chromatography (GC)-based direct quantitation method for measuring the titer of a sesquiterpene such as farnesene. The improved enzymes can also be further improved by genetic engineering methods such as induced mutations and the like. As a result, improvements of multiple enzyme properties that enhance the final enzyme performance are successively accomplished, and the most effective enzyme variants are identified.

5.2.3 Functional Disruption of the PDH-Bypass

Acetyl-CoA can be formed in the mitochondria by oxidative decarboxylation of pyruvate catalyzed by the PDH complex. However, due to the inability of *S. cerevisiae* to transport acetyl-CoA out of the mitochondria, the PDH bypass has an essential role in providing acetyl-CoA in the cytosolic compartment, and provides an alternative route to the PDH reaction for the conversion of pyruvate to acetyl-CoA. The PDH bypass involves the enzymes pyruvate decarboxylase (PDC; EC 4.1.1.1), acetaldehyde dehydrogenase (ACDH; EC 1.2.1.5 and EC 1.2.1.4), and acetyl-CoA synthetase (ACS; EC 6.2.1.1). Pyruvate decarboxylase catalyzes the decarboxylation of pyruvate to acetaldehyde and carbon dioxide. Acetaldehyde dehydrogenase oxidizes acetaldehyde to acetic acid. In *S. cerevisiae*, the family of aldehyde dehydrogenases contains five members. ALD2 (YMR170c), ALD3 (YMR169c), and ALD6 (YPL061w) correspond to the cytosolic isoforms, while ALD4 (YOR374w) and ALD5 (YER073w) encode the mitochondrial enzyme. The main cytosolic acetaldehyde dehydrogenase isoform is encoded by ALD6. The formation of acetyl-CoA from acetate is catalyzed by ACS and involves hydrolysis of ATP. Two structural genes, ACS1 and ACS2, encode ACS.

In some embodiments, the genetically modified host cell comprises a functional disruption in one or more genes of the PDH-bypass pathway. In some embodiments, disruption of the one or more genes of the PDH-bypass of the host cell results in a genetically modified microbial cell that is impaired in its ability to catalyze one or more of the following reactions: (1) the decarboxylation of pyruvate into acetaldehyde by pyruvate decarboxylase; (2) the conversion of acetaldehyde into acetate by acetaldehyde dehydrogenase; and (3) the synthesis of acetyl-CoA from acetate and CoA by acetyl-CoA synthetase.

In some embodiments, compared to a parent cell, a host cell comprises a functional disruption in one or more genes of the PDH-bypass pathway, wherein the activity of the reduced-function or non-functional PDH-bypass pathway alone or in combination with a weak ADA is not sufficient to support host cell growth, viability, and/or health.

In some embodiments, the activity or expression of one or more endogenous proteins of the PDH-bypass is reduced by at least about 50%. In another embodiment, the activity or expression of one or more endogenous proteins of the PDH-bypass is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction or deletion of the activity or expression of one or more endogenous proteins of the PDH-bypass.

As is understood by those skilled in the art, there are several mechanisms available for reducing or disrupting the activity of a protein, such as a protein of the PDH-bypass, including, but not limited to, the use of a regulated promoter, use of a weak constitutive promoter, disruption of one of the two copies of the gene encoding the protein in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologous gene with lower specific activity, the like or combinations thereof.

In some embodiments, the genetically modified host cell comprises a mutation in at least one gene encoding for a protein of the PDH-bypass, resulting in a reduction of activity of a polypeptide encoded by said gene. In another embodiment, the genetically modified host cell comprises a partial deletion of gene encoding for a protein of the PDH-bypass, resulting in a reduction of activity of a polypeptide encoded by the gene. In another embodiment, the genetically modified host cell comprises a complete deletion of a gene encoding for a protein of the PDH-bypass, resulting in a reduction of activity of a polypeptide encoded by the gene. In yet another embodiment, the genetically modified host cell comprises a modification of the regulatory region associated with the gene encoding a protein of the PDH-bypass, resulting in a reduction of expression of a polypeptide encoded by said gene. In yet another embodiment, the genetically modified host cell comprises a modification of the transcriptional regulator resulting in a reduction of transcription of a gene encoding a protein of the PDH-bypass. In yet another embodiment, the genetically modified host cell comprises mutations in all genes encoding for a protein of the PDH-bypass resulting in a reduction of activity of a polypeptide encoded by the gene (s). In one embodiment, the activity or expression of the protein of the PDH-bypass is reduced by at least about 50%. In another embodiment, the activity or expression of the protein of the PDH-bypass is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction of the activity or expression of the protein of the PDH-bypass.

In some embodiments, disruption of one or more genes of the PDH-bypass is achieved by using a "disruption construct" that is capable of specifically disrupting a gene of the PDH-bypass upon introduction of the construct into the microbial cell, thereby rendering the disrupted gene non-functional. In some embodiments, disruption of the target gene prevents the expression of a functional protein. In some embodiments, disruption of the target gene results in expression of a non-functional protein from the disrupted gene. In some embodiments, disruption of a gene of the PDH-bypass is achieved by integration of a "disrupting sequence" within the target gene locus by homologous recombination. In such embodiments, the disruption construct comprises a disrupting sequence flanked by a pair of nucleotide sequences that are homologous to a pair of nucleotide sequences of the target gene locus (homologous sequences). Upon replacement of the targeted portion of the target gene by the disruption construct, the disrupting sequence prevents the expression of a functional protein, or causes expression of a non-functional protein, from the target gene.

Disruption constructs capable of disrupting a gene of the PDH-bypass may be constructed using standard molecular biology techniques well known in the art. See, e.g., Sambrook et al., 2001, *Molecular Cloning—A Laboratory Manual*, 3rd edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY. Parameters of disruption constructs that may be varied in the practice of the present methods include, but are not limited to, the lengths of the homologous sequences; the nucleotide sequence of the homologous sequences; the length of the disrupting sequence; the nucleotide sequence of the disrupting sequence; and the nucleotide sequence of the target gene. In some embodiments, an effective range for the length of each homologous sequence is 50 to 5,000 base pairs. In particular embodiments, the length of each homologous sequence is about 500 base pairs. For a discussion of the length of homology required for gene targeting, see Hasty et al., *Mol Cell Biol* 11:5586-91 (1991). In some embodiments, the homologous sequences comprise coding sequences of the target gene. In other embodiments, the homologous sequences comprise upstream or downstream sequences of the target gene. Is some embodiments, one homologous sequence comprises a nucleotide sequence that is homologous to a nucleotide sequence located 5' of the coding sequence of the target gene, and the other homologous sequence comprises a nucleotide sequence that is homologous to a nucleotide sequence located 3' of the coding sequence of the target gene. In some embodiments, the disrupting sequence comprises a nucleotide sequence encoding a selectable marker that enables selection of microbial cells comprising the disrupting sequence. Thus, in such embodiments, the disruption construct has a dual function, i.e., to functionally disrupt the target gene and to provide a selectable marker for the identification of cells in which the target gene is functionally disrupted. In some embodiments, a termination codon is positioned in-frame with and downstream of the nucleotide sequence encoding the selectable marker to prevent translational read-through that might yield a fusion protein having some degree of activity of the wild type protein encoded by the target gene. In some embodiments, the length of the disrupting sequence is one base pair. Insertion of a single base pair can suffice to disrupt a target gene because insertion of the single base pair in a coding sequence could constitute a frame shift mutation that could prevent expression of a functional protein. In some embodiments, the sequence of the disruption sequence differs from the nucleotide sequence of the target gene located between the homologous sequences by a single base pair. Upon replacement of the nucleotide sequence within the target gene with the disrupting sequence, the single base pair substitution that is introduced could result in a single amino acid substitution at a critical site in the protein and the expression of a non-functional protein. It should be recognized, however, that disruptions effected using very short disrupting sequences are susceptible to reversion to the wild type sequence through spontaneous mutation, thus leading to restoration of PDH-bypass function to the host strain. Accordingly, in particular embodiments, the disrupting sequences are longer than one to a few base pairs. At the other extreme, a disrupting sequence of excessive length is unlikely to confer any advantage over a disrupting sequence of moderate length, and might diminish efficiency of transfection or targeting. Excessive length in this context is many times longer than the distance between the chosen homologous sequences in the target gene. Thus, in certain embodiments, the length for the disrupting sequence can be from 2 to 2,000 base pairs. In other embodiments, the length for the disrupting sequence is a length approximately equivalent to the distance between the regions of the target gene locus that match the homologous sequences in the disruption construct.

In some embodiments, the disruption construct is a linear DNA molecule. In other embodiments, the disruption construct is a circular DNA molecule. In some embodiments, the circular disruption construct comprises a pair of homologous sequences separated by a disrupting sequence, as described above. In some embodiments, the circular disruption construct comprises a single homologous sequence. Such circular disruption constructs, upon integration at the target gene locus, would become linearized, with a portion of the homologous sequence positioned at each end and the remaining segments of the disruption construct inserting into and disrupting the target gene without replacing any of the target gene nucleotide sequence. In particular embodiments, the single homologous sequence of a circular disruption construct is homologous to a sequence located within the coding sequence of the target gene.

Disruption constructs can be introduced into a microbial cell by any method known to one of skill in the art without limitation. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Particular methods for transforming yeast cells are well known in the art. See Hinnen et al., Proc. Natl. Acad. Sci. USA 75:1292-3 (1978); Cregg et al., Mol. Cell. Biol. 5:3376-3385 (1985). Exemplary techniques include, but are not limited to, spheroplasting, electroporation, PEG 1000 mediated transformation, and lithium acetate or lithium chloride mediated transformation.

5.2.3.1 ALD4 and ALD6

In some embodiments, one or more genes encoding aldehyde dehydrogenase (ACDH) activity are functionally disrupted in the host cell. In some embodiments, the aldehyde dehydrogenase is encoded by a gene selected from the group consisting of ALD2, ALD3, ALD4, ALD5, ALD6, and homologs and variants thereof.

In some embodiments, the genetically modified host cell comprises a functional disruption of ALD4. Representative ALD4 nucleotide sequences of *Saccharomyces cerevisiae* include accession number NM_001183794, and SEQ ID NO:7 as provided herein. Representative Ald4 protein sequences of *Saccharomyces cerevisiae* include accession number NP_015019.1 and SEQ ID NO:8 as provided herein.

In some embodiments, the genetically modified host cell comprises a functional disruption of cytosolic aldehyde dehydrogenase (ALD6). Ald6p functions in the native PDH-bypass to convert acetaldehyde to acetate. Representative ALD6 nucleotide sequences of *Saccharomyces cerevisiae* include accession number SCU56604, and SEQ ID NO:9 as provided herein. Representative Ald6 protein sequences of *Saccharomyces cerevisiae* include accession number AAB01219 and SEQ ID NO:10 as provided herein.

As would be understood in the art, naturally occurring homologs of aldehyde dehydrogenase in yeast other than *S. cerevisiae* can similarly be inactivated using the methods described herein.

As would be understood by one skilled in the art, the activity or expression of more than one aldehyde dehydrogenase can be reduced or eliminated. In one specific embodiment, the activity or expression of ALD4 and ALD6 or homologs or variants thereof is reduced or eliminated. In another specific embodiment, the activity or expression of ALD5 and ALD6 or homologs or variants thereof is reduced or eliminated. In yet another specific embodiment, the activity or expression of ALD4, ALD5, and ALD6 or homologs or variants thereof is reduced or eliminated. In yet another specific embodiment, the activity or expression of the cytosolically localized aldehyde dehydrogenases ALD2, ALD3, and ALD6 or homologs or variants thereof is reduced or eliminated. In yet another specific embodiment, the activity or expression of the mitochondrially localized aldehyde dehydrogenases, ALD4 and ALD5 or homologs or variants thereof, is reduced or eliminated.

5.2.3.2 ACS1 and ACS2

In some embodiments, one or more genes encoding acetyl-CoA synthetase (ACS) activity are functionally disrupted in the host cell. In some embodiments, the acetyl-CoA synthetase is encoded by a gene selected from the group consisting of ACS1, ACS2, and homologs and variants thereof.

In some embodiments, one or more genes encoding acetyl-CoA synthetase (ACS) activity is functionally disrupted in the host cell. ACS1 and ACS2 are both acetyl-CoA synthetase that con convert acetate to acetyl-CoA. ACS1 is expressed only under respiratory conditions, whereas ACS2 is expressed constitutively. When ACS2 is knocked out, strains are able to grow on respiratory conditions (e.g. ethanol, glycerol, or acetate media), but die on fermentable carbon sources (e.g. sucrose, glucose).

In some embodiments, the genetically modified host cell comprises a functional disruption of ACS1. The sequence of the ACS1 gene of *S. cerevisiae* has been previously described. See, e.g., Nagasu et al., *Gene* 37 (1-3):247-253 (1985). Representative ACS1 nucleotide sequences of *Saccharomyces cerevisiae* include accession number X66425, and SEQ ID NO:3 as provided herein. Representative Acs1 protein sequences of *Saccharomyces cerevisiae* include accession number AAC04979 and SEQ ID NO:4 as provided herein.

In some embodiments, the genetically modified host cell comprises a functional disruption of ACS2. The sequence of the ACS2 gene of *S. cerevisiae* has been previously described. See, e.g., Van den Berg et al., *Eur. J. Biochem.* 231(3):704-713 (1995). Representative ACS2 nucleotide sequences of *Saccharomyces cerevisiae* include accession number S79456, and SEQ ID NO:5 as provided herein. Representative Acs2 protein sequences of *Saccharomyces cerevisiae* include accession number CAA97725 and SEQ ID NO:6 as provided herein.

As would be understood in the art, naturally occurring homologs of acetyl-CoA synthetase in yeast other than *S. cerevisiae* can similarly be inactivated using the methods described herein.

In some embodiments, the host cell comprises a cytosolic acetyl-CoA synthetase activity that can convert acetate to acetyl-CoA under respiratory conditions (i.e., when the host cell is grown in the presence of e.g. ethanol, glycerol, or acetate). In some such embodiments, the host cell is a yeast cell that comprises ACS1 activity. In other embodiments, the host cell compared to a parent cell comprises no or reduced endogenous acetyl-CoA synthetase activity under respiratory conditions. In some such embodiments, the host cell is a yeast cell that compared to a parent cell comprises no or reduced ACS1 activity.

In some embodiments, the host cell comprises a cytosolic acetyl-coA synthetase activity that can convert acetate to acetyl-CoA under non-respiratory conditions (i.e., when the host cell is grown in the presence of fermentable carbon sources (e.g. sucrose, glucose)). In some such embodiments, the host cell is a yeast cell that comprises ACS2 activity. In other embodiments, the host cell compared to a parent cell comprises no or reduced endogenous acetyl-CoA synthetase activity under non-respiratory conditions. In some such embodiments, the host cell is a yeast cell that compared to a parent cell comprises no or reduced ACS2 activity.

5.2.4 Phophoketolase (PK) and Phosphotransacetylase (PTA)

In yeast, acetyl-CoA is biosynthesized from glucose via glycolysis, the tricarboxylic acid (TCA) cycle, oxidative phosphorylation, and pyruvate metabolism. However, in this biosynthetic pathway, $CO_2$ is lost during pyruvate metabolism by pyruvate carboxylase, and in the TCA cycle by pyruvate dehydrogenase and isocitrate dehydrogenase. In an industrial fermentation setting, one benefit of reducing flux through lower glycolysis is that less $CO_2$ is produced in converting pyruvate into acetaldehyde, and thus more carbon can be captured in the end product, thereby increasing the maximum theoretical yield. A second benefit is that less NADH is produced, and therefore significantly less oxygen is needed to reoxidize it. The loss of carbon atoms can theoretically be avoided by bypassing the TCA cycle. This can be accomplished by using phosphoketolase (PK) (enzyme classes EC 4.1.2.9, EC 4.1.2.22) in conjunction with phosphoacetyltransferase (PTA) (EC 2.3.1.8).

PK and PTA catalyze the reactions to convert fructose-6-phosphate (F6P) or xylulose-5-phosphate (X5P) to acetyl-CoA (FIG. 7). PK draws from the pentose phosphate intermediate xyulose 5-phosphate, or from the upper glycolysis intermediate D-fructose 6-phosphate (F6P); PK splits X5P into glyceraldehyde 3-phosphate (G3P) and acetyl phosphate, or F6P into erythrose 4-phosphate (E4P). PTA then converts the acetyl phosphate into acetyl-CoA. G3P can re-enter lower glycolysis, and E4P can re-enter the pentose phosphate pathway or glycolysis by cycling through the non-oxidative pentose phosphate pathway network of transaldolases and transketolases.

In some embodiments, the genetically modified host cell provided herein comprises a heterologous nucleotide sequence encoding a phosphoketolase. In some embodiments, the phosphoketolase is from *Leuconostoc mesenteroides* (Lee et al., *Biotechnol Lett.* 27(12); 853-858 (2005). Representative phosphoketolase nucleotide sequences of *Leuconostoc mesenteroides* includes accession number AY804190, and SEQ ID NO: 11 as provided herein. Representative phosphoketolase protein sequences of *Leuconostoc mesenteroides* include accession numbers YP_819405, AAV66077.1 and SEQ ID NO: 12 as provided herein. Other useful phosphoketolases include, but are not limited to, those from *Bifidobacterium dentium* ATCC 27678 (ABIX02000002.1:2350400 . . . 2352877; EDT46356.1); *Bifidobacterium animalis* (NC_017834.1:1127580 . . . 1130057; YP_006280131.1); and *Bifidobacterium pseudolongum* (AY518216.1:988 . . . 3465; AAR98788.1).

Phosphoketolases also useful in the compositions and methods provided herein include those molecules which are said to be "derivatives" of any of the phosphoketolases described herein. Such a "derivative" has the following characteristics: (1) it shares substantial homology with any of the phosphoketolases described herein; and (2) is capable of catalyzing the conversion of X5P into glyceraldehyde 3-phosphate (G3P) and acetyl phosphate; or F6P into erythrose 4-phosphate (E4P). A derivative of a phosphoketolase is said to share "substantial homology" with the phosphoketolase if the amino acid sequences of the derivative is at least 80%, and more preferably at least 90%, and most preferably at least 95%, the same as that of the phosphoketolase.

In some embodiments, the genetically modified host cell provided herein comprises a heterologous nucleotide sequence encoding a phosphotransacetylase. In some embodiments, the phosphotransacetylase is from *Clostridium kluyveri*. Representative phosphotransacetylase nucleotide sequences of *Clostridium kluyveri* includes accession number NC_009706.1:1428554 . . . 1429555, and SEQ ID NO: 13 as provided herein. Representative phosphotransacetylase protein sequences of *Clostridium kluyveri* include accession number YP_001394780 and SEQ ID NO: 14 as provided herein. Other useful phosphotransacetylases include, but are not limited to, those from *Lactobacillus reuteri* (NC_010609.1:460303 . . . 461277; YP_001841389.10); *Bacillus subtilis* (NC_014479.1:3671865 . . . 3672836; YP_003868063.1); and *Methanosarcina thermophile* (L23147.1:207.1208; AAA72041.1).

Phosphotransacetylases also useful in the compositions and methods provided herein include those molecules which are said to be "derivatives" of any of the phosphotransacetylases described herein. Such a "derivative" has the following characteristics: (1) it shares substantial homology with any of the phosphotransacetylases described herein; and (2) is capable of catalyzing the conversion of acetyl phosphate into acetyl-CoA. A derivative of a phosphotransacetylase is said to share "substantial homology" with the phosphotransacetylase if the amino acid sequences of the derivative is at least 80%, and more preferably at least 90%, and most preferably at least 95%, the same as that of the phosphotransacetylase.

5.2.5 MEV Pathway

In some embodiments, the host cell comprises one or more heterologous enzymes of the MEV pathway. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate.

In some embodiments, the one or more enzymes of the MEV pathway are selected from the group consisting of acetyl-CoA thiolase, acetoacetyl-CoA synthase, HMG-CoA synthase, HMG-CoA reductase, mevalonate kinase, phosphomevalonate kinase and mevalonate pyrophosphate decarboxylase. In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate. In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway. In some embodiments, the host cell comprises one or more heterologous nucleotide sequences encoding seven enzymes of the MEV pathway. In some embodiments, the host cell comprises a plurality of heterologous nucleic acids encoding all of the enzymes of the MEV pathway.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound.

5.2.5.1 Conversion of Acetyl-CoA to Acetoacetyl-CoA

In some embodiments, the genetically modified host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In host cells comprising a heterologous ADA and acetyl-CoA thiolase, the reversible reaction catazlyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Thus, in some embodiments, in order to provide a strong pull on acetyl-CoA to drive the forward reaction of ADA, the MEV pathway of the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci* USA 107 (25):11265-70 (2010). Representative AACS nucleotide sequences of *Streptomyces* sp. strain CL190 include accession number AB540131.1 and SEQ ID NO:15 as provided herein. Representative AACS protein sequences of *Streptomyces* sp. strain CL190 include accession numbers D7URV0, BAJ10048 and SEQ ID NO:16 as provided herein. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988 (AB212624; BAE78983); *Actinoplanes* sp. A40644 (AB113568; BAD07381); *Streptomyces* sp. C(NZ_ACEW010000640; ZP_05511702); *Nocardiopsis dassonvillei* DSM 43111 (NZ_ABUI01000023; ZP_04335288); *Mycobacterium ulcerans* Agy99 (NC_008611; YP_907152); *Mycobacterium marinum* M (NC_010612; YP_001851502); *Streptomyces* sp. Mg1 (NZ_DS570501; ZP_05002626); *Streptomyces* sp. AA4 (NZ_ACEV01000037; ZP_05478992); *S. roseosporus* NRRL 15998 (NZ_ABYB01000295; ZP_04696763); *Streptomyces* sp. ACTE (NZ_ADFD01000030; ZP_06275834); *S. viridochromogenes* DSM 40736 (NZ_ACEZ01000031; ZP_05529691); *Frankia* sp. CcI3 (NC_007777; YP_480101); *Nocardia brasiliensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthaseis said to share "substantial homology" with acetoacetyl-CoA synthase if the amino acid sequences of the derivative is at least 80%, and more preferably at least 90%, and most preferably at least 95%, the same as that of acetoacetyl-CoA synthase.

5.2.5.2 Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

5.2.5.3 Conversion of HMG-CoA to Mevalonate

In some embodiments, the host cell comprises a heterologous nucleotide sequence encoding an enzyme that can convert HMG-CoA into mevalonate, e.g., a HMG-CoA reductase. In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMG-CoA reductases are provided below.

TABLE 1

Co-factor specificities for select class II HMG-CoA reductases

| Source | Coenzyme specificity | $K_m^{NADPH}$ (μM) | $K_m^{NADH}$ (μM) |
|---|---|---|---|
| *P. mevalonii* | NADH | | 80 |
| *A. fulgidus* | NAD(P)H | 500 | 160 |
| *S. aureus* | NAD(P)H | 70 | 100 |
| *E. faecalis* | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii, A. fulgidus* or *S. aureus*. In particular embodiments, the HMG-CoA reductase is capable of only utilizing NADH as a cofactor, e.g., HMG-CoA reductase from *P. mevalonii, S. pomeroyi* or *D. acidovorans*.

In some embodiments, the NADH-using HMG-CoA reductase is from *Pseudomonas mevalonii*. The sequence of the wild-type mvaA gene of *Pseudomonas mevalonii*, which encodes HMG-CoA reductase (E.C. 1.1.1.88), has been previously described. See Beach and Rodwell, *J. Bacteriol.* 171: 2994-3001 (1989). Representative mvaA nucleotide sequences of *Pseudomonas mevalonii* include accession number M24015, and SEQ ID NO: 17 as provided herein. Representative HMG-CoA reductase protein sequences of *Pseudomonas mevalonii* include accession numbers AAA25837, P13702, MVAA_PSEMV and SEQ ID NO: 18 as provided herein.

In some embodiments, the NADH-using HMG-CoA reductase is from *Silicibacter pomeroyi*. Representative HMG-CoA reductase nucleotide sequences of *Silicibacter pomeroyi* include accession number NC_006569.1, and SEQ ID NO: 19 as provided herein. Representative HMG-CoA reductase protein sequences of *Silicibacter pomeroyi* include accession number YP_164994 and SEQ ID NO: 20 as provided herein.

In some embodiments, the NADH-using HMG-CoA reductase is from *Delftia acidovorans*. A representative HMG-CoA reductase nucleotide sequences of *Delftia acidovorans* includes NC_010002 REGION: complement (319980 . . . 321269), and SEQ ID NO: 21 as provided herein. Representative HMG-CoA reductase protein sequences of *Delftia acidovorans* include accession number YP_001561318 and SEQ ID NO: 22 as provided herein.

In some embodiments, the NADH-using HMG-CoA reductases is from *Solanum tuberosum* (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$ ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro (see, e.g., Example 1 and Section 6.1.1.3 below), and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteriol.* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171:2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGr and an NADPH-using HMG-CoA reductase. Illustrative examples of nucleotide sequences encoding an NADPH-using HMG-CoA reductase include, but are not limited to: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

5.2.5.4 Conversion of Mevalonate to Mevalonate-5-Phosphate

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

5.2.5.5 Conversion of Mevalonate-5-Phosphate to Mevalonate-5-Pyrophosphate

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

5.2.5.6 Conversion of Mevalonate-5-Pyrophosphate to IPP

In some embodiments, the host cell comprises a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

5.2.5.7 Conversion of IPP to DMAPP

In some embodiments, the host cell further comprises a heterologous nucleotide sequence encoding an enzyme that can convert IPP generated via the MEV pathway into dimethylallyl pyrophopsphate (DMAPP), e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

5.2.5.8 Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*), (AF182827; *Mentha×piperita*), (MPI249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans serovar Copenhageni* str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa* Temecula1).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis serovar israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides f. lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; Synechococcus elongates), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

5.2.5.9 Terpene Synthases

In some embodiments, the host cell further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the heterologous nucleotide encodes a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the heterologous nucleotide encodes a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla* frutescens), (AY473623; *Picea abies*), (DQ195274; *Picea sitchensis*), and (AF444798; *Perilla frutescens* var. crispa cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867*; Citrus limon*) and (AY055214, REGION: 48.1889*; Agastache rugosa*) and (−)-limonene synthases (DQ195275, REGION: 1.1905; *Picea sitchensis*), (AF006193, REGION: 73.1986*; Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908*; Abies grandis*), (AY195609*; Antirrhinum majus*), (AY195608*; Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes a ocimene synthase. Illustrative examples of suitable nucleotide sequences include, but are not limited to: (AY195607*; Antirrhinum majus*), (AY195609*; Antirrhinum majus*), (AY195608*; Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+) α-pinene synthase (AF543530, REGION: 1.1887; *Pinus taeda*), (−)α-pinene synthase (AF543527, REGION: 32.1921; *Pinus taeda*), and (+)/(−)α-pinene synthase (AGU87909, REGION: 6111892*; Abies grandis*).

In some embodiments, the heterologous nucleotide encodes a β-pinene synthase. Illustrative examples of suitable nucleotide sequences include, but are not limited to: (−)β-pinene synthases (AF276072, REGION: 1.1749; *Artemisia annua*) and (AF514288, REGION: 26.1834*; Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis.*

In some embodiments, the heterologous nucleotide encodes a γ-terpinene synthase. Illustrative examples of suitable nucleotide sequences include: (AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include, but are not limited to: (AY693650 from *Oscimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes a α-farnesene synthase. Illustrative examples of suitable nucleotide sequences include, but are not limited to DQ309034 from *Pyrus communis cultivar d'Anjou* (pear; gene name AFS1) and AY182241 from *Malus domestica* (apple; gene AFS1). Pechouus et al., *Planta* 219(1):84-94 (2004).

In some embodiments, the heterologous nucleotide encodes a β-farnesene synthase. Illustrative examples of suitable nucleotide sequences include but is not limited to accession number AF024615 from *Mentha×piperita* (peppermint; gene Tspa11), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to accession number AF529266 from *Zea mays* and YDR481C from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchouliol synthase. Illustrative examples of suitable nucleotide sequences include, but are not limited to AY508730 REGION: 1.1659 from *Pogostemon cablin.*

In some embodiments, the heterologous nucleotide encodes a nootkatone synthase. Illustrative examples of suitable nucleotide sequences include, but are not limited to AF441124 REGION: 1.1647 from *Citrus sinensis* and AY917195 REGION: 1.1653 from *Perilla frutescens.*

In some embodiments, the heterologous nucleotide encodes an abietadiene synthase. Illustrative examples of suitable nucleotide sequences include, but are not limited to: (U50768*; Abies grandis*) and (AY473621; *Picea abies*).

In some embodiments, the host cell produces a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

5.3 Methods of Making Genetically Modified Cells

Also provided herein are methods for producing a host cell that is genetically engineered to comprise one or more of the modifications described above, e.g., one or more nucleic heterologous nucleic acids encoding one or more enzymes selected from ADA, NADH-using HMG-CoA reductase, AACS, PK, PTA, and other mevalonate pathway enzymes. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The copy number of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the $KAN^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989*, Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996*, Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994*, Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S.*

*cerevisiae* and *S. uvarum, Kluyveromyces* spp., including *K. thermotolerans, K. lactis*, and *K. marxianus, Pichia* spp., *Hansenula* spp., including *H. polymorphs, Candida* spp., *Trichosporon* spp., *Yamadazyma* spp., including Y. spp. *stipitis, Torulaspora pretoriensis, Issatchenkia orientalis, Schizosaccharomyces* spp., including *S. pombe, Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous ADA genes, proteins, or enzymes, techniques may include, but are not limited to, cloning a gene by PCR using primers based on a published sequence of an ADA gene/enzyme or by degenerate PCR using degenerate primers designed to amplify a conserved region among ADA genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology*, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

5.4 Methods of Producing Isoprenoids

In another aspect, provided herein is a method for the production of an isoprenoid, the method comprising the steps of: (a) culturing a population of any of the genetically modified host cells described herein in a medium with a carbon source under conditions suitable for making an isoprenoid compound; and (b) recovering said isoprenoid compound from the medium.

In some embodiments, the genetically modified host cell comprises one or more modifications selected from the group consisting of: heterologous expression of an ADA, heterologous expression of an NADH-using HMG-CoA reductase, heterologous expression of an AACS, heterologous expression of a phosphoketolase, heterologous expression of a phosphotrancacetylase, and heterologous expression of one or more enzymes of the mevalonate pathway; and the genetically modified host cell produces an increased amount of the isoprenoid compound compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of isoprenoid that is greater than about 10 grams per liter of fermentation medium. In some such embodiments, the isoprenoid is produced in an amount from about 10 to about 50 grams, more than about 15 grams, more than about 20 grams, more than about 25 grams, or more than about 30 grams per liter of cell culture.

In some embodiments, the host cell produces an elevated level of isoprenoid that is greater than about 50 milligrams per gram of dry cell weight. In some such embodiments, the isoprenoid is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by a parent cell, on a per unit volume of cell culture basis.

In some embodiments, the host cell produces an elevated level of isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit dry cell weight basis.

In some embodiments, the host cell produces an elevated level of an isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit volume of cell culture per unit time basis.

In some embodiments, the host cell produces an elevated isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit dry cell weight per unit time basis.

In most embodiments, the production of the elevated level of isoprenoid by the host cell is inducible by an inducing compound. Such a host cell can be manipulated with ease in the absence of the inducing compound. The inducing compound is then added to induce the production of the elevated level of isoprenoid by the host cell. In other embodiments, production of the elevated level of isoprenoid by the host cell is inducible by changing culture conditions, such as, for example, the growth temperature, media constituents, and the like.

5.4.1 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing isoprenoids provided herein may be performed in a suitable culture medium (e.g., with or without pantothenate supplementation) in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing an isoprenoid can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or isoprenoid production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of isoprenoids. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

5.4.2 Recovery of Isoprenoids

Once the isoprenoid is produced by the host cell, it may be recovered or isolated for subsequent use using any suitable separation and purification methods known in the art. In some embodiments, an organic phase comprising the isoprenoid is separated from the fermentation by centrifugation. In other embodiments, an organic phase comprising the isoprenoid separates from the fermentation spontaneously. In other embodiments, an organic phase comprising the isoprenoid is separated from the fermentation by adding a deemulsifier and/or a nucleating agent into the fermentation reaction. Illustrative examples of deemulsifiers include flocculants and coagulants. Illustrative examples of nucleating agents include droplets of the isoprenoid itself and organic solvents such as dodecane, isopropyl myristrate, and methyl oleate.

The isoprenoid produced in these cells may be present in the culture supernatant and/or associated with the host cells. In embodiments where the isoprenoid is associated with the host cell, the recovery of the isoprenoid may comprise a method of permeabilizing or lysing the cells. Alternatively or simultaneously, the isoprenoid in the culture medium can be recovered using a recovery process including, but not limited to, chromatography, extraction, solvent extraction, membrane separation, electrodialysis, reverse osmosis, distillation, chemical derivatization and crystallization.

In some embodiments, the isoprenoid is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

6. EXAMPLES

6.1 Example 1

Identification and Characterization of NADH-Specific HMG-CoA Reductases

This example describes the identification and characterization of HMG-CoA reductases not previously known to have NADH cofactor specificity.

6.1.1 Materials and Methods 6.1.1.1 Strain Engineering

A wild-type *Saccharomyces cerevisiae* strain, (CEN.PK2, Mat a, ura3$^-$, TRP1$^+$, leu2$^-$, MAL2-8C, SUC2,) was used as a host for the expression of the mevalonate (MevT) pathway (whereby acetyl-CoA thiolase (ERG10) converts acetyl-CoA to acetoacetyl-CoA; HMG-CoA synthase (ERG13) converts acetoacetyl-CoA into HMG-CoA; and HMG-CoA reductase converts HMG-CoA into mevalonate (FIG. 1)).

This strain was transformed with a plasmid encoding either a heterologous class II HMG-CoA reductase derived from *Staphylococcus aureus* (ZP_06815052), *Herpetosiphon aurantiacus* (YP_001546303), *Pseudomonas mevalonii* (P13702), *Delftia acidovorans* (YP_001561318), *Menthanosaeta thermofila* (YP_843364) or *Silicibacter pomeoyri* (YP_164994); or an N-terminally truncated version of the *Saccharomyces cerevisiae* HMG-CoA reductase (tHMG-CoA reductase) (EEU05004). The class II HMG-CoA reductases were codon optimized for yeast expression and chemically synthesized with c-terminal FLAG-HIS tags, with the exception that the *P. mevalonii* HMG-CoA reductase was synthesized with the following additional modifications:

NotI site—GAL1 promotor—NdeI site—[*P. mevalonii* HMG-CoA reductase]- - - EcoRI site—FLAG tag—HIS tag—STOP codon—PGK1 terminator - - - NotI site This DNA was cloned into the NotI site of the pBluescript SK+ vector (Stratagene). The yeast Gal7 promoter was PCR amplified using the genomic DNA extract of a wild-type CENPK2 strain as template and using the oligonucleotides YT_164_30_Gal7F (which contains a SacI and a NotI restriction site at 5'-end) and YT_164_30_Gal7R (which contains NdeI restriction site at 3'-end) (see Table 2). The PCR product was cloned onto pCR II-TOPO vector (Invitrogen). Both plasmids were cut using SacI and NotI, and the excised Sc.GAL7 promoter was used to swap the Gal1 promoter upstream of the *P. mevalonii* HMG-CoA reductase gene. The resulting plasmid and pAM70 (SEQ ID NO:23), a yeast episomal vector pRS426 with a URA3 marker, were both digested with NotI. The plasmid pAM01147 (SEQ ID NO:24) was then constructed by ligating the NotI fragment into the NotI digested site of pAM70. This plasmid was used as a base plasmid to swap the *P. mevalonii* HMG-CoA reductase coding sequence for any HMG-CoA reductase coding sequence of interest (including the yeast tHMG-CoA reductase) by digesting the plasmid with NdeI and EcoRI and ligating a digested HMG-CoA reductase coding sequence of interest having NdeI and EcoRI sites at the 5'- and 3'-ends, respectively. Propagation of plasmid DNA was performed in *Escherichia coli* strain DH5α. Strain Y1389 was then transformed with the plasmids harboring coding sequences for different HMG-CoA reductases, and transformants were selected on CSM media plate without uracil containing 2% glucose. All DNA-mediated transformation into *S. cerevisiae* was conducted using the standard Lithium Acetate procedure as described by Gietz R W and Woods R A, *Guide to Yeast Genetics and Molecular and Cell Biology, Part B*. San Diego, Calif.: Academic Press Inc. pp. 87-96 (2002).

Genomic integration of Sc. acetoacetyl-CoA thiolase (ERG10) and Sc.HMG-CoA Synthase (ERG13) was targeted to the Ga180 locus of the host strain using the integration construct shown below (SEQ ID NO:25).

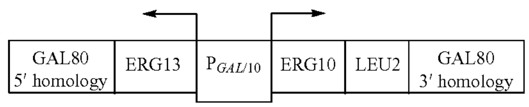

Each component of the integration construct was PCR amplified using 100 ng of Y002 genomic DNA as template. PCR amplification of the upstream GAL80 locus from positions-1000 to -1 was performed with oligonucleotides YT__164__36__001 and YT__164__36__003 (see Table 2). PCR amplification of the yeast ERG10 and ERG13 genes was done using the pair of oligonucleotides YT__164__36__002 and YT__164__36__005 for ERG13 and YT__164__36__006 and YT__164__36__009 for ERG10. The oligonucleotides YT__164__36__004 and YT__164__36__007 were used to amplify the GAL1/10 promoter, while primers YT__164__36__008 and YT__164__36__011 were used to amplify the LEU2 gene. PCR amplification of the downstream GAL80 locus positions 23 to 1000 (after the stop codon) was performed with oligonucleotides YT__164__36__010 and YT__164__36__012. One hundred fmol of each piece of DNA was added in a single tube and assembled by stitching PCR reaction (as described in U.S. Pat. No. 8,221,982, the contents of which are hereby incorporated by reference) using the primers YT__164__36__001 and YT__164__36__012. PCR products having the expected molecular weights were gel purified.

TABLE 2

| Primers used for strain engineering | | |
|---|---|---|
| Primer name | SEQ ID NO: | Primer Sequence |
| YT_164_36_001 | SEQ ID NO: 26 | GCCTGTCTACAGGATAAAGACGGG |
| YT_164_36_002 | SEQ ID NO: 27 | TCCCGTTCTTTCCACTCCCGTCTATATATATA TCATTGTTATTA |
| YT_164_36_003 | SEQ ID NO: 28 | TAATAACAATGATATATATATAGACGGGAGT GGAAAGAACGGGA |
| YT_164_36_004 | SEQ ID NO: 29 | CCAACAAAGTTTAGTTGAGAGTTTCATTTAT ATTGAATTTTCAAAAATTCTTAC |
| YT_164_36_005 | SEQ ID NO: 30 | GTAAGAATTTTTGAAAATTCAATATAAATGA AACTCTCAACTAAACTTTGTTGG |
| YT_164_36_006 | SEQ ID NO: 31 | GTCAAGGAGAAAAAACTATAATGTCTCAGA ACGTTTACATTGTATCGACTGCCAGAACCC |
| YT_164_36_007 | SEQ ID NO: 32 | GGGTTCTGGCAGTCGATACAATGTAAACGTT CTGAGACATTATAGTTTTTTCTCCTTGAC |
| YT_164_36_008 | SEQ ID NO: 33 | GTGTGCCTTTTGACTTACTTTTACGTTGAGCC ATTAGTATCA |
| YT_164_36_009 | SEQ ID NO: 34 | TGATACTAATGGCTCAACGTAAAAGTAAGTC AAAAGGCACAC |
| YT_164_36_010 | SEQ ID NO: 35 | GATATTTCTTGAATCAGGCGCCTTAGACCCC CCAGTGCAGCGAACGTTATAAAAAC |
| YT_164_36_011 | SEQ ID NO: 36 | GTTTTTATAACGTTCGCTGCACTGGGGGGTC TAAGGCGCCTGATTCAAGAAATATC |
| YT_164_36_012 | SEQ ID NO: 37 | AAATATGACCCCCAATATGAGAAATTAAGG C |
| YT_164_30_Gal3F | SEQ ID NO: 38 | GAGCTCGCGGCCGC GTACATACCTCTCTCCGTATCCTCGTAATCAT TTTCTTGT |
| YT_164_30_Gal3R | SEQ ID NO: 39 | CATATGACTATGTGT TGCCCTACCTTTTTACTTTTATTTTCTCTTT |
| YT_164_30_Gal7F | SEQ ID NO: 40 | GAGCTCGCGGCCGC GTGTCACAGCGAATTTCCTCACATGTAGGGA CCGAATTGT |
| YT_164_30_Gal7R | SEQ ID NO: 41 | CATATGTTTTGAGGGAATATTCAACTGTTTTT TTTATCATGTTGA |
| RYSE 0 | SEQ ID NO: 42 | GACGGCACGGCCACGCGTTTAAACCGCC |
| RYSE 19 | SEQ ID NO: 43 | CCCGCCAGGCGCTGGGGTTTAAACACC |

Derivatives of Y1389 transformed with different HMG-CoA reductases (as indicated above) were transformed with the ERG 10/ERG13 integration construct to create the strains listed below in Table 3. Transformants were selected on CSM containing 2% glucose media plate without uracil and leucine. All gene disruptions and replacements were confirmed by phenotypic analysis and colony PCR.

TABLE 3

| Strain Description | | |
|---|---|---|
| Strain # | Descrption | strain # after adh1 Knockout |
| Y1431 | MevT with *S. cerevisae* tHMG-CoA reductase | Y1804 |
| Y1432 | MevT with *S. aureus* HMG-CoA reductase | |
| Y1433 | MevT with *P. mevalonii* HMG-CoA reductase | Y1805 |
| Y1435 | MevT with *D. acidovorans* HMG-CoA reductase | Y1806 |
| Y1436 | MevT with *M. thermofila* HMG-CoA reductase | |
| Y1486 | MevT with *H. aurantiacus* HMG-CoA reductase | |
| Y1487 | MevT with *S. pomeroyi* HMG-CoA reductase | Y1807 |

For strains Y1431, Y1433, Y1435 and Y1487, the ADH1 gene was knocked out using the disruption construct shown below (SEQ ID NO:44):

| ADH1 5' homology | Kan A | ADH1 3' homology |
|---|---|---|

The disruption construct was generated by the methods of polynucleotide assembly described in U.S. Pat. No. 8,221,982. The ADH1 5' homology region of the integration construct was homologous to positions −563 to −77 of the ADH1 coding sequence, and the ADH1 3' homology region was homologous to positions 87 to 538 (after the stop codon of the ADH1 gene). Primers RYSE 0 and RYSE 19 were used to amplify the product. Strain Y1431, Y1433, Y1435 and Y1487 (Table 2) were transformed with the product, and transformants were selected on YPD media plate containing 2% glucose and G418 (Geneticin). The ADH1 gene disruption was confirmed by phenotypic analysis and colony PCR.

6.1.1.2 Cell Culture

A single colony of a given yeast strain was cultured in 3 ml of Yeast Nitrogen Base (YNB) media with 2% sucrose as an overnight starter culture. The next day, production flasks were prepared with an initial $OD_{600}$ of 0.05 diluted from the starter culture in 40 ml YNB-4% sucrose production culture media in 250 ml disposable PETG sterile flasks (Nalgene). The flasks were incubated at 30° C. by shaking at 250 RPM for the durations indicated below.

6.1.1.3 HMG-CoA reductase Activity Assay Using Cell-Free Extract

Yeast cells were grown for 48 hours HMG-CoA reductase activity assays (FIG. 8) or 72 hours for mevalonate assays (Table 4) and harvested by centrifugation in a 15 mL Falcon tube for 10 minutes at 4000×g in a swinging bucket rotor JS-5.3 with proper carriage for the Falcon tubes. The cell pellet was resuspended in 1 ml and washed once using cold lysis buffer (100 mM Tris pH 7.0 with Mini, EDTA free protease inhibitor tablet (Roche) added, 1 mM DTT and 1 mM EDTA). The cells were then transferred to a 2 mL plastic screw cap microfuge tube with O ring cap (Fisher Brand 520-GRD) and cells were lysed using disruption beads (Disruption beads, 0.5 Mm, Fisher) and a bead beater for 1 minute at 6 M/S. The tubes were immediately placed in an ice water bath for at least 5 minutes. Tubes were spun at a minimum of 8000×g for 20 minutes. The supernatant was then transferred to a new cold tube. Protein concentration was measured using the classic Bradford assay for proteins (Bradford M M A rapid and sensitive method for quantitation of microgram quantities of protein utilizing the principle of protein-dye binding. *Anal. Biochem* 72, 248-254 (1976)).

For HMG-CoA reducatase assays, the reaction buffer (100 mM phosphate buffer pH 7.0, 100 mM KCl, 1 mM DTT and 1 mM EDTA) was initially pre-incubated in a 96 well plate at 30° C. Either NADH or NADPH at a final concentration of 150 μM, a final concentration of 400 μM HMG-CoA and 5 mM final concentration of DTT was added to a total volume of 190 μl in each well. The assay was initiated by adding ten microliter of cell-free extract diluted to the range of linear activity. The reaction was monitored by measuring the decrease in absorbance of NADPH or NADH at 340 nm using Molecular Devices Spectramax M5 plate reader. The slope of the line of absorbance at 340 nm along with the protein concentration was used to calculate the specific activity of HMGr for each cell free extract.

6.1.1.4 Organic Acids and Alcohol Measurement

Samples for organic acids and alcohols assay were prepared by taking 1 ml of fermentation broth and transferring the samples to a 1.5 ml eppendorf tubes. Samples were spun for 1 min at 13,000 RPM using a table eppendorf centrifuges. The supernatant was then diluted (1:1 v/v) in 15 mM sulfuric acid. The mixture was vortexed and centrifuged for 1 min at 13,000 RPM. The clarified supernatant was transferred to a vial for HPLC analysis.

HPLC analysis was performed for glycerol and mevalonate content using HPLC Thermofisher and by ion exclusion chromatography using Column Waters IC-Pak 7.8 mm×300 mm, 7 μm, 50 Å (Waters) and with refractive index (R1) detection (Thermofisher). Elution was carried out isocratically using a 15 mM sulfuric acid aqueous mobile phase with 0.6 mL/min flow rate.

6.1.2 Results 6.1.2.1 Determination of Cofactor Specificity for Class II HMG-CoA Reductases As shown in FIG. 8, HMG-CoA reductases from *D. acidovorans* and *S. pomeroyi* exhibit high specificity for NADH and high specific activity in vitro. These HMG-CoA reductases displayed virtually no specific activity in the presence of NADPH, while specific activity approached 400 nmol/mg/min in the presence of NADH. Similarly, HMG-CoA reductase from *P. mevalonii* demonstrated selectivity for NADH as a cofactor, consistent with previously published reports. See, e.g., Hedl et al., *J. Bacteriol* 186(7):1927-1932 (2004). By contrast, HMG-CoA reductases from *S. cerevisiae, S. aureus* and *H. aurantiacus* showed no measurable activity in the presence of NADH, and HMG-CoA reductase from *M. thermofila* showed barely detectable activity in the presence of both NADPH and NADH. These results indicate that HMG-CoA reductases from *D. acidovorans* and *S. pomeroyi* are NADH-selective HMG-CoA reductases, similar to the HMG-CoA reductase from *P. mevalonii.*

In addition, Table 4 indicates that strains comprising a MevT pathway comprising an NADH-using HMG-CoA reductase (from *P. mevalonii, D. acidovorans* and *S. pomeroyi*, respectively) produced substantially less mevalonate than strains comprising a MevT pathway comprising an NADPH-using HMG-CoA reductase (from *S. cerevisiae, S. aureus* and *H. aurantiacus*, respectively). This suggests that in vivo, an additional source of NADH is required to utilize the full catalytic capacity of NADH-using HMG-CoA reductases towards mevalonate and downstream isoprenoid production.

TABLE 4

| Mevalonate production from NADPH-using HMG-CoA reductases vs. NADH-using HMG-CoA reductases | | |
|---|---|---|
| Source of HMG-CoA reductase | Mevalonate production (g/L) | Co-factor specificity |
| *S. cerevisiae* | 1.11 | NADPH |
| *S. aureus* | 1.74 | NADPH |
| *H. aurantiacus* | 1.84 | NADPH |
| *P. mevalonii* | 0.41 | NADH |
| *D. acidovorans* | 0.42 | NADH |
| *S. pomeoyri* | 0.57 | NADH |

6.1.2.2 Increased Intracellular NADH Improves NADH-Using HMG-CoA Reductase Activity As indicated in FIGS. 9-11, mevalonate production is substantially improved in cells comprising a MevT pathway comprising an NADH-using HMG-CoA reductase when a metabolic perturbation is introduced which increases the intracellular concentration of NADH. ADH1 reduces acetaldehyde to ethanol in an NADH-dependent manner. In an adh1Δbackground, host cells suffer reduced growth (FIG. 9) and increased glycerol production (FIG. 10), which is indicative of redox imbalance likely resulting from the accumulation of intracellular NADH. However, while cells comprising a MevT pathway comprising an NADPH-using HMG-CoA reductase (*S. cerevisiae* (Sc.) tHMG-CoA reductase) display reduced mevalonate production in the adh1Δbackground, cells comprising a MevT pathway comprising an NADH-using HMG-CoA reductase ((from *P. mevalonii, D. acidovorans* and *S. pomeroyi*, respectively) display substantial improvements in mevalonate production (FIG. 11), despite also showing signs of redox stress. These data suggest that NADH-using HMG-CoA reductases are able to utilize increased pools of intracellular NADH to boost mevalonate production. These results also suggest that in the absence of an increased intracellular source of NADH, NADH-using HMG-CoA reductases are cofactor limited.

Notably, previous published reports have indicated that the HMG-CoA reductase of *P. mevalonii* is utilized in the degradation of mevalonate. See Anderson et al., *J. Bacteriol*., (171 (12):6468-6472 (1989). *P. mevalonii* is among the few prokaryotes that have been identified as capable of subsisting on mevalonate as its sole carbon source. However, the results presented here demonstrate the unexpected utility of *P. mevalonii* HMG-CoA reductase for use in a biosynthetic pathway for mevalonate.

6.2 Example 2

Improved Isoprenoid Production and Redox Balancing with Alternate Routes to Acetyl-CoA and Alternate MEV Pathway Enzymes This example demonstrates that mevalonate and downstream isoprenoid production from the MEV pathway can be improved by utilizing alternate routes to cytolsolic acetyl-CoA production, e.g. via the heterologous expression of acetaldehyde dehydrogenase, acetylating (ADA, E.C. 1.2.1.10), in lieu of the wild-type PDH-bypass, and in various combinations with alternate MEV pathway enzymes. These results show that the redox imbalance introduced by the replacement of the NADPH-producing PDH-bypass enzymes with NADH-producing ADA can be alleviated in part by combining ADA expression with an NADH-using HMG-CoA reductase of the MEV pathway, and/or with heterologous expression of phosphoketolase and phosphotrancsacetylasse, which can also provide an additional alternate route to cytosolic acetyl-CoA production. These results further demonstrate that the catalytic capacity of ADA for providing acetyl-CoA substrate to the MEV pathway is substantially improved by providing a thermodynamically favorable downstream conversion of acetyl-CoA to acetoacetyl-CoA, such as that provided by acetyl-CoA:malonyl-CoA acyltransferase.

6.2.1 Materials and Methods 6.2.1.1 Strain Engineering

The strains listed in Table 5 were constructed to determine: (1) the effects on cell growth and heterologous isoprenoid production when ADA is paired with an NADH-using HMG-CoA reductase versus an NADPH-using HMG-CoA reductase; (2) the effect of phosphoketolase and phosphotransacetylase expression on the redox imbalance created by the expression of ADA; and (3) the effect of acetoacetyl-CoA synthase expression on mevalonate levels in strains expressing ADA.

TABLE 5

| Strain Name | Description |
|---|---|
| Y968 | Wildtype CEN.PK2 |
| Y12869 | acs1^ acs2^ ald6^ ; 2x Dz.eutE |
| Y12746 | acs1^ acs2^ ald6^ ; 2x Dz.eutE; 3x Lm.PK; 1x Ck.PTA |
| Y12869.ms63908 | Y12869 with construct ms63908 |
| Y12869.ms63909 | Y12869 with construct ms63909 |
| Y968.ms63908 | Y968 with construct ms63908 |
| Y968.ms63909 | Y968 with construct ms63909 |
| Y12869.ms63907.ms64472 | Y12869.ms63907 with construct ms64472 |
| Y12869.ms63909.ms64472 | Y12869.ms63909 with construct ms64472 |
| Y968.ms63907.ms64472 | Y968.ms63907 with construct ms64472 |
| Y968.ms63909.ms64472 | Y968.ms63909 with construct ms64472 |

| 6.2.1.1.1 | Y968 |
|---|---|

Y968 is wildtype *Saccharomyces cerevisiae* CEN.PK2, Matalpha. The starting strain for Y12869, Y12746, and all of their derivatives, was *Saccharomyces cerevisiae* strain (CEN.PK2, Mat alpha, ura3-52, trp1-289, leu2-3,122, his3^1), Y003. All DNA-mediated transformation into *S. cerevisiae* was conducted using the standard Lithium Acetate procedure as described by Gietz R W and Woods R A, *Guide to Yeast Genetics and Molecular and Cell Biology. Part B*. San Diego, Calif.: Academic Press Inc. pp. 87-96 (2002), and in all cases integration of the constructs were confirmed by PCR amplification of genomic DNA.

| 6.2.1.1.2 | Y12869 |
|---|---|

Y12869 was generated through three successive integrations into Y003. First, the gene ACS2 was deleted by introducing an integration construct (i2235; SEQ ID NO:45) consisting of the native *S. cerevisiae* LEU2 gene, flanked by sequences consisting of upstream and downstream nucleotide sequences of the ACS2 locus. Upon introduction of a *S. cerevisiae* host cell, this construct can integrate by homologous recombination into the ACS2 locus of the genome, functionally disrupting ACS2 by replacing the ACS2 coding sequence with its integrating sequence. Transformants were plated onto CSM—leu plates containing 2% EtOH as the sole carbon source, and were confirmed by PCR amplification. The resulting strain was Y4940.

Next, ALD6 was deleted and *Dickeya zeae* eutE was introduced in Y4940 with the integration construct (i74804; SEQ ID NO:46) pictured below.

| ALD6US | pTDH3 | Dz.eutE | tTEF2 | TRP1 | tTEF2 | Dz.eutE | pTDH3 | ALD6DS |
|---|---|---|---|---|---|---|---|---|

This integration construct comprises a selectable marker (TRP1), as well as two copies a yeast-codon-optimized sequence encoding the gene eutE from *Dickeya zeae* (NCBI Reference Sequence: YP_003003316.1) under control of the TDH3 promoter (840 basepairs upstream of the native *S. cerevisiae* TDH3 coding region), and the TEF2 terminator (508 basepairs downstream of the native *S. cerevisiae* TEF2 coding region). These components are flanked by upstream and downstream nucleotide sequences of the ALD6 locus. Upon introduction into a host cell, this construct integrates by homologous recombination into the host cell genome, functionally disrupting ALD6 by replacing the ALD6 coding sequence with its integrating sequence. The construct was assembled using the methods described in U.S. Pat. No. 8,221,982. The construct was transformed into Y4940, and transformants were selected on CSM-TRP plates with 2% glucose and confirmed by PCR amplification. The resulting strain was 12602.

Next, ACS1 was deleted in Y12602 by introducing an integration construct (i76220; SEQ ID NO:47) consisting of the upstream and downstream nucleotide sequences of ACS1, flanking the native *S. cerevisiae* HIS3 gene under its own promoter and terminator. Transformants were plated onto CSM—his plates containing 2% glucose as the sole carbon source, and were confirmed by PCR amplification. The resulting strain was Y12747.

Next, Y12747 was transformed with a PCR product amplified from the native URA3 sequence. This sequence restores the ura3-52 mutation. See Rose and Winston, *Mol Gen Genet.* 193:557-560 (1984). Transformants were plated onto CSM-ura plates containing 2% glucose as the sole carbon source, and were confirmed by PCR amplification. The resulting strain was Y12869.

| 6.2.1.1.3 | Y12746 |
|---|---|

Y12746 was generated through three successive integrations into Y4940. First, Y4940 was transformed with the integration construct (i73830; SEQ ID NO:48) pictured below.

| BUD9US | pTDH3 | Lm.PK | tTDH3 | URA3 | tPGK1 | Ck.PTA | pTDH3 | BUD9DS |
|---|---|---|---|---|---|---|---|---|

This integration construct comprises a selectable marker (URA3); a yeast codon-optimized version of phosphoketolase from *Leuconostoc mesenteroides* (NCBI Reference Sequence YP_819405.1) under the TDH3 promoter (870 bp upstream of the TDH3 coding sequence) and TDH3 terminator (259 bp downstream of the TDH3 coding sequence); a yeast codon-optimized version of *Clostridium kluyveri* phosphotransacetylase (NCBI Reference Sequence: YP_001394780.1) under control of the TDH3 promoter (870 bp upstream of the TDH3 coding sequence) and the PGK1 terminator (259 bp downstream of the PGK1 coding sequence); flanked by homologous sequences consisting of the upstream and downstream nucleotide sequences of the *S. cerevisiae* BUD9 locus. Upon introduction into a host cell, this construct integrates by homologous recombination into the host cell genome, functionally disrupting_BUD9 by replacing the BUD9 coding sequence with its integrating sequence. The construct was assembled using the methods described in U.S. Pat. No. 8,221,982. Transformants were selected on CSM-URA plates with 2% glucose.

The resulting strain was transformed with the construct (i74810; SEQ ID NO:49) shown below.

| ALD6US | pTDH3 | Lm.PK | tTDH3 | TRP1 | tTDH3 | Lm.PK | pTDH3 | ALD6DS |
|---|---|---|---|---|---|---|---|---|

This construct comprising a selectable marker (TRP1); two copies of phosphoketolase from *Leuconostoc mesenteroides* under the TDH3 promoter (870 bp upstream of the TDH3 coding sequence) and TDH3 terminator (259 bp downstream of the TDH3 coding sequence); flanked by homologous sequences consisting of the upstream and downstream nucleotide sequences of the ALD6 locus. Upon introduction into a host cell, this construct integrates by homologous recombination into the host cell genome, functionally disrupting ALD6 by replacing the ALD6 coding sequence with its integrating sequence. The construct was assembled using the methods described in U.S. Pat. No. 8,221,982. Transformants were selected on CSM-URA plates with 2% glucose and confirmed by PCR amplification.

Finally, the resulting strain was transformed with the construct (i76221; SEQ ID NO:50) shown below.

| ACS1US | pTDH3 | Dz.eutE | tTEF2 | HIS3 | tTEF2 | Dz.eutE | pTDH3 | ACS1DS |
|---|---|---|---|---|---|---|---|---|

This construct comprises a selectable marker (HIS3); as well as two copies a yeast-codon-optimized sequence encoding the gene eutE from *Dickeya Zeae* (NCBI Reference Sequence: YP_003003316.1) under control of the TDH3 promoter (840 basepairs upstream of the native *S. cerevisiae* TDH3 coding region) and the TEF2 terminator (508 basepairs downstream of the native *S. cerevisiae* TEF2 coding region). These components are flanked by upstream and downstream nucleotide sequences of the ACS1 locus. Upon introduction into a host cell, this construct integrates by homologous recombination into the host cell genome, functionally disrupting ACS1 by replacing the ACS1 coding sequence with its integrating sequence. The construct was assembled using the methods described in U.S. Pat. No. 8,221,982. Transformants were selected on CSM-HIS plates with 2% glucose and confirmed by PCR amplification. The resulting strain was Y12746.

| 6.2.1.1.4 | ms63907, ms63908, ms63909, and ms64472 integration constructs |
|---|---|

The ms63907 integration construct (i84022; SEQ ID NO:51) is shown below.

| HO US | GAL4 | Sp.HMGr | pGAL1 | pGAL10 | ERG10 | URA3 | ERG13 | pGAL10 | pGAL1 | Sp.HMGr | HO DS |
|---|---|---|---|---|---|---|---|---|---|---|---|

This construct comprises nucleotide sequences that encode a selectable marker (URA3); a copy of the native yeast GAL4 transcription factor under its own promoter; two native yeast enzymes of the mevalonate pathway (ERG10 which encodes Acetoacetyl-CoA thiolase, and ERG13, which encodes HMG-CoA synthase), as well as two copies of a yeast codon-optimized version of *Silicibacter pomeroyi* HMG-CoA reductase, all under galactose-inducible promoters (promoters of the *S. cerevisiae* genes GAL1 and GAL10, flanked by homologous sequences consisting of upstream and downstream nucleotide sequences of the *S. cerevisiae* HO endonuclease locus. Upon introduction into a host cell, the ms63907 construct integrates by homologous integration into the host cell genome, functionally disrupting HO by replacing the HO coding sequence with its integrating sequence. The construct was assembled using the methods described in U.S. Pat. No. 8,221,982. Transformants were selected on CSM-URA plates with 2% glucose and confirmed by PCR amplification.

The ms63908 integration construct (i84024; SEQ ID NO:52) is identical to ms63907, with two exceptions: first, ERG10 is replaced by a yeast codon-optimized version of the nphT7 gene of *Streptomyces* sp. CL190 encoding acetyl-CoA:malonyl-CoA acyltransferase (accession no. AB540131.1) fused to the AHR1 terminator (125 bp downstream of the AHR1 coding sequence in *S. cerevisiae*); second, the sequences encoding *S. pomeroyi* HMG-CoA reductase are replaced by tHMGr, the truncated HMG1 coding sequence which encodes the native *S. cerevisiae* HMG-CoA reductase.

The ms63909 integration construct (i84026; SEQ ID NO:53) is identical to ms63907, with one exception: the sequences encoding *S. pomeroyi* HMG-CoA reductase are replaced by tHMGr, the truncated HMG1 coding sequence which encodes the native *S. cerevisiae* HMG-CoA reductase.

The ms64472 integration construct (i85207; SEQ ID NO:54) is shown below.

| GAL80 US | pGAL7 | IDI1 | Aa.FS | pGAL1 | pGAL10 | ERG20 | URA3 | ERG8 | pGAL7 | ERG19 | pGAL10 | pGAL1 | ERG12 | GAL80 DS |
|---|---|---|---|---|---|---|---|---|---|---|---|---|---|---|

This construct comprises nucleotide sequences that encode a selectable marker (URA3); five native yeast enzymes of the ergosterol pathway (ERG12 which encodes mevalonate kinase, ERG8 which encodes phosphomevalonate kinase, ERG19 which encodes mevalonate pyrophosphate decarboxylase, IDI1 which encodes dimethylallyl diphosphate isomerase, and ERG20 which encodes farnesyl pyrophosphate synthetase), as well as an evolved, yeast codon-optimized version of *Artemisia annua* farnesene synthase, all under galactose-inducible promoters (Promoters of the *S. cerevisiae* genes GAL1, GAL10, and GAL7). These sequences are flanked by homologous sequences consisting of the upstream and downstream nucleotide sequences of GAL80. Upon introduction into a host cell, the ms64472 construct integrates by homologous integration into the host cell genome, functionally disrupting GAL80 by replacing the GAL80 coding sequence with its integrating sequence. The construct was assembled using the methods described in U.S. Pat. No. 8,221,982. Transformants were selected on CSM-URA plates with 2% glucose and confirmed by PCR amplification.

6.2.1.2 Quantitation of Mevalonate

Single colonies were inoculated in wells of a 96-well plate in seed media (15 g/L ammonium sulfate, 8 g/L potassium phosphate, 6.1 g/L magnesium sulfate, 150 mg/L EDTA, 57.5 mg/L zinc sulfate, 4.8 mg/L cobalt chloride, 3.24 mg/L manganese chloride, 5 mg/L copper sulfate, 29.4 mg/L calcium chloride, 27.8 mg/L iron sulfate, 4.8 mg/L sodium molybdate, 0.6 mg/L biotin, 12 mg/L calcium pantothenate, 12 mg/L nicotinic acid, 30 mg/L inositol, 12 mg/L thiamin hydrochloride, 12 mg/L pyridoxine hydrochloride, 0.24 mg/L para-aminobenzoic acid) with 50 mM succinate pH 5.0, and 20 g/L sucrose, and grown at 30 C for three days. Then, 14.4 ul of culture was subcultured into seed media with 50 mM succinate pH 5.0 and 40 g/L galactose, and grown at 30 C for 2 days.

To quantitate secreted mevalonate, whole cell broth was first spun down at 14,000 RPM for 5 min. 10 ul of clarified broth was then incubated with 190 ul of assay buffer (1 mM CoA, 2 mM NAD, purified and lyophilized *Pseudomonas mevalonii* HMG-CoA reductase at 0.2 mg/ml, purified and lyophilized *Pseudomonas mevalonii* HMG-CoA lyase at 0.1 mg/ml, 95 mM TrisCl pH8.5, 20 mM MgCl2, and 5 mM DTT). The sample was incubated for 30 minutes at 30 C, then assayed for 340 nM absorbance on a Beckman M5 plate reader. Mevalonate concentration was quantitated by plotting onto a standard curve generated with purified mevalonate.

6.2.1.3 Quantitation of Farnesene

Cultures were first grown as described above. To quantitate farnesene, 600 ul of 2-butoxyethanol was added to 150 ul of whole cell broth in three additions of 200 ul each, with 90 seconds of shaking at 1000 rpm on a 96-well plate shaker between each addition. The samples were then incubated for 40 minutes. 8 ul of the 2-butoxyethanol extract was mixed with 200 ul of isopropyl alcohol in a 96-well UV plate (Costar 3635), then read on a plate reader for absorbance 222.

6.2.1.4 Quantitation of Optical Density

In a 96-well assay plate, 8 ul of culture was mixed with diluent (20% PEG 200, 20% Ethanol, 2% Triton X-114) and incubated for 30 minutes at room temperature. The assay plate was vortexted before measuring $OD_{600}$ on a Beckman M5 plate reader.

6.2.1.5 Batch Fermentation

Inoculum cultures of Y967, Y12869, and Y12746 were grown from single colonies in 5 ml of seed media with 50 mM succinate pH 5.0, and 20 g/L sucrose. After 3 days of growth, the precultures were subcultured into 25 ml of seed media with 50 mM succinate pH 5.0 and 40 g/L sucrose to an initial optical density (OD) of 0.1. After 10 hours, the cultures were subcultured again into 50 ml of seed media with 50 mM succinate pH 5.0 and 40 g/L sucrose to an OD of 0.05. Cultures were grown at 30° C. When the OD was approximately 3, the 3 flasks were split in half and spun down and the media was discarded. The cultures were resuspended in 1.5 L seed media with 40 g/L glucose (without succinate) and transferred to the fermentor. Fermentation experiments were performed in a 2 L Biostat B plus vessel (Sartorius, Germany). Stirring was controlled at 1200 rpm and the fermentor was continuously sparged with 0.5 L/min air. The pH was maintained at 5.0 with 14.4 M $NH_4OH$ and the temperature was maintained at 30° C. Roughly every 1.5 hours, a sample was drawn to measure the OD, dry cell weight, and organic acids and sugars.

6.2.2 Results 6.2.2.1 ADA Strains Produce More Isoprenoid when Paired with an NADH-Using HMGr Versus an NADPH-Using HMGr FIG. 12A shows that strain Y12869, comprising a deletion of the PDH-bypass (acs1Δ acs2Δ ald6Δ) and heterologously expressing ADA (Dz.eutE), produces more farnesene when expressing a MEV pathway comprising an NADH-using HMGr (construct ms63907) than a MEV pathway comprising an NADPH-using HMGr (construct ms63909). In contrast, FIG. 12B shows that strain Y968, comprising an intact PDH-bypass, produces more farnesene when paired with an NADPH-using HMGr. These results demonstrate that utilization of ADA for isoprenoid production from the MEV pathway is improved when the MEV pathway comprises an NADH-using HMGr.

6.2.2.2 Expression of ADA Causes a Redox Imbalance which is Alleviated When PK and PTA Share Flux with Glycolysis Native yeast produce two NADH per glucose consumed through glycolysis. When fermented to ethanol, the two NADH are reoxidized to NAD+. However, a fraction of the glucose is converted to biomass rather than fermented to ethanol, resulting in an excess of NADH. This excess NADH is reoxidized to NAD+ through the reduction of dihydroxyacetone phosphate to glycerol 3-phosphate, which is hydrolyzed to glycerol. Strains which use the acylating acetaldehyde dehydrogenase in place of the native PDH-bypass produce NADH instead of NADPH, resulting in a further excess of NADH. For each glucose converted to biomass, a strain which uses ADA in place of the native PDH-bypass produces exactly twice as much NADH, meaning that twice as much glycerol must be produced in order to reoxidize the excess NADH. As shown in FIG. 13A, Y12869 (a strain which uses ADA in the place of the wildtype PDH-bypass) produces twice as much glycerol as Y968 (comprising an intact PDH-bypass) while consuming comparable levels of glucose in a batch glucose fermentation. These results demonstrate that Y12869 is redox imbalanced as predicted by the stoichiometry of the ADA reaction.

The addition of phosphoketolase and phosphotransacetylase to an ADA strain provides an alternative, non-glycolytic route to generating AcCoA from glucose, reducing the NADH produced through glycolysis and improving redox balance. As shown in FIG. 13B, Y12745 (a strain which carries phosphoketolase and phosphotransacetylase in addition to the ADA) produces half as much glycerol as Y12869, while consuming comparable levels of glucose in a batch glucose fermentation.

6.2.2.3 The ATP Savings in an ADA Strain Come at the Cost of Thermodynamic Driving Force, which is Alleviated by a Strong Downstream Pull on Acetyl-CoA The native PDH-bypass reaction for forming Acetyl-CoA is thermodynamically favorable because the reaction is coupled to the hydrolysis of ATP to AMP. In contrast, the acylating acetaldehyde dehydrogenase reaction is not coupled to ATP, and is much closer to equilibrium than the native PDH-bypass reactions for forming Acetyl-CoA. When using then native *S. cerevisiae* pathway genes for producing mevalonate, strains using the ADA produce much less mevalonate than strains using the wildtype PDH-bypass despite comparable kinetic properties of ADA and Ald6 in vitro. As shown in FIG. 14 ($1^{st}$ and 2nd column), mevalonate production in an ADA strain (Y12869.ms63909) is only ~30% that of a wildtype equivalent strain (Y968.ms63909), despite sufficient kinetic capacity measured in vitro. This result reflects the lack of a thermodynamic driving force behind the conversion of acetaldehyde to acetyl-CoA by ADA.

The Erg10 acetyl-CoA thiolase catalyzes the formation of acetoacetyl-CoA from two acetyl-CoA, a reaction that is thermodynamically unfavorable. Acetoacetyl-CoA synthase (i.e., acetyl-CoA:malonyl-CoA acyltransferase), encoded by nphT7, catalyzes the formation of acetoacetyl-CoA from acetyl-CoA and malonyl-CoA, a reaction that is thermodynamically favorable due to the decarboxylation of malonyl-CoA. Putting this thermodynamically favorable reaction directly downstream of AcCoA production provides a thermodynamic driving force that increases the forward activity of ADA. As shown in FIG. 14 (3rd and 4th column), when nphT7 is overexpressed in place of ERG10, Y968.ms63908 and Y12869.ms63908 make comparable levels of mevalonate. Moreover, they produce more substantially more mevalonate than equivalent strains which use ERG10 for the first step of the MEV pathway (Y968.ms63909 and Y12869.63909.).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A genetically modified yeast cell capable of producing an isoprenoid, the cell comprising:

(a) a nucleic acid encoding an NADH-using HMG-CoA reductase (HMGr) and optionally one or more heterologous nucleic acids encoding one or more enzymes of a mevalonate (MEV) pathway for making isopentenyl pyrophosphate;

(b) a heterologous nucleic acid encoding an acylating acetylaldehyde dehydrogenase (ADA, EC 1.2.1.10); and (c) a functional disruption of one or more enzymes of the native pyruvate dehydrogenase (PDH)-bypass selected from the group consisting of acetyl-CoA synthetase 1 (ACS1), acetyl-CoA synthetase 2 (ACS2), and aldehyde dehydrogenase 6 (ALD6), wherein the genetically modified yeast cell produces an increased amount of an isoprenoid compound compared to an yeast cell not comprising a heterologous nucleic acid sequence encoding said ADA.

2. The genetically modified host cell of claim 1, wherein the one or more enzymes of the MEV pathway comprise an enzyme that condenses acetyl-CoA with malonyl-CoA to form acetoacetyl-CoA.

3. The genetically modified host cell of claim 1, wherein the one or more enzymes of the MEV pathway comprise an acetyl-CoA:malonyl-CoA acyltransferase.

4. The genetically modified host cell of claim 1, wherein the one or more enzymes of the MEV pathway comprise an NADH-using enzyme that converts 3-hydroxy-3-methylglutaryl-CoA (HMG-CoA) to mevalonate.

5. The genetically modified host cell of claim 1, further comprising a heterologous nucleic acid encoding a phosphoketolase (PK).

6. The genetically modified host cell of claim 1, further comprising a heterologous nucleic acid encoding a phosphotransacetylase (PTA).

7. The genetically modified host cell of claim 1, wherein ACS1, ACS2 and ALD6 are functionally disrupted.

8. The genetically modified host cell of claim 1, wherein the one or more enzymes of the MEV pathway comprise an enzyme that condenses two molecules of acetyl-CoA to form acetoacetyl-CoA.

9. The genetically modified host cell of claim 1, wherein the one or more enzymes of the MEV pathway comprise an enzyme that condenses acetoacetyl-CoA with acetyl-CoA to form HMG-CoA.

10. The genetically modified host cell of claim 1, wherein the one or more enzymes of the MEV pathway comprise an NADPH-using enzyme that converts HMG-CoA to mevalonate.

11. The genetically modified host cell of claim 1, wherein the one or more enzymes of the MEV pathway comprise an enzyme that phosphorylates mevalonate to mevalonate 5-phosphate.

12. The genetically modified host cell of claim 1, wherein the one or more enzymes of the MEV pathway comprise an enzyme that converts mevalonate 5-phosphate to mevalonate 5-pyrophosphate.

13. The genetically modified host cell of claim 1, wherein the one or more enzymes of the MEV pathway comprise an enzyme that converts mevalonate 5-pyrophosphate to isopentenyl pyrophosphate.

14. The genetically modified host cell of claim 1, wherein the one or more enzymes of the MEV pathway are selected from HMG-CoA synthase, mevalonate kinase, phosphomevalonate kinase and mevalonate pyrophosphate decarboxylase.

15. The genetically modified host cell of claim 1, wherein the host cell comprises a plurality of heterologous nucleic acids encoding all of the enzymes of the MEV pathway.

16. The genetically modified host cell of claim 1, wherein the one or more heterologous nucleic acids encoding one or more enzymes of the MEV pathway are under control of a single transcriptional regulator.

17. The genetically modified host cell of claim 1, further comprising a heterologous nucleic acid encoding an enzyme that can convert isopentenyl pyrophosphate (IPP) into dimethylallyl pyrophosphate (DMAPP).

18. The genetically modified host cell of claim 1, further comprising a heterologous nucleic acid encoding an enzyme that can condense IPP and/or DMAPP molecules to form a polyprenyl compound.

19. The genetically modified host cell of claim 1, further comprising a heterologous nucleic acid encoding an enzyme that can modify IPP or a polyprenyl to form an isoprenoid compound.

20. The genetically modified host cell of claim 19, wherein the enzyme that can modify IPP or a polyprenyl to form an isoprenoid compound is selected from the group consisting of carene synthase, geraniol synthase, linalool synthase, limonene synthase, myrcene synthase, ocimene synthase, α-pinene synthase, β-pinene synthase, γ-terpinene synthase, terpinolene synthase, amorphadiene synthase, α-farnesene synthase, β-farnesene synthase, farnesol synthase, nerolidol synthase, patchouliol synthase, nootkatone synthase, and abietadiene synthase.

21. The genetically modified host cell of claim 19, wherein the isoprenoid is selected from the group consisting of a hemiterpene, monoterpene, diterpene, triterpene, tetraterpene, sesquiterpene, and polyterpene.

22. The genetically modified host cell of claim 19, wherein the isoprenoid is a $C_5$-$C_{20}$ isoprenoid.

23. The genetically modified host cell of claim 19, wherein the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

24. The genetically modified host cell of claim 1, wherein the yeast is *Saccharomyces cerevisiae.*

25. A method for producing an isoprenoid comprising:

(a) culturing a population of the genetically modified yeast cell of claim 1 in a medium with a carbon source under conditions suitable for making said isoprenoid compound; and (b) recovering said isoprenoid compound from the medium.

26. The method of claim 25, wherein the genetically modified yeast cell produces an increased amount of an isoprenoid compound compared to the same genetically modified yeast cell not comprising a heterologous nucleotide sequence encoding said ADA.

* * * * *

SEQUENCE LISTING

```
<160> NUMBER OF SEQ ID NOS: 54

<210> SEQ ID NO 1
<211> LENGTH: 1380
<212> TYPE: DNA
<213> ORGANISM: Dickeya zeae
<220> FEATURE:
<221> NAME/KEY: misc_feature
<222> LOCATION: (1)..(1380)
<223> OTHER INFORMATION: Dickeya zeae eutE gene sequence

<400> SEQUENCE: 1

atggagcatt cagttatcga accgacagtg cccatgccgc tgccagccat gtttgacgcg      60

ccatctggaa tcttttctag cctggacgat gcagtccagg cggcaaccct ggcacaacaa     120

cagttgtcgt ctgtggagtt acgccagcaa gttattaaag caattagagt tgcaggcgaa     180

cgctatgcac aggttctggc ggaaatggcg gtggctgaaa caggtatggg tcgggtagtg     240

gataaataca ttaaaaatgt ttcacaggct cgccatacac ccggcattga atgtctgagc     300

gcggaagttc tgacaggcga caatggcctg acactgattg aaaatgcccc ttggggagtg     360

gtggcttccg tgacgccaag cacgaaccca gccgccacag tcatcaataa tgcaatttcc     420

atgattgcgg cagggaattc agtcgttttt gcaccgcacc catccgccaa aaatgtgtcc     480

ttacgcacaa tatcgcttct taacaaagca attgtggcga caggtgggcc agaaaatctg     540

ctggtatccg tcgcaaatcc caacatcgaa acagctcaac gcctgttccg ttatccaggt     600

attggattac tcgtcgtaac aggtggtgag gcggtggtgg aagcggcgcg caaacacact     660

gataaacgtt taattgccgc aggcgccgga aaccccccag tagtcgttga cgaaacagcg     720

gatataccga aagccgctcg cgcaatagta aagggcgctt cgtttgacaa caatattatt     780

tgtgccgacg agaaagtatt aatcgtggtt gatcgcgtag ccgacgcctt attagccgaa     840

atgcaacgca acaatgctgt tttactgacg cctgaacaga cagaacgact tctgcccgct     900

ttgctgagcg atatagatga gcaggggaag ggacgcgtga accgcgatta tgtggggagg     960

gatgccgcta aactagcggc ggccattggt ttagaagtgt cagaacacac aagattatta    1020

cttgctgaaa cagatgctga tcatcctttt gcagtaaccg aattaatgat gcccgtattg    1080

cctgttatcc gtgtaaaaaa cgttgatgac gccattgccc tcgctgtaaa acttgagagt    1140

ggttgtcgtc acactgcagc aatgcattcg acaaacatta ggaacctgaa tcggatggca    1200

aatgctataa atacatcaat ttttgttaaa aatggtccgt gtatcgctgg gctgggcctg    1260

ggtggcgagg gctggacgtc gatgactata tctacaccca caggggaagg agttacctca    1320

gcacgcacct tcgtacgttt acgtagatgt gtattggttg acatgttcag aatcgcgtaa    1380


<210> SEQ ID NO 2
<211> LENGTH: 459
<212> TYPE: PRT
<213> ORGANISM: Dickeya zeae
```

```
<220> FEATURE:
<221> NAME/KEY: misc_feature
<222> LOCATION: (1)..(459)
<223> OTHER INFORMATION: Dickeya zeae eutE protein sequence

<400> SEQUENCE: 2

Met Glu His Ser Val Ile Glu Pro Thr Val Pro Met Pro Leu Pro Ala
1               5                   10                  15

Met Phe Asp Ala Pro Ser Gly Ile Phe Ser Ser Leu Asp Asp Ala Val
            20                  25                  30

Gln Ala Ala Thr Leu Ala Gln Gln Gln Leu Ser Ser Val Glu Leu Arg
        35                  40                  45

Gln Gln Val Ile Lys Ala Ile Arg Val Ala Gly Glu Arg Tyr Ala Gln
    50                  55                  60

Val Leu Ala Glu Met Ala Val Ala Glu Thr Gly Met Gly Arg Val Val
65                  70                  75                  80

Asp Lys Tyr Ile Lys Asn Val Ser Gln Ala Arg His Thr Pro Gly Ile
                85                  90                  95

Glu Cys Leu Ser Ala Glu Val Leu Thr Gly Asp Asn Gly Leu Thr Leu
            100                 105                 110

Ile Glu Asn Ala Pro Trp Gly Val Val Ala Ser Val Thr Pro Ser Thr
        115                 120                 125

Asn Pro Ala Ala Thr Val Ile Asn Asn Ala Ile Ser Met Ile Ala Ala
    130                 135                 140

Gly Asn Ser Val Val Phe Ala Pro His Pro Ser Ala Lys Asn Val Ser
145                 150                 155                 160

Leu Arg Thr Ile Ser Leu Leu Asn Lys Ala Ile Val Ala Thr Gly Gly
                165                 170                 175

Pro Glu Asn Leu Leu Val Ser Val Ala Asn Pro Asn Ile Glu Thr Ala
            180                 185                 190

Gln Arg Leu Phe Arg Tyr Pro Gly Ile Gly Leu Leu Val Val Thr Gly
        195                 200                 205

Gly Glu Ala Val Val Glu Ala Ala Arg Lys His Thr Asp Lys Arg Leu
    210                 215                 220

Ile Ala Ala Gly Ala Gly Asn Pro Pro Val Val Val Asp Glu Thr Ala
225                 230                 235                 240

Asp Ile Pro Lys Ala Ala Arg Ala Ile Val Lys Gly Ala Ser Phe Asp
                245                 250                 255

Asn Asn Ile Ile Cys Ala Asp Glu Lys Val Leu Ile Val Val Asp Arg
            260                 265                 270

Val Ala Asp Ala Leu Leu Ala Glu Met Gln Arg Asn Asn Ala Val Leu
        275                 280                 285

Leu Thr Pro Glu Gln Thr Glu Arg Leu Leu Pro Ala Leu Leu Ser Asp
    290                 295                 300

Ile Asp Glu Gln Gly Lys Gly Arg Val Asn Arg Asp Tyr Val Gly Arg
305                 310                 315                 320

Asp Ala Ala Lys Leu Ala Ala Ala Ile Gly Leu Glu Val Ser Glu His
                325                 330                 335

Thr Arg Leu Leu Leu Ala Glu Thr Asp Ala Asp His Pro Phe Ala Val
            340                 345                 350

Thr Glu Leu Met Met Pro Val Leu Pro Val Ile Arg Val Lys Asn Val
        355                 360                 365

Asp Asp Ala Ile Ala Leu Ala Val Lys Leu Glu Ser Gly Cys Arg His
    370                 375                 380
```

```
Thr Ala Ala Met His Ser Thr Asn Ile Arg Asn Leu Asn Arg Met Ala
385                 390                 395                 400

Asn Ala Ile Asn Thr Ser Ile Phe Val Lys Asn Gly Pro Cys Ile Ala
                405                 410                 415

Gly Leu Gly Leu Gly Gly Glu Gly Trp Thr Ser Met Thr Ile Ser Thr
            420                 425                 430

Pro Thr Gly Glu Gly Val Thr Ser Ala Arg Thr Phe Val Arg Leu Arg
        435                 440                 445

Arg Cys Val Leu Val Asp Met Phe Arg Ile Ala
    450                 455


<210> SEQ ID NO 3
<211> LENGTH: 2728
<212> TYPE: DNA
<213> ORGANISM: Saccharomyces cerevisiae
<220> FEATURE:
<221> NAME/KEY: misc_feature
<222> LOCATION: (1)..(2728)
<223> OTHER INFORMATION: Saccharomyces cerevisiae ACS1 nucleotide
      sequence

<400> SEQUENCE: 3

acctcccgcg acctccaaaa tcgaactacc ttcacaatgt cgccctctgc cgtacaatca     60

tcaaaactag aagaacagtc aagtgaaatt gacaagttga aagcaaaaat gtcccagtct    120

gcctccactg cgcagcagaa gaaggaacat gagtatgaac atttgacctc ggtcaagatc    180

gtgccacaac ggcccatctc agatagactg cagcccgcaa ttgctaccca ctattctcca    240

cacttggacg ggttgcagga ctatcagcgc ttgcacaagg agtctattga agaccctgct    300

aagttcttcg gttctaaagc tacccaattt ttaaactggt ctaagccatt cgataaggtg    360

ttcatcccag actctaaaac gggtaggccc tccttccaga acaatgcatg gttcctcaac    420

ggccaattaa acgcctgtta caactgtgtt gacagacatg ccttgaagac ccctaacaag    480

aaagccatta ttttcgaagg tgacgagcct ggccaaggct attccattac ctacaaggaa    540

ctacttgaag aagtttgtca agtggcacaa gtgctgactt actctatggg cgttcgcaag    600

ggcgatactg ttgccgtgta catgcctatg gtcccagaag caatcataac cttgttggcc    660

atttcccgta tcggcgccat tcactccgta gtctttgccg ggttttcttc caactccttg    720

agagatcgta tcaacgatgg ggactctaaa gttgtcatca ctacagatga atccaacaga    780

ggtggtaaag tcattgagac taaaagaatt gttgatgacg cgctaagaga gaccccaggc    840

gtgagacacg tcttggttta tagaaagacc aacaatccat ctgttgcttt ccatgccccc    900

agagatttag attgggcaac agaaaagaag aaatacaaga cctactatcc atgcacaccc    960

gttgattctg aggatccatt attcttgttg tatacgtctg gttctactgg tgcccccaag   1020

ggtgttcaac attctaccgc aggttacttg ctgggagctt tgttgaccat gcgctacact   1080

tttgacactc accaagaaga cgttttcttc acagctggag acattggctg gattacaggc   1140

cacacttatg tggtttatgg tcccttacta tatggttgtg ccactttggt ctttgaaggg   1200

actcctgcgt acccaaatta ctcccgttat tgggatatta ttgatgaaca caaagtcacc   1260

caattttatg ttgccccaac tgctttgcgt ttgttgaaaa gagctggtga ttcctacatc   1320

gaaaatcatt ccttaaaatc tttgcgttgc ttgggttcgg tcggtgaacc aattgctgct   1380

gaagtttggg agtggtactc tgaaaaaata ggtaaaaatg aaatccccat tgtagacacc   1440

tactggcaaa cagaatctgg ttcgcatctg gtcaccccgc tggctggtgg tgtcacacca   1500

atgaaaccgg gttctgcctc attccccttc ttcggtattg atgcagttgt tcttgaccct   1560
```

```
aacactggtg aagaacttaa taccagccac gcagagggtg tccttgccgt caaagctgca   1620

tggccatcat ttgcaagaac tatttggaaa aatcatgata ggtatctaga cacttatttg   1680

aacccttacc ctggctacta tttcactggt gatggtgctg caaaggataa ggatggttat   1740

atctggattt tgggtcgtgt agacgatgtg gtgaacgtct ctggtcaccg tctgtctacc   1800

gctgaaattg aggctgctat tatcgaagat ccaattgtgg ccgagtgtgc tgttgtcgga   1860

ttcaacgatg acttgactgg tcaagcagtt gctgcatttg tggtgttgaa aaacaaatct   1920

aattggtcca ccgcaacaga tgatgaatta caagatatca agaagcattt ggtctttact   1980

gttagaaaag acatcgggcc atttgccgca ccaaaattga tcattttagt ggatgacttg   2040

cccaagacaa gatctggcaa aattatgaga cgtattttaa gaaaaatcct agcaggagaa   2100

agtgaccaac taggcgacgt ttctacattg tcaaaccctg gcattgttag acatctaatt   2160

gattcggtca agttgtaatg atgatttctt tcctttttat attgacgact ttttttttt    2220

cgtgtgtttt tgttctctta taaccgagct gcttacttat tattatttca ccttctcttt   2280

ttatttatac ttataattat ttattcttta catactgtta caagaaactc ttttctacat   2340

taattgcata aagtgtcaat cagcacatcc tctatatcgc tatcaacaac aaatttgaca   2400

aacctgccta tatcttcagg aacaactgcc gcatcgctac caccactact tgtgaagtcc   2460

ctggagttta atatgcactg aaatttacct agccgtttta cacaagacca taatccatcc   2520

atgctatcgc agtatatgat tttgtgttcg tttttcgtct tgcgaaaggc atcctcaatg   2580

gcttgtttca ttgatccatc agtgtggctc gtaggtacca gcaaaaccac ttcatcagcg   2640

gcgtactcct cccactttat gggcagtcct tgtatcgact tgctcattat aatacatttg   2700

ctctatcccc gcgtgcttgg ccggccgt                                      2728
```

```
<210> SEQ ID NO 4
<211> LENGTH: 713
<212> TYPE: PRT
<213> ORGANISM: Saccharomyces cerevisiae
<220> FEATURE:
<221> NAME/KEY: misc_feature
<222> LOCATION: (1)..(713)
<223> OTHER INFORMATION: Saccharomyces cerevisiae ACS1 protein sequence

<400> SEQUENCE: 4

Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ser Thr Ala
            20                  25                  30

Gln Gln Lys Lys Glu His Glu Tyr Glu His Leu Thr Ser Val Lys Ile
        35                  40                  45

Val Pro Gln Arg Pro Ile Ser Asp Arg Leu Gln Pro Ala Ile Ala Thr
    50                  55                  60

His Tyr Ser Pro His Leu Asp Gly Leu Gln Asp Tyr Gln Arg Leu His
65                  70                  75                  80

Lys Glu Ser Ile Glu Asp Pro Ala Lys Phe Phe Gly Ser Lys Ala Thr
                85                  90                  95

Gln Phe Leu Asn Trp Ser Lys Pro Phe Asp Lys Val Phe Ile Pro Asp
            100                 105                 110

Ser Lys Thr Gly Arg Pro Ser Phe Gln Asn Asn Ala Trp Phe Leu Asn
        115                 120                 125

Gly Gln Leu Asn Ala Cys Tyr Asn Cys Val Asp Arg His Ala Leu Lys
    130                 135                 140
```

```
Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205

Ile Ser Arg Ile Gly Ala Ile His Ser Val Val Phe Ala Gly Phe Ser
    210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Lys Tyr Lys Thr Tyr Tyr
    290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
    370                 375                 380

Val Phe Glu Gly Thr Pro Ala Tyr Pro Asn Tyr Ser Arg Tyr Trp Asp
385                 390                 395                 400

Ile Ile Asp Glu His Lys Val Thr Gln Phe Tyr Val Ala Pro Thr Ala
                405                 410                 415

Leu Arg Leu Leu Lys Arg Ala Gly Asp Ser Tyr Ile Glu Asn His Ser
            420                 425                 430

Leu Lys Ser Leu Arg Cys Leu Gly Ser Val Gly Glu Pro Ile Ala Ala
        435                 440                 445

Glu Val Trp Glu Trp Tyr Ser Glu Lys Ile Gly Lys Asn Glu Ile Pro
    450                 455                 460

Ile Val Asp Thr Tyr Trp Gln Thr Glu Ser Gly Ser His Leu Val Thr
465                 470                 475                 480

Pro Leu Ala Gly Gly Val Thr Pro Met Lys Pro Gly Ser Ala Ser Phe
                485                 490                 495

Pro Phe Phe Gly Ile Asp Ala Val Val Leu Asp Pro Asn Thr Gly Glu
            500                 505                 510

Glu Leu Asn Thr Ser His Ala Glu Gly Val Leu Ala Val Lys Ala Ala
        515                 520                 525

Trp Pro Ser Phe Ala Arg Thr Ile Trp Lys Asn His Asp Arg Tyr Leu
    530                 535                 540

Asp Thr Tyr Leu Asn Pro Tyr Pro Gly Tyr Tyr Phe Thr Gly Asp Gly
545                 550                 555                 560

Ala Ala Lys Asp Lys Asp Gly Tyr Ile Trp Ile Leu Gly Arg Val Asp
                565                 570                 575
```

```
Asp Val Val Asn Val Ser Gly His Arg Leu Ser Thr Ala Glu Ile Glu
            580                 585                 590

Ala Ala Ile Ile Glu Asp Pro Ile Val Ala Glu Cys Ala Val Val Gly
        595                 600                 605

Phe Asn Asp Asp Leu Thr Gly Gln Ala Val Ala Ala Phe Val Val Leu
    610                 615                 620

Lys Asn Lys Ser Asn Trp Ser Thr Ala Thr Asp Asp Glu Leu Gln Asp
625                 630                 635                 640

Ile Lys Lys His Leu Val Phe Thr Val Arg Lys Asp Ile Gly Pro Phe
                645                 650                 655

Ala Ala Pro Lys Leu Ile Ile Leu Val Asp Asp Leu Pro Lys Thr Arg
            660                 665                 670

Ser Gly Lys Ile Met Arg Arg Ile Leu Arg Lys Ile Leu Ala Gly Glu
        675                 680                 685

Ser Asp Gln Leu Gly Asp Val Ser Thr Leu Ser Asn Pro Gly Ile Val
    690                 695                 700

Arg His Leu Ile Asp Ser Val Lys Leu
705                 710


<210> SEQ ID NO 5
<211> LENGTH: 2287
<212> TYPE: DNA
<213> ORGANISM: Saccharomyces cerevisiae
<220> FEATURE:
<221> NAME/KEY: misc_feature
<222> LOCATION: (1)..(2287)
<223> OTHER INFORMATION: Saccharomyces cerevisiae ACS2 nucleotide
      sequence

<400> SEQUENCE: 5

acctcccgcg acctccaaaa tcgaactacc ttcacaatga caatcaagga acataaagta     60

gtttatgaag ctcacaacgt aaaggctctt aaggctcctc aacatttta caacagccaa    120

cccggcaagg gttacgttac tgatatgcaa cattatcaag aaatgtatca acaatctatc    180

aatgagccag aaaaattctt tgataagatg gctaaggaat acttgcattg ggatgctcca    240

tacaccaaag ttcaatctgg ttcattgaac aatggtgatg ttgcatggtt tttgaacggt    300

aaattgaatg catcatacaa ttgtgttgac agacatgcct ttgctaatcc cgacaagcca    360

gctttgatct atgaagctga tgacgaatcc gacaacaaaa tcatcacatt tggtgaatta    420

ctcagaaaag tttcccaaat cgctggtgtc ttaaaaagct ggggcgttaa gaaaggtgac    480

acagtggcta tctatttgcc aatgattcca gaagcggtca ttgctatgtt ggctgtggct    540

cgtattggtg ctattcactc tgttgtcttt gctgggttct ccgctggttc gttgaaagat    600

cgtgtcgttg acgctaattc taaagtggtc atcacttgtg atgaaggtaa aagaggtggt    660

aagaccatca acactaaaaa aattgttgac gaaggtttga acggagtcga tttggtttcc    720

cgtatcttgg ttttccaaag aactggtact gaaggtattc caatgaaggc cggtagagat    780

tactggtggc atgaggaggc cgctaagcag agaacttacc tacctcctgt ttcatgtgac    840

gctgaagatc ctctattttt attatacact tccggttcca ctggttctcc aaagggtgtc    900

gttcacacta caggtggtta tttattaggt gccgctttaa caactagata cgtttttgat    960

attcacccag aagatgttct cttcactgcc ggtgacgtcg gctggatcac gggtcacacc   1020

tatgctctat atggtccatt aaccttgggt accgcctcaa taattttcga atccactcct   1080

gcctacccag attatggtag atattggaga attatccaac gtcacaaggc tacccatttc   1140

tatgtggctc caactgcttt aagattaatc aaacgtgtag gtgaagccga aattgccaaa   1200
```

-continued

```
tatgacactt cctcattacg tgtcttgggt tccgtcggtg aaccaatctc tccagactta   1260

tgggaatggt atcatgaaaa agtgggtaac aaaaactgtg tcatttgtga cactatgtgg   1320

caaacagagt ctggttctca tttaattgct cctttggcag gtgctgtccc aacaaaacct   1380

ggttctgcta ccgtgccatt ctttggtatt aacgcttgta tcattgaccc tgttacaggt   1440

gtggaattag aaggtaatga tgtcgaaggt gtccttgccg ttaaatcacc atggccatca   1500

atggctagat ctgtttggaa ccaccacgac cgttacatgg atacttactt gaaaccttat   1560

cctggtcact atttcacagg tgatggtgct ggtagagatc atgatggtta ctactggatc   1620

aggggtagag ttgacgacgt tgtaaatgtt tccggtcata gattatccac atcagaaatt   1680

gaagcatcta tctcaaatca cgaaaacgtc tcggaagctg ctgttgtcgg tattccagat   1740

gaattgaccg gtcaaaccgt cgttgcatat gtttccctaa aagatggtta tctacaaaac   1800

aacgctactg aaggtgatgc agaacacatc acaccagata atttacgtag agaattgatc   1860

ttacaagtta ggggtgagat tggtcctttc gcctcaccaa aaaccattat tctagttaga   1920

gatctaccaa gaacaaggtc aggaaagatt atgagaagag ttctaagaaa ggttgcttct   1980

aacgaagccg aacagctagg tgacctaact actttggcca acccagaagt tgtacctgcc   2040

atcatttctg ctgtagagaa ccaatttttc tctcaaaaaa agaaataact taaatgagaa   2100

aaatttcgta atgagataaa atttcgctcc ttttctgttt tctattttct attttcccaa   2160

cttttgctct attcagttat aaattactat ttatccatca gttaaaaaac aagatctttt   2220

actggtcagc taggaaagcg aaaatacaaa gactttatgc actatccccg cgtgcttggc   2280

cggccgt                                                             2287
```

```
<210> SEQ ID NO 6
<211> LENGTH: 683
<212> TYPE: PRT
<213> ORGANISM: Saccharomyces cerevisiae
<220> FEATURE:
<221> NAME/KEY: misc_feature
<222> LOCATION: (1)..(683)
<223> OTHER INFORMATION: Saccharomyces cerevisiae ACS2 protein sequence

<400> SEQUENCE: 6

Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly
            20                  25                  30

Tyr Val Thr Asp Met Gln His Tyr Gln Glu Met Tyr Gln Gln Ser Ile
        35                  40                  45

Asn Glu Pro Glu Lys Phe Phe Asp Lys Met Ala Lys Glu Tyr Leu His
    50                  55                  60

Trp Asp Ala Pro Tyr Thr Lys Val Gln Ser Gly Ser Leu Asn Asn Gly
65                  70                  75                  80

Asp Val Ala Trp Phe Leu Asn Gly Lys Leu Asn Ala Ser Tyr Asn Cys
                85                  90                  95

Val Asp Arg His Ala Phe Ala Asn Pro Asp Lys Pro Ala Leu Ile Tyr
            100                 105                 110

Glu Ala Asp Asp Glu Ser Asp Asn Lys Ile Ile Thr Phe Gly Glu Leu
        115                 120                 125

Leu Arg Lys Val Ser Gln Ile Ala Gly Val Leu Lys Ser Trp Gly Val
    130                 135                 140

Lys Lys Gly Asp Thr Val Ala Ile Tyr Leu Pro Met Ile Pro Glu Ala
145                 150                 155                 160
```

```
Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
            180                 185                 190

Ala Asn Ser Lys Val Val Ile Thr Cys Asp Glu Gly Lys Arg Gly Gly
        195                 200                 205

Lys Thr Ile Asn Thr Lys Lys Ile Val Asp Glu Gly Leu Asn Gly Val
    210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
            260                 265                 270

Leu Phe Leu Leu Tyr Thr Ser Gly Ser Thr Gly Ser Pro Lys Gly Val
        275                 280                 285

Val His Thr Thr Gly Gly Tyr Leu Leu Gly Ala Ala Leu Thr Thr Arg
    290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
            340                 345                 350

Tyr Gly Arg Tyr Trp Arg Ile Ile Gln Arg His Lys Ala Thr His Phe
        355                 360                 365

Tyr Val Ala Pro Thr Ala Leu Arg Leu Ile Lys Arg Val Gly Glu Ala
    370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
                405                 410                 415

Gly Asn Lys Asn Cys Val Ile Cys Asp Thr Met Trp Gln Thr Glu Ser
            420                 425                 430

Gly Ser His Leu Ile Ala Pro Leu Ala Gly Ala Val Pro Thr Lys Pro
        435                 440                 445

Gly Ser Ala Thr Val Pro Phe Phe Gly Ile Asn Ala Cys Ile Ile Asp
    450                 455                 460

Pro Val Thr Gly Val Glu Leu Glu Gly Asn Asp Val Glu Gly Val Leu
465                 470                 475                 480

Ala Val Lys Ser Pro Trp Pro Ser Met Ala Arg Ser Val Trp Asn His
                485                 490                 495

His Asp Arg Tyr Met Asp Thr Tyr Leu Lys Pro Tyr Pro Gly His Tyr
            500                 505                 510

Phe Thr Gly Asp Gly Ala Gly Arg Asp His Asp Gly Tyr Tyr Trp Ile
        515                 520                 525

Arg Gly Arg Val Asp Asp Val Val Asn Val Ser Gly His Arg Leu Ser
    530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val
                565                 570                 575

Ala Tyr Val Ser Leu Lys Asp Gly Tyr Leu Gln Asn Asn Ala Thr Glu
            580                 585                 590
```

```
Gly Asp Ala Glu His Ile Thr Pro Asp Asn Leu Arg Arg Glu Leu Ile
        595                 600                 605

Leu Gln Val Arg Gly Glu Ile Gly Pro Phe Ala Ser Pro Lys Thr Ile
    610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
                645                 650                 655

Leu Thr Thr Leu Ala Asn Pro Glu Val Val Pro Ala Ile Ile Ser Ala
            660                 665                 670

Val Glu Asn Gln Phe Phe Ser Gln Lys Lys Lys
        675                 680


<210> SEQ ID NO 7
<211> LENGTH: 1798
<212> TYPE: DNA
<213> ORGANISM: Saccharomyces cerevisiae
<220> FEATURE:
<221> NAME/KEY: misc_feature
<222> LOCATION: (1)..(1798)
<223> OTHER INFORMATION: Saccharomyces cerevisiae ALD4 nucleotide
      sequence

<400> SEQUENCE: 7

gcacccaggg acacacagca gcgaagtatt ttcagaatgt tcagtagatc tacgctctgc      60

ttaaagacgt ctgcatcctc cattgggaga cttcaattga gatatttctc acaccttcct     120

atgacagtgc ctatcaagct gcccaatggg ttggaatatg agcaaccaac ggggttgttc     180

atcaacaaca agtttgttcc ttctaaacag aacaagacct tcgaagtcat taacccttcc     240

acggaagaag aaatatgtca tatttatgaa ggtagagagg acgatgtgga agaggccgtg     300

caggccgccg accgtgcctt ctctaatggg tcttggaacg gtatcgaccc tattgacagg     360

ggtaaggctt tgtacaggtt agccgaatta attgaacagg acaaggatgt cattgcttcc     420

atcgagactt tggataacgg taaagctatc tcttcctcga gaggagatgt tgatttagtc     480

atcaactatt tgaaatcttc tgctggcttt gctgataaaa ttgatggtag aatgattgat     540

actggtagaa cccatttttc ttacactaag agacagcctt tgggtgtttg tgggcagatt     600

attccttgga atttcccact gttgatgtgg gcctggaaga ttgcccctgc tttggtcacc     660

ggtaacaccg tcgtgttgaa gactgccgaa tccacccccat tgtccgcttt gtatgtgtct     720

aaatacatcc cacaggcggg tattccacct ggtgtgatca acattgtatc cgggtttggt     780

aagattgtgg gtgaggccat tacaaaccat ccaaaaatca aaaaggttgc cttcacaggg     840

tccacggcta cgggtagaca catttaccag tccgcagccg caggcttgaa aaaagtgact     900

ttggagctgg gtggtaaatc accaaacatt gtcttcgcgg acgccgagtt gaaaaaagcc     960

gtgcaaaaca ttatccttgg tatctactac aattctggtg aggtctgttg tgcgggttca    1020

agggtgtatg ttgaagaatc tatttacgac aaattcattg aagagttcaa agccgcttct    1080

gaatccatca aggtgggcga cccattcgat gaatctactt tccaaggtgc acaaacctct    1140

caaatgcaac taaacaaaat cttgaaatac gttgacattg gtaagaatga aggtgctact    1200

ttgattaccg gtggtgaaag attaggtagc aagggttact tcattaagcc aactgtcttt    1260

ggtgacgtta aggaagacat gagaattgtc aaagaggaaa tctttggccc tgttgtcact    1320

gtaaccaaat tcaaatctgc cgacgaagtc attaacatgg cgaacgattc tgaatacggg    1380

ttggctgctg gtattcacac ctctaatatt aataccgcct taaaagtggc tgatagagtt    1440

aatgcgggta cggtctggat aaacacttat aacgatttcc accacgcagt tcctttcggt    1500
```

```
gggttcaatg catctggttt gggcagggaa atgtctgttg atgctttaca aaactacttg   1560

caagttaaag cggtccgtgc caaattggac gagtaaggtc atcaataagc ctggtgtcca   1620

atcgatgctt acatacataa aattaaatat tctgtctctg ttatatttcc acatgtcatc   1680

atttcaaata tatgtacttt aaagaaaata aaataaaaaa taaaattttt ttctcccgat   1740

aatcaatttt cttaattaat taattgcgtt acgaaacgcg atcgccgacg ccgccgat     1798


<210> SEQ ID NO 8
<211> LENGTH: 519
<212> TYPE: PRT
<213> ORGANISM: Saccharomyces cerevisiae
<220> FEATURE:
<221> NAME/KEY: misc_feature
<222> LOCATION: (1)..(519)
<223> OTHER INFORMATION: Saccharomyces cerevisiae ALD4 protein sequence

<400> SEQUENCE: 8

Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
            180                 185                 190

Phe Pro Leu Leu Met Trp Ala Trp Lys Ile Ala Pro Ala Leu Val Thr
        195                 200                 205

Gly Asn Thr Val Val Leu Lys Thr Ala Glu Ser Thr Pro Leu Ser Ala
    210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Lys Val Ala Phe Thr Gly Ser Thr Ala Thr
            260                 265                 270

Gly Arg His Ile Tyr Gln Ser Ala Ala Ala Gly Leu Lys Lys Val Thr
        275                 280                 285

Leu Glu Leu Gly Gly Lys Ser Pro Asn Ile Val Phe Ala Asp Ala Glu
    290                 295                 300
```

```
Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
                325                 330                 335

Tyr Asp Lys Phe Ile Glu Glu Phe Lys Ala Ala Ser Glu Ser Ile Lys
            340                 345                 350

Val Gly Asp Pro Phe Asp Glu Ser Thr Phe Gln Gly Ala Gln Thr Ser
        355                 360                 365

Gln Met Gln Leu Asn Lys Ile Leu Lys Tyr Val Asp Ile Gly Lys Asn
    370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
                405                 410                 415

Ile Val Lys Glu Glu Ile Phe Gly Pro Val Val Thr Val Thr Lys Phe
            420                 425                 430

Lys Ser Ala Asp Glu Val Ile Asn Met Ala Asn Asp Ser Glu Tyr Gly
        435                 440                 445

Leu Ala Ala Gly Ile His Thr Ser Asn Ile Asn Thr Ala Leu Lys Val
    450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
                485                 490                 495

Arg Glu Met Ser Val Asp Ala Leu Gln Asn Tyr Leu Gln Val Lys Ala
            500                 505                 510

Val Arg Ala Lys Leu Asp Glu
        515
```

<210> SEQ ID NO 9
<211> LENGTH: 2744
<212> TYPE: DNA
<213> ORGANISM: Saccharomyces cerevisiae
<220> FEATURE:
<221> NAME/KEY: misc_feature
<222> LOCATION: (1)..(2744)
<223> OTHER INFORMATION: Saccharomyces cerevisiae cytosolic aldehyde dehydrogenase 6 (ALD6) nucleotide sequence

<400> SEQUENCE: 9

```
catatggcgt atccaagccg aaaccctttg cctcatcccc acggaataag gcagccgaca     60

aaagaaaaac gaccgaaaag gaaccagaaa gaaaaaagag ggtgggcgcg ccgcggacgt    120

gtaaaaagat atgcatccag cttctatatc gctttaactt taccgttttg ggcatcggga    180

acgtatgtaa cattgatctc ctcttgggaa cggtgagtgc aacagatgcg atatagcacc    240

gaccatgtgg gcaaattcgt aataaattcg gggtgagggg gattcaagac aagcaacctt    300

gttagtcagc tcaaacagcg atttaacggt tgagtaacac atcaaaacac cgttcgaggt    360

caagcctggc gtgtttaaca agttcttgat atcatatata aatgtaataa gaagtttggt    420

aatattcaat tcgaagtgtt cagtctttta cttctcttgt tttatagaag aaaaaacatc    480

aagaaacatc tttaacatac acaaacacat actatcagaa tacaatgact aagctacact    540

ttgacactgc tgaaccagtc aagatcacac ttccaaatgg tttgacatac gagcaaccaa    600

ccggtctatt cattaacaac aagtttatga aagctcaaga cggtaagacc tatcccgtcg    660

aagatccttc cactgaaaac accgtttgtg aggtctcttc tgccaccact gaagatgttg    720

aatatgctat cgaatgtgcc gaccgtgctt tccacgacac tgaatgggct acccaagacc    780
```

```
caagagaaag aggccgtcta ctaagtaagt tggctgacga attggaaagc caaattgact    840

tggtttcttc cattgaagct ttggacaatg gtaaaacttt ggcctttaag gcccgtgggg    900

atgttaccat tgcaatcaac tgtctaagag atgctgctgc ctatgccgac aaagtcaacg    960

gtagaacaat caacaccggt gacggctaca tgaacttcac caccttagag ccaatcggtg   1020

tctgtggtca aattattcca tggaactttc caataatgat gttggcttgg aagatcgccc   1080

cagcattggc catgggtaac gtctgtatct tgaaacccgc tgctgtcaca cctttaaatg   1140

ccctatactt tgcttcttta tgtaagaagg ttggtattcc agctggtgtc gtcaacatcg   1200

ttccaggtcc tggtagaact gttggtgctg ctttgaccaa cgacccaaga atcagaaagc   1260

tggcttttac cggttctaca gaagtcggta agagtgttgc tgtcgactct tctgaatcta   1320

acttgaagaa aatcactttg gaactaggtg gtaagtccgc ccatttggtc tttgacgatg   1380

ctaacattaa gaagacttta ccaaatctag taaacggtat tttcaagaac gctggtcaaa   1440

tttgttcctc tggttctaga atttacgttc aagaaggtat ttacgacgaa ctattggctg   1500

ctttcaaggc ttacttggaa accgaaatca aagttggtaa tccatttgac aaggctaact   1560

tccaaggtgc tatcactaac cgtcaacaat tcgacacaat tatgaactac atcgatatcg   1620

gtaagaaaga aggcgccaag atcttaactg gtggcgaaaa agttggtgac aagggttact   1680

tcatcagacc aaccgttttc tacgatgtta atgaagacat gagaattgtt aaggaagaaa   1740

tttttggacc agttgtcact gtcgcaaagt tcaagacttt agaagaaggt gtcgaaatgg   1800

ctaacagctc tgaattcggt ctaggttctg gtatcgaaac agaatctttg agcacaggtt   1860

tgaaggtggc caagatgttg aaggccggta ccgtctggat caacacatac aacgattttg   1920

actccagagt tccattcggt ggtgttaagc aatctggtta cggtagagaa atgggtgaag   1980

aagtctacca tgcatacact gaagtaaaag ctgtcagaat taagttgtaa tgtaccaacc   2040

tgcatttctt tccgtcatat acacaaaata ctttcatata aacttacttg gtcttacgtc   2100

ataaataaat atgtatacat ataaattaaa aaatttggtt ttatattttt acaaaaagaa   2160

tcgtttactt catttctccc ttttaagcga tacaatccat gaaaaaagag aaaaagagag   2220

aacaggcttg tgccttcttt aaaacatccc acacaaaatc atattgaatt gaattttaca   2280

tcttaagcta gtgtacaaca actgctatat ccaaagaaaa ctaacgtgga ccgcttttag   2340

agttgagaaa aaggtttgaa aaaaatagca atacaaagac ttgtttcata tataaaatac   2400

agggagcaca ttgagctaat ataacataaa cactgcgaac caattccaat caaaaggtac   2460

acatgagagc attcccccga gtactgccat ttcgccatca gagatcatat aataacatcc   2520

ttcttcgaac agtaaggctt tttggttcat cactttcttc ttttgatttc tctaggcaaa   2580

tgcctaaggt ggaccctgac aataccgctg caatgctact acagaaaaac ttgatccaaa   2640

gaaacaacat gctctatggg tatggatcag ggacaatacg atgtactttg ctagactcaa   2700

ctggacgagc caaatcacca ttagtagaga taaaacgtga ggat                    2744
```

```
<210> SEQ ID NO 10
<211> LENGTH: 500
<212> TYPE: PRT
<213> ORGANISM: Saccharomyces cerevisiae
<220> FEATURE:
<221> NAME/KEY: misc_feature
<222> LOCATION: (1)..(500)
<223> OTHER INFORMATION: Saccharomyces cerevisiae cytosolic aldehyde
      dehydrogenase 6 (ALD6) protein sequence
```

<400> SEQUENCE: 10

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415
```

```
Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500
```

```
<210> SEQ ID NO 11
<211> LENGTH: 2749
<212> TYPE: DNA
<213> ORGANISM: Leuconostoc mesenteroides
<220> FEATURE:
<221> NAME/KEY: misc_feature
<222> LOCATION: (1)..(2749)
<223> OTHER INFORMATION: Leuconostoc mesenteroides Phosphoketolase (PK)
      gene sequence

<400> SEQUENCE: 11

gttacggaag aagtcgtggt ttacggtgtt tatgattctt gcaaaaaata aggagtactt     60

aatctcatgg cagatttcga ttcaaaagag tacttggaac ttgttgataa gtggtggcgc    120

gcaactaact atttgtcagc tgggatgatc tttttgaaga gcaacccatt gttctcagtt    180

actaatacac ctatcaaggc tgaagatgta aaagttaagc caatcggaca ctggggtact    240

atctcaggtc agacattctt gtatgcacat gctaaccgtt tgatcaacaa gtatggtttg    300

aacatgtttt acgttggtgg tcctggtcac ggtggccaag ttatggttac taacgcttac    360

ttagacggcg catatactga agattatcct gaaattactc aagatatcga aggtatgagc    420

cacttgttca agcgtttctc attccctggc ggtattggat cacacatgac agctcaaaca    480

cctggttcat tacacgaagg tggtgaattg ggctattcat tgagccacgc ttttggtgcc    540

gttttggaca atcctgacca agttgctttc gcagttgttg gtgatggtga agctgaaaca    600

ggtccttcaa tggcttcatg gcactcaatt aagtttttga atgctaagaa tgatggtgcc    660

gttttgcctg tcttggattt gaacggattc aagatttcaa acccaactat cttctcacgt    720

atgagtgatg aagaaatcac aaagttcttt gaaggtttgg gttattcacc tcgcttcatc    780

gaaaacgatg atattcatga ctacgcaaca tatcaccaac ttgcagcaaa cattttggat    840

caagctattg aagatattca agctattcaa aatgatgcac gtgaaaatgg taagtatcaa    900

gatggtgaaa tccctgcatg gccagtaatt attgctcgct tgccaaaggg ctggggtgga    960

ccaacgcacg atgcaagtaa caatcctatt gaaaactcat tccgtgcgca ccaagtgcca   1020

ttgcctcttg aacaacacga tcttgcaaca ttgcctgaat tcgaagactg gatgaactca   1080

tacaagcctg aagaattatt caatgctgat ggttctttga aggatgaatt gaaagctatc   1140

gctcctaagg gtgacaagcg tatgtcagct aaccctatta caaatggtgg tgctgatcgt   1200

tcagacttga agttgcctaa ctggagagaa ttcgctaacg atatcaatga tgatacacgt   1260

ggtaaggaat tcgctgatag caagcgcaat atggacatgg caacattgtc aaactacttg   1320

ggtgctgttt cacaattgaa cccaactcgt ttccgcttct tcggtcctga tgaaacaatg   1380

tcaaaccgtt tgtggggatt gttcaatgtt acaccacgtc aatggatgga agaaatcaag   1440

gaaccacaag atcaattgtt gagccctacg ggtcgcatta ttgattcaca attgtctgaa   1500
```

catcaagctg aaggttggct tgaaggatat actttgactg gtcgtgttgg aatcttcgca 1560
tcatacgagt cattcttgcg tgttgtcgat acaatggtta cgcaacactt caagtggttg 1620
cgtcacgctt cagaacaagc atggcgtaat gactatccat cattgaactt gattgcaact 1680
tcaactgctt tccaacaaga tcacaatgga tatactcacc aagatccagg tatgttgact 1740
cacttggctg aaaagaagtc taactttatt cgtgaatatt tgccagctga tggtaactca 1800
ttgttggctg ttcaagaacg tgctttctca gaacgtcata aggttaactt gttgattgct 1860
tctaagcaac cacgtcaaca atggtttaca gttgaagaag ctgaagtatt ggctaacgaa 1920
ggtttgaaga tcattgattg ggcttctact gcaccttcta gtgatgttga tattacattc 1980
gcatctgctg gtactgaacc aacaattgaa actttggctg ctttgtggtt gattaaccaa 2040
gcattcccag atgttaagtt ccgttatgtt aacgttgttg aattactacg tttgcaaaag 2100
aagtcagaac ctaacatgaa tgatgaacgt gaattatcag ccgaagaatt caacaagtat 2160
ttccaagctg atacaccagt tatcttcggt ttccatgctt atgaaaactt gattgaatca 2220
ttcttcttcg aacgtaagtt cacgggtgat gtatacgttc atggatatcg tgaagatggt 2280
gacatcacaa cgacatatga tatgcgtgta tattcacact tggatcgctt ccatcaagct 2340
aaggaagctg ctgaaatctt gtctgcaaat ggtaagattg atcaagctgc tgctgataca 2400
ttcatcgcta agatggatga tactttggca aagcatttcc aagttactcg taacgaaggt 2460
cgtgatatcg aagaattcac tgactggaca tggtcaccac ttaagtaatt taaaattatt 2520
ttatcaaaac caactattat ttttaatagt tggttttttt atggctaaat tgactacata 2580
ctaaacgaaa ccatgtaaaa gtgccacata gttttactta ataagttcct tttatttttt 2640
gatttgcaat gcaaaattgt aagcgtaata tgaataataa aaacccccaa ttagttagct 2700
aattgggggt tttgtaaatc accatatcag ccgctcatag tcttagacg 2749

<210> SEQ ID NO 12
<211> LENGTH: 813
<212> TYPE: PRT
<213> ORGANISM: Leuconostoc mesenteroides
<220> FEATURE:
<221> NAME/KEY: misc_feature
<222> LOCATION: (1)..(813)
<223> OTHER INFORMATION: Leuconostoc mesenteroides Phosphoketolase (PK) protein sequence

<400> SEQUENCE: 12

Met Ala Asp Phe Asp Ser Lys Glu Tyr Leu Glu Leu Val Asp Lys Trp
1 5 10 15

Trp Arg Ala Thr Asn Tyr Leu Ser Ala Gly Met Ile Phe Leu Lys Ser
20 25 30

Asn Pro Leu Phe Ser Val Thr Asn Thr Pro Ile Lys Ala Glu Asp Val
35 40 45

Lys Val Lys Pro Ile Gly His Trp Gly Thr Ile Ser Gly Gln Thr Phe
50 55 60

Leu Tyr Ala His Ala Asn Arg Leu Ile Asn Lys Tyr Gly Leu Asn Met
65 70 75 80

Phe Tyr Val Gly Gly Pro Gly His Gly Gly Gln Val Met Val Thr Asn
85 90 95

Ala Tyr Leu Asp Gly Ala Tyr Thr Glu Asp Tyr Pro Glu Ile Thr Gln
100 105 110

Asp Ile Glu Gly Met Ser His Leu Phe Lys Arg Phe Ser Phe Pro Gly
115 120 125

```
Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160

Asp Asn Pro Asp Gln Val Ala Phe Ala Val Val Gly Asp Gly Glu Ala
                165                 170                 175

Glu Thr Gly Pro Ser Met Ala Ser Trp His Ser Ile Lys Phe Leu Asn
            180                 185                 190

Ala Lys Asn Asp Gly Ala Val Leu Pro Val Leu Asp Leu Asn Gly Phe
        195                 200                 205

Lys Ile Ser Asn Pro Thr Ile Phe Ser Arg Met Ser Asp Glu Glu Ile
    210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Thr Tyr His Gln Leu Ala Ala Asn Ile
                245                 250                 255

Leu Asp Gln Ala Ile Glu Asp Ile Gln Ala Ile Gln Asn Asp Ala Arg
            260                 265                 270

Glu Asn Gly Lys Tyr Gln Asp Gly Glu Ile Pro Ala Trp Pro Val Ile
        275                 280                 285

Ile Ala Arg Leu Pro Lys Gly Trp Gly Gly Pro Thr His Asp Ala Ser
    290                 295                 300

Asn Asn Pro Ile Glu Asn Ser Phe Arg Ala His Gln Val Pro Leu Pro
305                 310                 315                 320

Leu Glu Gln His Asp Leu Ala Thr Leu Pro Glu Phe Glu Asp Trp Met
                325                 330                 335

Asn Ser Tyr Lys Pro Glu Glu Leu Phe Asn Ala Asp Gly Ser Leu Lys
            340                 345                 350

Asp Glu Leu Lys Ala Ile Ala Pro Lys Gly Asp Lys Arg Met Ser Ala
        355                 360                 365

Asn Pro Ile Thr Asn Gly Gly Ala Asp Arg Ser Asp Leu Lys Leu Pro
    370                 375                 380

Asn Trp Arg Glu Phe Ala Asn Asp Ile Asn Asp Asp Thr Arg Gly Lys
385                 390                 395                 400

Glu Phe Ala Asp Ser Lys Arg Asn Met Asp Met Ala Thr Leu Ser Asn
                405                 410                 415

Tyr Leu Gly Ala Val Ser Gln Leu Asn Pro Thr Arg Phe Arg Phe Phe
            420                 425                 430

Gly Pro Asp Glu Thr Met Ser Asn Arg Leu Trp Gly Leu Phe Asn Val
        435                 440                 445

Thr Pro Arg Gln Trp Met Glu Glu Ile Lys Glu Pro Gln Asp Gln Leu
    450                 455                 460

Leu Ser Pro Thr Gly Arg Ile Ile Asp Ser Gln Leu Ser Glu His Gln
465                 470                 475                 480

Ala Glu Gly Trp Leu Glu Gly Tyr Thr Leu Thr Gly Arg Val Gly Ile
                485                 490                 495

Phe Ala Ser Tyr Glu Ser Phe Leu Arg Val Val Asp Thr Met Val Thr
            500                 505                 510

Gln His Phe Lys Trp Leu Arg His Ala Ser Glu Gln Ala Trp Arg Asn
        515                 520                 525

Asp Tyr Pro Ser Leu Asn Leu Ile Ala Thr Ser Thr Ala Phe Gln Gln
    530                 535                 540

Asp His Asn Gly Tyr Thr His Gln Asp Pro Gly Met Leu Thr His Leu
545                 550                 555                 560
```

```
Ala Glu Lys Lys Ser Asn Phe Ile Arg Glu Tyr Leu Pro Ala Asp Gly
                565                 570                 575

Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
        595                 600                 605

Val Glu Glu Ala Glu Val Leu Ala Asn Glu Gly Leu Lys Ile Ile Asp
    610                 615                 620

Trp Ala Ser Thr Ala Pro Ser Ser Asp Val Asp Ile Thr Phe Ala Ser
625                 630                 635                 640

Ala Gly Thr Glu Pro Thr Ile Glu Thr Leu Ala Ala Leu Trp Leu Ile
                645                 650                 655

Asn Gln Ala Phe Pro Asp Val Lys Phe Arg Tyr Val Asn Val Val Glu
            660                 665                 670

Leu Leu Arg Leu Gln Lys Lys Ser Glu Pro Asn Met Asn Asp Glu Arg
        675                 680                 685

Glu Leu Ser Ala Glu Glu Phe Asn Lys Tyr Phe Gln Ala Asp Thr Pro
    690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
                725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Ala Glu Ile Leu Ser Ala Asn
        755                 760                 765

Gly Lys Ile Asp Gln Ala Ala Ala Asp Thr Phe Ile Ala Lys Met Asp
    770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
                805                 810
```

<210> SEQ ID NO 13
<211> LENGTH: 1002
<212> TYPE: DNA
<213> ORGANISM: Clostridium kluyveri
<220> FEATURE:
<221> NAME/KEY: misc_feature
<222> LOCATION: (1)..(1002)
<223> OTHER INFORMATION: Clostridium kluyveri Phosphotransacetylase (PTA) gene sequence

<400> SEQUENCE: 13

```
atgaaattaa tggaaaatat ttttggttta gccaaagcag ataagaaaaa aattgttttg     60

gcagaaggag aagaagaaag gaacattaga gcttccgaag aaataataag ggatggtatt    120

gcagatataa ttttagtagg aagtgaaagt gtaataaaag agaatgcagc taaatttggg    180

gttaacttag ctggagtgga aatagtagat cctgaaactt caagtaaaac tgcaggctat    240

gccaatgctt tttatgaaat tagaaagaat aaaggagtta cactggaaaa agcagataaa    300

atagttagag atcctatata ttttgcaaca atgatggtga aacttggaga tgcagatggt    360

ttagtttcag gtgcaataca tacaacggga gatcttttga gaccaggact tcaaatagtg    420

aagacagttc caggtgcttc tgtggtttcc agtgtatttt taatgagtgt accagattgt    480

gaatatggag aagatggatt cttgttattt gctgattgtg ctgtaaatgt atgtcctact    540

gctgaagaat tatcttcaat tgcaataact acagcagaaa ctgcaaaaaa tttgtgtaaa    600
```

```
atagaaccaa gagttgccat gctttcattt tctactatgg gaagtgctag tcatgaattg    660

gtagataaag ttacaaaagc aacaaaactt gctaaagaag ctagacctga tttggatata    720

gatggagaac ttcaattgga tgcttcccta gtaaaaaaag ttgcagactt aaaagctccg    780

ggcagtaaag tggcaggaaa agccaatgta cttatattcc ctgatataca agcaggaaat    840

ataggatata agttagttca aagatttgca aaagctgagg ctataggacc tatatgtcag    900

ggatttgcaa agcctataaa tgatttatca agaggctgca gcgttgatga tatagtaaag    960

gtagtggctg taactgcagt tcaagcacag gcacagggtt ag                      1002
```

<210> SEQ ID NO 14
<211> LENGTH: 333
<212> TYPE: PRT
<213> ORGANISM: Clostridium kluyveri
<220> FEATURE:
<221> NAME/KEY: misc_feature
<222> LOCATION: (1)..(333)
<223> OTHER INFORMATION: Clostridium kluyveri Phosphotransacetylase (PTA) protein sequence

<400> SEQUENCE: 14

```
Met Lys Leu Met Glu Asn Ile Phe Gly Leu Ala Lys Ala Asp Lys Lys
1               5                   10                  15

Lys Ile Val Leu Ala Glu Gly Glu Glu Glu Arg Asn Ile Arg Ala Ser
            20                  25                  30

Glu Glu Ile Ile Arg Asp Gly Ile Ala Asp Ile Ile Leu Val Gly Ser
        35                  40                  45

Glu Ser Val Ile Lys Glu Asn Ala Ala Lys Phe Gly Val Asn Leu Ala
    50                  55                  60

Gly Val Glu Ile Val Asp Pro Glu Thr Ser Ser Lys Thr Ala Gly Tyr
65                  70                  75                  80

Ala Asn Ala Phe Tyr Glu Ile Arg Lys Asn Lys Gly Val Thr Leu Glu
                85                  90                  95

Lys Ala Asp Lys Ile Val Arg Asp Pro Ile Tyr Phe Ala Thr Met Met
            100                 105                 110

Val Lys Leu Gly Asp Ala Asp Gly Leu Val Ser Gly Ala Ile His Thr
        115                 120                 125

Thr Gly Asp Leu Leu Arg Pro Gly Leu Gln Ile Val Lys Thr Val Pro
    130                 135                 140

Gly Ala Ser Val Val Ser Ser Val Phe Leu Met Ser Val Pro Asp Cys
145                 150                 155                 160

Glu Tyr Gly Glu Asp Gly Phe Leu Leu Phe Ala Asp Cys Ala Val Asn
                165                 170                 175

Val Cys Pro Thr Ala Glu Glu Leu Ser Ser Ile Ala Ile Thr Thr Ala
            180                 185                 190

Glu Thr Ala Lys Asn Leu Cys Lys Ile Glu Pro Arg Val Ala Met Leu
        195                 200                 205

Ser Phe Ser Thr Met Gly Ser Ala Ser His Glu Leu Val Asp Lys Val
    210                 215                 220

Thr Lys Ala Thr Lys Leu Ala Lys Glu Ala Arg Pro Asp Leu Asp Ile
225                 230                 235                 240

Asp Gly Glu Leu Gln Leu Asp Ala Ser Leu Val Lys Lys Val Ala Asp
                245                 250                 255

Leu Lys Ala Pro Gly Ser Lys Val Ala Gly Lys Ala Asn Val Leu Ile
            260                 265                 270

Phe Pro Asp Ile Gln Ala Gly Asn Ile Gly Tyr Lys Leu Val Gln Arg
        275                 280                 285
```

```
Phe Ala Lys Ala Glu Ala Ile Gly Pro Ile Cys Gln Gly Phe Ala Lys
    290                 295                 300

Pro Ile Asn Asp Leu Ser Arg Gly Cys Ser Val Asp Asp Ile Val Lys
305                 310                 315                 320

Val Val Ala Val Thr Ala Val Gln Ala Gln Ala Gln Gly
                325                 330


<210> SEQ ID NO 15
<211> LENGTH: 2137
<212> TYPE: DNA
<213> ORGANISM: Streptomyces sp. CL190
<220> FEATURE:
<221> NAME/KEY: misc_feature
<222> LOCATION: (1)..(2137)
<223> OTHER INFORMATION: Streptomyces sp. CL190 nphT7 gene sequence

<400> SEQUENCE: 15

cctgcaggcc gtcgagggcg cctggaagga ctacgcggag caggacggcc ggtcgctgga     60

ggagttcgcg gcgttcgtct accaccagcc gttcacgaag atggcctaca aggcgcaccg    120

ccacctgctg aacttcaacg gctacgacac cgacaaggac gccatcgagg gcgccctcgg    180

ccagacgacg gcgtacaaca acgtcatcgg caacagctac accgcgtcgg tgtacctggg    240

cctggccgcc ctgctcgacc aggcggacga cctgacgggc cgttccatcg gcttcctgag    300

ctacggctcg ggcagcgtcg ccgagttctt ctcgggcacc gtcgtcgccg ggtaccgcga    360

gcgtctgcgc accgaggcga accaggaggc gatcgcccgg cgcaagagcg tcgactacgc    420

cacctaccgc gagctgcacg agtacacgct cccgtccgac ggcggcgacc acgccacccc    480

ggtgcagacc accggcccct tccggctggc cgggatcaac gaccacaagc gcatctacga    540

ggcgcgctag cgacacccct cggcaacggg gtgcgccact gttcggcgca ccccgtgccg    600

ggctttcgca cagctattca cgaccatttg aggggcgggc agccgcatga ccgacgtccg    660

attccgcatt atcggtacgg gtgcctacgt accggaacgg atcgtctcca acgatgaagt    720

cggcgcgccg gccggggtgg acgacgactg gatcacccgc aagaccggta tccggcagcg    780

tcgctgggcc gccgacgacc aggccacctc ggacctggcc acggccgcgg ggcgggcagc    840

gctgaaagcg gcgggcatca cgcccgagca gctgaccgtg atcgcggtcg ccacctccac    900

gccggaccgg ccgcagccgc ccacggcggc ctatgtccag caccacctcg gtgcgaccgg    960

cactgcggcg ttcgacgtca acgcggtctg ctccggcacc gtgttcgcgc tgtcctcggt   1020

ggcgggcacc ctcgtgtacc ggggcggtta cgcgctggtc atcggcgcgg acctgtactc   1080

gcgcatcctc aacccggccg accgcaagac ggtcgtgctg ttcggggacg gcgccggcgc   1140

aatggtcctc gggccgacct cgaccggcac gggccccatc gtccggcgcg tcgccctgca   1200

caccttcggc ggcctcaccg acctgatccg tgtgcccgcg ggcggcagcc gccagccgct   1260

ggacacggat ggcctcgacg cgggactgca gtacttcgcg atggacgggc gtgaggtgcg   1320

ccgcttcgtc acggagcacc tgccgcagct gatcaagggc ttcctgcacg aggccggggt   1380

cgacgccgcc gacatcagcc acttcgtgcc gcatcaggcc aacggtgtca tgctcgacga   1440

ggtcttcggc gagctgcatc tgccgcgggc gaccatgcac cggacggtcg agacctacgg   1500

caacacggga gcggcctcca tcccgatcac catggacgcg gccgtgcgcg ccggttcctt   1560

ccggccgggc gagctggtcc tgctggccgg gttcggcggc ggcatggccg cgagcttcgc   1620

cctgatcgag tggtagtcgc ccgtaccacc acagcggtcc ggcgccacct gttccctgcg   1680

ccgggccgcc ctcggggcct ttaggcccca caccgcccca gccgacggat tcagtcgcgg   1740

cagtacctca gatgtccgct gcgacggcgt cccggagagc ccgggcgaga tcgcgggccc   1800
```

```
ccttctgctc gtccccggcc cctcccgcga gcaccacccg cggcggacgg ccgccgtcct   1860

ccgcgatacg ccgggcgagg tcgcaggcga gcacgccgga cccggagaag ccccccagca   1920

ccagcgaccg gccgactccg tgcgcggcca gggcaggctg cgcgccgtcg acgtcggtga   1980

gcagcaccag gagctcctgc ggcccggcgt agaggtcggc cagccggtcg tagcaggtcg   2040

cgggcgcgcc cggcggcggg atcagacaga tcgtgcccgc ccgctcgtgc ctcgccgccc   2100

gcagcgtgac cagcggaatg tcccgcccag ctccgga                            2137


<210> SEQ ID NO 16
<211> LENGTH: 325
<212> TYPE: PRT
<213> ORGANISM: Streptomyces sp. CL190
<220> FEATURE:
<221> NAME/KEY: misc_feature
<222> LOCATION: (1)..(325)
<223> OTHER INFORMATION: Streptomyces sp. CL190 acetyl-CoA:malonyl-CoA
      acyltransferase protein sequence

<400> SEQUENCE: 16

Arg Phe Arg Ile Ile Gly Thr Gly Ala Tyr Val Pro Glu Arg Ile Val
1               5                   10                  15

Ser Asn Asp Glu Val Gly Ala Pro Ala Gly Val Asp Asp Asp Trp Ile
            20                  25                  30

Thr Arg Lys Thr Gly Ile Arg Gln Arg Arg Trp Ala Ala Asp Asp Gln
        35                  40                  45

Ala Thr Ser Asp Leu Ala Thr Ala Ala Gly Arg Ala Ala Leu Lys Ala
    50                  55                  60

Ala Gly Ile Thr Pro Glu Gln Leu Thr Val Ile Ala Val Ala Thr Ser
65                  70                  75                  80

Thr Pro Asp Arg Pro Gln Pro Pro Thr Ala Ala Tyr Val Gln His His
                85                  90                  95

Leu Gly Ala Thr Gly Thr Ala Ala Phe Asp Val Asn Ala Val Cys Ser
            100                 105                 110

Gly Thr Val Phe Ala Leu Ser Ser Val Ala Gly Thr Leu Val Tyr Arg
        115                 120                 125

Gly Gly Tyr Ala Leu Val Ile Gly Ala Asp Leu Tyr Ser Arg Ile Leu
    130                 135                 140

Asn Pro Ala Asp Arg Lys Thr Val Val Leu Phe Gly Asp Gly Ala Gly
145                 150                 155                 160

Ala Met Val Leu Gly Pro Thr Ser Thr Gly Thr Gly Pro Ile Val Arg
                165                 170                 175

Arg Val Ala Leu His Thr Phe Gly Gly Leu Thr Asp Leu Ile Arg Val
            180                 185                 190

Pro Ala Gly Gly Ser Arg Gln Pro Leu Asp Thr Asp Gly Leu Asp Ala
        195                 200                 205

Gly Leu Gln Tyr Phe Ala Met Asp Gly Arg Glu Val Arg Arg Phe Val
    210                 215                 220

Thr Glu His Leu Pro Gln Leu Ile Lys Gly Phe Leu His Glu Ala Gly
225                 230                 235                 240

Val Asp Ala Ala Asp Ile Ser His Phe Val Pro His Gln Ala Asn Gly
                245                 250                 255

Val Met Leu Asp Glu Val Phe Gly Glu Leu His Leu Pro Arg Ala Thr
            260                 265                 270

Met His Arg Thr Val Glu Thr Tyr Gly Asn Thr Gly Ala Ala Ser Ile
        275                 280                 285
```

```
Pro Ile Thr Met Asp Ala Ala Val Arg Ala Gly Ser Phe Arg Pro Gly
    290                 295                 300

Glu Leu Val Leu Leu Ala Gly Phe Gly Gly Gly Met Ala Ala Ser Phe
305                 310                 315                 320

Ala Leu Ile Glu Trp
                325


<210> SEQ ID NO 17
<211> LENGTH: 1287
<212> TYPE: DNA
<213> ORGANISM: Pseudomonas mevalonii
<220> FEATURE:
<221> NAME/KEY: misc_feature
<222> LOCATION: (1)..(1287)
<223> OTHER INFORMATION: Pseudomonas mevalonii HMG-CoA reductase (mvaA)
      gene sequence

<400> SEQUENCE: 17

atgagcctcg attcccgcct gcccgctttc cgtaacctgt cccctgccgc gcgcctggac     60

cacatcggcc agttgctcgg cctgagccac gacgatgtca gcctgctggc caacgccggt    120

gccctgccga tggacatcgc caacggcatg atcgaaaacg tcatcggcac cttcgagctg    180

ccctatgccg tggccagcaa cttccagatc aatggccgtg atgtgctggt gccgctggtg    240

gtggaagagc cctcgatcgt cgccgctgct tcgtacatgg ccaagctggc ccgtgccaac    300

ggcggcttca ccacctccag cagcgccccg ctgatgcatg cccaggtaca gatcgtcggc    360

atacaggacc cgctcaatgc acgcctgagc ctgctgcgcc gcaaagacga aatcattgaa    420

ctggccaacc gcaaggacca gttgctcaac agcctcggcg gcggctgccg cgacatcgaa    480

gtgcacacct tcgccgatac ccgcgtggc ccgatgctgg tggcgcacct gatcgtcgat    540

gtacgcgatg ccatgggcgc caacaccgtc aataccatgg ccgaggccgt tgcgccgctg    600

atggaagcca tcaccggggg ccaggtacgc ctgcgcattc tgtccaacct ggccgacctg    660

cgcctggcca gggcccaggt gcggattact ccgcagcaac tggaaacggc cgaattcagt    720

ggcgaggcag tgatcgaagg catcctcgac gcctacgcct tcgctgcggt cgacccttac    780

cgcgcggcca cccacaacaa gggcatcatg aatggcatcg acccactgat cgtcgccact    840

ggcaacgact ggcgtgcagt ggaagccggc gcccatgcgt atgcctgccg cagtggtcac    900

tacggctcgc tgaccacctg ggaaaaggac aacaacggcc atttggtcgg caccctggaa    960

atgccgatgc ccgtaggcct ggtcggcggc gccaccaaaa cccatccgct ggcgcaactg   1020

tcgctgcgca tcctcggcgt gaaaacagcc caggcgctcg ctgagattgc cgtggccgta   1080

ggcctggcgc aaaacctcgg ggccatgcgc gccctggcca ccgaaggcat ccagcgcggc   1140

cacatggccc tgcatgcgcg caatattgcc gtggtggcgg gcgcccgagg cgatgaggtg   1200

gactgggttg cccggcagtt ggtggaatac cacgacgtgc gcgccgaccg cgccgtagca   1260

ctgctgaaac aaaagcgcgg ccaatga                                        1287


<210> SEQ ID NO 18
<211> LENGTH: 428
<212> TYPE: PRT
<213> ORGANISM: Pseudomonas mevalonii
<220> FEATURE:
<221> NAME/KEY: misc_feature
<222> LOCATION: (1)..(428)
<223> OTHER INFORMATION: Pseudomonas mevalonii hydroxymethylglutaryl-CoA
      reductase protein sequence
```

```
<400> SEQUENCE: 18

Met Ser Leu Asp Ser Arg Leu Pro Ala Phe Arg Asn Leu Ser Pro Ala
1               5                   10                  15

Ala Arg Leu Asp His Ile Gly Gln Leu Leu Gly Leu Ser His Asp Asp
            20                  25                  30

Val Ser Leu Leu Ala Asn Ala Gly Ala Leu Pro Met Asp Ile Ala Asn
        35                  40                  45

Gly Met Ile Glu Asn Val Ile Gly Thr Phe Glu Leu Pro Tyr Ala Val
    50                  55                  60

Ala Ser Asn Phe Gln Ile Asn Gly Arg Asp Val Leu Val Pro Leu Val
65                  70                  75                  80

Val Glu Glu Pro Ser Ile Val Ala Ala Ala Ser Tyr Met Ala Lys Leu
                85                  90                  95

Ala Arg Ala Asn Gly Gly Phe Thr Thr Ser Ser Ser Ala Pro Leu Met
            100                 105                 110

His Ala Gln Val Gln Ile Val Gly Ile Gln Asp Pro Leu Asn Ala Arg
        115                 120                 125

Leu Ser Leu Leu Arg Arg Lys Asp Glu Ile Ile Glu Leu Ala Asn Arg
    130                 135                 140

Lys Asp Gln Leu Leu Asn Ser Leu Gly Gly Gly Cys Arg Asp Ile Glu
145                 150                 155                 160

Val His Thr Phe Ala Asp Thr Pro Arg Gly Pro Met Leu Val Ala His
                165                 170                 175

Leu Ile Val Asp Val Arg Asp Ala Met Gly Ala Asn Thr Val Asn Thr
            180                 185                 190

Met Ala Glu Ala Val Ala Pro Leu Met Glu Ala Ile Thr Gly Gly Gln
        195                 200                 205

Val Arg Leu Arg Ile Leu Ser Asn Leu Ala Asp Leu Arg Leu Ala Arg
    210                 215                 220

Ala Gln Val Arg Ile Thr Pro Gln Gln Leu Glu Thr Ala Glu Phe Ser
225                 230                 235                 240

Gly Glu Ala Val Ile Glu Gly Ile Leu Asp Ala Tyr Ala Phe Ala Ala
                245                 250                 255

Val Asp Pro Tyr Arg Ala Ala Thr His Asn Lys Gly Ile Met Asn Gly
            260                 265                 270

Ile Asp Pro Leu Ile Val Ala Thr Gly Asn Asp Trp Arg Ala Val Glu
        275                 280                 285

Ala Gly Ala His Ala Tyr Ala Cys Arg Ser Gly His Tyr Gly Ser Leu
    290                 295                 300

Thr Thr Trp Glu Lys Asp Asn Asn Gly His Leu Val Gly Thr Leu Glu
305                 310                 315                 320

Met Pro Met Pro Val Gly Leu Val Gly Gly Ala Thr Lys Thr His Pro
                325                 330                 335

Leu Ala Gln Leu Ser Leu Arg Ile Leu Gly Val Lys Thr Ala Gln Ala
            340                 345                 350

Leu Ala Glu Ile Ala Val Ala Val Gly Leu Ala Gln Asn Leu Gly Ala
        355                 360                 365

Met Arg Ala Leu Ala Thr Glu Gly Ile Gln Arg Gly His Met Ala Leu
    370                 375                 380

His Ala Arg Asn Ile Ala Val Val Ala Gly Ala Arg Gly Asp Glu Val
385                 390                 395                 400
```

```
Asp Trp Val Ala Arg Gln Leu Val Glu Tyr His Asp Val Arg Ala Asp
              405                 410                 415

Arg Ala Val Ala Leu Leu Lys Gln Lys Arg Gly Gln
          420                 425
```

<210> SEQ ID NO 19
<211> LENGTH: 1302
<212> TYPE: DNA
<213> ORGANISM: Silicibacter pomeroyi
<220> FEATURE:
<221> NAME/KEY: misc_feature
<222> LOCATION: (1)..(1302)
<223> OTHER INFORMATION: Silicibacter pomeroyi hydroxymethylglutaryl-CoA reductase gene sequence

<400> SEQUENCE: 19

```
atgacaggca agacgggtca catcgatggt ttgaactcgc gcattgaaaa gatgcgagat      60

ctcgaccccg cacaacggct ggtgcgcgtt gccgaggcgg cgggcctcga gcccgaggcg     120

atcagcgcgc tggcgggtaa cggcgccctg cccctctcgc tggccaacgg gatgatcgag     180

aacgtcatcg gcaaattcga actgccgctg ggcgtggcca cgaatttcac tgtgaacggc     240

cgcgactatc tgatcccgat ggcggtcgaa gagccctcgg tggtggcggc cgcgtcctat     300

atggcgcgta tcgcgcgcga gaatggcgga ttcaccgcgc atggcaccgc gcccttgatg     360

cgcgcccaga tccaggtggt cgggttgggt gatcccgagg gcgcccggca gcgtctcctc     420

gcccacaagg ccgcgttcat ggaggcggcg gacgctgtcg atccggtgct tgtcgggctg     480

ggtggcggct gccgcgatat cgaggttcac gtgttccggg atacgccggt gggcgcgatg     540

gtcgtcctgc acctgatcgt cgatgtgcgc gacgcgatgg gggccaatac ggtcaacacg     600

atggccgaac ggctggcccc cgaggtcgag cggattgccg gtggcaccgt gcggctgcgc     660

atcctgtcga acctcgccga cctgcgattg gtccgggcgc gggtggaact ggccccggaa     720

acactgacaa cgcagggcta tgacggcgcc gacgtggcgc ggggcatggt cgaggcctgc     780

gcgcttgcca tcgtcgaccc ctatcgcgcg gcgacccata acaaggggat catgaacggc     840

atcgacccgg tcgtcgtcgc caccggcaat gactggcgcg cgatcgaggc gggtgcccat     900

gcctatgccg cccgcacggg tcattatacc tcgctgaccc gctgggaact ggcgaatgac     960

gggcggcttg tgggcacgat cgaactgccc ctggcgcttg gccttgtcgg cggcgcgacc    1020

aagacgcacc cgaccgcacg ggcggcgctg gccctgatgc aggtagagac tgcaaccgaa    1080

ctggcccagg tcaccgccgc cgtgggtctg gcgcagaaca tggccgccat ccgcgcgctg    1140

gcgaccgaag gcatccagcg cggtcacatg acccttcatg cgcgcaacat cgcgatcatg    1200

gccggcgcaa caggcgccga tatcgaccgc gtcacccggg tcattgtcga agcgggcgac    1260

gtcagcgtgg cccgtgcaaa acaggtgctg gaaaacacct ga                       1302
```

<210> SEQ ID NO 20
<211> LENGTH: 433
<212> TYPE: PRT
<213> ORGANISM: Silicibacter pomeroyi
<220> FEATURE:
<221> NAME/KEY: misc_feature
<222> LOCATION: (1)..(433)
<223> OTHER INFORMATION: Silicibacter pomeroyi hydroxymethylglutaryl-CoA reductase protein sequence

<400> SEQUENCE: 20

```
Met Thr Gly Lys Thr Gly His Ile Asp Gly Leu Asn Ser Arg Ile Glu
1               5                   10                  15

Lys Met Arg Asp Leu Asp Pro Ala Gln Arg Leu Val Arg Val Ala Glu
            20                  25                  30

Ala Ala Gly Leu Glu Pro Glu Ala Ile Ser Ala Leu Ala Gly Asn Gly
        35                  40                  45

Ala Leu Pro Leu Ser Leu Ala Asn Gly Met Ile Glu Asn Val Ile Gly
    50                  55                  60

Lys Phe Glu Leu Pro Leu Gly Val Ala Thr Asn Phe Thr Val Asn Gly
65                  70                  75                  80

Arg Asp Tyr Leu Ile Pro Met Ala Val Glu Glu Pro Ser Val Val Ala
                85                  90                  95

Ala Ala Ser Tyr Met Ala Arg Ile Ala Arg Glu Asn Gly Gly Phe Thr
            100                 105                 110

Ala His Gly Thr Ala Pro Leu Met Arg Ala Gln Ile Gln Val Val Gly
        115                 120                 125

Leu Gly Asp Pro Glu Gly Ala Arg Gln Arg Leu Leu Ala His Lys Ala
    130                 135                 140

Ala Phe Met Glu Ala Ala Asp Ala Val Asp Pro Val Leu Val Gly Leu
145                 150                 155                 160

Gly Gly Gly Cys Arg Asp Ile Glu Val His Val Phe Arg Asp Thr Pro
                165                 170                 175

Val Gly Ala Met Val Val Leu His Leu Ile Val Asp Val Arg Asp Ala
            180                 185                 190

Met Gly Ala Asn Thr Val Asn Thr Met Ala Glu Arg Leu Ala Pro Glu
        195                 200                 205

Val Glu Arg Ile Ala Gly Gly Thr Val Arg Leu Arg Ile Leu Ser Asn
    210                 215                 220

Leu Ala Asp Leu Arg Leu Val Arg Ala Arg Val Glu Leu Ala Pro Glu
225                 230                 235                 240

Thr Leu Thr Thr Gln Gly Tyr Asp Gly Ala Asp Val Ala Arg Gly Met
                245                 250                 255

Val Glu Ala Cys Ala Leu Ala Ile Val Asp Pro Tyr Arg Ala Ala Thr
            260                 265                 270

His Asn Lys Gly Ile Met Asn Gly Ile Asp Pro Val Val Val Ala Thr
        275                 280                 285

Gly Asn Asp Trp Arg Ala Ile Glu Ala Gly Ala His Ala Tyr Ala Ala
    290                 295                 300

Arg Thr Gly His Tyr Thr Ser Leu Thr Arg Trp Glu Leu Ala Asn Asp
305                 310                 315                 320

Gly Arg Leu Val Gly Thr Ile Glu Leu Pro Leu Ala Leu Gly Leu Val
                325                 330                 335

Gly Gly Ala Thr Lys Thr His Pro Thr Ala Arg Ala Ala Leu Ala Leu
            340                 345                 350

Met Gln Val Glu Thr Ala Thr Glu Leu Ala Gln Val Thr Ala Ala Val
        355                 360                 365

Gly Leu Ala Gln Asn Met Ala Ala Ile Arg Ala Leu Ala Thr Glu Gly
    370                 375                 380

Ile Gln Arg Gly His Met Thr Leu His Ala Arg Asn Ile Ala Ile Met
385                 390                 395                 400

Ala Gly Ala Thr Gly Ala Asp Ile Asp Arg Val Thr Arg Val Ile Val
                405                 410                 415
```

```
Glu Ala Gly Asp Val Ser Val Ala Arg Ala Lys Gln Val Leu Glu Asn
            420                 425                 430

Thr


<210> SEQ ID NO 21
<211> LENGTH: 1290
<212> TYPE: DNA
<213> ORGANISM: Delftia acidovorans
<220> FEATURE:
<221> NAME/KEY: misc_feature
<222> LOCATION: (1)..(1290)
<223> OTHER INFORMATION: Delftia acidovorans hydroxymethylglutaryl-CoA
      reductase nucleotide sequence

<400> SEQUENCE: 21

atggttgccg attcgcgact gcccaatttc cgcgccctca caccggccca gcgccgggat      60

ttcctggccg atgcctgcgg cctgtccgat gccgagcgcg ccctgctcgc tgcccccggt     120

gccctgcccc tggcgctggc cgacggcatg atcgagaacg tgttcggcag cttcgagctg     180

ccgctgggcg tggccggcaa cttccgcgtc aacggccgcg acgtgctggt gcccatggcg     240

gtggaggagc cctcggtggt ggccgccgcc tcgtacatgg ccaagctggc gcgcgaggac     300

gggggctttc agacctcaag cacgctgccg ctgatgcgcg cccaggtcca ggtgctgggc     360

gtgaccgatc cacacggcgc gcgcctggcc gtgctgcagg cgcgtgcgca gatcatcgag     420

cgcgccaaca gccgcgacaa ggtgctgatc ggcctgggcg gcggctgcaa ggacatcgag     480

gtccatgtct tccccgacac gccgcgcggc cccatgctgg tggtccacct gatcgtggac     540

gtgcgcgacg ccatgggcgc caacaccgtc aacaccatgg ccgaatcggt ggcgcccctg     600

gtcgagaaga tcacgggcgg cagcgtgcgg ctgcgcatcc tgtccaacct ggccgacctg     660

cggctggccc gcgcccgcgt gcggctcacg ccgcagaccc tggccacgca ggatcgcagc     720

ggcgaggaga tcatcgaagg cgtgctggac gcctatacct tcgcggccat cgacccctac     780

cgcgcggcca cgcacaacaa gggaatcatg aacggcatcg accccgtcat cgtggccacg     840

ggcaacgact ggcgcgcggt cgaggccggc gcccatgcct atgccagccg cagcggcagc     900

tacacctcgc tgacgcgctg ggaaaaggat gccggcggcg ccctggtcgg cagcatcgag     960

ctgcccatgc cggtgggcct tgtcggcggc gccaccaaga cccatccgct ggcacgcctg    1020

gcgctgaaga tcatggacct gcagtccgcc cagcagctgg gcgagatcgc cgccgccgtg    1080

ggcctggcgc agaacctggg cgccctgcgc gccctggcca ccgaaggcat tcagcgcggc    1140

cacatggccc tgcacgcccg caacatcgcc ctggtggccg gcgccacggg cgacgaggtc    1200

gatgccgtgg cgcgccagct ggccgccgag cacgacgtgc gcaccgaccg cgcgctggaa    1260

gtgctggccg cgctgcgcgc cagggcctga                                     1290


<210> SEQ ID NO 22
<211> LENGTH: 429
<212> TYPE: PRT
<213> ORGANISM: Delftia acidovorans
<220> FEATURE:
<221> NAME/KEY: misc_feature
<222> LOCATION: (1)..(429)
<223> OTHER INFORMATION: Delftia acidovorans hydroxymethylglutaryl-CoA
      reductase protein sequence

<400> SEQUENCE: 22

Met Val Ala Asp Ser Arg Leu Pro Asn Phe Arg Ala Leu Thr Pro Ala
1               5                   10                  15

Gln Arg Arg Asp Phe Leu Ala Asp Ala Cys Gly Leu Ser Asp Ala Glu
            20                  25                  30
```

```
Arg Ala Leu Leu Ala Ala Pro Gly Ala Leu Pro Leu Ala Leu Ala Asp
        35                  40                  45

Gly Met Ile Glu Asn Val Phe Gly Ser Phe Glu Leu Pro Leu Gly Val
    50                  55                  60

Ala Gly Asn Phe Arg Val Asn Gly Arg Asp Val Leu Val Pro Met Ala
65                  70                  75                  80

Val Glu Glu Pro Ser Val Val Ala Ala Ala Ser Tyr Met Ala Lys Leu
                85                  90                  95

Ala Arg Glu Asp Gly Gly Phe Gln Thr Ser Ser Thr Leu Pro Leu Met
            100                 105                 110

Arg Ala Gln Val Gln Val Leu Gly Val Thr Asp Pro His Gly Ala Arg
        115                 120                 125

Leu Ala Val Leu Gln Ala Arg Ala Gln Ile Ile Glu Arg Ala Asn Ser
    130                 135                 140

Arg Asp Lys Val Leu Ile Gly Leu Gly Gly Gly Cys Lys Asp Ile Glu
145                 150                 155                 160

Val His Val Phe Pro Asp Thr Pro Arg Gly Pro Met Leu Val Val His
                165                 170                 175

Leu Ile Val Asp Val Arg Asp Ala Met Gly Ala Asn Thr Val Asn Thr
            180                 185                 190

Met Ala Glu Ser Val Ala Pro Leu Val Glu Lys Ile Thr Gly Gly Ser
        195                 200                 205

Val Arg Leu Arg Ile Leu Ser Asn Leu Ala Asp Leu Arg Leu Ala Arg
    210                 215                 220

Ala Arg Val Arg Leu Thr Pro Gln Thr Leu Ala Thr Gln Asp Arg Ser
225                 230                 235                 240

Gly Glu Glu Ile Ile Glu Gly Val Leu Asp Ala Tyr Thr Phe Ala Ala
                245                 250                 255

Ile Asp Pro Tyr Arg Ala Ala Thr His Asn Lys Gly Ile Met Asn Gly
            260                 265                 270

Ile Asp Pro Val Ile Val Ala Thr Gly Asn Asp Trp Arg Ala Val Glu
        275                 280                 285

Ala Gly Ala His Ala Tyr Ala Ser Arg Ser Gly Ser Tyr Thr Ser Leu
    290                 295                 300

Thr Arg Trp Glu Lys Asp Ala Gly Gly Ala Leu Val Gly Ser Ile Glu
305                 310                 315                 320

Leu Pro Met Pro Val Gly Leu Val Gly Gly Ala Thr Lys Thr His Pro
                325                 330                 335

Leu Ala Arg Leu Ala Leu Lys Ile Met Asp Leu Gln Ser Ala Gln Gln
            340                 345                 350

Leu Gly Glu Ile Ala Ala Ala Val Gly Leu Ala Gln Asn Leu Gly Ala
        355                 360                 365

Leu Arg Ala Leu Ala Thr Glu Gly Ile Gln Arg Gly His Met Ala Leu
    370                 375                 380

His Ala Arg Asn Ile Ala Leu Val Ala Gly Ala Thr Gly Asp Glu Val
385                 390                 395                 400

Asp Ala Val Ala Arg Gln Leu Ala Ala Glu His Asp Val Arg Thr Asp
                405                 410                 415

Arg Ala Leu Glu Val Leu Ala Ala Leu Arg Ala Arg Ala
            420                 425
```

<210> SEQ ID NO 23
<211> LENGTH: 5726
<212> TYPE: DNA
<213> ORGANISM: Artificial Sequence
<220> FEATURE:
<223> OTHER INFORMATION: Synthetic construct: pAM70 plasmid

<400> SEQUENCE: 23

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020

ccggtgtggg tttagatgac aagggagacg cattgggtca acagtataga accgtggatg   1080

atgtggtctc tacaggatct gacattatta ttgttggaag aggactattt gcaaagggaa   1140

gggatgctaa ggtagagggt gaacgttaca gaaaagcagg ctgggaagca tatttgagaa   1200

gatgcggcca gcaaaactaa aaaactgtat tataagtaaa tgcatgtata ctaaactcac   1260

aaattagagc ttcaatttaa ttatatcagt tattacccta tgcggtgtga aataccgcac   1320

agatgcgtaa ggagaaaata ccgcatcagg aaattgtaaa cgttaatatt ttgttaaaat   1380

tcgcgttaaa tttttgttaa atcagctcat tttttaacca ataggccgaa atcggcaaaa   1440

tcccttataa atcaaaagaa tagaccgaga tagggttgag tgttgttcca gtttggaaca   1500

agagtccact attaaagaac gtggactcca acgtcaaagg gcgaaaaacc gtctatcagg   1560

gcgatggccc actacgtgaa ccatcaccct aatcaagttt tttggggtcg aggtgccgta   1620

aagcactaaa tcggaaccct aaagggagcc cccgatttag agcttgacgg ggaaagccgg   1680

cgaacgtggc gagaaaggaa gggaagaaag cgaaaggagc gggcgctagg gcgctggcaa   1740

gtgtagcggt cacgctgcgc gtaaccacca cacccgccgc gcttaatgcg ccgctacagg   1800

gcgcgtcgcg ccattcgcca ttcaggctgc gcaactgttg ggaagggcga tcggtgcggg   1860

cctcttcgct attacgccag ctggcgaaag ggggatgtgc tgcaaggcga ttaagttggg   1920

taacgccagg gttttcccag tcacgacgtt gtaaaacgac ggccagtgag cgcgcgtaat   1980

acgactcact atagggcgaa ttgggtaccg ggcccccccct cgaggtcgac ggtatcgata   2040

agcttgatat cgaattcctg cagcccgggg gatccactag ttctagagcg gccgccaccg   2100

cggtggagct ccagcttttg ttccctttag tgagggttaa ttgcgcgctt ggcgtaatca   2160

tggtcatagc tgtttcctgt gtgaaattgt tatccgctca caattccaca caacatagga   2220

gccggaagca taaagtgtaa agcctggggt gcctaatgag tgaggtaact cacattaatt   2280
```

-continued

```
gcgttgcgct cactgcccgc tttccagtcg ggaaacctgt cgtgccagct gcattaatga   2340
atcggccaac gcgcggggag aggcggtttg cgtattgggc gctcttccgc ttcctcgctc   2400
actgactcgc tgcgctcggt cgttcggctg cggcgagcgg tatcagctca ctcaaaggcg   2460
gtaatacggt tatccacaga atcaggggat aacgcaggaa agaacatgtg agcaaaaggc   2520
cagcaaaagg ccaggaaccg taaaaaggcc gcgttgctgg cgtttttcca taggctccgc   2580
ccccctgacg agcatcacaa aaatcgacgc tcaagtcaga ggtggcgaaa cccgacagga   2640
ctataaagat accaggcgtt tccccctgga agctccctcg tgcgctctcc tgttccgacc   2700
ctgccgctta ccggatacct gtccgccttt ctcccttcgg gaagcgtggc gctttctcat   2760
agctcacgct gtaggtatct cagttcggtg taggtcgttc gctccaagct gggctgtgtg   2820
cacgaacccc ccgttcagcc cgaccgctgc gccttatccg gtaactatcg tcttgagtcc   2880
aacccggtaa gacacgactt atcgccactg gcagcagcca ctggtaacag gattagcaga   2940
gcgaggtatg taggcggtgc tacagagttc ttgaagtggt ggcctaacta cggctacact   3000
agaaggacag tatttggtat ctgcgctctg ctgaagccag ttaccttcgg aaaaagagtt   3060
ggtagctctt gatccggcaa acaaaccacc gctggtagcg gtggtttttt tgtttgcaag   3120
cagcagatta cgcgcagaaa aaaaggatct caagaagatc ctttgatctt ttctacgggg   3180
tctgacgctc agtggaacga aaactcacgt taagggattt tggtcatgag attatcaaaa   3240
aggatcttca cctagatcct tttaaattaa aaatgaagtt ttaaatcaat ctaaagtata   3300
tatgagtaaa cttggtctga cagttaccaa tgcttaatca gtgaggcacc tatctcagcg   3360
atctgtctat ttcgttcatc catagttgcc tgactccccg tcgtgtagat aactacgata   3420
cgggagggct taccatctgg ccccagtgct gcaatgatac cgcgagaccc acgctcaccg   3480
gctccagatt tatcagcaat aaaccagcca gccggaaggg ccgagcgcag aagtggtcct   3540
gcaactttat ccgcctccat ccagtctatt aattgttgcc gggaagctag agtaagtagt   3600
tcgccagtta atagtttgcg caacgttgtt gccattgcta caggcatcgt ggtgtcacgc   3660
tcgtcgtttg gtatggcttc attcagctcc ggttcccaac gatcaaggcg agttacatga   3720
tcccccatgt tgtgcaaaaa agcggttagc tccttcggtc ctccgatcgt tgtcagaagt   3780
aagttggccg cagtgttatc actcatggtt atggcagcac tgcataattc tcttactgtc   3840
atgccatccg taagatgctt ttctgtgact ggtgagtact caaccaagtc attctgagaa   3900
tagtgtatgc ggcgaccgag ttgctcttgc ccggcgtcaa tacgggataa taccgcgcca   3960
catagcagaa ctttaaaagt gctcatcatt ggaaaacgtt cttcggggcg aaaactctca   4020
aggatcttac cgctgttgag atccagttcg atgtaaccca ctcgtgcacc caactgatct   4080
tcagcatctt ttactttcac cagcgtttct gggtgagcaa aaacaggaag gcaaaatgcc   4140
gcaaaaaagg gaataagggc gacacggaaa tgttgaatac tcatactctt cctttttcaa   4200
tattattgaa gcatttatca gggttattgt ctcatgagcg gatacatatt tgaatgtatt   4260
tagaaaaata aacaaatagg ggttccgcgc acatttcccc gaaaagtgcc acctgaacga   4320
agcatctgtg cttcattttg tagaacaaaa atgcaacgcg agagcgctaa tttttcaaac   4380
aaagaatctg agctgcattt ttacagaaca gaaatgcaac gcgaaagcgc tattttacca   4440
acgaagaatc tgtgcttcat ttttgtaaaa caaaaatgca acgcgagagc gctaattttt   4500
caaacaaaga atctgagctg catttttaca gaacagaaat gcaacgcgag agcgctattt   4560
taccaacaaa gaatctatac ttcttttttg ttctacaaaa atgcatcccg agagcgctat   4620
ttttctaaca aagcatctta gattactttt tttctccttt gtgcgctcta taatgcagtc   4680
```

```
tcttgataac tttttgcact gtaggtccgt taaggttaga agaaggctac tttggtgtct   4740

attttctctt ccataaaaaa agcctgactc cacttcccgc gtttactgat tactagcgaa   4800

gctgcgggtg catttttca agataaaggc atccccgatt atattctata ccgatgtgga   4860

ttgcgcatac tttgtgaaca gaaagtgata gcgttgatga ttcttcattg gtcagaaaat   4920

tatgaacggt ttcttctatt ttgtctctat atactacgta taggaaatgt ttacattttc   4980

gtattgtttt cgattcactc tatgaatagt tcttactaca attttttgt ctaaagagta   5040

atactagaga taaacataaa aaatgtagag gtcgagttta gatgcaagtt caaggagcga   5100

aaggtggatg ggtaggttat atagggatat agcacagaga tatatagcaa agagatactt   5160

ttgagcaatg tttgtggaag cggtattcgc aatattttag tagctcgtta cagtccggtg   5220

cgtttttggt tttttgaaag tgcgtcttca gagcgctttt ggttttcaaa agcgctctga   5280

agttcctata ctttctagag aataggaact tcggaatagg aacttcaaag cgtttccgaa   5340

aacgagcgct tccgaaaatg caacgcgagc tgcgcacata cagctcactg ttcacgtcgc   5400

acctatatct gcgtgttgcc tgtatatata tatacatgag aagaacggca tagtgcgtgt   5460

ttatgcttaa atgcgtactt atatgcgtct atttatgtag gatgaaaggt agtctagtac   5520

ctcctgtgat attatcccat tccatgcggg gtatcgtatg cttccttcag cactaccctt   5580

tagctgttct atatgctgcc actcctcaat tggattagtc tcatccttca atgctatcat   5640

ttcctttgat attggatcat actaagaaac cattattatc atgacattaa cctataaaaa   5700

taggcgtatc acgaggccct ttcgtc                                        5726
```

<210> SEQ ID NO 24
<211> LENGTH: 8125
<212> TYPE: DNA
<213> ORGANISM: Artificial Sequence
<220> FEATURE:
<223> OTHER INFORMATION: Synthetic construct: pAM01147 plasmid

<400> SEQUENCE: 24

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat cattttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020
```

-continued

```
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggcccccccct cgaggtcgac ggtatcgata   2040
agcttgatat cgaattcctg cagcccgggg gatccactag ttctagagcg gccgcttatt   2100
gcagaagatt agactttttt tgttgcaagt gggatgagct tggagcagga agaatacact   2160
atactggatc taaagagtac aatagatgga taagaatatt ggcagcgcaa aaggcttca    2220
agcttacaca acacggttta tttcgaaata atatccttct cgaaagcttt aacgaacgca   2280
gaattttcga gttattaaac ttaaaatacg ctgaacccga acatagaaat atcgaatggg   2340
aaaaaaaaac tgcataaagg cattaaaaga ggagcgaatt tttttttaat aaaaatctta   2400
ataatcatta aaagataaat aatagtctat atatacgtat ataaataaaa aatattcaaa   2460
aaataaaata aactattatt ttagcgtaaa ggatggggaa agagaaaaga aaaaaattga   2520
tctatcgatt tcaattcaat tcaattcagt ggtgatggtg atgatgccct ttatcgtcat   2580
cgtccttata atcgaattcc tggcctctct tttgttttag aagtgcgacg gcacgatctg   2640
ctctgacatc gtgatattca actaattgtc tggcaaccca atcgacttcg tcgccccttg   2700
cacctgctac aaccgctata ttcctcgcat gcaaggccat gtgacccctt tgaatacctt   2760
cagttgctaa agccctcatt gcacccaaat tttgagcaag accaacagcc acagcgatct   2820
ctgccaaggc ttgggcagtt ttaactccta atattcttaa agataattga gccagagggt   2880
gggtcttcgt tgcaccacct actaatccaa ccggcatcgg catctccaga gtaccgacta   2940
aatgaccatt attatccttc tcccaagtag ttagagaacc ataatgtccg gacctacaag   3000
cgtacgcgtg agccccagcc tctacggctc tccaatcgtt accagtagca acaattagtg   3060
gatctatgcc gttcataata cctttattat gtgtagcggc tctgtatggg tcaacagcgg   3120
cgaaagcata agcgtctaga ataccttcaa tcacagcctc ccccgaaaat tccgctgttt   3180
ccaattgctg tggggttatt cttacttgtg cacgagctaa tcttagatca gctaaattag   3240
acaagatcct tagacgcact tgaccgccag taattgcctc cattaatggt gcgacggctt   3300
cagccattgt gtttactgtg ttcgccccca ttgcatcacg aacatctacg attaagtgag   3360
caactaacat aggtcctcta ggagtgtcag cgaatgtatg cacttcgatg tctctacaac   3420
```

```
caccacctaa cgaatttaac aattgatctt ttctattagc caattctatt atctcatctt   3480

ttcttctcaa caatgaaagt ctggcgttta aaggatcttg tataccaacg atttgtactt   3540

gagcatgcat aagtggggct gaactgctgg tggtgaaacc tccgttcgct cttgccaatt   3600

tagccatgta tgatgctgct gcaactatag atggttcctc aacgactagt gggaccaaaa   3660

catccctacc attaatttga aaattcgaag caacggcgta cggaagttcg aaagtaccta   3720

taacattttc gatcatacca ttagcgatgt ccataggcaa tgctccagcg ttggccaaca   3780

aagaaacgtc atcatggctt aatcccaata gttgtcctat gtgatctaaa cgagcagccg   3840

gactcaggtt tctgaatgct ggcaatctgc tatctaaaga catatgtttt gagggaatat   3900

tcaactgttt ttttttatca tgttgatgct ctgcataata atgcccataa atatttccga   3960

cctgctttta tatctttgct agccaaacta actgaacata gctacacatt attttcagct   4020

tggctatttt gtgaacactg tatagccagt ccttcggatc acggtcaaca gttgtccgag   4080

cgctttttgg accctttccc ttatttttgg gttaaggaaa atgacagaaa atatatctaa   4140

tgagccttcg ctcaacagtg ctccgaagta tagctttcca aaaggagagg caaagcaatt   4200

taagaatgta tgaacaaaat aaaggggaaa aattaccccc tctactttac caaacgaata   4260

ctaccaataa tatttacaac ttttccttat gatttttttca ctgaagcgct tcgcaatagt   4320

tgtgagcgat atcaaaagta acgaaatgaa cttcgcggct cgtgctatat tcttgttgct   4380

accgtccata tctttccata gattttcaat ctttgatgtc tccatggtgg tacagagaac   4440

ttgtaaacaa ttcggtccct acatgtgagg aaattcgctg tgacacgcgg ccgccaccgc   4500

ggtggagctc cagcttttgt tccctttagt gagggttaat tgcgcgcttg gcgtaatcat   4560

ggtcatagct gtttcctgtg tgaaattgtt atccgctcac aattccacac aacataggag   4620

ccggaagcat aaagtgtaaa gcctggggtg cctaatgagt gaggtaactc acattaattg   4680

cgttgcgctc actgcccgct ttccagtcgg gaaacctgtc gtgccagctg cattaatgaa   4740

tcggccaacg cgcggggaga ggcggtttgc gtattgggcg ctcttccgct tcctcgctca   4800

ctgactcgct gcgctcggtc gttcggctgc ggcgagcggt atcagctcac tcaaaggcgg   4860

taatacggtt atccacagaa tcaggggata acgcaggaaa gaacatgtga gcaaaaggcc   4920

agcaaaaggc caggaaccgt aaaaaggccg cgttgctggc gtttttccat aggctccgcc   4980

cccctgacga gcatcacaaa aatcgacgct caagtcagag gtggcgaaac ccgacaggac   5040

tataaagata ccaggcgttt ccccctggaa gctccctcgt gcgctctcct gttccgaccc   5100

tgccgcttac cggatacctg tccgcctttc tcccttcggg aagcgtggcg ctttctcata   5160

gctcacgctg taggtatctc agttcggtgt aggtcgttcg ctccaagctg ggctgtgtgc   5220

acgaaccccc cgttcagccc gaccgctgcg ccttatccgg taactatcgt cttgagtcca   5280

acccggtaag acacgactta tcgccactgg cagcagccac tggtaacagg attagcagag   5340

cgaggtatgt aggcggtgct acagagttct tgaagtggtg gcctaactac ggctacacta   5400

gaaggacagt atttggtatc tgcgctctgc tgaagccagt taccttcgga aaaagagttg   5460

gtagctcttg atccggcaaa caaaccaccg ctggtagcgg tggttttttt gtttgcaagc   5520

agcagattac gcgcagaaaa aaaggatctc aagaagatcc tttgatcttt tctacggggt   5580

ctgacgctca gtggaacgaa aactcacgtt aagggatttt ggtcatgaga ttatcaaaaa   5640

ggatcttcac ctagatcctt ttaaattaaa aatgaagttt taaatcaatc taaagtatat   5700

atgagtaaac ttggtctgac agttaccaat gcttaatcag tgaggcacct atctcagcga   5760

tctgtctatt tcgttcatcc atagttgcct gactccccgt cgtgtagata actacgatac   5820
```

```
gggagggctt accatctggc cccagtgctg caatgatacc gcgagaccca cgctcaccgg   5880
ctccagattt atcagcaata aaccagccag ccggaagggc cgagcgcaga agtggtcctg   5940
caactttatc cgcctccatc cagtctatta attgttgccg ggaagctaga gtaagtagtt   6000
cgccagttaa tagtttgcgc aacgttgttg ccattgctac aggcatcgtg gtgtcacgct   6060
cgtcgtttgg tatggcttca ttcagctccg gttcccaacg atcaaggcga gttacatgat   6120
cccccatgtt gtgcaaaaaa gcggttagct ccttcggtcc tccgatcgtt gtcagaagta   6180
agttggccgc agtgttatca ctcatggtta tggcagcact gcataattct cttactgtca   6240
tgccatccgt aagatgcttt tctgtgactg gtgagtactc aaccaagtca ttctgagaat   6300
agtgtatgcg gcgaccgagt tgctcttgcc cggcgtcaat acgggataat accgcgccac   6360
atagcagaac tttaaaagtg ctcatcattg gaaaacgttc ttcggggcga aaactctcaa   6420
ggatcttacc gctgttgaga tccagttcga tgtaacccac tcgtgcaccc aactgatctt   6480
cagcatcttt tactttcacc agcgtttctg ggtgagcaaa aacaggaagg caaaatgccg   6540
caaaaaaggg aataagggcg acacggaaat gttgaatact catactcttc ctttttcaat   6600
attattgaag catttatcag ggttattgtc tcatgagcgg atacatattt gaatgtattt   6660
agaaaaataa acaaataggg gttccgcgca catttccccg aaaagtgcca cctgaacgaa   6720
gcatctgtgc ttcattttgt agaacaaaaa tgcaacgcga gagcgctaat ttttcaaaca   6780
aagaatctga gctgcatttt tacagaacag aaatgcaacg cgaaagcgct attttaccaa   6840
cgaagaatct gtgcttcatt tttgtaaaac aaaaatgcaa cgcgagagcg ctaatttttc   6900
aaacaaagaa tctgagctgc atttttacag aacagaaatg caacgcgaga gcgctatttt   6960
accaacaaag aatctatact tcttttttgt tctacaaaaa tgcatcccga gagcgctatt   7020
tttctaacaa agcatcttag attacttttt ttctcctttg tgcgctctat aatgcagtct   7080
cttgataact ttttgcactg taggtccgtt aaggttagaa gaaggctact ttggtgtcta   7140
ttttctcttc cataaaaaaa gcctgactcc acttcccgcg tttactgatt actagcgaag   7200
ctgcgggtgc atttttcaa gataaaggca tccccgatta tattctatac cgatgtggat   7260
tgcgcatact ttgtgaacag aaagtgatag cgttgatgat tcttcattgg tcagaaaatt   7320
atgaacggtt tcttctattt tgtctctata tactacgtat aggaaatgtt tacattttcg   7380
tattgttttc gattcactct atgaatagtt cttactacaa tttttttgtc taaagagtaa   7440
tactagagat aaacataaaa aatgtagagg tcgagtttag atgcaagttc aaggagcgaa   7500
aggtggatgg gtaggttata tagggatata gcacagagat atatagcaaa gagatacttt   7560
tgagcaatgt ttgtggaagc ggtattcgca atattttagt agctcgttac agtccggtgc   7620
gtttttggtt ttttgaaagt gcgtcttcag agcgcttttg gttttcaaaa gcgctctgaa   7680
gttcctatac tttctagaga ataggaactt cggaatagga acttcaaagc gtttccgaaa   7740
acgagcgctt ccgaaaatgc aacgcgagct gcgcacatac agctcactgt tcacgtcgca   7800
cctatatctg cgtgttgcct gtatatatat atacatgaga agaacggcat agtgcgtgtt   7860
tatgcttaaa tgcgtactta tatgcgtcta tttatgtagg atgaaaggta gtctagtacc   7920
tcctgtgata ttatcccatt ccatgcgggg tatcgtatgc ttccttcagc actacccttt   7980
agctgttcta tatgctgcca ctcctcaatt ggattagtct catccttcaa tgctatcatt   8040
tcctttgata ttggatcata ctaagaaacc attattatca tgacattaac ctataaaaat   8100
aggcgtatca cgaggccctt tcgtc                                         8125
```

<210> SEQ ID NO 25
<211> LENGTH: 10881
<212> TYPE: DNA
<213> ORGANISM: Artificial Sequence
<220> FEATURE:
<223> OTHER INFORMATION: Synthetic construct: ERG10-ERG13 integration construct

<400> SEQUENCE: 25

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagctat    240

ttaggtgaca ctatagaata ctcaagctat gcatcaagct tggtaccgag ctcggatcca    300

ctagtaacgg ccgccagtgt gctggaattc gcccttaaat atgacccccca atatgagaaa    360

ttaaggctag attattctca ggaaaaagct tttcatcttg aaatgctgca attatgtcgg    420

gtcccatttc tccacactta gcatctctct tataatgccc acagactaag ttccaatctc    480

ttagaaaagt ttcaccctga aaccttgtaa gctttctatg atgcacttca tgaacctgtt    540

gggaagcctt ggccttaccg cttaaataat cctggaagga tagctttggt gcttgaatag    600

ctccttcatc taaaaaagat gcaaattcct cgatgtccgt ttccttaatt acataaagct    660

tcatgtcagg aataacaaaa aaataaagcc attcatcgtg ttgttttggc cttggaataa    720

attcattttg caaatgcacc gcatttatta gtattcctgg agaaccacct aaatgggagc    780

gcaatttact aatggcatta tatggccgat ttgtattagt atccaaatta tgattccatg    840

ctaccttcca tggttgagca aacctatcac ccggtgataa cagcaaaaca tgcttattgt    900

aattgggcgt tctatgagga agcttgatat gaggatctaa tggatcagtt tttgaaggca    960

gccttgcgtt tatttcttgg caataacagt ttgtttgatc attttgagca cgggtatgaa   1020

gatcaggaac gctaatatgt ttgaagctat gatggaagga tgcccgctgc tgcaaagttt   1080

tgacagttat acgtagcatt ttattttttg tgtcagtgca ccttctctca cttttctact   1140

aaggaaattt gatatttcaa atgtagtatg ctaataaata agaacacccg catgcacgaa   1200

aaagggaaat ttaaaactag ttaggtaaac aaagttcaga acaagaaatg atatggttgt   1260

tttacataga tatatactca gtattcgttt ttataacgtt cgctgcactg gggggtctaa   1320

ggcgcctgat tcaagaaata tcttgaccgc agttaactgt gggaatactc aggtatcgta   1380

agatgcaaga gttcgaatct cttagcaacc attatttttt tcctcaacat aacgagaaca   1440

cacaggggcg ctatcgcaca gaatcaaatt cgatgactgg aaattttttg ttaatttcag   1500

aggtcgcctg acgcatatac ctttttcaac tgaaaaattg ggagaaaaag gaaaggtgag   1560

agcgccggaa ccggcttttc atatagaata gagaagcgtt catgactaaa tgcttgcatc   1620

acaatacttg aagttgacaa tattatttaa ggacctattg ttttttccaa taggtggtta   1680

gcaatcgtct tactttctaa cttttcttac cttttacatt tcagcaatat atatatatat   1740

atttcaagga tataccattc taatgtctgc ccctaagaag atcgtcgttt tgccaggtga   1800

ccacgttggt caagaaatca cagccgaagc cattaaggtt cttaaagcta tttctgatgt   1860

tcgttccaat gtcaagttcg atttcgaaaa tcatttaatt ggtggtgctg ctatcgatgc   1920

tacaggtgtt ccacttccag atgaggcgct ggaagcctcc aagaaggctg atgccgtttt   1980

gttaggtgct gtgggtggtc ctaaatgggg taccggtagt gttagacctg aacaaggttt   2040

actaaaaatc cgtaaagaac ttcaattgta cgccaactta agaccatgta actttgcatc   2100
```

-continued

```
cgactctctt ttagacttat ctccaatcaa gccacaattt gctaaaggta ctgacttcgt   2160
tgttgtcaga gaattagtgg gaggtattta ctttggtaag agaaaggaag acgatggtga   2220
tggtgtcgct tgggatagtg aacaatacac cgttccagaa gtgcaaagaa tcacaagaat   2280
ggccgctttc atggccctac aacatgagcc accattgcct atttggtcct tggataaagc   2340
taatgttttg gcctcttcaa gattatggag aaaaactgtg gaggaaacca tcaagaacga   2400
attccctaca ttgaaggttc aacatcaatt gattgattct gccgccatga tcctagttaa   2460
gaacccaacc cacctaaatg gtattataat caccagcaac atgtttggtg atatcatctc   2520
cgatgaagcc tccgttatcc caggttcctt gggtttgttg ccatctgcgt ccttggcctc   2580
tttgccagac aagaacaccg catttggttt gtacgaacca tgccacggtt ctgctccaga   2640
tttgccaaag aataaggtca accctatcgc cactatcttg tctgctgcaa tgatgttgaa   2700
attgtcattg aacttgcctg aagaaggtaa ggccattgaa gatgcagtta aaaaggtttt   2760
ggatgcaggt atcagaactg gtgatttagg tggttccaac agtaccaccg aagtcggtga   2820
tgctgtcgcc gaagaagtta agaaaatcct tgcttaaaaa gattctcttt ttttatgata   2880
tttgtacata aactttataa atgaaattca taatagaaac gacacgaaat tacaaaatgg   2940
aatatgttca tagggtagac gaaactatat acgcaatcta catacattta tcaagaagga   3000
gaaaaaggag gatgtaaagg aatacaggta agcaaattga tactaatggc tcaacgtaaa   3060
agtaagtcaa aaggcacacc tcagcgtttg agtacctgaa aaacgatgaa tcgcaaataa   3120
aactttaaat tatgcctgtt atacataaag ccatttatat atttatgtat tttatgaaaa   3180
agatcatgag aaaatcgcag aacgtaatca tatcttttca atgacaatag aggaagcacc   3240
accaccacca ttacaaatgg cggcaacacc gatcttacct ccttcttgct gtaagatgga   3300
tagcagtgta acaaccactc tagcaccaga acaacccaat gggtgaccta gagcaacagc   3360
accaccatat acattaacct tagatgggtc tagcttcaaa atcttagtgt tcaccaaacc   3420
gacaaccgaa aaggcttcat tgaattcaaa gtaatcaaca gaattgatgt cttcgatgcc   3480
agcatgtttc aaagcctttg gaactgcaag agatggagcc catgtaaaat cagctggttg   3540
atgagcggcc tcaccccaac ctttgataat agccaaaggc ttcaaattct tttccttcaa   3600
aactttttcg gaaaccaaga tgacggctgc agcaccatcg ttgattggag aagcgttagc   3660
ggcagtaaca gtaccgtttt ctttttggaa aacagtcctt gcagatctca atttttcaac   3720
gtgtaatcta gcaggttcct cgtccttcgt gacttgagta tcaggcttac ctctaaatcc   3780
cttaatggta acaggtacaa tttcattgtc gaatttacct tccttttgag atttttgaga   3840
tttttggtag gattcgatgg caaaattgtc ttgttgttct ctagtaatat cccaatcacg   3900
ggcacacttt tctgcgtgta cacccatggc tagaccatcg tacgcatcgt tcaacccatc   3960
tctttcgaca ccatcaacaa gaacagtttg gccaaatttg gcacccgcac gggctgctgg   4020
catgtagtat ggtgcgttag tcatagattc acaaccacca gctacgacaa catcagcatt   4080
accacatttg atggattgag cacccaaaat gattgccttc atagcggatg cacagacctt   4140
gttaactgtg cttgcaacga tatgattact caaaccggca gccaaagcaa cttgtctggc   4200
cggagcttgg cccaaattgg cagaaagaac gttaccaaaa ataatttcgt caaaatcctt   4260
ggatgcatcc aattctggaa ccttagccaa ggcgcctttt aaagcaacag cacccaattc   4320
cactgctgtc ttggaggata gagaaccctg gaatgaacca attggggttc tggcagtcga   4380
tacaatgtaa acgttctgag acattatagt tttttctcct tgacgttaaa gtatagaggt   4440
atattaacaa ttttttgttg atacttttat gacatttgaa taagaagtaa tacaaaccga   4500
```

-continued

```
aaatgttgaa agtattagtt aaagtggtta tgcagctttt gcatttatat atctgttaat   4560

agatcaaaaa tcatcgcttc gctgattaat taccccagaa ataaggctaa aaaactaatc   4620

gcattattat cctatggttg ttaatttgat tcgttgattt gaaggtttgt ggggccaggt   4680

tactgccaat tttcctcttt cataaccata aaagctagta ttgtagaatc tttattgttc   4740

ggagcagtgc ggcgcgaggc acatctgcgt ttcaggaacg cgaccggtga agaccaggac   4800

gcacggagga gagtcttccg tcggagggct gtcgcccgct cggcggcttc taatccgtac   4860

ttcaatatag caatgagcag ttaagcgtat tactgaaagt tccaaagaga aggttttttt   4920

aggctaagat aatggggctc tttacatttc cacaacatat aagtaagatt agatatggat   4980

atgtatatgg tggtattgcc atgtaatatg attattaaac ttctttgcgt ccatccaaaa   5040

aaaaagtaag aatttttgaa aattcaatat aaatgaaact ctcaactaaa ctttgttggt   5100

gtggtattaa aggaagactt aggccgcaaa agcaacaaca attacacaat acaaacttgc   5160

aaatgactga actaaaaaaa caaaagaccg ctgaacaaaa aaccagacct caaaatgtcg   5220

gtattaaagg tatccaaatt tacatcccaa ctcaatgtgt caaccaatct gagctagaga   5280

aatttgatgg cgtttctcaa ggtaaataca caattggtct gggccaaacc aacatgtctt   5340

ttgtcaatga cagagaagat atctactcga tgtccctaac tgttttgtct aagttgatca   5400

agagttacaa catcgacacc aacaaaattg gtagattaga agtcggtact gaaactctga   5460

ttgacaagtc caagtctgtc aagtctgtct tgatgcaatt gtttggtgaa aacactgacg   5520

tcgaaggtat tgacacgctt aatgcctgtt acggtggtac caacgcgttg ttcaactctt   5580

tgaactggat tgaatctaac gcatgggatg gtagagacgc cattgtagtt tgcggtgata   5640

ttgccatcta cgataagggt gccgcaagac caaccggtgg tgccggtact gttgctatgt   5700

ggatcggtcc tgatgctcca attgtatttg actctgtaag agcttcttac atggaacacg   5760

cctacgattt ttacaagcca gatttcacca gcgaatatcc ttacgtcgat ggtcattttt   5820

cattaacttg ttacgtcaag gctcttgatc aagtttacaa gagttattcc aagaaggcta   5880

tttctaaagg gttggttagc gatcccgctg gttcggatgc tttgaacgtt ttgaaatatt   5940

tcgactacaa cgttttccat gttccaacct gtaaattggt cacaaaatca tacggtagat   6000

tactatataa cgatttcaga gccaatcctc aattgttccc agaagttgac gccgaattag   6060

ctactcgcga ttatgacgaa tctttaaccg ataagaacat tgaaaaaact tttgttaatg   6120

ttgctaagcc attccacaaa gagagagttg cccaatcttt gattgttcca acaaacacag   6180

gtaacatgta caccgcatct gtttatgccg cctttgcatc tctattaaac tatgttggat   6240

ctgacgactt acaaggcaag cgtgttggtt tattttctta cggttccggt ttagctgcat   6300

ctctatattc ttgcaaaatt gttggtgacg tccaacatat tatcaaggaa ttagatatta   6360

ctaacaaatt agccaagaga atcaccgaaa ctccaaagga ttacgaagct gccatcgaat   6420

tgagagaaaa tgcccatttg aagaagaact tcaaacctca aggttccatt gagcatttgc   6480

aaagtggtgt ttactacttg accaacatcg atgacaaatt tagaagatct tacgatgtta   6540

aaaaataatc ttccccccatc gattgcatct tgctgaaccc ccttcataaa tgctttattt   6600

ttttggcagc ctgctttttt tagctctcat ttaatagagt agttttttaa tctatatact   6660

aggaaaactc tttatttaat aacaatgata tatatataga cgggagtgga aagaacggga   6720

aaccaactat cgagattgta tacgctggtc ggcaaggacc agcagtgaca tgtgatgtat   6780

atatattcag gttcaaaaaa aaaagttatg agcttttggt tattatgaat gtagcagaca   6840

ttttgaggtc gttcgggcga gagtgcgccg gtaaatgaag aaaatatagg atattattaa   6900
```

```
tattagaatt aaactattat attgcagggg agagaagaaa ggggtataaa tatatattac   6960
aaagcggaaa acttgcgcca tttaaacaga gacatcgtcc gggcgctcgt gtgattttct   7020
tatagtgaag aagttaatac ctttaggttg gttttccgta gcagcagtgg cagtgaccgg   7080
attagcattg gaagaaggcc ccactatgct tgcactttgt tgcatgtctt caggtccagt   7140
ggcagtcaat attgggtcag ttgcttgctc cttctctcta tggaagggat tccatctgga   7200
ggaggttctg tatcttgaat tgtcgatgga gtaagtagag gccaaccttg ccctaacaga   7260
ccagaagacc agcaggataa attccacgat acataaaaag acacttgccc aagccatacc   7320
catcatagag gcacccaatt gggcactacg atgatcgtca tggaaagcat tctttgccat   7380
ggcagaggcg gccgtttgca agacaacggc tgccgtattg aagacaaacc caaaagacat   7440
gaggataagc accatctctg aaagcatctt cgagcaccaa gtcaaaacgt aaaggataaa   7500
cgacacacct acaaaggcaa gcgcaatcca aaagaaacaa aatgaaaatc tagtcaggta   7560
gtaaaaagcg tctcttttgg aaataaactg gtgagggaca ttgatgtgtg tgttgaagtt   7620
atctactggg gaaatggggt atgcaggtgc caaattgctt gtgcaggtat ccgacccgtc   7680
tttatcctgt agacaggcaa gggcgaattc tgcagatatc catcacactg gcggccgctc   7740
gagcatgcat ctagagggcc caattcgccc tatagtgagt cgtattacaa ttcactggcc   7800
gtcgttttac aacgtcgtga ctgggaaaac cctggcgtta cccaacttaa tcgccttgca   7860
gcacatcccc ctttcgccag ctggcgtaat agcgaagagg cccgcaccga tcgcccttcc   7920
caacagttgc gcagcctata cgtacggcag tttaaggttt acacctataa aagagagagc   7980
cgttatcgtc tgtttgtgga tgtacagagt gatattattg acacgccggg gcgacggatg   8040
gtgatccccc tggccagtgc acgtctgctg tcagataaag tctcccgtga actttacccg   8100
gtggtgcata tcggggatga aagctggcgc atgatgacca ccgatatggc cagtgtgccg   8160
gtctccgtta tcggggaaga agtggctgat ctcagccacc gcgaaaatga catcaaaaac   8220
gccattaacc tgatgttctg gggaatataa atgtcaggca tgagattatc aaaaaggatc   8280
ttcacctaga tccttttcac gtagaaagcc agtccgcaga aacggtgctg accccggatg   8340
aatgtcagct actgggctat ctggacaagg gaaaacgcaa gcgcaaagag aaagcaggta   8400
gcttgcagtg ggcttacatg gcgatagcta gactgggcgg ttttatggac agcaagcgaa   8460
ccggaattgc cagctggggc gccctctggt aaggttggga agccctgcaa agtaaactgg   8520
atggctttct cgccgccaag gatctgatgg cgcaggggat caagctctga tcaagagaca   8580
ggatgaggat cgtttcgcat gattgaacaa gatggattgc acgcaggttc tccggccgct   8640
tgggtggaga ggctattcgg ctatgactgg gcacaacaga caatcggctg ctctgatgcc   8700
gccgtgttcc ggctgtcagc gcaggggcgc ccggttcttt ttgtcaagac cgacctgtcc   8760
ggtgccctga atgaactgca agacgaggca gcgcggctat cgtggctggc cacgacgggc   8820
gttccttgcg cagctgtgct cgacgttgtc actgaagcgg gaagggactg gctgctattg   8880
ggcgaagtgc cggggcagga tctcctgtca tctcaccttg ctcctgccga gaaagtatcc   8940
atcatggctg atgcaatgcg gcggctgcat acgcttgatc cggctacctg cccattcgac   9000
caccaagcga aacatcgcat cgagcgagca cgtactcgga tggaagccgg tcttgtcgat   9060
caggatgatc tggacgaaga gcatcagggg ctcgcgccag ccgaactgtt cgccaggctc   9120
aaggcgagca tgcccgacgg cgaggatctc gtcgtgaccc atggcgatgc ctgcttgccg   9180
aatatcatgg tggaaaatgg ccgcttttct ggattcatcg actgtggccg gctgggtgtg   9240
gcggaccgct atcaggacat agcgttggct acccgtgata ttgctgaaga gcttggcggc   9300
```

```
gaatgggctg accgcttcct cgtgctttac ggtatcgccg ctcccgattc gcagcgcatc   9360

gccttctatc gccttcttga cgagttcttc tgaattatta acgcttacaa tttcctgatg   9420

cggtattttc tccttacgca tctgtgcggt atttcacacc gcatacaggt ggcacttttc   9480

ggggaaatgt gcgcggaacc cctatttgtt tatttttcta aatacattca aatatgtatc   9540

cgctcatgag acaataaccc tgataaatgc ttcaataata gcacgtgagg agggccacca   9600

tggccaagtt gaccagtgcc gttccggtgc tcaccgcgcg cgacgtcgcc ggagcggtcg   9660

agttctggac cgaccggctc gggttctccc gggacttcgt ggaggacgac ttcgccggtg   9720

tggtccggga cgacgtgacc ctgttcatca gcgcggtcca ggaccaggtg gtgccggaca   9780

acaccctggc ctgggtgtgg gtgcgcggcc tggacgagct gtacgccgag tggtcggagg   9840

tcgtgtccac gaacttccgg gacgcctccg ggccggccat gaccgagatc ggcgagcagc   9900

cgtgggggcg ggagttcgcc ctgcgcgacc cggccggcaa ctgcgtgcac ttcgtggccg   9960

aggagcagga ctgacacgtg ctaaaacttc atttttaatt taaaaggatc taggtgaaga  10020

tcctttttga taatctcatg accaaaatcc cttaacgtga gttttcgttc cactgagcgt  10080

cagaccccgt agaaaagatc aaaggatctt cttgagatcc tttttttctg cgcgtaatct  10140

gctgcttgca aacaaaaaaa ccaccgctac cagcggtggt ttgtttgccg gatcaagagc  10200

taccaactct ttttccgaag gtaactggct tcagcagagc gcagatacca aatactgtcc  10260

ttctagtgta gccgtagtta ggccaccact tcaagaactc tgtagcaccg cctacatacc  10320

tcgctctgct aatcctgtta ccagtggctg ctgccagtgg cgataagtcg tgtcttaccg  10380

ggttggactc aagacgatag ttaccggata aggcgcagcg gtcgggctga acggggggtt  10440

cgtgcacaca gcccagcttg gagcgaacga cctacaccga actgagatac ctacagcgtg  10500

agctatgaga aagcgccacg cttcccgaag ggagaaaggc ggacaggtat ccggtaagcg  10560

gcagggtcgg aacaggagag cgcacgaggg agcttccagg gggaaacgcc tggtatcttt  10620

atagtcctgt cgggtttcgc cacctctgac ttgagcgtcg atttttgtga tgctcgtcag  10680

gggggcggag cctatggaaa aacgccagca acgcggcctt tttacggttc ctggcctttt  10740

gctggccttt tgctcacatg ttctttcctg cgttatcccc tgattctgtg gataaccgta  10800

ttaccgcctt tgagtgagct gataccgctc gccgcagccg aacgaccgag cgcagcgagt  10860

cagtgagcga ggaagcggaa g                                            10881
```

<210> SEQ ID NO 26
<211> LENGTH: 24
<212> TYPE: DNA
<213> ORGANISM: Artificial Sequence
<220> FEATURE:
<223> OTHER INFORMATION: Synthetic primer YT_164_36_001

<400> SEQUENCE: 26

```
gcctgtctac aggataaaga cggg                                             24
```

<210> SEQ ID NO 27
<211> LENGTH: 44
<212> TYPE: DNA
<213> ORGANISM: Artificial Sequence
<220> FEATURE:
<223> OTHER INFORMATION: Synthetic primer YT_164_36_002

<400> SEQUENCE: 27

```
tcccgttctt tccactcccg tctatatata tatcattgtt atta                       44
```

<210> SEQ ID NO 28
<211> LENGTH: 44
<212> TYPE: DNA
<213> ORGANISM: Artificial Sequence
<220> FEATURE:
<223> OTHER INFORMATION: Synthetic primer YT_164_36_003

<400> SEQUENCE: 28
taataacaat gatatatata tagacgggag tggaaagaac ggga 44

<210> SEQ ID NO 29
<211> LENGTH: 54
<212> TYPE: DNA
<213> ORGANISM: Artificial Sequence
<220> FEATURE:
<223> OTHER INFORMATION: Synthetic primer YT_164_36_004

<400> SEQUENCE: 29
ccaacaaagt ttagttgaga gtttcattta tattgaattt tcaaaaattc ttac 54

<210> SEQ ID NO 30
<211> LENGTH: 54
<212> TYPE: DNA
<213> ORGANISM: Artificial Sequence
<220> FEATURE:
<223> OTHER INFORMATION: Synthetic primer YT_164_36_005

<400> SEQUENCE: 30
gtaagaattt ttgaaaattc aatataaatg aaactctcaa ctaaactttg ttgg 54

<210> SEQ ID NO 31
<211> LENGTH: 60
<212> TYPE: DNA
<213> ORGANISM: Artificial Sequence
<220> FEATURE:
<223> OTHER INFORMATION: Synthetic primer YT_164_36_006

<400> SEQUENCE: 31
gtcaaggaga aaaaactata atgtctcaga acgtttacat tgtatcgact gccagaaccc 60

<210> SEQ ID NO 32
<211> LENGTH: 60
<212> TYPE: DNA
<213> ORGANISM: Artificial Sequence
<220> FEATURE:
<223> OTHER INFORMATION: Synthetic primer YT_164_36_007

<400> SEQUENCE: 32
gggttctggc agtcgataca atgtaaacgt tctgagacat tatagttttt tctccttgac 60

<210> SEQ ID NO 33
<211> LENGTH: 42
<212> TYPE: DNA
<213> ORGANISM: Artificial Sequence
<220> FEATURE:
<223> OTHER INFORMATION: Synthetic primer YT_164_36_008

<400> SEQUENCE: 33
gtgtgccttt tgacttactt ttacgttgag ccattagtat ca 42

<210> SEQ ID NO 34
<211> LENGTH: 42
<212> TYPE: DNA
<213> ORGANISM: Artificial Sequence
<220> FEATURE:
<223> OTHER INFORMATION: Synthetic primer YT_164_36_009

<400> SEQUENCE: 34
tgatactaat ggctcaacgt aaaagtaagt caaaaggcac ac 42

<210> SEQ ID NO 35
<211> LENGTH: 56
<212> TYPE: DNA
<213> ORGANISM: Artificial Sequence
<220> FEATURE:
<223> OTHER INFORMATION: Synthetic primer YT_164_36_010

<400> SEQUENCE: 35
gatatttctt gaatcaggcg ccttagaccc cccagtgcag cgaacgttat aaaaac 56

<210> SEQ ID NO 36
<211> LENGTH: 56
<212> TYPE: DNA
<213> ORGANISM: Artificial Sequence
<220> FEATURE:
<223> OTHER INFORMATION: Synthetic primer YT_164_36_011

<400> SEQUENCE: 36
gtttttataa cgttcgctgc actggggggt ctaaggcgcc tgattcaaga aatatc 56

<210> SEQ ID NO 37
<211> LENGTH: 31
<212> TYPE: DNA
<213> ORGANISM: Artificial Sequence
<220> FEATURE:
<223> OTHER INFORMATION: Synthetic construct: Linker YT_164_36_012

<400> SEQUENCE: 37
aaatatgacc cccaatatga gaaattaagg c 31

<210> SEQ ID NO 38
<211> LENGTH: 54
<212> TYPE: DNA
<213> ORGANISM: Artificial Sequence
<220> FEATURE:
<223> OTHER INFORMATION: Synthetic primer YT_164_30_Gal3F

<400> SEQUENCE: 38
gagctcgcgg ccgcgtacat acctctctcc gtatcctcgt aatcattttc ttgt 54

<210> SEQ ID NO 39
<211> LENGTH: 46
<212> TYPE: DNA
<213> ORGANISM: Artificial Sequence
<220> FEATURE:
<223> OTHER INFORMATION: Synthetic primer YT_164_30_Gal3R

<400> SEQUENCE: 39
catatgacta tgtgttgccc taccttttta cttttatttt ctcttt 46

<210> SEQ ID NO 40
<211> LENGTH: 54
<212> TYPE: DNA
<213> ORGANISM: Artificial Sequence
<220> FEATURE:
<223> OTHER INFORMATION: Synthetic primer YT_164_30_Gal7F

<400> SEQUENCE: 40
gagctcgcgg ccgcgtgtca cagcgaattt cctcacatgt agggaccgaa ttgt 54

<210> SEQ ID NO 41
<211> LENGTH: 46
<212> TYPE: DNA
<213> ORGANISM: Artificial Sequence
<220> FEATURE:
<223> OTHER INFORMATION: Synthetic primer YT_164_30_Gal7R

<400> SEQUENCE: 41
catatgtttt gagggaatat tcaactgttt ttttttatca tgttga 46

<210> SEQ ID NO 42
<211> LENGTH: 28
<212> TYPE: DNA
<213> ORGANISM: Artificial Sequence
<220> FEATURE:
<223> OTHER INFORMATION: Synthetic construct: RYSE Linker 0

<400> SEQUENCE: 42
gacggcacgg ccacgcgttt aaaccgcc 28

<210> SEQ ID NO 43
<211> LENGTH: 27
<212> TYPE: DNA
<213> ORGANISM: Artificial Sequence
<220> FEATURE:
<223> OTHER INFORMATION: Synthetic construct: RYSE Linker 19

<400> SEQUENCE: 43
cccgccaggc gctggggttt aaacacc 27

<210> SEQ ID NO 44
<211> LENGTH: 2738
<212> TYPE: DNA
<213> ORGANISM: Artificial Sequence
<220> FEATURE:
<223> OTHER INFORMATION: Synthetic construct: Kan A-ADH1 disruption construct

<400> SEQUENCE: 44
gacggcacgg ccacgcgttt aaaccgccaa tgggctaaac aagactacac caattacact 60
gcctcattga tggtggtaca taacgaacta atactgtagc cctagacttg atagccatca 120
tcatatcgaa gtttcactac cctttttcca tttgccatct attgaagtaa taataggcgc 180
atgcaacttc ttttcttttt ttttcttttc tctctccccc gttgttgtct caccatatcc 240
gcaatgacaa aaaaatgatg gaagacacta aaggaaaaaa ttaacgacaa agacagcacc 300
aacagatgtc gttgttccag agctgatgag gggtatctcg aagcacacga aactttttcc 360
ttccttcatt cacgcacact actctctaat gagcaacggt atacggcctt ccttccagtt 420
acttgaattt gaaataaaaa aaagtttgct gtcttgctat caagtataaa tagacctgca 480
attattaatc ttttgtttcc tcgtcattgt tctcgctcac acgcggccag gggagcctc 540 gacactagta atacacatca tcgtcctaca agttcatcaa agtgttggac agacaactat 600
accagcatgg atctcttgta tcggttcttt tctcccgctc tctcgcaata acaatgaaca 660
ctgggtcaat catagcctac acaggtgaac agagtagcgt ttatacaggg tttatacggt 720
gattcctacg gcaaaaattt ttcatttcta aaaaaaaaaa gaaaaatttt tctttccaac 780
gctagaagga aaagaaaaat ctaattaaat tgatttggtg attttctgag agttcccttt 840
ttcatatatc gaattttgaa tataaaagga gatcgaaaaa atttttctat tcaatctgtt 900
ttctggtttt atttgatagt ttttttgtgt attattatta tggattagta ctggtttata 960
tgggtttttc tgtataactt ctttttattt tagtttgttt aatcttattt tgagttacat 1020

```
tatagttccc taactgcaag agaagtaaca ttaaaaatgg gtaaggaaaa gactcacgtt   1080

tcgaggccgc gattaaattc caacatggat gctgatttat atgggtataa atgggctcgc   1140

gataatgtcg ggcaatcagg tgcgacaatc tatcgattgt atgggaagcc cgatgcgcca   1200

gagttgtttc tgaaacatgg caaaggtagc gttgccaatg atgttacaga tgagatggtc   1260

agactaaact ggctgacgga atttatgcct cttccgacca tcaagcattt tatccgtact   1320

cctgatgatg catggttact caccactgcg atccccggca aaacagcatt ccaggtatta   1380

gaagaatatc ctgattcagg tgaaaatatt gttgatgcgc tggcagtgtt cctgcgccgg   1440

ttgcattcga ttcctgtttg taattgtcct tttaacagcg atcgcgtatt tcgtctcgct   1500

caggcgcaat cacgaatgaa taacggtttg gttgatgcga gtgattttga tgacgagcgt   1560

aatggctggc ctgttgaaca agtctggaaa gaaatgcata agcttttgcc attctcaccg   1620

gattcagtcg tcactcatgg tgatttctca cttgataacc ttatttttga cgaggggaaa   1680

ttaataggtt gtattgatgt tggacgagtc ggaatcgcag accgatacca ggatcttgcc   1740

atcctatgga actgcctcgg tgagttttct ccttcattac agaaacggct ttttcaaaaa   1800

tatggtattg ataatcctga tatgaataaa ttgcagtttc atttgatgct cgatgagttt   1860

ttctaagttt aacttgatac tactagattt tttctcttca tttataaaat ttttggttat   1920

aattgaagct ttagaagtat gaaaaaatcc ttttttttca ttctttgcaa ccaaaataag   1980

aagcttcttt tattcattga aatgatgaat ataaacctaa caaaagaaaa agactcgaat   2040

atcaaacatt aaaaaaaaat aaaagaggtt atctgttttc ccatttagtt ggagtttgca   2100

ttttctaata gatagaactc tcaattaatg tggatttagt ttctctgttc gttttttttt   2160

gttttgttct cactgtattt acatttctat ttagtattta gttattcata taatcttaac   2220

ttctcgagga gctccgctcg tccaacgccg gcggaccttt taaaacgaaa attcttattc   2280

ttgagtaact ctttcctgta ggtcaggttg ctttctcagg tatagcatga ggtcgctctt   2340

attgaccaca cctctaccgg catgccgagc aaatgcctgc aaatcgctcc ccatttcacc   2400

caattgtaga tatgctaact ccagcaatga gttgatgaat ctcggtgtgt attttatgtc   2460

ctcagaggac aacacctgtt gtaatcgttc ttccacacgg atccacagcc tagccttcag   2520

ttgggctcta tcttcatcgt cattcattgc atctactagc cccttacctg agcttcaaga   2580

cgttatatcg cttttatgta tcatgatctt atcttgagat atgaatacat aaatatattt   2640

actcaagtgt atacgtgcat gcttttttta cggcagcatt ttttttcaa ctctgatcgc   2700

ccctttactg cggtgtttaa accccagcgc ctggcggg                           2738
```

<210> SEQ ID NO 45
<211> LENGTH: 3059
<212> TYPE: DNA
<213> ORGANISM: Artificial Sequence
<220> FEATURE:
<223> OTHER INFORMATION: Synthetic construct: i2235 integration construct

<400> SEQUENCE: 45

```
gacggcacgg ccacgcgttt aaaccgcctc gatatttcct gtgagaagtt taaatccact     60

aaggtttttc attgttgctg cagatgtgtt tttccattca tcctgaaata tgcactgcta    120

ttccgcattc cattccccta gtcttttttta gttctttccg ttcgaccttc atcgaaaaat    180

gacaaaacgc gttaggaaca acaaccaatt gcaaacaagc agtgaaacaa aaccatcaag    240

gcccgaaaat acaagtgtgt actaatacag taagtaggtc aaatacgcaa tgaccaaaga    300

tgccgtgaat ctagatgctt acaccgtgag cttcatgcct ttctataccg agtatcaagg    360
```

-continued

```
accaaccgaa gagtttaagg attacaaatt cgaagatact atttactttc gtggcaagga    420
actgaagagg gaaaagtctg cgacgccttc cagtagcgat aacacaacta gtaatacctt    480
cagtaatggc gccatcctct cgggaaacac aataactggc aagatagttt cagtgaataa    540
ttacgaaaga gagggcactg atcgcaacga attggcgcga ttgcaagaat tgatctccct    600
catcgatgtc ataaatcagt aaatataagc tcacacgcgg ccaggggggag cccgttgagc    660
cattagtatc aatttgctta cctgtattcc tttactatcc tccttttttct ccttcttgat    720
aaatgtatgt agattgcgta tatagtttcg tctaccctat gaacatattc cattttgtaa    780
tttcgtgtcg tttctattat gaatttcatt tataaagttt atgtacaaat atcataaaaa    840
aagagaatct ttttaagcaa ggattttctt aacttcttcg gcgacagcat caccgacttc    900
ggtggtactg ttggaaccac ctaaatcacc agttctgata cctgcatcca aaaccttttt    960
aactgcatct tcaatggcct taccttcttc aggcaagttc aatgacaatt tcaacatcat   1020
tgcagcagac aagatagtgg cgatagggtc aaccttattc tttggcaaat ctggagcaga   1080
accgtggcat ggttcgtaca aaccaaatgc ggtgttcttg tctggcaaag aggccaagga   1140
cgcagatggc aacaaaccca aggaacctgg gataacggag gcttcatcgg agatgatatc   1200
accaaacatg ttgctggtga ttataatacc atttaggtgg gttgggttct taactaggat   1260
catggcggca gaatcaatca attgatgttg aaccttcaat gtagggaatt cgttcttgat   1320
ggtttcctcc acagtttttc tccataatct tgaagaggcc aaaacattag ctttatccaa   1380
ggaccaaata ggcaatggtg gctcatgttg tagggccatg aaagcggcca ttcttgtgat   1440
tctttgcact tctggaacgg tgtattgttc actatcccaa gcgacaccat caccatcgtc   1500
ttcctttctc ttaccaaagt aaatacctcc cactaattct ctgacaacaa cgaagtcagt   1560
acctttagca aattgtggct tgattggaga taagtctaaa agagagtcgg atgcaaagtt   1620
acatggtctt aagttggcgt acaattgaag ttctttacgg atttttagta aaccttgttc   1680
aggtctaaca ctaccggtac cccatttagg accacccaca gcacctaaca aaacggcatc   1740
aaccttcttg gaggcttcca gcgcctcatc tggaagtggg acacctgtag catcgatagc   1800
agcaccacca attaaatgat tttcgaaatc gaacttgaca ttggaacgaa catcagaaat   1860
agctttaaga accttaatgg cttcggctgt gatttcttga ccaacgtggt cacctggcaa   1920
aacgacgatc ttcttagggg cagacatagg ggcagacatt agaatggtat atccttgaaa   1980
tatatatata tattgctgaa atgtaaaagg taagaaaagt tagaaagtaa gacgattgct   2040
aaccacctat tggaaaaaac aataggtcct taaataatat tgtcaacttc aagtattgtg   2100
atgcaagcat ttagtcatga acgcttctct attctatatg aaaagccggt tccggcctct   2160
cacctttcct ttttctccca atttttcagt tgaaaaaggt atatgcgtca ggcgacctct   2220
gaaattaaca aaaaatttcc agtcatcgaa tttgattctg tgcgatagcg cccctgtgtg   2280
ttctcgttat gttgaggaaa aaaataatgg ttgctaagag attcgaactc ttgcatctta   2340
cgatacctga gtattcccac agttaactgc ggtcaagata tttcttgaat caggcgcctc   2400
gctcgtccaa cgccggcgga cctcttaaat gagaaaaatt tcgtaatgag ataaaatttc   2460
gctccttttc tgttttctat tttctatttt cccaactttt gctctattca gttataaatt   2520
actatttatc catcagttaa aaaacaagat cttttactgg tcagctagga aagcgaaaat   2580
acaaagactt tatgcactta gtgatatata tgtatagata tatccatttt tacgcactta   2640
tcatatatct tagttatcta aatacaatct agttattcgt acacaatcgc ccctgttatc   2700
cctatagtgg gaataaagta atgcactgtg acggggttct tcgcccggga tagggtaaaa   2760
```

```
ggatattgcc gtttcaagaa acttcgggga taatcgaata agataccgag aaagctattg   2820

ttcgttgtgc acgtaggatg tatattgaac aagcatgacc agaatctgat gcattacgag   2880

aaggttacgg gatgatatca gacctccgaa gtccatgttg caaaatgtgc cgactttccg   2940

cggcgctatt tggcacaaat ttcaggagaa acatcactgt cggtgttata gaattccatc   3000

tatattgttt tccccgtagg catacgtcga gcggtgttta aaccccagcg cctggcggg    3059
```

<210> SEQ ID NO 46
<211> LENGTH: 8106
<212> TYPE: DNA
<213> ORGANISM: Artificial Sequence
<220> FEATURE:
<223> OTHER INFORMATION: Synthetic construct: i74804 integration construct

<400> SEQUENCE: 46

```
gacggcacgg ccacgcgttt aaaccgcccg ctcgcctcat ccccacggga ataaggcagc     60

cgacaaaaga aaaacgaccg aaaaggaacc agaaagaaaa aagagggtgg gcgcgccgcg    120

gacgtgtaaa aagatatgca tccagcttct atatcgcttt aactttaccg ttttgggcat    180

cgggaacgta tgtaacattg atctcctctt gggaacggtg agtgcaacga atgcgatata    240

gcaccgacca tgtgggcaaa ttcgtaataa attcggggtg agggggattc aagacaagca    300

accttgttag tcagctcaaa cagcgattta acggttgagt aacacatcaa aacaccgttc    360

gaggtcaagc ctggcgtgtt taacaagttc ttgatatcat atataaatgt aataagaagt    420

ttggtaatat tcaattcgaa gtgttcagtc ttttacttct cttgttttat agaagaaaaa    480

acatcaagaa acatctttaa catacacaaa cacatactat cagaatacac gctcgtccaa    540

cgccggcgga cctttcagac gcgactgcct catcagtaag acccgttgaa aagaacttac    600

ctgaaaaaaa cgaatatata ctagcgttga atgttagcgt caacaacaag aagtttaatg    660

acgcggaggc caaggcaaaa agattccttg attacgtaag ggagttagaa tcattttgaa    720

taaaaaacac gctttttcag ttcgagttta tcattatcaa tactgccatt tcaaagaata    780

cgtaaataat taatagtagt gattttccta actttattta gtcaaaaaat tagcctttta    840

attctgctgt aacccgtaca tgcccaaaat agggggcggg ttacacagaa tatataacat    900

cgtaggtgtc tgggtgaaca gtttattcct ggcatccact aaatataatg gagcccgctt    960

tttaagctgg catccagaaa aaaaaagaat cccagcacca aaatattgtt ttcttcacca   1020

accatcagtt cataggtcca ttctcttagc gcaactacag agaacagggg cacaaacagg   1080

caaaaaacgg gcacaacctc aatggagtga tgcaacctgc ctggagtaaa tgatgacaca   1140

aggcaattga cccacgcatg tatctatctc attttcttac accttctatt accttctgct   1200

ctctctgatt tggaaaaagc tgaaaaaaaa ggttgaaacc agttccctga aattattccc   1260

ctacttgact aataagtata taaagacggt aggtattgat tgtaattctg taaatctatt   1320

tcttaaactt cttaaattct acttttatag ttagtctttt ttttagtttt aaaacaccaa   1380

gaacttagtt tcgacctccc gcgacctcca aaatcgaact accttcacaa tggaacattc   1440

tgtaatcgaa ccaactgtgc ccatgccgct accagccatg tttgacgctc catctggtat   1500

ttttagctct ttggacgacg ctgtgcaagc agccacctta gcccaacaac aactaagttc   1560

agttgagttg cgtcagcaag taatcaaagc cataagagtg gccggagaaa ggtatgcaca   1620

agttttggct gaaatggcag ttgctgaaac tggtatgggt agggtggtgg ataagtacat   1680

taagaatgtc tctcaagctc gtcatacgcc tggtatagaa tgtttatcgg ccgaggttct   1740

tacgggtgat aatggcctaa cattgattga aaatgcccct tggggagtcg tagcttcagt   1800
```

```
cacgccaagc acaaatccag cagctacggt aattaataat gcaatctcaa tgattgcagc   1860
ggggaattca gtcgtgttcg caccacatcc ttctgccaaa aacgtctcac taaggactat   1920
ttctttactc aacaaggcca ttgtcgctac cggcggccca gaaaatttac tagttagtgt   1980
ggcaaaccct aacatcgaaa ctgcacagag attattcaga tatccgggta ttggattgtt   2040
agttgtgaca ggtggtgaag ccgtcgttga agccgctagg aagcatacag ataaaaggtt   2100
aattgcagcc ggcgctggta atcctcctgt tgttgtggac gaaactgctg acatacctaa   2160
agccgcaaga gcaattgtca agggtgcttc tttcgacaac aacataattt gtgctgatga   2220
aaaagttttg attgtggtag acagagttgc agatgcacta ttggcagaaa tgcaaagaaa   2280
taacgccgtc ttacttacac ccgaacagac cgaaagacta ctacccgctc ttttgtccga   2340
tattgacgaa cagggcaaag gacgtgtgaa tagagattat gttggaagag atgcggctaa   2400
attagcagcg gctattggtc tggaagttag cgaacatact cgtctactcc tggcagagac   2460
agacgctgat catccattcg ccgtgacgga gctgatgatg ccagtgttac cagtaataag   2520
agtcaagaat gtagatgatg caatcgcatt ggcagttaag ctagagtcag gctgcagaca   2580
cacagctgcg atgcactcta ctaatataag aaacttaaat agaatggcta atgccatcaa   2640
tacctctatc tttgtaaaaa atggtccatg tattgcaggt ttgggtttag gcggtgaagg   2700
ttggacttca atgactatta gcactccgac cggtgaaggt gttacaagcg ctcgtacctt   2760
tgtcagatta agaaggtgtg tcttagtcga catgtttcgg attgcttaag cggccgcgag   2820
taataattat tgcttccata taatattttt atatacctct tatttttatg tattagttaa   2880
ttaagtattt ttatctatct gcttatcatt ttcttttcat ataggggggg ttggtgtttt   2940
cttgcccatc agattgatgt cctccaactc ggcactattt tacaaagggt ttttttgtaa   3000
gagaaggaga agacagatac taaaccatac gttactcgaa acaaaaaaaa aaaaaatgga   3060
aaaagctgct atcaacaaaa gacggcctca tcaaacctaa agaaaccatg tcagcgtatg   3120
tatatacctt gtaatttacg tttccttaaa tcttctttct actaacgttt tcattattct   3180
atactctatg accaataaaa acagactgta ctttcaaaat ttacccagta ggccagcaaa   3240
taaagaaaat tataccagat tacttctgaa acacattaat cccaacaaca agtatgccat   3300
taatccgtcg ctaccccatc cccgcgtgct tggccggccg tacactgagt aatggtagtt   3360
ataagaaaga gaccgagtta gggacagtta gaggcggtgg agatattcct tatggcatgt   3420
ctggcgatga taaaactttt caaacggcag ccccgatcta aaagagctga cagggaaatg   3480
gtcagaaaaa gaaacgtgca cccgcccgtc tggacgcgcc gctcacccgc acggcagaga   3540
ccaatcagta aaaatcaacg gttaacgaca ttactatata tataatatag gaagcattta   3600
atagaacagc atcgtaatat atgtgtactt tgcagttatg acgccagatg gcagtagtgg   3660
aagatattct ttattgaaaa atagcttgtc accttacgta caatcttgat ccggagcttt   3720
tctttttttg ccgattaaga attcggtcga aaaaagaaaa ggagagggcc aagagggagg   3780
gcattggtga ctattgagca cgtgagtata cgtgattaag cacacaaagg cagcttggag   3840
tatgtctgtt attaatttca caggtagttc tggtccattg gtgaaagttt gcggcttgca   3900
gagcacagag gccgcagaat gtgctctaga ttccgatgct gacttgctgg gtattatatg   3960
tgtgcccaat agaaagagaa caattgaccc ggttattgca aggaaaattt caagtcttgt   4020
aaaagcatat aaaaatagtt caggcactcc gaaatacttg gttggcgtgt ttcgtaatca   4080
acctaaggag gatgttttgg ctctggtcaa tgattacggc attgatatcg tccaactgca   4140
tggagatgag tcgtggcaag aataccaaga gttcctcggt ttgccagtta ttaaaagact   4200
```

```
cgtatttcca aaagactgca acatactact cagtgcagct tcacagaaac ctcattcgtt   4260
tattcccttg tttgattcag aagcaggtgg gacaggtgaa cttttggatt ggaactcgat   4320
ttctgactgg gttggaaggc aagagagccc cgaaagctta cattttatgt tagctggtgg   4380
actgacgcca gaaaatgttg gtgatgcgct tagattaaat ggcgttattg gtgttgatgt   4440
aagcggaggt gtggagacaa atggtgtaaa agactctaac aaaatagcaa atttcgtcaa   4500
aaatgctaag aaataggtta ttactgagta gtatttattt aagtattgtt tgtgcacttg   4560
cctgcaggcc ttttgaaaag caagcataaa agatctaaac ataaaatctg taaaataaca   4620
agatgtaaag ataatgctaa atcatttggc tttttgattg attgtacagg aaaatataca   4680
tcgcaggggg ttgactttta ccatttcacc gcaatggaat caaacttgtt gaagagaatg   4740
ttcacaggcg catacgctac aatgacacgg ccggccaagc acgcggggat ggggtagcga   4800
cggattaatg gcatacttgt tgttgggatt aatgtgtttc agaagtaatc tggtataatt   4860
ttctttattt gctggcctac tgggtaaatt ttgaaagtac agtctgtttt tattggtcat   4920
agagtataga ataatgaaaa cgttagtaga aagaagattt aaggaaacgt aaattacaag   4980
gtatatacat acgctgacat ggtttcttta ggtttgatga ggccgtcttt tgttgatagc   5040
agctttttcc attttttttt tttttgtttc gagtaacgta tggtttagta tctgtcttct   5100
ccttctctta caaaaaaacc ctttgtaaaa tagtgccgag ttggaggaca tcaatctgat   5160
gggcaagaaa acaccaaccc cccctatatg aaaagaaaat gataagcaga tagataaaaa   5220
tacttaatta actaatacat aaaaataaga ggtatataaa aatattatat ggaagcaata   5280
attattactc gcggccgctt aagcaatccg aaacatgtcg actaagacac accttcttaa   5340
tctgacaaag gtacgagcgc ttgtaacacc ttcaccggtc ggagtgctaa tagtcattga   5400
agtccaacct tcaccgccta aacccaaacc tgcaatacat ggaccatttt ttacaaagat   5460
agaggtattg atggcattag ccattctatt taagtttctt atattagtag agtgcatcgc   5520
agctgtgtgt ctgcagcctg actctagctt aactgccaat gcgattgcat catctacatt   5580
cttgactctt attactggta acactggcat catcagctcc gtcacggcga atggatgatc   5640
agcgtctgtc tctgccagga gtagacgagt atgttcgcta acttccagac caatagccgc   5700
tgctaattta gccgcatctc ttccaacata atctctattc acacgtcctt tgccctgttc   5760
gtcaatatcg gacaaaagag cgggtagtag tctttcggtc tgttcgggtg taagtaagac   5820
ggcgttattt ctttgcattt ctgccaatag tgcatctgca actctgtcta ccacaatcaa   5880
aactttttca tcagcacaaa ttatgttgtt gtcgaaagaa gcacccttga caattgctct   5940
tgcggcttta ggtatgtcag cagtttcgtc cacaacaaca ggaggattac cagcgccggc   6000
tgcaattaac cttttatctg tatgcttcct agcggcttca acgacggctt caccacctgt   6060
cacaactaac aatccaatac ccggatatct gaataatctc tgtgcagttt cgatgttagg   6120
gtttgccaca ctaactagta aattttctgg gccgccggta gcgacaatgg ccttgttgag   6180
taaagaaata gtccttagtg agacgttttt ggcagaagga tgtggtgcga acacgactga   6240
attccccgct gcaatcattg agattgcatt attaattacc gtagctgctg gatttgtgct   6300
tggcgtgact gaagctacga ctccccaagg ggcattttca atcaatgtta ggccattatc   6360
acccgtaaga acctcggccg ataaacattc tataccaggc gtatgacgag cttgagagac   6420
attcttaatg tacttatcca ccaccctacc cataccagtt tcagcaactg ccatttcagc   6480
caaaacttgt gcataccttt ctccggccac tcttatggct ttgattactt gctgacgcaa   6540
ctcaactgaa cttagttgtt gttgggctaa ggtggctgct tgcacagcgt cgtccaaaga   6600
```

```
gctaaaaata ccagatggag cgtcaaacat ggctggtagc ggcatgggca cagttggttc   6660

gattacagaa tgttccattg tgaaggtagt tcgattttgg aggtcgcggg aggtcgaaac   6720

taagttcttg gtgttttaaa actaaaaaaa agactaacta taaaagtaga atttaagaag   6780

tttaagaaat agatttacag aattacaatc aatacctacc gtctttatat acttattagt   6840

caagtagggg aataatttca gggaactggt ttcaaccttt tttttcagct ttttccaaat   6900

cagagagagc agaaggtaat agaaggtgta agaaaatgag atagatacat gcgtgggtca   6960

attgccttgt gtcatcattt actccaggca ggttgcatca ctccattgag gttgtgcccg   7020

tttttgcct gtttgtgccc ctgttctctg tagttgcgct aagagaatgg acctatgaac   7080

tgatggttgg tgaagaaaac aatattttgg tgctgggatt cttttttttt ctggatgcca   7140

gcttaaaaag cgggctccat tatatttagt ggatgccagg aataaactgt tcacccagac   7200

acctacgatg ttatatattc tgtgtaaccc gccccctatt ttgggcatgt acgggttaca   7260

gcagaattaa aaggctaatt ttttgactaa ataaagttag gaaaatcact actattaatt   7320

atttacgtat tctttgaaat ggcagtattg ataatgataa actcgaactg aaaaagcgtg   7380

tttttattc aaaatgattc taactccctt acgtaatcaa ggaatctttt tgccttggcc   7440

tccgcgtcat taaacttctt gttgttgacg ctaacattca acgctagtat atattcgttt   7500

ttttcaggta agttcttttc aacgggtctt actgatgagg cagtcgcgtc tgaaaggtcc   7560

gccggcgttg gacgagcgtg taccaacctg catttctttc cgtcatatac acaaaatact   7620

ttcatataaa cttacttggt cttacgtcat aaataaatat gtatacatat aaattaaaaa   7680

atttggtttt atatttttac aaaaagaatc gtttacttca tttctccctt ttaagcgata   7740

caatccatga aaaaagagaa aaagagagaa caggcttgtg ccttctttaa aacatcccac   7800

acaaaatcat attgaattga attttacatc ttaagctagt gtacaacaac tgctatatcc   7860

aaagaaaact aacgtggacc gcttttagag ttgagaaaaa ggtttgaaaa aaatagcaat   7920

acaaagactt gtttcatata taaaatacag ggagcacatt gagctaatat aacataaaca   7980

ctgcgaacca attccaatca aaaggtacac atgagagcat tcccccgagt actgccattt   8040

cgccatcaga gatcatataa taacatcctt cttcgaacgg cggtttaaac gcgtggccgt   8100

gccgtc                                                               8106
```

```
<210> SEQ ID NO 47
<211> LENGTH: 2404
<212> TYPE: DNA
<213> ORGANISM: Artificial Sequence
<220> FEATURE:
<223> OTHER INFORMATION: Synthetic construct: i76220 integration
      construct

<400> SEQUENCE: 47

gacggcacgg ccacgcgttt aaaccgccgc acgtgtatgt acggctgtgt aaatatgata     60

atcatctcgg acgaacggcg tagtactctc catcccctaa aaatgttcac gtgtgactgc    120

tccatttcgc cggatgtcga gatgaccccc ccccctcaaa aggcactcac ctgctgacat    180

gccgtggcaa atgattgggg tcatcctttt tttctgttat ctctaagatc caaagaaaag    240

taaaaaaaaa aggttggggt acgaattgcc gccgagcctc cgatgccatt attcaatggg    300

tattgcagtt ggggtatagt tcctcggtgg caaatagttc tcccttcatt ttgtatataa    360

actgggcggc tattctaagc atatttctcc cttaggttat ctggtagtac gttatatctt    420

gttcttatat tttctatcta taagcaaaac caaacatatc aaaactacta gaaagacatt    480

gccccactgt gttcgctcgt ccaacgccgg cggacctttc tcgacgtggg ccttttttctt    540
```

```
gccatatgga tccgctgcac ggtcctgttc cctagcatgt acgtgagcgt atttcctttt    600

aaaccacgac gctttgtctt cattcaacgt ttcccattgt ttttttctac tattgctttg    660

ctgtgggaaa aacttatcga aagatgacga ctttttctta attctcgttt taagagcttg    720

gtgagcgcta ggagtcactg ccaggtatcg tttgaacacg gcattagtca gggaagtcat    780

aacacagtcc tttcccgcaa ttttcttttt ctattactct tggcctcctc tagtacactc    840

tatatttttt tatgcctcgg taatgatttt catttttttt tttccaccta gcggatgact    900

cttttttttt cttagcgatt ggcattatca cataatgaat tatacattat ataaagtaat    960

gtgatttctt cgaagaatat actaaaaaat gagcaggcaa gataaacgaa ggcaaagatg   1020

acagagcaga aagccctagt aaagcgtatt acaaatgaaa ccaagattca gattgcgatc   1080

tctttaaagg gtggtcccct agcgatagag cactcgatct tcccagaaaa agaggcagaa   1140

gcagtagcag aacaggccac acaatcgcaa gtgattaacg tccacacagg tatagggttt   1200

ctggaccata tgatacatgc tctggccaag cattccggct ggtcgctaat cgttgagtgc   1260

attggtgact tacacataga cgaccatcac accactgaag actgcgggat tgctctcggt   1320

caagctttta aagaggccct aggggccgtg cgtggagtaa aaaggtttgg atcaggattt   1380

gcgcctttgg atgaggcact ttccagagcg gtggtagatc tttcgaacag gccgtacgca   1440

gttgtcgaac ttggtttgca aagggagaaa gtaggagatc tctcttgcga gatgatcccg   1500

cattttcttg aaagctttgc agaggctagc agaattaccc tccacgttga ttgtctgcga   1560

ggcaagaatg atcatcaccg tagtgagagt gcgttcaagg ctcttgcggt tgccataaga   1620

gaagccacct cgcccaatgg taccaacgat gttccctcca ccaaaggtgt tcttatgtag   1680

tgacaccgat tatttaaagc tgcagcatac gatatatata catgtgtata tatgtatacc   1740

tatgaatgtc agtaagtatg tatacgaaca gtatgatact gaagatgaca aggtaatgca   1800

tcattctata cgtgtcattc tgaacgaggc gcgctttcct tttttctttt tgctttttct   1860

tttttttct cttgaactcg aggtccgccg gcgttggacg agcgtgatga tttctttcct   1920

ttttatattg acgacttttt tttttcgtg tgtttttgtt ctcttataac cgagctgctt    1980

acttattatt atttcacctt ctctttttat ttatacttat aattatttat tctttacata   2040

ctgttacaag aaactctttt ctacattaat tgcataaagt gtcaatcagc acatcctcta   2100

tatcgctatc aacaacaaat ttgacaaacc tgcctatatc ttcaggaaca actgccgcat   2160

cgctaccacc actacttgtg aagtccctgg agtttaatat gcactgaaat ttacctagcc   2220

gttttacaca agaccataat ccatccatgc tatcgcagta tatgattttg tgttcgtttt   2280

tcgtcttgcg aaaggcatcc tcaatggctt gtttcattga tccatcagtg tggctcgtag   2340

gtaccagcaa aaccacttca tcagcggcgt actcctggcg gtttaaacgc gtggccgtgc   2400

cgtc                                                                2404
```

<210> SEQ ID NO 48
<211> LENGTH: 8536
<212> TYPE: DNA
<213> ORGANISM: Artificial Sequence
<220> FEATURE:
<223> OTHER INFORMATION: Synthetic construct: i73830 integration construct

<400> SEQUENCE: 48

```
gacggcacgg ccacgcgttt aaaccgccac ccagccaagg tagtctaaaa gctaatttct     60

ctaaaaggga gaaagttggt gattttttat ctcgcattat tatatatgca agaatagtta    120

aggtatagtt ataaagtttt atcttaattg ccacatacgt acattgacac gtagaaggac    180
```

```
tccattattt ttttcattct agcatactat tattccttgt aacgtcccag agtattccat    240

ttaattgtcc tccatttctt aacggtgacg aaggatcacc atacaacaac tactaaagat    300

tatagtacac tctcaccttg caactattta tctgacattt gccttacttt tatctccagc    360

ttcccctcga ttttattttt caatttgatt tctaaagctt tttgcttagg cataccaaac    420

catccactca tttaacacct tatttttttt ttcgaagaca gcatccaact ttatacgttc    480

actacctttt tttttacaac aatttcattc ttcatcctat gaacgctcgt ccaacgccgg    540

cggacctttc agacgcgact gcctcatcag taagacccgt tgaaaagaac ttacctgaaa    600

aaaacgaata tatactagcg ttgaatgtta gcgtcaacaa caagaagttt aatgacgcgg    660

aggccaaggc aaaaagattc cttgattacg taagggagtt agaatcattt tgaataaaaa    720

acacgctttt tcagttcgag tttatcatta tcaatactgc catttcaaag aatacgtaaa    780

taattaatag tagtgatttt cctaacttta tttagtcaaa aaattagcct tttaattctg    840

ctgtaacccg tacatgccca aaataggggg cgggttacac agaatatata acatcgtagg    900

tgtctgggtg aacagtttat tcctggcatc cactaaatat aatggagccc gctttttaag    960

ctggcatcca gaaaaaaaaa gaatcccagc accaaaatat tgttttcttc accaaccatc   1020

agttcatagg tccattctct tagcgcaact acagagaaca ggggcacaaa caggcaaaaa   1080

acgggcacaa cctcaatgga gtgatgcaac ctgcctggag taaatgatga cacaaggcaa   1140

ttgacccacg catgtatcta tctcattttc ttacaccttc tattaccttc tgctctctct   1200

gatttggaaa aagctgaaaa aaaaggttga aaccagttcc ctgaaattat tcccctactt   1260

gactaataag tatataaaga cggtaggtat tgattgtaat tctgtaaatc tatttcttaa   1320

acttcttaaa ttctactttt atagttagtc tttttttag ttttaaaaca ccaagaactt   1380

agtttcgacc tcccgcgacc tccaaaatcg aactaccttc acaatggctg atttcgattc   1440

taaagaatac ttggagttag ttgacaagtg gtggcgtgcc accaactact tgtccgctgg   1500

tatgattttc ttgaagtcca acccattatt ctctgttact aatacccccaa tcaaggccga  1560

agatgtcaaa gttaaaccaa ttggtcactg ggtactatt tccggtcaaa ctttcttata   1620

cgcccacgct aaccgtttga ttaacaagta cggtctcaac atgttttacg ttggtggtcc   1680

aggtcacggt ggtcaagtca tggttactaa cgcctactta gacggtgcct acaccgaaga   1740

ttacccagaa attactcaag acatcgaagg tatgtctcat ttgttcaagc gtttctcttt   1800

ccctggtggt attggttccc atatgaccgc tcaaactcca ggttccttgc acgaaggtgg   1860

tgaattgggt tactctttgt cccatgcttt cggtgctgtt ttggacaacc cagaccaagt   1920

tgcttttgct gtcgttggtg atggtgaagc tgaaactggt ccatctatgg cctcttggca   1980

ttccattaag ttcttaaatg ccaagaacga tggtgccgtt ttgccagttt tggatttaaa   2040

cggtttcaag atttccaatc caaccatttt ttctagaatg tctgatgaag aaattactaa   2100

gttcttcgaa ggtttgggtt attcccctag attcattgaa aatgatgaca ttcacgacta   2160

cgccacctac caccaattgg ccgctaacat cttagatcaa gccatcgaag acattcaagc   2220

tattcaaaat gacgccagag agaatggtaa atatcaagat ggtgaaattc cagcttggcc   2280

tgttattatc gctagattgc caaagggttg ggtggtcca acccacgatg cttctaataa   2340

tccaattgaa aactctttca gagctcacca agttccatta ccattggaac aacacgattt   2400

ggccaccttg ccagaattcg aagattggat gaactcttac aagccagaag aattattcaa   2460

cgctgatggt tccttgaagg atgagttgaa agctattgcc ccaaagggtg ataagagaat   2520

gtctgctaac ccaatcacca acggtggtgc tgacagatcc gacttgaaat tgccaaattg   2580
```

```
gagagaattc gctaacgaca tcaacgacga taccagaggt aaggaattcg ctgactctaa   2640
gagaaacatg gatatggcta ctttatccaa ctatttaggt gccgtttctc aattgaaccc   2700
aaccagattc agattcttcg gtccagatga aaccatgtcc aacagattgt ggggtttgtt   2760
taatgttacc ccacgtcaat ggatggaaga aatcaaggaa ccacaagatc aattgttgtc   2820
tccaactggt cgtatcatcg attcccaatt gtctgaacac caagctgaag gttggttgga   2880
aggttacact ttgactggta gagttggtat ctttgcctct tacgaatctt tcttgagagt   2940
tgttgatacc atggtcactc aacatttcaa gtggttgcgt cacgcttccg aacaagcttg   3000
gagaaatgac tatccatcct taaatttgat cgctacctct accgctttcc aacaagatca   3060
taacggttat actcaccaag accctggtat gttaactcat ttggccgaga agaagtctaa   3120
cttcattaga gaatatttgc cagccgacgg taactctttg ttagccgttc aagagagagc   3180
tttctctgaa agacataagg ttaacttatt gatcgcttct aaacaaccaa gacaacaatg   3240
gttcactgtt gaagaagctg aagtcttagc taacgaaggt ttgaagatta tcgattgggc   3300
ttctactgct ccatcttccg atgttgatat tacttttgct tctgccggta ctgaaccaac   3360
cattgagact ttggccgcct tatggttgat taatcaagct ttccctgacg ttaagtttag   3420
atacgttaac gttgttgaat tgttaagatt gcaaaagaaa tctgaaccaa acatgaacga   3480
cgaaagagaa ttatctgccg aagaatttaa taagtacttc caagccgaca ctccagttat   3540
cttcggtttc cacgcttacg aaaacttgat tgaatctttc tttttcgaga gaaagttcac   3600
cggtgatgtc tatgttcacg gttatagaga agatggtgat atcactacca cctacgatat   3660
gagagtctat tcccacttgg atcgtttcca tcaagccaag gaagccgccg aaatcttgtc   3720
tgctaacggt aaaatcgacc aagccgctgc cgacaccttt attgctaaga tggacgacac   3780
tttggccaaa cacttccaag ttactagaaa tgaaggtaga gatattgaag aattcactga   3840
ctggacttgg tctccattga agtaagtgaa tttactttaa atcttgcatt taaataaatt   3900
ttctttttat agctttatga cttagtttca atttatatac tattttaatg acattttcga   3960
ttcattgatt gaaagctttg tgttttttct tgatgcgcta ttgcattgtt cttgtctttt   4020
tcgccacatg taatatctgt agtagatacc tgatacattg tggatgctga gtgaaatttt   4080
agttaataat ggaggcgctc ttaataattt tggggatatt ggcttatccc cgcgtgcttg   4140
gccggccgta cgaaaatcgt tattgtcttg aaggtgaaat ttctactctt attaatggtg   4200
aacgttaagc tgatgctatg atggaagctg attggtctta acttgcttgt catcttgcta   4260
atggtcattg gctcgtgtta ttacttaagt tatttgtact cgttttgaac gtaatgctaa   4320
tgatcatctt atggaataat agtgagtggt ttcagggtcc ataaagcttt tcaattcatc   4380
tttttttttt ttgttctttt ttttgattcc ggtttctttg aaattttttt gattcggtaa   4440
tctccgagca gaaggaagaa cgaaggaagg agcacagact tagattggta tatatacgca   4500
tatgtggtgt tgaagaaaca tgaaattgcc cagtattctt aacccaactg cacagaacaa   4560
aaacctgcag gaaacgaaga taaatcatgt cgaaagctac atataaggaa cgtgctgcta   4620
ctcatcctag tcctgttgct gccaagctat ttaatatcat gcacgaaaag caaacaaact   4680
tgtgtgcttc attggatgtt cgtaccacca aggaattact ggagttagtt gaagcattag   4740
gtcccaaaat ttgtttacta aaaacacatg tggatatctt gactgatttt tccatggagg   4800
gcacagttaa gccgctaaag gcattatccg ccaagtacaa tttttactc ttcgaagaca   4860
gaaaatttgc tgacattggt aatacagtca aattgcagta ctctgcgggt gtatacagaa   4920
tagcagaatg ggcagacatt acgaatgcac acggtgtggt gggcccaggt attgttagcg   4980
```

```
gtttgaagca ggcggcggaa gaagtaacaa aggaacctag aggccttttg atgttagcag   5040

aattgtcatg caagggctcc ctagctactg gagaatatac taagggtact gttgacattg   5100

cgaagagtga caaagatttt gttatcggct ttattgctca aagagacatg ggtggaagag   5160

atgaaggtta cgattggttg attatgacac ccggtgtggg tttagatgac aagggagacg   5220

cattgggtca acagtataga accgtggatg atgtggtctc tacaggatct gacattatta   5280

ttgttggaag aggactattt gcaaagggaa gggatgctaa ggtagagggt gaacgttaca   5340

gaaaagcagg ctgggaagca tatttgagaa gatgcggcca gcaaaactaa aaaactgtat   5400

tataagtaaa tgcatgtata ctaaactcac aaattagagc ttcaatttaa ttatatcagt   5460

tattaccacg aaaatcgtta ttgtcttgaa ggtgaaattt ctactcttat taatggtgaa   5520

cgttaagctg atgctatgat ggaagctgat tggtcttaac ttgcttgtca tcttgctaat   5580

ggtcatatgg ctcgtgttat tacttaagtt atttgtactc gttttgaacg taatgctaat   5640

gatcatctta tggaataata gtgaacggcc ggccaagcac gcggggatgg gatgagcttg   5700

gagcaggaag aatacactat actggatcta aagagtacaa tagatggata agaatattgg   5760

cagcgcaaaa aggcttcaag cttacacaac acggtttatt tcgaaataat atccttctcg   5820

aaagctttaa cgaacgcaga attttcgagt tattaaactt aaaatacgct gaacccgaac   5880

atagaaatat cgaatgggaa aaaaaaactg cataaaggca ttaaaagagg agcgaatttt   5940

tttttaataa aaatcttaat aatcattaaa agataaataa tagtctatat atacgtatat   6000

aaataaaaaa tattcaaaaa ataaaataaa ctattatttt agcgtaaagg atggggaaag   6060

agaaaagaaa aaaattgatc tatcgatttc aattcaattc aatagatctt tatccttgtg   6120

cttgtgcctg aactgcggta acggcaacaa ctttgacgat gtcgtcgact gaacatcccc   6180

ttgacaaatc gttgataggt ttggcaaatc cctgacatat aggaccgatg gcttcggcct   6240

ttgcgaatct ttggaccaac ttgtatccga tgtttcctgc ctggatgtct gggaagatca   6300

agacatttgc cttaccagcg actttagatc caggggcttt caaatctgcg accttcttaa   6360

ccaatgaggc gtctaactgc aattcaccgt cgatgtctaa gtcaggccta gcctccttag   6420

ccaattttgt tgcctttgta accttgtcga ctaattcatg tgaggctgat cccatggttg   6480

agaatgacaa catggctacc cttggctcga tcttgcacaa attctttgca gtctcagcag   6540

tggtaattgc gattgaagat aactcttcag cggtaggaca aacatttaca gcgcagtcag   6600

cgaataacaa aaaaccgtcc tctccatact cgcagtcagg tactgacatc aagaagactg   6660

atgagacgac agatgcacct ggtactgttt tgacaatctg caaaccaggc cttaacaagt   6720

ctcctgtagt atgtatagca ccagatacca aaccgtcagc gtcacctaac ttgaccatca   6780

ttgttgcgaa gtagattggg tccctgacga ttttgtcagc cttctccaag gtgactccct   6840

tgtttttttct gatctcgtag aaagcgttgg cgtaaccggc ggtcttagaa gaagtttctg   6900

ggtcgactat ctctactccg gccaaattta ctccgaattt tgcggcgttt tccttaatga   6960

cagactctga accgaccaag attatgtcgg caataccgtc cctaataatc tcctctgaag   7020

ccctgatgtt cctctcttcc tcaccctctg ccaaaacgat ttcttcttg tcggccttgg   7080

ccaatccgaa gatattctcc atcaatttca ttgtgaaggt agttcgattt tggaggtcgc   7140

gggaggtcga aactaagttc ttggtgtttt aaaactaaaa aaaagactaa ctataaaagt   7200

agaatttaag aagtttaaga aatagattta cagaattaca atcaatacct accgtcttta   7260

tatacttatt agtcaagtag gggaataatt tcagggaact ggtttcaacc ttttttttca   7320

gctttttcca aatcagagag agcagaaggt aatagaaggt gtaagaaaat gagatagata   7380
```

```
catgcgtggg tcaattgcct tgtgtcatca tttactccag gcaggttgca tcactccatt   7440

gaggttgtgc ccgtttttttg cctgtttgtg cccctgttct ctgtagttgc gctaagagaa   7500

tggacctatg aactgatggt tggtgaagaa aacaatattt tggtgctggg attcttttttt   7560

tttctggatg ccagcttaaa aagcgggctc cattatattt agtggatgcc aggaataaac   7620

tgttcaccca gacacctacg atgttatata ttctgtgtaa cccgcccccct attttgggca   7680

tgtacgggtt acagcagaat taaaaggcta atttttttgac taaataaagt taggaaaatc   7740

actactatta attatttacg tattctttga aatggcagta ttgataatga taaactcgaa   7800

ctgaaaaagc gtgtttttta ttcaaaatga ttctaactcc cttacgtaat caaggaatct   7860

ttttgccttg gcctccgcgt cattaaactt cttgttgttg acgctaacat tcaacgctag   7920

tatatattcg tttttttcag gtaagttctt ttcaacgggt cttactgatg aggcagtcgc   7980

gtctgaaagg tccgccggcg ttggacgagc gctccatgct ggacttactc gtcgaagatt   8040

tcctgctact ctctatataa ttagacaccc atgttataga tttcagaaaa caatgtaata   8100

atatatggta gcctcctgaa actaccaagg gaaaaatctc aacaccaaga gctcatattc   8160

gttggaatag cgataatatc tctttacctc aatcttatat gcatgttatt tgctcttata   8220

attggtctct atttagggaa aaaagtcggt ttgagagctt ctcgcgatgt gaaatctcaa   8280

tttgaactgc acgccaaagc tagcccattt cacgaacacc agaaagaaga aatccccaag   8340

gatcgcatga cagagtatgc tctctcatat cgttgagtat gaatgccaat acactgatca   8400

gctttacaag aaacgtaaaa tctggcacga tggtagactg aaatactttc agttaaacaa   8460

cagattcatg ctttatacgg aaaaggataa cgttttgtta gctagtgagg cggtttaaac   8520

gcgtggccgt gccgtc                                                 8536
```

<210> SEQ ID NO 49
<211> LENGTH: 9734
<212> TYPE: DNA
<213> ORGANISM: Artificial Sequence
<220> FEATURE:
<223> OTHER INFORMATION: Synthetic construct: i74810 integration construct

<400> SEQUENCE: 49

```
gacggcacgg ccacgcgttt aaaccgcccg ctcgcctcat ccccacggga ataaggcagc     60

cgacaaaaga aaaacgaccg aaaaggaacc agaaagaaaa aagagggtgg gcgcgccgcg    120

gacgtgtaaa aagatatgca tccagcttct atatcgcttt aactttaccg ttttgggcat    180

cgggaacgta tgtaacattg atctcctctt gggaacggtg agtgcaacga atgcgatata    240

gcaccgacca tgtgggcaaa ttcgtaataa attcggggtg agggggattc aagacaagca    300

accttgttag tcagctcaaa cagcgattta acggttgagt aacacatcaa aacaccgttc    360

gaggtcaagc ctggcgtgtt taacaagttc ttgatatcat atataaatgt aataagaagt    420

ttggtaatat tcaattcgaa gtgttcagtc ttttacttct cttgttttat agaagaaaaa    480

acatcaagaa acatctttaa catacacaaa cacatactat cagaatacac gctcgtccaa    540

cgccggcgga cctttcagac gcgactgcct catcagtaag acccgttgaa aagaacttac    600

ctgaaaaaaa cgaatatata ctagcgttga atgttagcgt caacaacaag aagtttaatg    660

acgcggaggc caaggcaaaa agattccttg attacgtaag ggagttagaa tcattttgaa    720

taaaaaacac gctttttcag ttcgagttta tcattatcaa tactgccatt tcaaagaata    780

cgtaaataat taatagtagt gattttccta actttattta gtcaaaaaat tagccttta     840

attctgctgt aacccgtaca tgcccaaaat agggggcggg ttacacagaa tatataacat    900
```

-continued

```
cgtaggtgtc tgggtgaaca gtttattcct ggcatccact aaatataatg gagcccgctt    960

tttaagctgg catccagaaa aaaaaagaat cccagcacca aaatattgtt ttcttcacca   1020

accatcagtt catagtccca ttctcttagc gcaactacag agaacagggg cacaaacagg   1080

caaaaaacgg gcacaacctc aatggagtga tgcaacctgc ctggagtaaa tgatgacaca   1140

aggcaattga cccacgcatg tatctatctc attttcttac accttctatt accttctgct   1200

ctctctgatt tggaaaaagc tgaaaaaaaa ggttgaaacc agttccctga aattattccc   1260

ctacttgact aataagtata taaagacggt aggtattgat tgtaattctg taaatctatt   1320

tcttaaactt cttaaattct acttttatag ttagtctttt ttttagtttt aaaacaccaa   1380

gaacttagtt tcgacctccc gcgacctcca aaatcgaact accttcacaa tggctgattt   1440

cgattctaaa gaatacttgg agttagttga caagtggtgg cgtgccacca actacttgtc   1500

cgctggtatg attttcttga agtccaaccc attattctct gttactaata ccccaatcaa   1560

ggccgaagat gtcaaagtta aaccaattgg tcactggggt actatttccg gtcaaacttt   1620

cttatacgcc cacgctaacc gtttgattaa caagtacggt ctcaacatgt tttacgttgg   1680

tggtccaggt cacggtggtc aagtcatggt tactaacgcc tacttagacg gtgcctacac   1740

cgaagattac ccagaaatta ctcaagacat cgaaggtatg tctcatttgt tcaagcgttt   1800

ctctttccct ggtggtattg gttcccatat gaccgctcaa actccaggtt ccttgcacga   1860

aggtggtgaa ttgggttact ctttgtccca tgctttcggt gctgttttgg acaacccaga   1920

ccaagttgct tttgctgtcg ttggtgatgg tgaagctgaa actggtccat ctatggcctc   1980

ttggcattcc attaagttct taaatgccaa gaacgatggt gccgttttgc cagttttgga   2040

tttaaacggt ttcaagattt ccaatccaac catttttttct agaatgtctg atgaagaaat   2100

tactaagttc ttcgaaggtt tgggttattc ccctagattc attgaaaatg atgacattca   2160

cgactacgcc acctaccacc aattggccgc taacatctta gatcaagcca tcgaagacat   2220

tcaagctatt caaaatgacg ccagagagaa tggtaaatat caagatggtg aaattccagc   2280

ttggcctgtt attatcgcta gattgccaaa gggttggggt ggtccaaccc acgatgcttc   2340

taataatcca attgaaaact ctttcagagc tcaccaagtt ccattaccat tggaacaaca   2400

cgatttggcc accttgccag aattcgaaga ttggatgaac tcttacaagc cagaagaatt   2460

attcaacgct gatggttcct tgaaggatga gttgaaagct attgccccaa agggtgataa   2520

gagaatgtct gctaacccaa tcaccaacgg tggtgctgac agatccgact tgaaattgcc   2580

aaattggaga gaattcgcta acgacatcaa cgacgatacc agaggtaagg aattcgctga   2640

ctctaagaga aacatggata tggctacttt atccaactat ttaggtgccg tttctcaatt   2700

gaacccaacc agattcagat tcttcggtcc agatgaaacc atgtccaaca gattgtgggg   2760

tttgtttaat gttaccccac gtcaatggat ggaagaaatc aaggaaccac aagatcaatt   2820

gttgtctcca actggtcgta tcatcgattc ccaattgtct gaacaccaag ctgaaggttg   2880

gttggaaggt tacactttga ctggtagagt tggtatcttt gcctcttacg aatctttctt   2940

gagagttgtt gataccatgg tcactcaaca tttcaagtgg ttgcgtcacg cttccgaaca   3000

agcttggaga aatgactatc catccttaaa tttgatcgct acctctaccg ctttccaaca   3060

agatcataac ggttatactc accaagaccc tggtatgtta actcatttgg ccgagaagaa   3120

gtctaacttc attagagaat atttgccagc cgacggtaac tctttgttag ccgttcaaga   3180

gagagctttc tctgaaagac ataaggttaa cttattgatc gcttctaaac aaccaagaca   3240

acaatggttc actgttgaag aagctgaagt cttagctaac gaaggtttga agattatcga   3300
```

```
ttgggcttct actgctccat cttccgatgt tgatattact tttgcttctg ccggtactga   3360
accaaccatt gagactttgg ccgccttatg gttgattaat caagctttcc ctgacgttaa   3420
gtttagatac gttaacgttg ttgaattgtt aagattgcaa aagaaatctg aaccaaacat   3480
gaacgacgaa agagaattat ctgccgaaga atttaataag tacttccaag ccgacactcc   3540
agttatcttc ggtttccacg cttacgaaaa cttgattgaa tctttctttt tcgagagaaa   3600
gttcaccggt gatgtctatg ttcacggtta tagagaagat ggtgatatca ctaccaccta   3660
cgatatgaga gtctattccc acttggatcg tttccatcaa gccaaggaag ccgccgaaat   3720
cttgtctgct aacggtaaaa tcgaccaagc cgctgccgac acctttattg ctaagatgga   3780
cgacactttg gccaaacact tccaagttac tagaaatgaa ggtagagata ttgaagaatt   3840
cactgactgg acttggtctc cattgaagta agtgaattta ctttaaatct tgcatttaaa   3900
taaattttct ttttatagct ttatgactta gtttcaattt atatactatt ttaatgacat   3960
tttcgattca ttgattgaaa gctttgtgtt ttttcttgat gcgctattgc attgttcttg   4020
tctttttcgc cacatgtaat atctgtagta gatacctgat acattgtgga tgctgagtga   4080
aattttagtt aataatggag gcgctcttaa taattttggg gatattggct tatccccgcg   4140
tgcttggccg gccgtacact gagtaatggt agttataaga aagagaccga gttagggaca   4200
gttagaggcg gtggagatat tccttatggc atgtctggcg atgataaaac ttttcaaacg   4260
gcagccccga tctaaaagag ctgacaggga aatggtcaga aaaagaaacg tgcacccgcc   4320
cgtctggacg cgccgctcac ccgcacggca gagaccaatc agtaaaaatc aacggttaac   4380
gacattacta tatatataat ataggaagca tttaatagaa cagcatcgta atatatgtgt   4440
actttgcagt tatgacgcca gatggcagta gtggaagata ttctttattg aaaaatagct   4500
tgtcacctta cgtacaatct tgatccggag cttttctttt tttgccgatt aagaattcgg   4560
tcgaaaaaag aaaaggagag ggccaagagg gagggcattg gtgactattg agcacgtgag   4620
tatacgtgat taagcacaca aaggcagctt ggagtatgtc tgttattaat ttcacaggta   4680
gttctggtcc attggtgaaa gtttgcggct tgcagagcac agaggccgca gaatgtgctc   4740
tagattccga tgctgacttg ctgggtatta tatgtgtgcc caatagaaag agaacaattg   4800
acccggttat tgcaaggaaa atttcaagtc ttgtaaaagc atataaaaat agttcaggca   4860
ctccgaaata cttggttggc gtgtttcgta atcaacctaa ggaggatgtt ttggctctgg   4920
tcaatgatta cggcattgat atcgtccaac tgcatggaga tgagtcgtgg caagaatacc   4980
aagagttcct cggtttgcca gttattaaaa gactcgtatt tccaaaagac tgcaacatac   5040
tactcagtgc agcttcacag aaacctcatt cgtttattcc cttgtttgat tcagaagcag   5100
gtgggacagg tgaacttttg gattggaact cgatttctga ctgggttgga aggcaagaga   5160
gccccgaaag cttacatttt atgttagctg gtggactgac gccagaaaat gttggtgatg   5220
cgcttagatt aaatggcgtt attggtgttg atgtaagcgg aggtgtggag acaaatggtg   5280
taaaagactc taacaaaata gcaaatttcg tcaaaaatgc taagaaatag gttattactg   5340
agtagtattt atttaagtat tgtttgtgca cttgcctgca ggccttttga aaagcaagca   5400
taaaagatct aaacataaaa tctgtaaaat aacaagatgt aaagataatg ctaaatcatt   5460
tggctttttg attgattgta caggaaaata tacatcgcag gggggttgact tttaccattt   5520
caccgcaatg gaatcaaact tgttgaagag aatgttcaca ggcgcatacg ctacaatgac   5580
acggccggcc aagcacgcgg ggataagcca atatccccaa aattattaag agcgcctcca   5640
ttattaacta aaatttcact cagcatccac aatgtatcag gtatctacta cagatattac   5700
```

atgtggcgaa aaagacaaga acaatgcaat agcgcatcaa gaaaaaacac aaagctttca 5760
atcaatgaat cgaaaatgtc attaaaatag tatataaatt gaaactaagt cataaagcta 5820
taaaaagaaa atttatttaa atgcaagatt taaagtaaat tcacttactt caatggagac 5880
caagtccagt cagtgaattc ttcaatatct ctaccttcat ttctagtaac ttggaagtgt 5940
ttggccaaag tgtcgtccat cttagcaata aaggtgtcgg cagcggcttg gtcgatttta 6000
ccgttagcag acaagatttc ggcggcttcc ttggcttgat ggaaacgatc caagtgggaa 6060
tagactctca tatcgtaggt ggtagtgata tcaccatctt ctctataacc gtgaacatag 6120
acatcaccgg tgaactttct ctcgaaaaag aaagattcaa tcaagttttc gtaagcgtgg 6180
aaaccgaaga taactggagt gtcggcttgg aagtacttat taaattcttc ggcagataat 6240
tctctttcgt cgttcatgtt tggttcagat ttcttttgca atcttaacaa ttcaacaacg 6300
ttaacgtatc taaacttaac gtcagggaaa gcttgattaa tcaaccataa ggcggccaaa 6360
gtctcaatgg ttggttcagt accggcagaa gcaaaagtaa tatcaacatc ggaagatgga 6420
gcagtagaag cccaatcgat aatcttcaaa ccttcgttag ctaagacttc agcttcttca 6480
acagtgaacc attgttgtct tggttgttta gaagcgatca ataagttaac cttatgtctt 6540
tcagagaaag ctctctcttg aacggctaac aaagagttac cgtcggctgg caaatattct 6600
ctaatgaagt tagacttctt ctcggccaaa tgagttaaca taccagggtc ttggtgagta 6660
taaccgttat gatcttgttg gaaagcggta gaggtagcga tcaaatttaa ggatggatag 6720
tcatttctcc aagcttgttc ggaagcgtga cgcaaccact tgaaatgttg agtgaccatg 6780
gtatcaacaa ctctcaagaa agattcgtaa gaggcaaaga taccaactct accagtcaaa 6840
gtgtaacctt ccaaccaacc ttcagcttgg tgttcagaca attgggaatc gatgatacga 6900
ccagttggag acaacaattg atcttgtggt tccttgattt cttccatcca ttgacgtggg 6960
gtaacattaa acaaacccca caatctgttg gacatggttt catctggacc gaagaatctg 7020
aatctggttg ggttcaattg agaaacggca cctaaatagt tggataaagt agccatatcc 7080
atgtttctct tagagtcagc gaattcctta cctctggtat cgtcgttgat gtcgttagcg 7140
aattctctcc aatttggcaa tttcaagtcg gatctgtcag caccaccgtt ggtgattggg 7200
ttagcagaca ttctcttatc accctttggg gcaatagctt tcaactcatc cttcaaggaa 7260
ccatcagcgt tgaataattc ttctggcttg taagagttca tccaatcttc gaattctggc 7320
aaggtggcca aatcgtgttg ttccaatggt aatggaactt ggtgagctct gaaagagttt 7380
tcaattggat tattagaagc atcgtgggtt ggaccacccc aaccctttgg caatctagcg 7440
ataataacag gccaagctgg aatttcacca tcttgatatt taccattctc tctggcgtca 7500
ttttgaatag cttgaatgtc ttcgatggct tgatctaaga tgttagcggc caattggtgg 7560
taggtggcgt agtcgtgaat gtcatcattt tcaatgaatc taggggaata acccaaacct 7620
tcgaagaact tagtaatttc ttcatcagac attctagaaa aaatggttgg attggaaatc 7680
ttgaaaccgt ttaaatccaa aactggcaaa acggcaccat cgttcttggc atttaagaac 7740
ttaatggaat gccaagaggc catagatgga ccagtttcag cttcaccatc accaacgaca 7800
gcaaaagcaa cttggtctgg gttgtccaaa acagcaccga aagcatggga caaagagtaa 7860
cccaattcac caccttcgtg caaggaacct ggagtttgag cggtcatatg ggaaccaata 7920
ccaccaggga aagagaaacg cttgaacaaa tgagacatac cttcgatgtc ttgagtaatt 7980
tctgggtaat cttcggtgta ggcaccgtct aagtaggcgt tagtaaccat gacttgacca 8040
ccgtgacctg gaccaccaac gtaaaacatg ttgagaccgt acttgttaat caaacggtta 8100

```
gcgtgggcgt ataagaaagt ttgaccggaa atagtacccc agtgaccaat tggtttaact   8160

ttgacatctt cggccttgat tggggtatta gtaacagaga ataatgggtt ggacttcaag   8220

aaaatcatac cagcggacaa gtagttggtg gcacgccacc acttgtcaac taactccaag   8280

tattctttag aatcgaaatc agccattgtg aaggtagttc gattttggag gtcgcgggag   8340

gtcgaaacta agttcttggt gttttaaaac taaaaaaaag actaactata aaagtagaat   8400

ttaagaagtt taagaaatag atttacagaa ttacaatcaa tacctaccgt ctttatatac   8460

ttattagtca agtaggggaa taatttcagg gaactggttt caaccttttt tttcagcttt   8520

ttccaaatca gagagagcag aaggtaatag aaggtgtaag aaaatgagat agatacatgc   8580

gtgggtcaat tgccttgtgt catcatttac tccaggcagg ttgcatcact ccattgaggt   8640

tgtgcccgtt ttttgcctgt ttgtgcccct gttctctgta gttgcgctaa gagaatggac   8700

ctatgaactg atggttggtg aagaaaacaa tattttggtg ctgggattct ttttttttct   8760

ggatgccagc ttaaaaagcg ggctccatta tatttagtgg atgccaggaa taaactgttc   8820

acccagacac ctacgatgtt atatattctg tgtaacccgc cccctatttt gggcatgtac   8880

gggttacagc agaattaaaa ggctaatttt ttgactaaat aaagttagga aaatcactac   8940

tattaattat ttacgtattc tttgaaatgg cagtattgat aatgataaac tcgaactgaa   9000

aaagcgtgtt ttttattcaa aatgattcta actcccttac gtaatcaagg aatctttttg   9060

ccttggcctc cgcgtcatta aacttcttgt tgttgacgct aacattcaac gctagtatat   9120

attcgttttt ttcaggtaag ttcttttcaa cgggtcttac tgatgaggca gtcgcgtctg   9180

aaaggtccgc cggcgttgga cgagcgtgta ccaacctgca tttctttccg tcatatacac   9240

aaaatacttt catataaact tacttggtct tacgtcataa ataaatatgt atacatataa   9300

attaaaaaat ttggttttat atttttacaa aaagaatcgt ttacttcatt tctccctttt   9360

aagcgataca atccatgaaa aaagagaaaa agagagaaca ggcttgtgcc ttctttaaaa   9420

catcccacac aaaatcatat tgaattgaat tttacatctt aagctagtgt acaacaactg   9480

ctatatccaa agaaaactaa cgtggaccgc ttttagagtt gagaaaaagg tttgaaaaaa   9540

atagcaatac aaagacttgt ttcatatata aaatacaggg agcacattga gctaatataa   9600

cataaacact gcgaaccaat tccaatcaaa aggtacacat gagagcattc ccccgagtac   9660

tgccatttcg ccatcagaga tcatataata acatccttct tcgaacggcg gtttaaacgc   9720

gtggccgtgc cgtc                                                     9734
```

```
<210> SEQ ID NO 50
<211> LENGTH: 7980
<212> TYPE: DNA
<213> ORGANISM: Artificial Sequence
<220> FEATURE:
<223> OTHER INFORMATION: Synthetic construct: i76221 integration
      construct

<400> SEQUENCE: 50
```

```
gacggcacgg ccacgcgttt aaaccgccgc acgtgtatgt acggctgtgt aaatatgata     60

atcatctcgg acgaacggcg tagtactctc catcccctaa aaatgttcac gtgtgactgc    120

tccatttcgc cggatgtcga gatgaccccc ccccctcaaa aggcactcac ctgctgacat    180

gccgtggcaa atgattgggg tcatcctttt tttctgttat ctctaagatc caaagaaaag    240

taaaaaaaaa aggttggggt acgaattgcc gccgagcctc cgatgccatt attcaatggg    300

tattgcagtt ggggtatagt tcctcggtgg caaatagttc tcccttcatt ttgtatataa    360

actgggcggc tattctaagc atatttctcc cttaggttat ctggtagtac gttatatctt    420
```

-continued

```
gttcttatat tttctatcta taagcaaaac caaacatatc aaaactacta gaaagacatt    480
gccccactgt gttcgctcgt ccaacgccgg cggacctttc agacgcgact gcctcatcag    540
taagacccgt tgaaaagaac ttacctgaaa aaaacgaata tatactagcg ttgaatgtta    600
gcgtcaacaa caagaagttt aatgacgcgg aggccaaggc aaaaagattc cttgattacg    660
taagggagtt agaatcattt tgaataaaaa acacgctttt tcagttcgag tttatcatta    720
tcaatactgc catttcaaag aatacgtaaa taattaatag tagtgatttt cctaacttta    780
tttagtcaaa aaattagcct tttaattctg ctgtaacccg tacatgccca aaataggggg    840
cgggttacac agaatatata acatcgtagg tgtctgggtg aacagtttat tcctggcatc    900
cactaaatat aatggagccc gctttttaag ctggcatcca gaaaaaaaaa gaatcccagc    960
accaaaatat tgttttcttc accaaccatc agttcatagg tccattctct tagcgcaact   1020
acagagaaca ggggcacaaa caggcaaaaa acgggcacaa cctcaatgga gtgatgcaac   1080
ctgcctggag taaatgatga cacaaggcaa ttgacccacg catgtatcta tctcattttc   1140
ttacaccttc tattaccttc tgctctctct gatttggaaa aagctgaaaa aaaaggttga   1200
aaccagttcc ctgaaattat tcccctactt gactaataag tatataaaga cggtaggtat   1260
tgattgtaat tctgtaaatc tatttcttaa acttcttaaa ttctactttt atagttagtc   1320
ttttttttag ttttaaaaca ccaagaactt agtttcgacc tcccgcgacc tccaaaatcg   1380
aactaccttc acaatggaac attctgtaat cgaaccaact gtgcccatgc cgctaccagc   1440
catgtttgac gctccatctg gtatttttag ctctttggac gacgctgtgc aagcagccac   1500
cttagcccaa caacaactaa gttcagttga gttgcgtcag caagtaatca aagccataag   1560
agtggccgga gaaaggtatg cacaagtttt ggctgaaatg gcagttgctg aaactggtat   1620
gggtagggtg gtggataagt acattaagaa tgtctctcaa gctcgtcata cgcctggtat   1680
agaatgttta tcggccgagg ttcttacggg tgataatggc ctaacattga ttgaaaatgc   1740
cccttgggga gtcgtagctt cagtcacgcc aagcacaaat ccagcagcta cggtaattaa   1800
taatgcaatc tcaatgattg cagcggggaa ttcagtcgtg ttcgcaccac atccttctgc   1860
caaaaacgtc tcactaagga ctatttcttt actcaacaag gccattgtcg ctaccggcgg   1920
cccagaaaat ttactagtta gtgtggcaaa ccctaacatc gaaactgcac agagattatt   1980
cagatatccg ggtattggat tgttagttgt gacaggtggt gaagccgtcg ttgaagccgc   2040
taggaagcat acagataaaa ggttaattgc agccggcgct ggtaatcctc ctgttgttgt   2100
ggacgaaact gctgacatac ctaaagccgc aagagcaatt gtcaagggtg cttctttcga   2160
caacaacata atttgtgctg atgaaaaagt tttgattgtg gtagacagag ttgcagatgc   2220
actattggca gaaatgcaaa gaaataacgc cgtcttactt acacccgaac agaccgaaag   2280
actactaccc gctcttttgt ccgatattga cgaacagggc aaaggacgtg tgaatagaga   2340
ttatgttgga agagatgcgg ctaaattagc agcggctatt ggtctggaag ttagcgaaca   2400
tactcgtcta ctcctggcag agacagacgc tgatcatcca ttcgccgtga cggagctgat   2460
gatgccagtg ttaccagtaa taagagtcaa gaatgtagat gatgcaatcg cattggcagt   2520
taagctagag tcaggctgca gacacacagc tgcgatgcac tctactaata taagaaactt   2580
aaatagaatg gctaatgcca tcaatacctc tatctttgta aaaaatggtc catgtattgc   2640
aggtttgggt ttaggcggtg aaggttggac ttcaatgact attagcactc cgaccggtga   2700
aggtgttaca agcgctcgta cctttgtcag attaagaagg tgtgtcttag tcgacatgtt   2760
tcggattgct taagcggccg cgagtaataa ttattgcttc catataatat ttttatatac   2820
```

```
ctcttatttt tatgtattag ttaattaagt atttttatct atctgcttat cattttcttt   2880
tcatataggg ggggttggtg ttttcttgcc catcagattg atgtcctcca actcggcact   2940
attttacaaa gggttttttt gtaagagaag gagaagacag atactaaacc atacgttact   3000
cgaaacaaaa aaaaaaaaaa tggaaaaagc tgctatcaac aaaagacggc ctcatcaaac   3060
ctaaagaaac catgtcagcg tatgtatata ccttgtaatt tacgtttcct taaatcttct   3120
ttctactaac gttttcatta ttctatactc tatgaccaat aaaaacagac tgtactttca   3180
aaatttaccc agtaggccag caaataaaga aaattatacc agattacttc tgaaacacat   3240
taatcccaac aacaagtatg ccattaatcc gtcgctaccc catccccgcg tgcttggccg   3300
gccgtttctc gacgtgggcc tttttcttgc catatggatc cgctgcacgg tcctgttccc   3360
tagcatgtac gtgagcgtat ttccttttaa accacgacgc tttgtcttca ttcaacgttt   3420
cccattgttt ttttctacta ttgctttgct gtgggaaaaa cttatcgaaa gatgacgact   3480
ttttcttaat tctcgtttta agagcttggt gagcgctagg agtcactgcc aggtatcgtt   3540
tgaacacggc attagtcagg gaagtcataa cacagtcctt tcccgcaatt ttctttttct   3600
attactcttg gcctcctcta gtacactcta tattttttta tgcctcggta atgattttca   3660
tttttttttt tccacctagc ggatgactct tttttttct tagcgattgg cattatcaca   3720
taatgaatta tacattatat aaagtaatgt gatttcttcg aagaatatac taaaaaatga   3780
gcaggcaaga taaacgaagg caaagatgac agagcagaaa gccctagtaa agcgtattac   3840
aaatgaaacc aagattcaga ttgcgatctc tttaaagggt ggtcccctag cgatagagca   3900
ctcgatcttc ccagaaaaag aggcagaagc agtagcagaa caggccacac aatcgcaagt   3960
gattaacgtc cacacaggta tagggtttct ggaccatatg atacatgctc tggccaagca   4020
ttccggctgg tcgctaatcg ttgagtgcat tggtgactta cacatagacg accatcacac   4080
cactgaagac tgcgggattg ctctcggtca agcttttaaa gaggccctag gggccgtgcg   4140
tggagtaaaa aggtttggat caggatttgc gcctttggat gaggcacttt ccagagcggt   4200
ggtagatctt tcgaacaggc cgtacgcagt tgtcgaactt ggtttgcaaa gggagaaagt   4260
aggagatctc tcttgcgaga tgatcccgca ttttcttgaa agctttgcag aggctagcag   4320
aattaccctc cacgttgatt gtctgcgagg caagaatgat catcaccgta gtgagagtgc   4380
gttcaaggct cttgcggttg ccataagaga agccacctcg cccaatggta ccaacgatgt   4440
tccctccacc aaaggtgttc ttatgtagtg acaccgatta tttaaagctg cagcatacga   4500
tatatataca tgtgtatata tgtataccta tgaatgtcag taagtatgta tacgaacagt   4560
atgatactga agatgacaag gtaatgcatc attctatacg tgtcattctg aacgaggcgc   4620
gctttccttt tttctttttg ctttttcttt ttttttctct tgaactcgac ggccggccaa   4680
gcacgcgggg atggggtagc gacggattaa tggcatactt gttgttggga ttaatgtgtt   4740
tcagaagtaa tctggtataa ttttctttat ttgctggcct actgggtaaa ttttgaaagt   4800
acagtctgtt tttattggtc atagagtata gaataatgaa aacgttagta gaaagaagat   4860
ttaaggaaac gtaaattaca aggtatatac atacgctgac atggtttctt taggtttgat   4920
gaggccgtct tttgttgata gcagcttttt ccattttttt tttttttgtt tcgagtaacg   4980
tatggtttag tatctgtctt ctccttctct tacaaaaaaa ccctttgtaa aatagtgccg   5040
agttggagga catcaatctg atgggcaaga aaacaccaac ccccccctata tgaaaagaaa   5100
atgataagca gatagataaa aatacttaat taactaatac ataaaaataa gaggtatata   5160
aaaatattat atggaagcaa taattattac tcgcggccgc ttaagcaatc cgaaacatgt   5220
```

-continued

```
cgactaagac acaccttctt aatctgacaa aggtacgagc gcttgtaaca ccttcaccgg   5280
tcggagtgct aatagtcatt gaagtccaac cttcaccgcc taaacccaaa cctgcaatac   5340
atggaccatt ttttacaaag atagaggtat tgatggcatt agccattcta tttaagtttc   5400
ttatattagt agagtgcatc gcagctgtgt gtctgcagcc tgactctagc ttaactgcca   5460
atgcgattgc atcatctaca ttcttgactc ttattactgg taacactggc atcatcagct   5520
ccgtcacggc gaatggatga tcagcgtctg tctctgccag gagtagacga gtatgttcgc   5580
taacttccag accaatagcc gctgctaatt tagccgcatc tcttccaaca taatctctat   5640
tcacacgtcc tttgccctgt tcgtcaatat cggacaaaag agcgggtagt agtctttcgg   5700
tctgttcggg tgtaagtaag acggcgttat ttctttgcat ttctgccaat agtgcatctg   5760
caactctgtc taccacaatc aaaacttttt catcagcaca aattatgttg ttgtcgaaag   5820
aagcaccctt gacaattgct cttgcggctt taggtatgtc agcagtttcg tccacaacaa   5880
caggaggatt accagcgccg gctgcaatta accttttatc tgtatgcttc ctagcggctt   5940
caacgacggc ttcaccacct gtcacaacta acaatccaat acccggatat ctgaataatc   6000
tctgtgcagt ttcgatgtta gggtttgcca cactaactag taaattttct gggccgccgg   6060
tagcgacaat ggccttgttg agtaaagaaa tagtccttag tgagacgttt ttggcagaag   6120
gatgtggtgc gaacacgact gaattccccg ctgcaatcat tgagattgca ttattaatta   6180
ccgtagctgc tggatttgtg cttggcgtga ctgaagctac gactccccaa ggggcatttt   6240
caatcaatgt taggccatta tcacccgtaa gaacctcggc cgataaacat tctataccag   6300
gcgtatgacg agcttgagag acattcttaa tgtacttatc caccacccta cccataccag   6360
tttcagcaac tgccatttca gccaaaactt gtgcatacct ttctccggcc actcttatgg   6420
ctttgattac ttgctgacgc aactcaactg aacttagttg ttgttgggct aaggtggctg   6480
cttgcacagc gtcgtccaaa gagctaaaaa taccagatgg agcgtcaaac atggctggta   6540
gcggcatggg cacagttggt tcgattacag aatgttccat tgtgaaggta gttcgatttt   6600
ggaggtcgcg ggaggtcgaa actaagttct tggtgtttta aaactaaaaa aaagactaac   6660
tataaaagta gaatttaaga agtttaagaa atagatttac agaattacaa tcaataccta   6720
ccgtctttat atacttatta gtcaagtagg ggaataattt cagggaactg gtttcaacct   6780
ttttttcag ctttttccaa atcagagaga gcagaaggta atagaaggtg taagaaaatg    6840
agatagatac atgcgtgggt caattgcctt gtgtcatcat ttactccagg caggttgcat   6900
cactccattg aggttgtgcc cgtttttttgc ctgtttgtgc ccctgttctc tgtagttgcg   6960
ctaagagaat ggacctatga actgatggtt ggtgaagaaa acaatatttt ggtgctggga   7020
ttcttttttt ttctggatgc cagcttaaaa agcgggctcc attatattta gtggatgcca   7080
ggaataaact gttcacccag acacctacga tgttatatat tctgtgtaac ccgcccccta   7140
ttttgggcat gtacgggtta cagcagaatt aaaaggctaa ttttttgact aaataaagtt   7200
aggaaaatca ctactattaa ttatttacgt attctttgaa atggcagtat tgataatgat   7260
aaactcgaac tgaaaaagcg tgttttttat tcaaaatgat tctaactccc ttacgtaatc   7320
aaggaatctt tttgccttgg cctccgcgtc attaaacttc ttgttgttga cgctaacatt   7380
caacgctagt atatattcgt ttttttcagg taagttcttt tcaacgggtc ttactgatga   7440
ggcagtcgcg tctgaaaggt ccgccggcgt tggacgagcg tgatgatttc tttccttttt   7500
atattgacga cttttttttt ttcgtgtgtt tttgttctct tataaccgag ctgcttactt   7560
attattattt caccttctct ttttatttat acttataatt atttattctt tacatactgt   7620
```

```
tacaagaaac tcttttctac attaattgca taaagtgtca atcagcacat cctctatatc   7680

gctatcaaca acaaatttga caaacctgcc tatatcttca ggaacaactg ccgcatcgct   7740

accaccacta cttgtgaagt ccctggagtt taatatgcac tgaaatttac ctagccgttt   7800

tacacaagac cataatccat ccatgctatc gcagtatatg attttgtgtt cgtttttcgt   7860

cttgcgaaag gcatcctcaa tggcttgttt cattgatcca tcagtgtggc tcgtaggtac   7920

cagcaaaacc acttcatcag cggcgtactc ctggcggttt aaacgcgtgg ccgtgccgtc   7980
```

<210> SEQ ID NO 51
<211> LENGTH: 13266
<212> TYPE: DNA
<213> ORGANISM: Artificial Sequence
<220> FEATURE:
<223> OTHER INFORMATION: Synthetic construct: i84022 integration construct

<400> SEQUENCE: 51

```
gacggcacgg ccacgcgttt aaaccgccaa gtgatgtaac taaatacacg attaccatgg     60

aaattaacgt acctttttttg tgcgtgtatt gaaatattat gacatattac agaaagggtt    120

cgcaagtcct gtttctatgc ctttctctta gtaattcacg aaataaacct atggtttacg    180

aaatgatcca cgaaaatcat gttattattt acatcaacat atcgcgaaaa ttcatgtcat    240

gtccacatta acatcattgc agagcaacaa ttcattttca tagagaaatt tgctactatc    300

acccactagt actaccattg gtacctacta ctttgaattg tactaccgct gggcgttatt    360

aggtgtgaaa ccacgaaaag ttcaccataa cttcgaataa agtcgcggaa aaaagtaaac    420

agctattgct actcaaatga ggtttgcaga agcttgttga agcatgatga agcgttctaa    480

acgcactatt catcattaaa tatttaaagc tcataaaatt gtattcaatt cctattctaa    540

atggctttta tttctattac aactattagc tctaaatcca tatcctcata agcagcaatc    600

aattctatct atactttaaa cgctcgtcca acgccggcgg acctgatgtg tattactagt    660

gtcgacgaca gcattcgccc agtatttttt ttattctaca aaccttctat aatttcaaag    720

tatttacata attctgtatc agtttaatca ccataatatc gttttctttg tttagtgcaa    780

ttaatttttc ctattgttac ttcgggcctt tttctgtttt atgagctatt ttttccgtca    840

tccttccgga tccagatttt cagcttcatc tccagattgt gtctacgtaa tgcacgccat    900

cattttaaga gaggacctcc cgcgacctcc aaaatcgaac taccttcaca atgaaacttc    960

ttagtagtat tgagcaggcg tgtgacatct gtagattgaa gaaattgaaa tgtagtaagg   1020

agaagcccaa atgtgcgaaa tgccttaaaa ataattggga atgcagatat agtccgaaga   1080

cgaagcgcag tccccttacc cgcgcgcacc ttacggaggt cgagagtcgc cttgagcgcc   1140

ttgagcaact ttccttcttt atcttcccca gagaggattt ggatatgatc cttaagatgg   1200

acagtcttca agacattaag gcgcttctta cggggctttt cgtgcaggac aacgtcaaca   1260

aggacgcggt gacggaccgc cttgccagtg tcgaaaccga catgcccctt acgcttcgcc   1320

aacaccgcat ttccgccacg agtagtagtg aggaatcctc caataagggg cagcgccaac   1380

ttaccgtgag tatcgatagt gcggcccacc acgacaatag tacgatcccc cttgacttca   1440

tgccgcgcga cgccttgcac gggttcgact ggagtgagga agacgatatg agtgacggtc   1500

ttccgtttct taagaccgat ccgaataaca acggtttttt cggtgatggg agtttgcttt   1560

gcatcttgag aagtatcggt ttcaagcccg agaactatac caatagtaat gtcaatcgct   1620

tgcccacgat gatcaccgac cgctataccc ttgccagtcg cagtacgacg agtagacttt   1680

tgcagtccta cttgaacaac ttccatccgt attgtcccat tgtccatagt cccaccctta   1740
```

```
tgatgcttta caacaatcaa atcgagattg ccagtaaaga ccagtggcag attttgttca   1800
attgtattct tgcgatcggg gcgtggtgca ttgaaggtga gagtaccgac attgacgtct   1860
tctattacca gaacgccaag agtcacctta cctccaaagt gtttgaaagt gggagtatta   1920
tccttgtcac ggcgcttcac ttgcttagta gatacacgca atggcgccaa aagacgaaca   1980
cctcctacaa cttccattcc ttcagtattc gcatggcgat tagtcttggt cttaaccgcg   2040
atttgccgag tagtttttcc gactcctcca tccttgagca gcgcagaaga atctggtgga   2100
gtgtgtatag ttgggaaatt cagcttagtc ttttgtacgg gagaagtatt caattgagtc   2160
aaaacacgat tagttttccc agtagtgtgg atgacgtcca aagaacgacg acggggccga   2220
cgatttacca cggtattatc gagacggcgc gcttgcttca ggtctttacg aagatttacg   2280
agcttgataa gacggtgacc gcggagaagt cccccatttg cgcgaagaag tgtcttatga   2340
tctgcaacga aatcgaagaa gtcagtcgcc aagcgccgaa attccttcag atggacatca   2400
gtacgacggc ccttacgaac cttcttaaag agcatccctg gcttagtttc acgcgctttg   2460
agcttaaatg gaagcaactt agtttgatta tctacgtgct tcgcgacttc tttaccaact   2520
tcacgcaaaa gaaaagtcag cttgagcaag accagaacga ccaccagtcc tacgaggtca   2580
agagatgtag tattatgctt tccgacgcgg cgcagcgcac cgtcatgagt gtgtcctcct   2640
acatggataa ccacaacgtg acgccgtact tcgcgtggaa ctgcagttac tatcttttta   2700
acgcggtgct tgtgccgatt aaaacccttt tgagtaatag taagagtaac gccgaaaaca   2760
atgaaacggc gcagcttctt cagcagatca ataccgtcct tatgcttctt aagaagcttg   2820
cgaccttcaa gattcaaacc tgcgagaagt atatccaggt gcttgaggaa gtgtgcgccc   2880
ccttccttct tagtcaatgc gcgattccgc ttccccacat ttcctacaat aactccaacg   2940
ggtccgcgat caagaacatc gtggggagtg cgaccattgc gcagtatccc accttgcccg   3000
aagagaacgt gaataacatt tccgtcaagt acgtcagtcc cggtagtgtg ggtcccagtc   3060
ccgtcccgct taagagtggg gcgtcctttt ccgaccttgt gaaacttctt agtaatagac   3120
cgccgagtag aaatagtccg gtcacgattc cgcgctccac gcccagtcac agaagtgtga   3180
ccccccttcct tggtcagcaa cagcaacttc agagtcttgt cccgcttacg cccagtgccc   3240
ttttcggggg tgcgaacttc aaccagtccg gtaacatcgc cgactccagt cttagtttta   3300
cctttaccaa ttcctccaat gggcccaatt tgattacgac ccagacgaac agtcaggcct   3360
tgagtcagcc gatcgcgagt agtaatgtcc acgacaattt tatgaacaac gagattaccg   3420
cctccaagat cgacgacggg aacaacagta agccgcttag tcccgggtgg accgatcaga   3480
ccgcctacaa tgccttcggg attaccacgg gtatgttcaa cacgaccacg atggacgacg   3540
tgtacaatta cctttttgac gacgaggaca cgccgccgaa tccgaagaag gaatgagcca   3600
attggtgcgg caattgataa taacgaaaat gtcttttaat gatctgggta taatgaggaa   3660
ttttccgaac gtttttactt tatatatata tatacatgta acatatattc tatacgctat   3720
atcgagaaaa cgcgatggtg ggtgactttt caactcggcg tatccccgcg tgcttggccg   3780
gccgtagtta tgacaattac aacaacagaa ttctttctat atatgcacga acttgtaata   3840
tggaagaaat tatgacgtac aaactataaa gtaaatattt tacgtaacac atggtgctgt   3900
tgtgcttctt tttcaagaga ataccaatga cgtatgacta agtttatgta ttttccaaaa   3960
cctgtttagc cctggcgaca gatacgtctc cggcttcaac gatgaccctg gtgaccctgt   4020
caatgtcggc tccggtggca ccggccatga ttgcgatgtt ccttgcgtgt aaggtcatgt   4080
gtcccctttg gattccctcg gttgccaagg ccctaattgc ggccatattc tgagccaaac   4140
```

-continued

```
caacggcggc agtaacctgg gccaactcag tagcggtttc gacctgcatt aaggccaaag   4200
cggccctagc tgtagggtga gtcttggtgg ctcctcctac caaacccaag gccaaaggca   4260
attcaatggt accgaccaac ctaccgtcgt tggccaactc ccaccttgtc aaagaggtgt   4320
aatgtccggt cctggcggcg taggcgtggg ctccagcttc gatggccctc cagtcgttac   4380
ctgttgcgac gacgactggg tcaattccgt tcataattcc cttgttatgg gttgcggccc   4440
tgtaagggtc gactattgct aaggcgcagg cttcaaccat tccccttgca acgtcggcac   4500
catcgtatcc ctgggtggtc aaagtctcag ggctaactc aaccctggct cttaccaacc    4560
tcaagtcggc caagttagac aaaatcctca acctgacggt tccaccagcg atcctctcta   4620
cctctggagc taacctttca gccatggtgt taactgtgtt ggcacccatg gcgtctctga   4680
catcaacaat caagtgcaat acgaccattg caccaacagg ggtgtcccta aaaacatgga   4740
cctcaatgtc tctgcaacca ccacctaaac caaccaaaac tggatctacg gcatctgctg   4800
cttccatgaa agcagcctta tggccaaca acctttgcct agctccttct gggtctccta    4860
atccgacaac ttggatttgg gccctcatta aaggtgcagt tccgtgtgcg gtgaatccac   4920
cgttctctct agctatcctt gccatatatg aggctgcggc aacaacagat ggttcctcga   4980
ctgccatagg tattaagtag tcccttccgt tgacggtgaa gttggtggcg acacccaatg   5040
gcaactcaaa ttttccgata acattctcga tcataccgtt ggccaatgac aaaggcaaag   5100
caccgttacc ggccaatgca gaaatggctt caggttccaa tcctgcggct tcggcaaccc   5160
taactaacct ctgagcagga tccaagtccc tcatcttctc gatccttgag ttcaatccgt   5220
cgatgtgacc tgtctttcca gtcattgtaa agttagttgg ttgcgcgact tcgggtgggg   5280
taagtataga ggtatattaa caatttttg ttgatacttt tatgacattt gaataagaag    5340
taatacaaac cgaaaatgtt gaaagtatta gttaaagtgg ttatgcagct tttgcattta   5400
tatatctgtt aatagatcaa aaatcatcgc ttcgctgatt aattacccca gaaataaggc   5460
taaaaaacta atcgcattat tatcctatgg ttgttaattt gattcgttga tttgaaggtt   5520
tgtggggcca ggttactgcc aatttttcct cttcataacc ataaaagcta gtattgtaga   5580
atctttattg ttcggagcag tgcggcgcga ggcacatctg cgtttcagga acgcgaccgg   5640
tgaagaccag gacgcacgga ggagagtctt ccgtcggagg gctgtcgccc gctcggcggc   5700
ttctaatccg tacttcaata tagcaatgag cagttaagcg tattactgaa agttccaaag   5760
agaaggtttt tttaggctaa gataatgggg ctctttacat ttccacaaca tataagtaag   5820
attagatatg gatatgtata tggtggtatt gccatgtaat atgattatta aacttctttg   5880
cgtccatcca aaaaaaaagt aacgcacgca cactcccgac agacaactag cttgataatg   5940
tctcagaacg tttacattgt atcgactgcc agaaccccaa ttggttcatt ccagggttct   6000
ctatcctcca agacagcagt ggaattgggt gctgttgctt taaaaggcgc cttggctaag   6060
gttccagaat tggatgcatc caaggatttt gacgaaatta tttttggtaa cgttctttct   6120
gccaatttgg gccaagctcc ggccagacaa gttgctttgg ctgccggttt gagtaatcat   6180
atcgttgcaa gcacagttaa caaggtctgt gcatccgcta tgaaggcaat cattttgggt   6240
gctcaatcca tcaaatgtgg taatgctgat gttgtcgtag ctggtggttg tgaatctatg   6300
actaacgcac catactacat gccagcagcc cgtgcgggtg ccaaatttgg ccaaactgtt   6360
cttgttgatg gtgtcgaaag agatgggttg aacgatgcgt acgatggtct agccatgggt   6420
gtacacgcag aaaagtgtgc ccgtgattgg gatattacta gagaacaaca agacaatttt   6480
gccatcgaat cctaccaaaa atctcaaaaa tctcaaaagg aaggtaaatt cgacaatgaa   6540
```

-continued

```
attgtacctg ttaccattaa gggatttaga ggtaagcctg atactcaagt cacgaaggac   6600
gaggaacctg ctagattaca cgttgaaaaa ttgagatctg caaggactgt tttccaaaaa   6660
gaaaacggta ctgttactgc cgctaacgct tctccaatca acgatggtgc tgcagccgtc   6720
atcttggttt ccgaaaaagt tttgaaggaa aagaatttga agcctttggc tattatcaaa   6780
ggttggggtg aggccgctca tcaaccagct gattttacat gggctccatc tcttgcagtt   6840
ccaaaggctt tgaaacatgc tggcatcgaa gacatcaatt ctgttgatta ctttgaattc   6900
aatgaagcct tttcggttgt cggtttggtg aacactaaga ttttgaagct agacccatct   6960
aaggttaatg tatatggtgg tgctgttgct ctaggtcacc cattgggttg ttctggtgct   7020
agagtggttg ttacactgct atccatctta cagcaagaag gaggtaagat cggtgttgcc   7080
gccatttgta atggtggtgg tggtgcttcc tctattgtca ttgaaaagat atgattacgt   7140
tctgcgattt tctcatgatc tttttcataa aatacataaa tatataaatg gctttatgta   7200
taacaggcat aatttaaagt tttatttgcg attcatcgtt tttcaggtac tcaaacgctg   7260
aggtgtgcct tttgacttac ttttccgcct tggcaagctg gccgaacctg caggccgcga   7320
gcgccgatac gaaaatcgtt attgtcttga aggtgaaatt tctactctta ttaatggtga   7380
acgttaagct gatgctatga tggaagctga ttggtcttaa cttgcttgtc atcttgctaa   7440
tggtcattgg ctcgtgttat tacttaagtt atttgtactc gttttgaacg taatgctaat   7500
gatcatctta tggaataata gtgagtggtt tcagggtcca taaagctttt caattcatct   7560
ttttttttt tgttcttttt tttgattccg gtttctttga aatttttttg attcggtaat   7620
ctccgagcag aaggaagaac gaaggaagga gcacagactt agattggtat atatacgcat   7680
atgtggtgtt gaagaaacat gaaattgccc agtattctta acccaactgc acagaacaaa   7740
aacctgcagg aaacgaagat aaatcatgtc gaaagctaca tataaggaac gtgctgctac   7800
tcatcctagt cctgttgctg ccaagctatt taatatcatg cacgaaaagc aaacaaactt   7860
gtgtgcttca ttggatgttc gtaccaccaa ggaattactg gagttagttg aagcattagg   7920
tcccaaaatt tgtttactaa aaacacatgt ggatatcttg actgattttt ccatggaggg   7980
cacagttaag ccgctaaagg cattatccgc caagtacaat tttttactct tcgaagacag   8040
aaaatttgct gacattggta atacagtcaa attgcagtac tctgcgggtg tatacagaat   8100
agcagaatgg gcagacatta cgaatgcaca cggtgtggtg ggcccaggta ttgttagcgg   8160
tttgaagcag gcggcggaag aagtaacaaa ggaacctaga ggcctttttga tgttagcaga   8220
attgtcatgc aagggctccc tagctactgg agaatatact aagggtactg ttgacattgc   8280
gaagagtgac aaagattttg ttatcggctt tattgctcaa agagacatgg gtggaagaga   8340
tgaaggttac gattggttga ttatgacacc cggtgtgggt ttagatgaca agggagacgc   8400
attgggtcaa cagtatagaa ccgtggatga tgtggtctct acaggatctg acattattat   8460
tgttggaaga ggactatttg caaagggaag ggatgctaag gtagagggtg aacgttacag   8520
aaaagcaggc tgggaagcat atttgagaag atgcggccag caaaactaaa aaactgtatt   8580
ataagtaaat gcatgtatac taaactcaca aattagagct tcaatttaat tatatcagtt   8640
attaccacga aaatcgttat tgtcttgaag gtgaaatttc tactcttatt aatggtgaac   8700
gttaagctga tgctatgatg gaagctgatt ggtcttaact tgcttgtcat cttgctaatg   8760
gtcatatggc tcgtgttatt acttaagtta tttgtactcg ttttgaacgt aatgctaatg   8820
atcatcttat ggaataatag tgaacggccg gccaagcacg cggggattga atgagaaaaa   8880
aaatcggttg ggcttaactt taaagaaaaa agttgagatt agatttattg tgttataaat   8940
```

```
atagatatac aattctttat aaaaaaaata tatatatata tcattgttat taaataaaga    9000
gttttcctag tatatagatt aaaaaactac tctattaaat gagagctaaa aaaagcaggc    9060
tgccaaaaaa ataaagcatt tatgaagggg gttcagcaag atgcaatcga tgggggaaga    9120
ttatttttta acatcgtaag atcttctaaa tttgtcatcg atgttggtca agtagtaaac    9180
accactttgc aaatgctcaa tggaaccttg aggtttgaag ttcttcttca aatgggcatt    9240
ttctctcaat tcgatggcag cttcgtaatc ctttggagtt tcggtgattc tcttggctaa    9300
tttgttagta atatctaatt ccttgataat atgttggacg tcaccaacaa ttttgcaaga    9360
atatagagat gcagctaaac cggaaccgta agaaaataaa ccaacacgct tgccttgtaa    9420
gtcgtcagat ccaacatagt ttaatagaga tgcaaaggcg gcataaacag atgcggtgta    9480
catgttacct gtgtttgttg gaacaatcaa agattgggca actctctctt tgtggaatgg    9540
cttagcaaca ttaacaaaag ttttttcaat gttcttatcg gttaaagatt cgtcataatc    9600
gcgagtagct aattcggcgt caacttctgg gaacaattga ggattggctc tgaaatcgtt    9660
atatagtaat ctaccgtatg attttgtgac caatttacag gttggaacat ggaaaacgtt    9720
gtagtcgaaa tatttcaaaa cgttcaaagc atccgaacca gcgggatcgc taaccaaccc    9780
tttagaaata gccttcttgg aataactctt gtaaacttga tcaagagcct tgacgtaaca    9840
agttaatgaa aaatgaccat cgacgtaagg atattcgctg gtgaaatctg gcttgtaaaa    9900
atcgtaggcg tgttccatgt aagaagctct tacagagtca aatacaattg gagcatcagg    9960
accgatccac atagcaacag taccggcacc accggttggt cttgcggcac ccttatcgta   10020
gatggcaata tcaccgcaaa ctacaatggc gtctctacca tcccatgcgt tagattcaat   10080
ccagttcaaa gagttgaaca acgcgttggt accaccgtaa caggcattaa gcgtgtcaat   10140
accttcgacg tcagtgtttt caccaaacaa ttgcatcaag acagacttga cagacttgga   10200
cttgtcaatc agagtttcag taccgacttc taatctacca attttgttgg tgtcgatgtt   10260
gtaactcttg atcaacttag acaaaacagt tagggacatc gagtagatat cttctctgtc   10320
attgacaaaa gacatgttgg tttggcccag accaattgtg tatttacctt gagaaacgcc   10380
atcaaatttc tctagctcag attggttgac acattgagtt gggatgtaaa tttggatacc   10440
tttaataccg acattttgag gtctggtttt ttgttcagcg gtcttttgtt tttttagttc   10500
agtcatttgc aagtttgtat tgtgtaattg ttgttgcttt tgcggcctaa gtcttccttt   10560
aataccacac caacaaagtt tagttgagag tttcattgtg aaggtagttc gattttggag   10620
gtcgcgggag gttacttttt ttttggatgg acgcaaagaa gtttaataat catattacat   10680
ggcaatacca ccatatacat atccatatct aatcttactt atatgttgtg gaaatgtaaa   10740
gagccccatt atcttagcct aaaaaaacct tctctttgga actttcagta atacgcttaa   10800
ctgctcattg ctatattgaa gtacggatta gaagccgccg agcgggcgac agccctccga   10860
cggaagactc tcctccgtgc gtcctggtct tcaccggtcg cgttcctgaa acgcagatgt   10920
gcctcgcgcc gcactgctcc gaacaataaa gattctacaa tactagcttt tatggttatg   10980
aagaggaaaa attggcagta acctggcccc acaaaccttc aaatcaacga atcaaattaa   11040
caaccatagg ataataatgc gattagtttt ttagccttat ttctggggta attaatcagc   11100
gaagcgatga tttttgatct attaacagat atataaatgc aaaagctgca taaccacttt   11160
aactaatact ttcaacattt tcggtttgta ttacttctta ttcaaatgtc ataaaagtat   11220
caacaaaaaa ttgttaatat acctctatac ttaccccacc cgaagtcgcg caaccaacta   11280
actttacaat gactggaaag acaggtcaca tcgacggatt gaactcaagg atcgagaaga   11340
```

```
tgagggactt ggatcctgct cagaggttag ttagggttgc cgaagccgca ggattggaac  11400

ctgaagccat ttctgcattg gccggtaacg gtgctttgcc tttgtcattg gccaacggta  11460

tgatcgagaa tgttatcgga aaatttgagt tgccattggg tgtcgccacc aacttcaccg  11520

tcaacggaag ggactactta atacctatgg cagtcgagga accatctgtt gttgccgcag  11580

cctcatatat ggcaaggata gctagagaga acggtggatt caccgcacac ggaactgcac  11640

ctttaatgag ggcccaaatc caagttgtcg gattaggaga cccagaagga gctaggcaaa  11700

ggttgttggc ccataaggct gctttcatgg aagcagcaga tgccgtagat ccagttttgg  11760

ttggtttagg tggtggttgc agagacattg aggtccatgt ttttagggac acccctgttg  11820

gtgcaatggt cgtattgcac ttgattgttg atgtcagaga cgccatgggt gccaacacag  11880

ttaacaccat ggctgaaagg ttagctccag aggtagagag gatcgctggt ggaaccgtca  11940

ggttgaggat tttgtctaac ttggccgact tgaggttggt aagagccagg gttgagttag  12000

cccctgagac tttgaccacc cagggatacg atggtgccga cgttgcaagg ggaatggttg  12060

aagcctgcgc cttagcaata gtcgaccctt acagggccgc aacccataac aagggaatta  12120

tgaacggaat tgacccagtc gtcgtcgcaa caggtaacga ctggagggcc atcgaagctg  12180

gagcccacgc ctacgccgcc aggaccggac attacacctc tttgacaagg tgggagttgg  12240

ccaacgacgg taggttggtc ggtaccattg aattgccttt ggccttgggt ttggtaggag  12300

gagccaccaa gactcaccct acagctaggg ccgctttggc cttaatgcag gtcgaaaccg  12360

ctactgagtt ggcccaggtt actgccgccg ttggtttggc tcagaatatg gccgcaatta  12420

gggccttggc aaccgaggga atccaaaggg gacacatgac cttacacgca aggaacatcg  12480

caatcatggc cggtgccacc ggagccgaca ttgacagggt caccagggtc atcgttgaag  12540

ccggagacgt atctgtcgcc agggctaaac aggttttgga aaatacataa acttagtcat  12600

acgtcattgg tattctcttg aaaaagaagc acaacagcac catgtgttac gtaaaatatt  12660

tactttatag tttgtacgtc ataatttctt ccatattaca agttcgtgca tatatagaaa  12720

gaattctgtt gttgtaattg tcataactag gtccgccggc gttggacgag cgaatgtgta  12780

tattagttta aaaagttgta tgtaataaaa gtaaaattta atattttgga tgaaaaaaac  12840

catttttaga ctttttctta actagaatgc tggagtagaa atacgccatc tcaagataca  12900

aaaagcgtta ccggcactga tttgtttcaa ccagtatata gattattatt gggtcttgat  12960

caactttcct cagacatatc agtaacagtt atcaagctaa atatttacgc gaaagaaaaa  13020

caaatatttt aattgtgata cttgtgaatt ttattttatt aaggatacaa agttaagaga  13080

aaacaaaatt tatatacaat ataagtaata ttcatatata tgtgatgaat gcagtcttaa  13140

cgagaagaca tggccttggt gacaactctc ttcaaaccaa cttcagcctt tctcaattca  13200

tcagcagatg ggtcttcgat ttgcaaagca gccaaagcgg cggtttaaac gcgtggccgt  13260

gccgtc                                                              13266
```

<210> SEQ ID NO 52
<211> LENGTH: 13712
<212> TYPE: DNA
<213> ORGANISM: Artificial Sequence
<220> FEATURE:
<223> OTHER INFORMATION: Synthetic construct: i84024 integration construct

<400> SEQUENCE: 52

```
gacggcacgg ccacgcgttt aaaccgccaa gtgatgtaac taaatacacg attaccatgg     60

aaattaacgt accttttttg tgcgtgtatt gaaatattat gacatattac agaaagggtt    120
```

-continued

```
cgcaagtcct gtttctatgc ctttctctta gtaattcacg aaataaacct atggtttacg    180
aaatgatcca cgaaaatcat gttattattt acatcaacat atcgcgaaaa ttcatgtcat    240
gtccacatta acatcattgc agagcaacaa ttcattttca tagagaaatt tgctactatc    300
acccactagt actaccattg gtacctacta ctttgaattg tactaccgct gggcgttatt    360
aggtgtgaaa ccacgaaaag ttcaccataa cttcgaataa agtcgcggaa aaaagtaaac    420
agctattgct actcaaatga ggtttgcaga agcttgttga agcatgatga agcgttctaa    480
acgcactatt catcattaaa tatttaaagc tcataaaatt gtattcaatt cctattctaa    540
atggctttta tttctattac aactattagc tctaaatcca tatcctcata agcagcaatc    600
aattctatct atactttaaa cgctcgtcca acgccggcgg acctgatgtg tattactagt    660
gtcgacgaca gcattcgccc agtatttttt ttattctaca aaccttctat aatttcaaag    720
tatttacata attctgtatc agtttaatca ccataatatc gttttctttg tttagtgcaa    780
ttaatttttc ctattgttac ttcgggcctt tttctgtttt atgagctatt ttttccgtca    840
tccttccgga tccagatttt cagcttcatc tccagattgt gtctacgtaa tgcacgccat    900
cattttaaga gaggacctcc cgcgacctcc aaaatcgaac taccttcaca atgaaacttc    960
ttagtagtat tgagcaggcg tgtgacatct gtagattgaa gaaattgaaa tgtagtaagg   1020
agaagcccaa atgtgcgaaa tgccttaaaa ataattggga atgcagatat agtccgaaga   1080
cgaagcgcag tccccttacc cgcgcgcacc ttacggaggt cgagagtcgc cttgagcgcc   1140
ttgagcaact tttccttctt atcttcccca gagaggattt ggatatgatc cttaagatgg   1200
acagtcttca agacattaag gcgcttctta cggggctttt cgtgcaggac aacgtcaaca   1260
aggacgcggt gacggaccgc cttgccagtg tcgaaaccga catgcccctt acgcttcgcc   1320
aacaccgcat ttccgccacg agtagtagtg aggaatcctc caataagggg cagcgccaac   1380
ttaccgtgag tatcgatagt gcggcccacc acgacaatag tacgatcccc cttgacttca   1440
tgccgcgcga cgccttgcac gggttcgact ggagtgagga agacgatatg agtgacggtc   1500
ttccgtttct taagaccgat ccgaataaca acggtttttt cggtgatggg agtttgcttt   1560
gcatcttgag aagtatcggt ttcaagcccg agaactatac caatagtaat gtcaatcgct   1620
tgcccacgat gatcaccgac cgctataccc ttgccagtcg cagtacgacg agtagacttt   1680
tgcagtccta cttgaacaac ttccatccgt attgtcccat tgtccatagt cccaccctta   1740
tgatgcttta caacaatcaa atcgagattg ccagtaaaga ccagtggcag attttgttca   1800
attgtattct tgcgatcggg gcgtggtgca ttgaaggtga gagtaccgac attgacgtct   1860
tctattacca gaacgccaag agtcacctta cctccaaagt gtttgaaagt gggagtatta   1920
tccttgtcac ggcgcttcac ttgcttagta gatacacgca atggcgccaa aagacgaaca   1980
cctcctacaa cttccattcc ttcagtattc gcatggcgat tagtcttggt cttaaccgcg   2040
atttgccgag tagtttttcc gactcctcca tccttgagca gcgcagaaga atctggtgga   2100
gtgtgtatag ttgggaaatt cagcttagtc ttttgtacgg gagaagtatt caattgagtc   2160
aaaacacgat tagttttccc agtagtgtgg atgacgtcca aagaacgacg acggggccga   2220
cgatttacca cggtattatc gagacggcgc gcttgcttca ggtctttacg aagatttacg   2280
agcttgataa gacggtgacc gcggagaagt cccccatttg cgcgaagaag tgtcttatga   2340
tctgcaacga aatcgaagaa gtcagtcgcc aagcgccgaa attccttcag atggacatca   2400
gtacgacggc ccttacgaac cttcttaaag agcatccctg gcttagtttc acgcgctttg   2460
agcttaaatg gaagcaactt agtttgatta tctacgtgct tcgcgacttc tttaccaact   2520
```

```
tcacgcaaaa gaaaagtcag cttgagcaag accagaacga ccaccagtcc tacgaggtca   2580
agagatgtag tattatgctt tccgacgcgg cgcagcgcac cgtcatgagt gtgtcctcct   2640
acatggataa ccacaacgtg acgccgtact tcgcgtggaa ctgcagttac tatcttttta   2700
acgcggtgct tgtgccgatt aaaacccttt tgagtaatag taagagtaac gccgaaaaca   2760
atgaaacggc gcagcttctt cagcagatca ataccgtcct tatgcttctt aagaagcttg   2820
cgaccttcaa gattcaaacc tgcgagaagt atatccaggt gcttgaggaa gtgtgcgccc   2880
ccttccttct tagtcaatgc gcgattccgc ttccccacat ttcctacaat aactccaacg   2940
ggtccgcgat caagaacatc gtggggagtg cgaccattgc gcagtatccc accttgcccg   3000
aagagaacgt gaataacatt tccgtcaagt acgtcagtcc cggtagtgtg ggtcccagtc   3060
ccgtcccgct taagagtggg gcgtcctttt ccgaccttgt gaaacttctt agtaatagac   3120
cgccgagtag aaatagtccg gtcacgattc cgcgctccac gcccagtcac agaagtgtga   3180
ccccccttcct tggtcagcaa cagcaacttc agagtcttgt cccgcttacg cccagtgccc   3240
ttttcggggg tgcgaacttc aaccagtccg gtaacatcgc cgactccagt cttagtttta   3300
cctttaccaa ttcctccaat gggcccaatt tgattacgac ccagacgaac agtcaggcct   3360
tgagtcagcc gatcgcgagt agtaatgtcc acgacaattt tatgaacaac gagattaccg   3420
cctccaagat cgacgacggg aacaacagta agccgcttag tcccgggtgg accgatcaga   3480
ccgcctacaa tgccttcggg attaccacgg gtatgttcaa cacgaccacg atggacgacg   3540
tgtacaatta ccttttttgac gacgaggaca cgccgccgaa tccgaagaag gaatgagcca   3600
attggtgcgg caattgataa taacgaaaat gtcttttaat gatctgggta taatgaggaa   3660
ttttccgaac gtttttactt tatatatata tatacatgta acatatattc tatacgctat   3720
atcgagaaaa cgcgatggtg gggtgacttt caactcggcg tatccccgcg tgcttggccg   3780
gccgtccgca tgactcaaga gaagcatgtg gtttttgagt ttttttcgtt gaattttcag   3840
gtaaagctca atagttatga caattacaac aacagaattc tttctatata tgcacgaact   3900
tgtaatatgg aagaaattat gacgtacaaa ctataaagta aatattttac gtaacacatg   3960
gtgctgttgt gcttcttttt caagagaata ccaatgacgt atgactaagt ttaggattta   4020
atgcaggtga cggacccatc tttcaaacga tttatatcag tggcgtccaa attgttaggt   4080
tttgttggtt cagcaggttt cctgttgtgg gtcatatgac tttgaaccaa atggccggct   4140
gctagggcag cacataagga taattcacct gccaagacgg cacaggcaac tattcttgct   4200
aattgacgtg cgttggtacc aggagcggta gcatgtgggc ctcttacacc taataagtcc   4260
aacatggcac cttgtggttc tagaacagta ccaccaccga tggtacctac ttcgatggat   4320
ggcatggata cggaaattct caaatcaccg tccacttctt tcatcaatgt tatacagttg   4380
gaactttcga cattttgtgc aggatcttgt cctaatgcca agaaaacagc tgtcactaaa   4440
ttagctgcat gtgcgttaaa tccaccaaca gacccagcca ttgcagatcc aaccaaattc   4500
ttagcaatgt tcaactcaac caatgcggaa acatcacttt ttaacacttt tctgacaaca   4560
tcaccaggaa tagtagcttc tgcgacgaca ctcttaccac gaccttcgat ccagttgatg   4620
gcagctggtt ttttgtcggt acagtagtta ccagaaacgg agacaacctc catatcttcc   4680
cagccatact cttctaccat ttgctttaat gagtattcga caccccttaga aatcatattc   4740
atacccattg cgtcaccagt agttgttcta aatctcatga agagtaaatc tcctgctaga   4800
caagtttgaa tatgttgcag acgtgcaaat cttgatgtag agttaaaagc ttttttaatt   4860
gcgttttgtc cctcttctga gtctaaccat atcttacagg caccagatct tttcaaagtt   4920
```

```
gggaaacgga ctactgggcc tcttgtcata ccatccttag ttaaaacagt tgttgcacca   4980

ccgccagcat tgattgcctt acagccacgc atggcagaag ctaccaaaca accctctgta   5040

gttgccattg gtatatgata agatgtacca tcgataacca aggggcctat aacaccaacg   5100

ggcaaaggca tgtaacctat aacattttca caacaagcgc caaatacgcg gtcgtagtca   5160

taatttttat atggtaaacg atcagatgct aatacaggag cttctgccaa aattgaaaga   5220

gccttcctac gtaccgcaac cgctctcgta gtatcaccta atttttctc caaagcgtac    5280

aaaggtaact taccgtgaat aaccaaggca gcgacctctt tgttcttcaa ttgttttgta   5340

tttccactac ttaataatgc ttctaattct tctaaaggac gtattttctt atccaagctt   5400

tcaatatcgc gggaatcatc ttcctcacta gatgatgaag gtcctgatga gctcgattgc   5460

gcagatgata aacttttgac tttcgatcca gaaatgactg ttttattggt taaaactggt   5520

gtagaagcct tttgtacagg agcagtaaaa gacttcttgg tgacttcagt cttcaccaat   5580

tggtctgcag ccattgtaaa gttagttggt tgcgcgactt cgggtggggt aagtatagag   5640

gtatattaac aatttttgt tgatactttt atgacattg aataagaagt aatacaaacc     5700

gaaaatgttg aaagtattag ttaaagtggt tatgcagctt ttgcatttat atatctgtta   5760

atagatcaaa aatcatcgct tcgctgatta attaccccag aaataaggct aaaaaactaa   5820

tcgcattatt atcctatggt tgttaatttg attcgttgat ttgaaggttt gtggggccag   5880

gttactgcca atttttcctc ttcataacca taaaagctag tattgtagaa tctttattgt   5940

tcggagcagt gcggcgcgag gcacatctgc gtttcaggaa cgcgaccggt gaagaccagg   6000

acgcacggag gagagtcttc cgtcggaggg ctgtcgcccg ctcggcggct tctaatccgt   6060

acttcaatat agcaatgagc agttaagcgt attactgaaa gttccaaaga gaaggttttt   6120

ttaggctaag ataatggggc tctttacatt tccacaacat ataagtaaga ttagatatgg   6180

atatgtatat ggtggtattg ccatgtaata tgattattaa acttctttgc gtccatccaa   6240

aaaaaaagta acgcacgcac actcccgaca gacaactagc ttgataatga ctgatgttcg   6300

tttcagaatc atcggtaccg gtgcctatgt tccagaaaga attgtttcta acgacgaagt   6360

tggtgctcca gctggtgttg atgacgactg gatcaccaga aagactggta tcagacaaag   6420

aagatgggct gctgatgacc aagctacttc tgacttagct actgctgctg gtagagccgc   6480

cttgaaggct gctggtatta ctccagaaca attgactgtt atcgctgttg ctacctccac   6540

tccagataga ccacaaccac ctaccgctgc ctacgttcaa caccacttgg gtgctactgg   6600

tactgctgct ttcgacgtta acgctgtttg ttccggtact gttttcgcct tatcttctgt   6660

cgccggtacc ttggtctaca gaggtggtta tgctttggtt atcggtgctg acttgtactc   6720

cagaatcttg aatccagctg acagaaagac cgttgttttg ttcggtgatg gtgctggtgc   6780

tatggttttg ggtccaactt ctactggtac tggtccaatc gttagaagag tcgctttaca   6840

cacctttggt ggtttaaccg atttgattag agttccagct ggtggttcta gacaaccatt   6900

ggacactgac ggtttggacg ccggtttgca atactttgcc atggacggta gagaagttag   6960

acgtttcgtc actgaacatt tgccacaatt gatcaaaggt ttcttgcatg aagctggtgt   7020

tgacgctgct gatatttctc atttcgtccc acatcaagcc aacggtgtta tgttggacga   7080

agtttttggt gaattgcatt tgccaagagc taccatgcac agaactgttg aaacttacgg   7140

taataccggt gctgcttcca ttccaattac tatggacgct gctgttagag ccggttcctt   7200

tagaccaggt gaattggtct tattggctgg ttttggtggt ggtatggccg cctctttcgc   7260

cttgattgaa tggtagatgc tatgtaatag acaataaaac catgtttata taaaaaaaat   7320
```

-continued tcaaaataga aaacgattct gtacaaggag tatttttttt ttgttctagt gtgtttatat 7380
tatccttggc taagaggcac taacctgcag gccgcgagcg ccgatacgaa aatcgttatt 7440
gtcttgaagg tgaaatttct actcttatta atggtgaacg ttaagctgat gctatgatgg 7500
aagctgattg gtcttaactt gcttgtcatc ttgctaatgg tcattggctc gtgttattac 7560
ttaagttatt tgtactcgtt ttgaacgtaa tgctaatgat catcttatgg aataatagtg 7620
agtggtttca gggtccataa agcttttcaa ttcatctttt tttttttgt tcttttttt 7680 gattccggtt tctttgaaat ttttttgatt cggtaatctc cgagcagaag gaagaacgaa 7740
ggaaggagca cagacttaga ttggtatata tacgcatatg tggtgttgaa gaaacatgaa 7800
attgcccagt attcttaacc caactgcaca gaacaaaaac ctgcaggaaa cgaagataaa 7860
tcatgtcgaa agctacatat aaggaacgtg ctgctactca tcctagtcct gttgctgcca 7920
agctatttaa tatcatgcac gaaaagcaaa caaacttgtg tgcttcattg gatgttcgta 7980
ccaccaagga attactggag ttagttgaag cattaggtcc caaaatttgt ttactaaaaa 8040
cacatgtgga tatcttgact gatttttcca tggagggcac agttaagccg ctaaaggcat 8100
tatccgccaa gtacaatttt ttactcttcg aagacagaaa atttgctgac attggtaata 8160
cagtcaaatt gcagtactct gcgggtgtat acagaatagc agaatgggca gacattacga 8220
atgcacacgg tgtggtgggc ccaggtattg ttagcggttt gaagcaggcg gcggaagaag 8280
taacaaagga acctagaggc cttttgatgt tagcagaatt gtcatgcaag ggctccctag 8340
ctactggaga atatactaag ggtactgttg acattgcgaa gagtgacaaa gattttgtta 8400
tcggctttat tgctcaaaga gacatgggtg gaagagatga aggttacgat tggttgatta 8460
tgacacccgg tgtgggttta gatgacaagg gagacgcatt gggtcaacag tatagaaccg 8520
tggatgatgt ggtctctaca ggatctgaca ttattattgt tggaagagga ctatttgcaa 8580
agggaaggga tgctaaggta gagggtgaac gttacagaaa agcaggctgg gaagcatatt 8640
tgagaagatg cggccagcaa aactaaaaaa ctgtattata agtaaatgca tgtatactaa 8700
actcacaaat tagagcttca atttaattat atcagttatt accacgaaaa tcgttattgt 8760
cttgaaggtg aaatttctac tcttattaat ggtgaacgtt aagctgatgc tatgatggaa 8820
gctgattggt cttaacttgc ttgtcatctt gctaatggtc atatggctcg tgttattact 8880
taagttattt gtactcgttt tgaacgtaat gctaatgatc atcttatgga ataatagtga 8940
acggccggcc aagcacgcgg ggattgaatg agaaaaaaaa tcggttgggc ttaactttaa 9000
agaaaaaagt tgagattaga tttattgtgt tataaatata gatatacaat tctttataaa 9060
aaaaatatat atatatatca ttgttattaa ataaagagtt ttcctagtat atagattaaa 9120
aaactactct attaaatgag agctaaaaaa agcaggctgc caaaaaaata aagcatttat 9180
gaagggggtt cagcaagatg caatcgatgg gggaagatta ttttttaaca tcgtaagatc 9240
ttctaaattt gtcatcgatg ttggtcaagt agtaaacacc actttgcaaa tgctcaatgg 9300
aaccttgagg tttgaagttc ttcttcaaat gggcattttc tctcaattcg atggcagctt 9360
cgtaatcctt tggagtttcg gtgattctct tggctaattt gttagtaata tctaattcct 9420
tgataatatg ttggacgtca ccaacaattt tgcaagaata tagagatgca gctaaaccgg 9480
aaccgtaaga aaataaacca acacgcttgc cttgtaagtc gtcagatcca acatagttta 9540
atagagatgc aaaggcggca taaacagatg cggtgtacat gttacctgtg tttgttggaa 9600
caatcaaaga ttgggcaact ctctctttgt ggaatggctt agcaacatta acaaaagttt 9660
tttcaatgtt cttatcggtt aaagattcgt cataatcgcg agtagctaat tcggcgtcaa 9720

```
cttctgggaa caattgagga ttggctctga aatcgttata tagtaatcta ccgtatgatt   9780
ttgtgaccaa tttacaggtt ggaacatgga aaacgttgta gtcgaaatat ttcaaaacgt   9840
tcaaagcatc cgaaccagcg ggatcgctaa ccaacccttt agaaatagcc ttcttggaat   9900
aactcttgta aacttgatca agagccttga cgtaacaagt taatgaaaaa tgaccatcga   9960
cgtaaggata ttcgctggtg aaatctggct tgtaaaaatc gtaggcgtgt tccatgtaag  10020
aagctcttac agagtcaaat acaattggag catcaggacc gatccacata gcaacagtac  10080
cggcaccacc ggttggtctt gcggcaccct tatcgtagat ggcaatatca ccgcaaacta  10140
caatggcgtc tctaccatcc catgcgttag attcaatcca gttcaaagag ttgaacaacg  10200
cgttggtacc accgtaacag gcattaagcg tgtcaatacc ttcgacgtca gtgttttcac  10260
caaacaattg catcaagaca gacttgacag acttggactt gtcaatcaga gtttcagtac  10320
cgacttctaa tctaccaatt ttgttggtgt cgatgttgta actcttgatc aacttagaca  10380
aaacagttag ggacatcgag tagatatctt ctctgtcatt gacaaaagac atgttggttt  10440
ggcccagacc aattgtgtat ttaccttgag aaacgccatc aaatttctct agctcagatt  10500
ggttgacaca ttgagttggg atgtaaattt ggataccttt aataccgaca ttttgaggtc  10560
tggtttttg ttcagcggtc ttttgttttt ttagttcagt catttgcaag tttgtattgt  10620
gtaattgttg ttgcttttgc ggcctaagtc ttcctttaat accacaccaa caaagtttag  10680
ttgagagttt cattgtgaag gtagttcgat tttggaggtc gcgggaggtt actttttttt  10740
tggatggacg caaagaagtt taataatcat attacatggc aataccacca tatacatatc  10800
catatctaat cttacttata tgttgtggaa atgtaaagag ccccattatc ttagcctaaa  10860
aaaaccttct ctttggaact ttcagtaata cgcttaactg ctcattgcta tattgaagta  10920
cggattagaa gccgccgagc gggcgacagc cctccgacgg aagactctcc tccgtgcgtc  10980
ctggtcttca ccggtcgcgt tcctgaaacg cagatgtgcc tcgcgccgca ctgctccgaa  11040
caataaagat tctacaatac tagcttttat ggttatgaag aggaaaaatt ggcagtaacc  11100
tggccccaca aaccttcaaa tcaacgaatc aaattaacaa ccataggata ataatgcgat  11160
tagtttttta gccttatttc tggggtaatt aatcagcgaa gcgatgattt ttgatctatt  11220
aacagatata taaatgcaaa agctgcataa ccactttaac taatactttc aacattttcg  11280
gtttgtatta cttcttattc aaatgtcata aaagtatcaa caaaaaattg ttaatatacc  11340
tctatactta ccccacccga agtcgcgcaa ccaactaact ttacaatggc tgcagaccaa  11400
ttggtgaaga ctgaagtcac caagaagtct tttactgctc ctgtacaaaa ggcttctaca  11460
ccagttttaa ccaataaaac agtcatttct ggatcgaaag tcaaaagttt atcatctgcg  11520
caatcgagct catcaggacc ttcatcatct agtgaggaag atgattcccg cgatattgaa  11580
agcttggata agaaaatacg tcctttagaa gaattagaag cattattaag tagtggaaat  11640
acaaaacaat tgaagaacaa agaggtcgct gccttggtta ttcacggtaa gttacctttg  11700
tacgctttgg agaaaaaatt aggtgatact acgagagcgg ttgcggtacg taggaaggct  11760
ctttcaattt tggcagaagc tcctgtatta gcatctgatc gtttaccata taaaaattat  11820
gactacgacc gcgtatttgg cgcttgttgt gaaaatgtta taggttacat gcctttgccc  11880
gttggtgtta taggcccctt ggttatcgat ggtacatctt atcatatacc aatggcaact  11940
acagagggtt gtttggtagc ttctgccatg cgtggctgta aggcaatcaa tgctggcggt  12000
ggtgcaacaa ctgttttaac taaggatggt atgacaagag gcccagtagt ccgtttccca  12060
actttgaaaa gatctggtgc ctgtaagata tggttagact cagaagaggg acaaaacgca  12120
```

```
attaaaaaag cttttaactc tacatcaaga tttgcacgtc tgcaacatat tcaaacttgt  12180

ctagcaggag atttactctt catgagattt agaacaacta ctggtgacgc aatgggtatg  12240

aatatgattt ctaagggtgt cgaatactca ttaaagcaaa tggtagaaga gtatggctgg  12300

gaagatatgg aggttgtctc cgtttctggt aactactgta ccgacaaaaa accagctgcc  12360

atcaactgga tcgaaggtcg tggtaagagt gtcgtcgcag aagctactat tcctggtgat  12420

gttgtcagaa aagtgttaaa aagtgatgtt tccgcattgg ttgagttgaa cattgctaag  12480

aatttggttg gatctgcaat ggctgggtct gttggtggat ttaacgcaca tgcagctaat  12540

ttagtgacag ctgttttctt ggcattagga caagatcctg cacaaaatgt cgaaagttcc  12600

aactgtataa cattgatgaa agaagtggac ggtgatttga gaatttccgt atccatgcca  12660

tccatcgaag taggtaccat cggtggtggt actgttctag aaccacaagg tgccatgttg  12720

gacttattag gtgtaagagg cccacatgct accgctcctg gtaccaacgc acgtcaatta  12780

gcaagaatag ttgcctgtgc cgtcttggca ggtgaattat ccttatgtgc tgccctagca  12840

gccggccatt tggttcaaag tcatatgacc cacaacagga aacctgctga accaacaaaa  12900

cctaacaatt tggacgccac tgatataaat cgtttgaaag atgggtccgt cacctgcatt  12960

aaatcctaaa cttagtcata cgtcattggt attctcttga aaaagaagca caacagcacc  13020

atgtgttacg taaaatattt actttatagt ttgtacgtca taatttcttc catattacaa  13080

gttcgtgcat atatagaaag aattctgttg ttgtaattgt cataactatt gagctttacc  13140

tgaaaattca acgaaaaaaa ctcaaaaacc acatgcttct cttgagtcat gcggaggtcc  13200

gccggcgttg gacgagcgaa tgtgtatatt agtttaaaaa gttgtatgta ataaaagtaa  13260

aatttaatat tttggatgaa aaaaaccatt tttagacttt ttcttaacta gaatgctgga  13320

gtagaaatac gccatctcaa gatacaaaaa gcgttaccgg cactgatttg tttcaaccag  13380

tatatagatt attattgggt cttgatcaac tttcctcaga catatcagta acagttatca  13440

agctaaatat ttacgcgaaa gaaaaacaaa tattttaatt gtgatacttg tgaattttat  13500

tttattaagg atacaaagtt aagagaaaac aaaatttata tacaatataa gtaatattca  13560

tatatatgtg atgaatgcag tcttaacgag aagacatggc cttggtgaca actctcttca  13620

aaccaacttc agcctttctc aattcatcag cagatgggtc ttcgatttgc aaagcagcca  13680

aagcggcggt ttaaacgcgt ggccgtgccg tc                                13712
```

<210> SEQ ID NO 53
<211> LENGTH: 13964
<212> TYPE: DNA
<213> ORGANISM: Artificial Sequence
<220> FEATURE:
<223> OTHER INFORMATION: Synthetic construct: i84026 integration construct

<400> SEQUENCE: 53

```
gacggcacgg ccacgcgttt aaaccgccaa gtgatgtaac taaatacacg attaccatgg     60

aaattaacgt accttttttg tgcgtgtatt gaaatattat gacatattac agaaagggtt    120

cgcaagtcct gtttctatgc ctttctctta gtaattcacg aaataaacct atggtttacg    180

aaatgatcca cgaaaatcat gttattattt acatcaacat atcgcgaaaa ttcatgtcat    240

gtccacatta acatcattgc agagcaacaa ttcattttca tagagaaatt tgctactatc    300

acccactagt actaccattg gtacctacta ctttgaattg tactaccgct gggcgttatt    360

aggtgtgaaa ccacgaaaag ttcaccataa cttcgaataa agtcgcggaa aaaagtaaac    420

agctattgct actcaaatga ggtttgcaga agcttgttga agcatgatga agcgttctaa    480
```

```
acgcactatt catcattaaa tatttaaagc tcataaaatt gtattcaatt cctattctaa    540

atggctttta tttctattac aactattagc tctaaatcca tatcctcata agcagcaatc    600

aattctatct atactttaaa cgctcgtcca acgccggcgg acctgatgtg tattactagt    660

gtcgacgaca gcattcgccc agtatttttt ttattctaca aaccttctat aatttcaaag    720

tatttacata attctgtatc agtttaatca ccataatatc gttttctttg tttagtgcaa    780

ttaatttttc ctattgttac ttcgggcctt tttctgtttt atgagctatt ttttccgtca    840

tccttccgga tccagatttt cagcttcatc tccagattgt gtctacgtaa tgcacgccat    900

cattttaaga gaggacctcc cgcgacctcc aaaatcgaac taccttcaca atgaaacttc    960

ttagtagtat tgagcaggcg tgtgacatct gtagattgaa gaaattgaaa tgtagtaagg   1020

agaagcccaa atgtgcgaaa tgccttaaaa ataattggga atgcagatat agtccgaaga   1080

cgaagcgcag tccccttacc cgcgcgcacc ttacggaggt cgagagtcgc cttgagcgcc   1140

ttgagcaact tttccttctt atcttcccca gagaggattt ggatatgatc cttaagatgg   1200

acagtcttca agacattaag gcgcttctta cggggctttt cgtgcaggac aacgtcaaca   1260

aggacgcggt gacggaccgc cttgccagtg tcgaaaccga catgcccctt acgcttcgcc   1320

aacaccgcat ttccgccacg agtagtagtg aggaatcctc caataagggg cagcgccaac   1380

ttaccgtgag tatcgatagt gcggcccacc acgacaatag tacgatcccc cttgacttca   1440

tgccgcgcga cgccttgcac gggttcgact ggagtgagga agacgatatg agtgacggtc   1500

ttccgtttct taagaccgat ccgaataaca acggtttttt cggtgatggg agtttgcttt   1560

gcatcttgag aagtatcggt ttcaagcccg agaactatac caatagtaat gtcaatcgct   1620

tgcccacgat gatcaccgac cgctataccc ttgccagtcg cagtacgacg agtagacttt   1680

tgcagtccta cttgaacaac ttccatccgt attgtcccat tgtccatagt cccaccctta   1740

tgatgcttta caacaatcaa atcgagattg ccagtaaaga ccagtggcag attttgttca   1800

attgtattct tgcgatcggg gcgtggtgca ttgaaggtga gagtaccgac attgacgtct   1860

tctattacca gaacgccaag agtcacctta cctccaaagt gtttgaaagt gggagtatta   1920

tccttgtcac ggcgcttcac ttgcttagta gatacacgca atggcgccaa aagacgaaca   1980

cctcctacaa cttccattcc ttcagtattc gcatggcgat tagtcttggt cttaaccgcg   2040

atttgccgag tagtttttcc gactcctcca tccttgagca gcgcagaaga atctggtgga   2100

gtgtgtatag ttgggaaatt cagcttagtc ttttgtacgg gagaagtatt caattgagtc   2160

aaaacacgat tagttttccc agtagtgtgg atgacgtcca aagaacgacg acggggccga   2220

cgatttacca cggtattatc gagacggcgc gcttgcttca ggtctttacg aagatttacg   2280

agcttgataa gacggtgacc gcggagaagt cccccatttg cgcgaagaag tgtcttatga   2340

tctgcaacga aatcgaagaa gtcagtcgcc aagcgccgaa attccttcag atggacatca   2400

gtacgacggc ccttacgaac cttcttaaag agcatccctg gcttagtttc acgcgctttg   2460

agcttaaatg gaagcaactt agtttgatta tctacgtgct tcgcgacttc tttaccaact   2520

tcacgcaaaa gaaaagtcag cttgagcaag accagaacga ccaccagtcc tacgaggtca   2580

agagatgtag tattatgctt tccgacgcgg cgcagcgcac cgtcatgagt gtgtcctcct   2640

acatggataa ccacaacgtg acgccgtact tcgcgtggaa ctgcagttac tatcttttta   2700

acgcggtgct tgtgccgatt aaaacccttt tgagtaatag taagagtaac gccgaaaaca   2760

atgaaacggc gcagcttctt cagcagatca ataccgtcct tatgcttctt aagaagcttg   2820

cgaccttcaa gattcaaacc tgcgagaagt atatccaggt gcttgaggaa gtgtgcgccc   2880
```

-continued

```
ccttccttct tagtcaatgc gcgattccgc ttccccacat ttcctacaat aactccaacg   2940
ggtccgcgat caagaacatc gtggggagtg cgaccattgc gcagtatccc accttgcccg   3000
aagagaacgt gaataacatt tccgtcaagt acgtcagtcc cggtagtgtg ggtcccagtc   3060
ccgtcccgct taagagtggg gcgtcctttt ccgaccttgt gaaacttctt agtaatagac   3120
cgccgagtag aaatagtccg gtcacgattc cgcgctccac gcccagtcac agaagtgtga   3180
ccccccttcct tggtcagcaa cagcaacttc agagtcttgt cccgcttacg cccagtgccc   3240
ttttcggggg tgcgaacttc aaccagtccg gtaacatcgc cgactccagt cttagtttta   3300
cctttaccaa ttcctccaat gggcccaatt tgattacgac ccagacgaac agtcaggcct   3360
tgagtcagcc gatcgcgagt agtaatgtcc acgacaattt tatgaacaac gagattaccg   3420
cctccaagat cgacgacggg aacaacagta agccgcttag tcccgggtgg accgatcaga   3480
ccgcctacaa tgccttcggg attaccacgg gtatgttcaa cacgaccacg atggacgacg   3540
tgtacaatta cctttttgac gacgaggaca cgccgccgaa tccgaagaag gaatgagcca   3600
attggtgcgg caattgataa taacgaaaat gtcttttaat gatctgggta taatgaggaa   3660
ttttccgaac gtttttactt tatatatata tatacatgta acatatattc tatacgctat   3720
atcgagaaaa cgcgatggtg gggtgacttt caactcggcg tatccccgcg tgcttggccg   3780
gccgtccgca tgactcaaga gaagcatgtg gtttttgagt ttttttcgtt gaattttcag   3840
gtaaagctca atagttatga caattacaac aacagaattc tttctatata tgcacgaact   3900
tgtaatatgg aagaaattat gacgtacaaa ctataaagta aatattttac gtaacacatg   3960
gtgctgttgt gcttcttttt caagagaata ccaatgacgt atgactaagt ttaggattta   4020
atgcaggtga cggacccatc tttcaaacga tttatatcag tggcgtccaa attgttaggt   4080
tttgttggtt cagcaggttt cctgttgtgg gtcatatgac tttgaaccaa atggccggct   4140
gctagggcag cacataagga taattcacct gccaagacgg cacaggcaac tattcttgct   4200
aattgacgtg cgttggtacc aggagcggta gcatgtgggc ctcttacacc taataagtcc   4260
aacatggcac cttgtggttc tagaacagta ccaccaccga tggtacctac ttcgatggat   4320
ggcatggata cggaaattct caaatcaccg tccacttctt tcatcaatgt tatacagttg   4380
gaactttcga cattttgtgc aggatcttgt cctaatgcca agaaaacagc tgtcactaaa   4440
ttagctgcat gtgcgttaaa tccaccaaca gacccagcca ttgcagatcc aaccaaattc   4500
ttagcaatgt tcaactcaac caatgcggaa acatcacttt ttaacacttt tctgacaaca   4560
tcaccaggaa tagtagcttc tgcgacgaca ctcttaccac gaccttcgat ccagttgatg   4620
gcagctggtt ttttgtcggt acagtagtta ccagaaacgg agacaacctc catatcttcc   4680
cagccatact cttctaccat ttgctttaat gagtattcga caccccttaga aatcatattc   4740
atacccattg cgtcaccagt agttgttcta aatctcatga agagtaaatc tcctgctaga   4800
caagtttgaa tatgttgcag acgtgcaaat cttgatgtag agttaaaagc ttttttaatt   4860
gcgttttgtc cctcttctga gtctaaccat atcttacagg caccagatct tttcaaagtt   4920
gggaaacgga ctactgggcc tcttgtcata ccatccttag ttaaaacagt tgttgcacca   4980
ccgccagcat tgattgcctt acagccacgc atggcagaag ctaccaaaca accctctgta   5040
gttgccattg gtatatgata agatgtacca tcgataacca aggggcctat aacaccaacg   5100
ggcaaaggca tgtaacctat aacattttca caacaagcgc caaatacgcg gtcgtagtca   5160
taatttttat atggtaaacg atcagatgct aatacaggag cttctgccaa aattgaaaga   5220
gccttcctac gtaccgcaac cgctctcgta gtatcaccta attttttctc caaagcgtac   5280
```

-continued

```
aaaggtaact taccgtgaat aaccaaggca gcgacctctt tgttcttcaa ttgttttgta   5340
tttccactac ttaataatgc ttctaattct tctaaaggac gtattttctt atccaagctt   5400
tcaatatcgc gggaatcatc ttcctcacta gatgatgaag gtcctgatga gctcgattgc   5460
gcagatgata aacttttgac tttcgatcca gaaatgactg ttttattggt taaaactggt   5520
gtagaagcct tttgtacagg agcagtaaaa gacttcttgg tgacttcagt cttcaccaat   5580
tggtctgcag ccattgtaaa gttagttggt tgcgcgactt cgggtggggt aagtatagag   5640
gtatattaac aatttttttgt tgatactttt atgacatttg aataagaagt aatacaaacc   5700
gaaaatgttg aaagtattag ttaaagtggt tatgcagctt ttgcatttat atatctgtta   5760
atagatcaaa aatcatcgct tcgctgatta attaccccag aaataaggct aaaaaactaa   5820
tcgcattatt atcctatggt tgttaatttg attcgttgat ttgaaggttt gtggggccag   5880
gttactgcca atttttcctc ttcataacca taaaagctag tattgtagaa tctttattgt   5940
tcggagcagt gcggcgcgag gcacatctgc gtttcaggaa cgcgaccggt gaagaccagg   6000
acgcacggag gagagtcttc cgtcggaggg ctgtcgcccg ctcggcggct tctaatccgt   6060
acttcaatat agcaatgagc agttaagcgt attactgaaa gttccaaaga gaaggttttt   6120
ttaggctaag ataatggggc tctttacatt tccacaacat ataagtaaga ttagatatgg   6180
atatgtatat ggtggtattg ccatgtaata tgattattaa acttctttgc gtccatccaa   6240
aaaaaaagta acgcacgcac actcccgaca gacaactagc ttgataatgt ctcagaacgt   6300
ttacattgta tcgactgcca gaaccccaat tggttcattc cagggttctc tatcctccaa   6360
gacagcagtg gaattgggtg ctgttgcttt aaaaggcgcc ttggctaagg ttccagaatt   6420
ggatgcatcc aaggattttg acgaaattat ttttggtaac gttctttctg ccaatttggg   6480
ccaagctccg gccagacaag ttgctttggc tgccggtttg agtaatcata tcgttgcaag   6540
cacagttaac aaggtctgtg catccgctat gaaggcaatc attttgggtg ctcaatccat   6600
caaatgtggt aatgctgatg ttgtcgtagc tggtggttgt gaatctatga ctaacgcacc   6660
atactacatg ccagcagccc gtgcgggtgc caaatttggc caaactgttc ttgttgatgg   6720
tgtcgaaaga gatgggttga acgatgcgta cgatggtcta gccatgggtg tacacgcaga   6780
aaagtgtgcc cgtgattggg atattactag agaacaacaa gacaattttg ccatcgaatc   6840
ctaccaaaaa tctcaaaaat ctcaaaagga aggtaaattc gacaatgaaa ttgtacctgt   6900
taccattaag ggatttagag gtaagcctga tactcaagtc acgaaggacg aggaacctgc   6960
tagattacac gttgaaaaat tgagatctgc aaggactgtt ttccaaaaag aaaacggtac   7020
tgttactgcc gctaacgctt ctccaatcaa cgatggtgct gcagccgtca tcttggtttc   7080
cgaaaaagtt ttgaaggaaa agaatttgaa gcctttggct attatcaaag gttggggtga   7140
ggccgctcat caaccagctg attttacatg ggctccatct cttgcagttc caaaggcttt   7200
gaaacatgct ggcatcgaag acatcaattc tgttgattac tttgaattca atgaagcctt   7260
ttcggttgtc ggtttggtga acactaagat tttgaagcta gacccatcta aggttaatgt   7320
atatggtggt gctgttgctc taggtcaccc attgggttgt tctggtgcta gagtggttgt   7380
tacactgcta tccatcttac agcaagaagg aggtaagatc ggtgttgccg ccatttgtaa   7440
tggtggtggt ggtgcttcct ctattgtcat tgaaaagata tgattacgtt ctgcgatttt   7500
ctcatgatct tttcataaa atacataaat atataaatgg ctttatgtat aacaggcata   7560
atttaaagtt ttatttgcga ttcatcgttt ttcaggtact caaacgctga ggtgtgcctt   7620
ttgacttact tttccgcctt ggcaagctgg ccgaacctgc aggccgcgag cgccgatacg   7680
```

```
aaaatcgtta ttgtcttgaa ggtgaaattt ctactcttat taatggtgaa cgttaagctg   7740
atgctatgat ggaagctgat tggtcttaac ttgcttgtca tcttgctaat ggtcattggc   7800
tcgtgttatt acttaagtta tttgtactcg ttttgaacgt aatgctaatg atcatcttat   7860
ggaataatag tgagtggttt cagggtccat aaagcttttc aattcatctt ttttttttt   7920
gttctttttt ttgattccgg tttctttgaa atttttttga ttcggtaatc tccgagcaga   7980
aggaagaacg aaggaaggag cacagactta gattggtata tatacgcata tgtggtgttg   8040
aagaaacatg aaattgccca gtattcttaa cccaactgca cagaacaaaa acctgcagga   8100
aacgaagata aatcatgtcg aaagctacat ataaggaacg tgctgctact catcctagtc   8160
ctgttgctgc caagctattt aatatcatgc acgaaaagca aacaaacttg tgtgcttcat   8220
tggatgttcg taccaccaag gaattactgg agttagttga agcattaggt cccaaaattt   8280
gtttactaaa aacacatgtg gatatcttga ctgatttttc catggagggc acagttaagc   8340
cgctaaaggc attatccgcc aagtacaatt ttttactctt cgaagacaga aaatttgctg   8400
acattggtaa tacagtcaaa ttgcagtact ctgcgggtgt atacagaata gcagaatggg   8460
cagacattac gaatgcacac ggtgtggtgg gcccaggtat tgttagcggt ttgaagcagg   8520
cggcggaaga agtaacaaag gaacctagag gccttttgat gttagcagaa ttgtcatgca   8580
agggctccct agctactgga gaatatacta agggtactgt tgacattgcg aagagtgaca   8640
aagattttgt tatcggcttt attgctcaaa gagacatggg tggaagagat gaaggttacg   8700
attggttgat tatgacaccc ggtgtgggtt tagatgacaa gggagacgca ttgggtcaac   8760
agtatagaac cgtggatgat gtggtctcta caggatctga cattattatt gttggaagag   8820
gactatttgc aaagggaagg gatgctaagg tagagggtga acgttacaga aaagcaggct   8880
gggaagcata tttgagaaga tgcggccagc aaaactaaaa aactgtatta taagtaaatg   8940
catgtatact aaactcacaa attagagctt caatttaatt atatcagtta ttaccacgaa   9000
aatcgttatt gtcttgaagg tgaaatttct actcttatta atggtgaacg ttaagctgat   9060
gctatgatgg aagctgattg gtcttaactt gcttgtcatc ttgctaatgg tcatatggct   9120
cgtgttatta cttaagttat ttgtactcgt tttgaacgta atgctaatga tcatcttatg   9180
gaataatagt gaacggccgg ccaagcacgc ggggattgaa tgagaaaaaa aatcggttgg   9240
gcttaacttt aaagaaaaaa gttgagatta gatttattgt gttataaata tagatataca   9300
attctttata aaaaaaatat atatatatat cattgttatt aaataaagag ttttcctagt   9360
atatagatta aaaaactact ctattaaatg agagctaaaa aaagcaggct gccaaaaaaa   9420
taaagcattt atgaaggggg ttcagcaaga tgcaatcgat gggggaagat tattttttaa   9480
catcgtaaga tcttctaaat ttgtcatcga tgttggtcaa gtagtaaaca ccactttgca   9540
aatgctcaat ggaaccttga ggtttgaagt tcttcttcaa atgggcattt tctctcaatt   9600
cgatggcagc ttcgtaatcc tttggagttt cggtgattct cttggctaat ttgttagtaa   9660
tatctaattc cttgataata tgttggacgt caccaacaat tttgcaagaa tatagagatg   9720
cagctaaacc ggaaccgtaa gaaaataaac caacacgctt gccttgtaag tcgtcagatc   9780
caacatagtt taatagagat gcaaaggcgg cataaacaga tgcggtgtac atgttacctg   9840
tgtttgttgg aacaatcaaa gattgggcaa ctctctcttt gtggaatggc ttagcaacat   9900
taacaaaagt tttttcaatg ttcttatcgg ttaaagattc gtcataatcg cgagtagcta   9960
attcggcgtc aacttctggg aacaattgag gattggctct gaaatcgtta tatagtaatc  10020
taccgtatga ttttgtgacc aatttacagg ttggaacatg gaaaacgttg tagtcgaaat  10080
```

```
atttcaaaac gttcaaagca tccgaaccag cgggatcgct aaccaaccct ttagaaatag  10140
ccttcttgga ataactcttg taaacttgat caagagcctt gacgtaacaa gttaatgaaa  10200
aatgaccatc gacgtaagga tattcgctgg tgaaatctgg cttgtaaaaa tcgtaggcgt  10260
gttccatgta agaagctctt acagagtcaa atacaattgg agcatcagga ccgatccaca  10320
tagcaacagt accggcacca ccggttggtc ttgcggcacc cttatcgtag atggcaatat  10380
caccgcaaac tacaatggcg tctctaccat cccatgcgtt agattcaatc cagttcaaag  10440
agttgaacaa cgcgttggta ccaccgtaac aggcattaag cgtgtcaata ccttcgacgt  10500
cagtgttttc accaaacaat tgcatcaaga cagacttgac agacttggac ttgtcaatca  10560
gagtttcagt accgacttct aatctaccaa ttttgttggt gtcgatgttg taactcttga  10620
tcaacttaga caaaacagtt agggacatcg agtagatatc ttctctgtca ttgacaaaag  10680
acatgttggt ttggcccaga ccaattgtgt atttaccttg agaaacgcca tcaaatttct  10740
ctagctcaga ttggttgaca cattgagttg ggatgtaaat ttggatacct ttaataccga  10800
cattttgagg tctggttttt tgttcagcgg tcttttgttt ttttagttca gtcatttgca  10860
agtttgtatt gtgtaattgt tgttgctttt gcggcctaag tcttccttta ataccacacc  10920
aacaaagttt agttgagagt ttcattgtga aggtagttcg attttggagg tcgcgggagg  10980
ttactttttt tttggatgga cgcaaagaag tttaataatc atattacatg gcaataccac  11040
catatacata tccatatcta atcttactta tatgttgtgg aaatgtaaag agccccatta  11100
tcttagccta aaaaaacctt ctctttggaa ctttcagtaa tacgcttaac tgctcattgc  11160
tatattgaag tacggattag aagccgccga gcgggcgaca gccctccgac ggaagactct  11220
cctccgtgcg tcctggtctt caccggtcgc gttcctgaaa cgcagatgtg cctcgcgccg  11280
cactgctccg aacaataaag attctacaat actagctttt atggttatga agaggaaaaa  11340
ttggcagtaa cctggcccca caaaccttca aatcaacgaa tcaaattaac aaccatagga  11400
taataatgcg attagttttt tagccttatt tctggggtaa ttaatcagcg aagcgatgat  11460
ttttgatcta ttaacagata tataaatgca aaagctgcat aaccacttta actaatactt  11520
tcaacatttt cggtttgtat tacttcttat tcaaatgtca taaaagtatc aacaaaaaat  11580
tgttaatata cctctatact taccccaccc gaagtcgcgc aaccaactaa ctttacaatg  11640
gctgcagacc aattggtgaa gactgaagtc accaagaagt cttttactgc tcctgtacaa  11700
aaggcttcta caccagtttt aaccaataaa acagtcattt ctggatcgaa agtcaaaagt  11760
ttatcatctg cgcaatcgag ctcatcagga ccttcatcat ctagtgagga agatgattcc  11820
cgcgatattg aaagcttgga taagaaaata cgtcctttag aagaattaga agcattatta  11880
agtagtggaa atacaaaaca attgaagaac aaagaggtcg ctgccttggt tattcacggt  11940
aagttacctt tgtacgcttt ggagaaaaaa ttaggtgata ctacgagagc ggttgcggta  12000
cgtaggaagg ctctttcaat tttggcagaa gctcctgtat tagcatctga tcgtttacca  12060
tataaaaatt atgactacga ccgcgtattt ggcgcttgtt gtgaaaatgt tataggttac  12120
atgcctttgc ccgttggtgt tataggcccc ttggttatcg atggtacatc ttatcatata  12180
ccaatggcaa ctacagaggg ttgtttggta gcttctgcca tgcgtggctg taaggcaatc  12240
aatgctggcg gtggtgcaac aactgtttta actaaggatg gtatgacaag aggcccagta  12300
gtccgtttcc caactttgaa aagatctggt gcctgtaaga tatggttaga ctcagaagag  12360
ggacaaaacg caattaaaaa agcttttaac tctacatcaa gatttgcacg tctgcaacat  12420
attcaaactt gtctagcagg agatttactc ttcatgagat ttagaacaac tactggtgac  12480
```

```
gcaatgggta tgaatatgat ttctaagggt gtcgaatact cattaaagca aatggtagaa  12540

gagtatggct gggaagatat ggaggttgtc tccgtttctg gtaactactg taccgacaaa  12600

aaaccagctg ccatcaactg gatcgaaggt cgtggtaaga gtgtcgtcgc agaagctact  12660

attcctggtg atgttgtcag aaaagtgtta aaaagtgatg tttccgcatt ggttgagttg  12720

aacattgcta agaatttggt tggatctgca atggctgggt ctgttggtgg atttaacgca  12780

catgcagcta atttagtgac agctgttttc ttggcattag gacaagatcc tgcacaaaat  12840

gtcgaaagtt ccaactgtat aacattgatg aaagaagtgg acggtgattt gagaatttcc  12900

gtatccatgc catccatcga agtaggtacc atcggtggtg gtactgttct agaaccacaa  12960

ggtgccatgt tggacttatt aggtgtaaga ggcccacatg ctaccgctcc tggtaccaac  13020

gcacgtcaat tagcaagaat agttgcctgt gccgtcttgg caggtgaatt atccttatgt  13080

gctgccctag cagccggcca tttggttcaa agtcatatga cccacaacag gaaacctgct  13140

gaaccaacaa aacctaacaa tttggacgcc actgatataa atcgtttgaa agatgggtcc  13200

gtcacctgca ttaaatccta aacttagtca tacgtcattg gtattctctt gaaaaagaag  13260

cacaacagca ccatgtgtta cgtaaaatat ttactttata gtttgtacgt cataatttct  13320

tccatattac aagttcgtgc atatatagaa agaattctgt tgttgtaatt gtcataacta  13380

ttgagcttta cctgaaaatt caacgaaaaa aactcaaaaa ccacatgctt ctcttgagtc  13440

atgcggaggt ccgccggcgt tggacgagcg aatgtgtata ttagtttaaa aagttgtatg  13500

taataaaagt aaaatttaat attttggatg aaaaaaacca tttttagact tttcttaac  13560

tagaatgctg gagtagaaat acgccatctc aagatacaaa aagcgttacc ggcactgatt  13620

tgtttcaacc agtatataga ttattattgg gtcttgatca actttcctca gacatatcag  13680

taacagttat caagctaaat atttacgcga aagaaaaaca aatattttaa ttgtgatact  13740

tgtgaatttt attttattaa ggatacaaag ttaagagaaa acaaaattta tatacaatat  13800

aagtaatatt catatatatg tgatgaatgc agtcttaacg agaagacatg gccttggtga  13860

caactctctt caaaccaact tcagcctttc tcaattcatc agcagatggg tcttcgattt  13920

gcaaagcagc caaagcggcg gtttaaacgc gtggccgtgc cgtc                  13964
```

<210> SEQ ID NO 54
<211> LENGTH: 13963
<212> TYPE: DNA
<213> ORGANISM: Artificial Sequence
<220> FEATURE:
<223> OTHER INFORMATION: Synthetic construct: i85207 integration construct

<400> SEQUENCE: 54

```
gacggcacgg ccacgcgttt aaaccgccag ggcaaggttg gcctctactt actccatcga     60

caattcaaga tacagaacct cctccagatg gaatcccttc catagagaga aggagcaagc    120

aactgaccca atattgactg ccactggacc tgaagacatg caacaaagtg caagcatagt    180

ggggccttct tccaatgcta atccggtcac tgccactgct gctacggaaa accaacctaa    240

aggtattaac ttcttcacta taagaaaatc acacgagcgc ccggacgatg tctctgttta    300

aatggcgcaa gttttccgct ttgtaatata tatttatacc cctttcttct ctcccctgca    360

atataatagt ttaattctaa tattaataat atcctatatt ttcttcattt accggcgcac    420

tctcgcccga acgacctcaa aatgtctgct acattcataa taaccaaaag ctcataactt    480

tttttttga acctgaatat atatacatca catgtcactg ctggtccttg ccgaccagcg    540

tatacaatct cgatagttgg tttcccgttc tttccactcc cgtccgctcg tccaacgccg    600
```

```
gcggaccttc acatgtaggg accgaattgt ttacaagttc tctgtaccac catggagaca    660

tcaaagattg aaaatctatg gaaagatatg gacggtagca acaagaatat agcacgagcc    720

gcgaagttca tttcgttact tttgatatcg ctcacaacta ttgcgaagcg cttcagtgaa    780

aaaatcataa ggaaaagttg taaatattat tggtagtatt cgtttggtaa agtagagggg    840

gtaatttttc ccctttattt tgttcataca ttcttaaatt gctttgcctc tccttttgga    900

aagctatact tcggagcact gttgagcgaa ggctcattag atatattttc tgtcattttc    960

cttaacccaa aaataaggga aagggtccaa aaagcgctcg gacaactgtt gaccgtgatc   1020

cgaaggactg gctatacagt gttcacaaaa tagccaagct gaaaataatg tgtagctatg   1080

ttcagttagt ttggctagca aagatataaa agcaggtcgg aaatatttat gggcattatt   1140

atgcagagca tcaacatgat aaaaaaacct cccgcgacct ccaaaatcga actaccttca   1200

caatgactgc cgacaacaat agtatgcccc atggtgcagt atctagttac gccaaattag   1260

tgcaaaacca aacacctgaa gacattttgg aagagtttcc tgaaattatt ccattacaac   1320

aaagacctaa tacccgatct agtgagacgt caaatgacga aagcggagaa acatgttttt   1380

ctggtcatga tgaggagcaa attaagttaa tgaatgaaaa ttgtattgtt ttggattggg   1440

acgataatgc tattggtgcc ggtaccaaga aagtttgtca tttaatggaa aatattgaaa   1500

agggtttact acatcgtgca ttctccgtct ttattttcaa tgaacaaggt gaattacttt   1560

tacaacaaag agccactgaa aaaataactt tccctgatct ttggactaac acatgctgct   1620

ctcatccact atgtattgat gacgaattag gtttgaaggg taagctagac gataagatta   1680

agggcgctat tactgcggcg gtgagaaaac tagatcatga attaggtatt ccagaagatg   1740

aaactaagac aaggggtaag tttcactttt taaacagaat ccattacatg gcaccaagca   1800

atgaaccatg gggtgaacat gaaattgatt acatcctatt ttataagatc aacgctaaag   1860

aaaacttgac tgtcaaccca aacgtcaatg aagttagaga cttcaaatgg gtttcaccaa   1920

atgatttgaa aactatgttt gctgacccaa gttacaagtt tacgccttgg tttaagatta   1980

tttgcgagaa ttacttattc aactggtggg agcaattaga tgacctttct gaagtggaaa   2040

atgacaggca aattcataga atgctataac aacgcgtcaa taatataggc tacataaaaa   2100

tcataataac tttgttatca tagcaaaatg tgatataaaa cgtttcattt cacctgaaaa   2160

atagtaaaaa taggcgacaa aaatccttag taatatgtaa actttatttt ctttatttat   2220

ttacagaact ctgaatatac attgattgtt cacatttttt ttttctcttc tcaatttccc   2280

ttgattatat tcaaaaggtt attggcctct tgaatgtttc ccactgaatc cccgcgtgct   2340

tggccggccg tggagcgacc tcatgctata cctgagaaag caacctgacc tacaggaaag   2400

agttactcaa gaataagaat tttcgtttta aaacctaaga gtcactttaa aatttgtata   2460

cacttatttt ttttataact tatttaataa taaaaatcat aaatcataag aaattcgctc   2520

aaacgaccat tggatggaca aagaaggact tcatgtaaga tttcatgtca ccttcggcgt   2580

gagtgaaacc atcgttaaca gagtataaaa cttcacacat tctagccaag ttgatagctg   2640

gcattaacaa agggaatgga acggcggttg gtctcaaaga ttctctgtta ataaccttcc   2700

aggcgtcttc gacttttcta gagatgtatt cacaggcttc ttcttcagaa gcaccggatt   2760

ccttagaata acattcgatg gaggaggcaa catgacctct ttcttgttct tctttatgag   2820

agacaatatc atccatcaat ctaatgataa cacaagaagc ttcaacaata ggtgggtagg   2880

aagaaaccca tttaaaagtg tcctcgttaa caatgtcacc tctaccaacg taagatctag   2940

cagtgatcaa accgtaggta ccggtaacca tggaaacaga catgtactct tccaaagtag   3000
```

-continued

```
gcatgtaacc ttctttcaac catctggctt caaccaagta gtttctgacc aattccttag   3060
ccatttcctt aacgtagtgg atttgataag ccttaccttc cttttctaaa gattcttcca   3120
tttcaacgtg caagttaacc aattcttggt agatcaactt catgtattct ggcaacatgt   3180
ccaaacaaga aatggaccac ttctcaacgg cttgagtgaa aatttccaat tcttcgtagg   3240
taccgtagtt gtcgaaggta tcatccaaaa cgaccaacca catacaagac ttcatcaaga   3300
acattctggt tctggcatgt tgtggttcat agtaaataga caaaatccag aagtaacctt   3360
cgacaactct atcacgaacg aatggcaatt tgttttgcaa gtctaaatct ttccaccact   3420
tgcagatgtg agacaattct ttcttatgca tggattgcaa aacagagaaa tctaacttag   3480
ccaacttcaa caaaacctcg tcgtgagaag tttcttgttg gtaaattggc atatagtgta   3540
aagcttcgat tctggccaat cttcttctca atggttgctt caaggcttgg tggatttggg   3600
ttcttaagga agagtcacaa gatggatcct tggcaataat gtccaagtga accttagaga   3660
attccaaagc gttgtccaag atggtttcat cttcgactct catgaaagca gcttcgtaca   3720
aggccaagat accttgagcg tcgttacaca aagattcctt aaatttacct ttttcgtcca   3780
taaagtcctt gaaaacacca gaggagacat tgaaaccttg ttgacgcaac aaacgaaacc   3840
acaaggagat agattgtaaa ttttccttat cgacccattg ttcaccgtaa gtgacatgga   3900
tatgttgtaa agcttcttcg atttcttctt caaaatggta agcaatacct aaacgttgaa   3960
cagcattgat taattcgatc aacttaacat gttgcatagg ttcgttagaa cccttaatag   4020
taatcaattc cttcttaact tcctccttta actcttcgac taattgcttc ttcataacca   4080
agtcctctgg ttcatcgtaa gtcaaaaatt gatcacccca aatggaagcg ttgaagttag   4140
cggtatgtct aataacgtct ggcttggtag aatccttatc atcgacaaca attggggaag   4200
tagatggaga ggaagaaaca gaggaaatag gcaaagtgga cattgtaaag ttagttggtt   4260
gcgcgacttc gggtggggta agtatagagg tatattaaca attttttgtt gatactttta   4320
tgacatttga ataagaagta atacaaaccg aaaatgttga aagtattagt taaagtggtt   4380
atgcagcttt tgcatttata tatctgttaa tagatcaaaa atcatcgctt cgctgattaa   4440
ttaccccaga aataaggcta aaaaactaat cgcattatta tcctatggtt gttaatttga   4500
ttcgttgatt tgaaggtttg tggggccagg ttactgccaa tttttcctct tcataaccat   4560
aaaagctagt attgtagaat ctttattgtt cggagcagtg cggcgcgagg cacatctgcg   4620
tttcaggaac gcgaccggtg aagaccagga cgcacggagg agagtcttcc gtcggagggc   4680
tgtcgcccgc tcggcggctt ctaatccgta cttcaatata gcaatgagca gttaagcgta   4740
ttactgaaag ttccaaagag aaggtttttt taggctaaga taatggggct ctttacattt   4800
ccacaacata taagtaagat tagatatgga tatgtatatg gtggtattgc catgtaatat   4860
gattattaaa cttctttgcg tccatccaaa aaaaaagtaa cgcacgcaca ctcccgacag   4920
acaactagct tgataatggc ttcagaaaaa gaaattagga gagagagatt cttgaacgtt   4980
ttccctaaat tagtagagga attgaacgca tcgcttttgg cttacggtat gcctaaggaa   5040
gcatgtgact ggtatgccca ctcattgaac tacaacactc caggcggtaa gttaaataga   5100
ggtttgtccg ttgtggacac gtatgctatt ctctccaaca agaccgttga acaattgggg   5160
caagaagaat acgaaaaggt tgctattcta ggttggtgca ttgagttgtt gcaggcttac   5220
ttcttggtcg ccgatgatat gatggacaag tccattacca gaagaggcca accatgttgg   5280
tacaaggttc ctgaagttgg ggaaattgcc atcaatgacg cattcatgtt agaggctgct   5340
atctacaagc ttttgaaatc tcacttcaga aacgaaaaat actacataga tatcaccgaa   5400
```

-continued

```
ttgttccatg aagtcacctt ccaaaccgaa ttgggccaat tgatggactt aatcactgca   5460
cctgaagaca aagtcgactt gagtaagttc tccctaaaga agcactcctt catagttact   5520
ttcaagactg cttactattc tttctacttg cctgtcgcat tggctatgta cgttgccggt   5580
atcacagatg aaaaggattt gaaacaagcc agagatgtct tgattccatt gggtgaatat   5640
ttccaaattc aagatgacta cttagactgc ttcggtaccc cagaacagat cggtaagatc   5700
ggtacagata tccaagataa caaatgttct tgggtaatca acaaggcatt agaacttgct   5760
tccgcagaac aaagaaagac tttagacgaa aattacggta agaaggactc agtcgcagaa   5820
gccaaatgca aaaagatttt caatgacttg aaaatcgacc agttatacca cgaatatgaa   5880
gagtctgttg ccaaggattt gaaggccaag atctcccaag tcgacgagtc tcgtggcttc   5940
aaagccgacg tcttaactgc gtttttgaac aaggtttaca agagaagtaa atagaactaa   6000
cgctaatcga taaaacatta gatttcagat tagataagga ccatgtataa gaaatatata   6060
cttccactat aatatagtat aagcttacag atagtatctc tcgatctacc gttccacgtg   6120
actagtccaa gaacctgcag gccgcgagcg ccgatacgaa aatcgttatt gtcttgaagg   6180
tgaaatttct actcttatta atggtgaacg ttaagctgat gctatgatgg aagctgattg   6240
gtcttaactt gcttgtcatc ttgctaatgg tcattggctc gtgttattac ttaagttatt   6300
tgtactcgtt ttgaacgtaa tgctaatgat catcttatgg aataatagtg agtggtttca   6360
gggtccataa agcttttcaa ttcatctttt tttttttgt tcttttttt gattccggtt   6420
tctttgaaat ttttttgatt cggtaatctc cgagcagaag gaagaacgaa ggaaggagca   6480
cagacttaga ttggtatata tacgcatatg tggtgttgaa gaaacatgaa attgcccagt   6540
attcttaacc caactgcaca gaacaaaaac ctgcaggaaa cgaagataaa tcatgtcgaa   6600
agctacatat aaggaacgtg ctgctactca tcctagtcct gttgctgcca agctatttaa   6660
tatcatgcac gaaaagcaaa caaacttgtg tgcttcattg gatgttcgta ccaccaagga   6720
attactggag ttagttgaag cattaggtcc caaaatttgt ttactaaaaa cacatgtgga   6780
tatcttgact gatttttcca tggagggcac agttaagccg ctaaaggcat tatccgccaa   6840
gtacaatttt ttactcttcg aagacagaaa atttgctgac attggtaata cagtcaaatt   6900
gcagtactct gcgggtgtat acagaatagc agaatgggca gacattacga atgcacacgg   6960
tgtggtgggc ccaggtattg ttagcggttt gaagcaggcg gcggaagaag taacaaagga   7020
acctagaggc cttttgatgt tagcagaatt gtcatgcaag ggctccctag ctactggaga   7080
atatactaag ggtactgttg acattgcgaa gagtgacaaa gattttgtta tcggctttat   7140
tgctcaaaga gacatgggtg gaagagatga aggttacgat tggttgatta tgacacccgg   7200
tgtgggttta gatgacaagg gagacgcatt gggtcaacag tatagaaccg tggatgatgt   7260
ggtctctaca ggatctgaca ttattattgt tggaagagga ctatttgcaa agggaaggga   7320
tgctaaggta gagggtgaac gttacagaaa agcaggctgg gaagcatatt tgagaagatg   7380
cggccagcaa aactaaaaaa ctgtattata agtaaatgca tgtatactaa actcacaaat   7440
tagagcttca atttaattat atcagttatt accacgaaaa tcgttattgt cttgaaggtg   7500
aaatttctac tcttattaat ggtgaacgtt aagctgatgc tatgatggaa gctgattggt   7560
cttaacttgc ttgtcatctt gctaatggtc atatggctcg tgttattact taagttattt   7620
gtactcgttt tgaacgtaat gctaatgatc atcttatgga ataatagtga atcggcgctc   7680
gcggcctgca ggtttcctca tcctagtatg tatagcttgt acccattaaa cgaattttat   7740
catgccgccg aaaggaacaa tttcaagtac tatcggaaga tgaatggtta gatgttaagc   7800
```

```
gcggtcactt caaacttcac atttataaag atgtcacatg gaccactatt atctacctta   7860
agttatttat caagataagt ttccggatct ttttctttcc taacacccca gtcagcctga   7920
gttacatcca gccattgaac cttagaaaat cttttgtcat cagcggtttg agccctaaga   7980
tcaacatctt gcttagcaat cactgcaatg gcgtcataac caccagcacc aggtattaag   8040
caagtaagaa ctccttttaa ggtctggcaa tcatccaata agctagtttg tacgggaggt   8100
tcgatatcgg caccagattc tttagttatt tttctaaagg aacgtctaat tgtggcaact   8160
gcatctctaa cttctgtgat ctcaggatac ttttgacagg tacagtcatt cctctcaaga   8220
gactcaaata tctgatcgct gtaatcgtca tgagtctcgt gtaagcgatc tagtttagat   8280
agtccatcca taaatctaga atttgcatga tcgagttctg tatatatttt caagctttcc   8340
ggcatatgcg aatcatacca attttttacc ttctggacca gttttactgt ttctgaacca   8400
ttcttaatat cgcccatcca taaagttaat cccgaaggta aatggttact tttaatcgtt   8460
atattccagt cttcttcatt aaccaaatgc gccagtttac tgccgtaagt agcacttcca   8520
atatctggca aattagagat taatgcgggt gggaatcttc tatatctgat agatccatat   8580
gctgccgccg ctacatcaaa cccgcttcca attttaccct gagcttgaca atgagcaact   8640
tgtgataaat tatgaataac ttctctatat ttgtctacat tattttccag gtccgataca   8700
aaaaaggagg ccaaagctgt agttaaaact gtgactaaac ctgccgagga gcccagccct   8760
gttttgggaa cttcttcaat tctgtgcgaa tgaaaactca atcttctgtt gccacgatgt   8820
tcggtaacgc tgtcctcctg agaatggtag gcatcatcag agaaaatatc aataacgaac   8880
aagtttctat tgcagtagtc gtccatgtta ggcttaaagt agctaaatac gttagcgata   8940
actttttcaa tgaaagggtt cttagatccg cctatcgaaa caggaatgaa gccagtttta   9000
ggacttatat ggtacagcca ctccccatct ttaaattgtt tacttttcac acgcacttca   9060
aacttatcag actcttgcaa tgaaccgtaa ggatgggcta cagcatgcat tcttgccgat   9120
aatccgacta caaatgcttc atatttcgga tctaaaacta aatatccacc agctagtaac   9180
gctttccctg ggcactgaa ggctctcaac tctgacatta tcaagctagt tgtctgtcgg    9240
gagtgtgcgt gcgttttttt atcatgttga tgctctgcat aataatgccc ataaatattt   9300
ccgacctgct tttatatctt tgctagccaa actaactgaa catagctaca cattattttc   9360
agcttggcta ttttgtgaac actgtatagc cagtccttcg gatcacggtc aacagttgtc   9420
cgagcgcttt ttggaccctt tcccttattt ttgggttaag gaaaatgaca gaaaatatat   9480
ctaatgagcc ttcgctcaac agtgctccga agtatagctt tccaaaagga gaggcaaagc   9540
aatttaagaa tgtatgaaca aaataaaggg gaaaaattac cccctctact ttaccaaacg   9600
aatactacca ataatattta caacttttcc ttatgatttt ttcactgaag cgcttcgcaa   9660
tagttgtgag cgatatcaaa agtaacgaaa tgaacttcgc ggctcgtgct atattcttgt   9720
tgctaccgtc catatctttc catagatttt caatctttga tgtctccatg gtggtacaga   9780
gaacttgtaa acaattcggt ccctacatgt gaacggccgg ccaagcacgc ggggatccga   9840
agcatgtagg gaggtcatga tatgaaaaag caaaagagta ggcatcaaaa agtttctcat   9900
tcaagtggta actgctgtta aaattaagat atttataaat tgaagcttgg tcgttccgac   9960
caataccgta gggaaacgta aattagctat tgtaaaaaaa ggaaaagaaa agaaaagaaa  10020
aatgttacat atcgaattga tcttattcct ttggtagacc agtctttgcg tcaatcaaag  10080
attcgtttgt ttcttgtggg cctgaaccga cttgagttaa aatcactctg gcaacatcct  10140
tttgcaactc aagatccaat tcacgtgcag taaagttaga tgattcaaat tgatggttga  10200
```

-continued

```
aagcctcaag ctgctcagta gtaaatttct tgtcccatcc aggaacagag ccaaacaatt  10260
tatagataaa tgcaaagagt ttcgactcat tttcagctaa gtagtacaac acagcatttg  10320
gacctgcatc aaacgtgtat gcaacgattg tttctccgta aaactgatta atggtgtggc  10380
accaactgat gatacgcttg gaagtgtcat tcatgtagaa tattggaggg aaagagtcca  10440
aacatgtggc atggaaagag ttggaatcca tcattgtttc ctttgcaaag gtggcgaaat  10500
ctttttcaac aatggcttta cgcatgactt caaatctctt tggtacgaca tgttcaattc  10560
tttctttaaa tagttcggag gttgccacgg tcaattgcat accctgagtg gaactcacat  10620
cctttttaat atcgctgaca actaggacac aagctttcat ctgaggccag tcagagctgt  10680
ctgcgatttg tactgccatg gaatcatgac catcttcagc ttttcccatt tcccaggcca  10740
cgtatccgcc aaacaacgat ctacaagctg aaccagaccc ctttcttgct attctagata  10800
tttctgaagt tgactgtggt aattggtata acttagcaat tgcagagacc aatgcagcaa  10860
agccagcagc ggaggaagct aaaccagctg ctgtaggaaa gttattttcg gagacaatgt  10920
ggagtttcca ttgagataat gtgggcaatg aggcgtcctt cgattccatt tcctttctta  10980
attggcgtag gtcgcgcaga caattttgag ttctttcatt gtcgatgctg tgtggttctc  11040
catttaacca caaagtgtcg cgttcaaact caggtgcagt agccgcagag gtcaacgttc  11100
tgaggtcatc ttgcgataaa gtcactgata tggacgaatt ggtgggcaga ttcaacttcg  11160
tgtccctttt cccccaatac ttaagggttg cgatgttgac gggtgcggta acggatgctg  11220
tgtaaacggt cattgtgaag gtagttcgat tttggaggtc gcgggaggtt actttttttt  11280
tggatggacg caaagaagtt taataatcat attacatggc aataccacca tatacatatc  11340
catatctaat cttacttata tgttgtggaa atgtaaagag ccccattatc ttagcctaaa  11400
aaaaccttct ctttggaact ttcagtaata cgcttaactg ctcattgcta tattgaagta  11460
cggattagaa gccgccgagc gggcgacagc cctccgacgg aagactctcc tccgtgcgtc  11520
ctggtcttca ccggtcgcgt tcctgaaacg cagatgtgcc tcgcgccgca ctgctccgaa  11580
caataaagat tctacaatac tagcttttat ggttatgaag aggaaaaatt ggcagtaacc  11640
tggccccaca aaccttcaaa tcaacgaatc aaattaacaa ccataggata ataatgcgat  11700
tagtttttta gccttatttc tggggtaatt aatcagcgaa gcgatgattt ttgatctatt  11760
aacagatata taaatgcaaa agctgcataa ccactttaac taatactttc aacattttcg  11820
gtttgtatta cttcttattc aaatgtcata aaagtatcaa caaaaaattg ttaatatacc  11880
tctatactta ccccacccga agtcgcgcaa ccaactaact ttacaatgtc attaccgttc  11940
ttaacttctg caccgggaaa ggttattatt tttggtgaac actctgctgt gtacaacaag  12000
cctgccgtcg ctgctagtgt gtctgcgttg agaacctacc tgctaataag cgagtcatct  12060
gcaccagata ctattgaatt ggacttcccg gacattagct ttaatcataa gtggtccatc  12120
aatgatttca atgccatcac cgaggatcaa gtaaactccc aaaaattggc caaggctcaa  12180
caagccaccg atggcttgtc tcaggaactc gttagtcttt tggatccgtt gttagctcaa  12240
ctatccgaat ccttccacta ccatgcagcg ttttgtttcc tgtatatgtt tgtttgccta  12300
tgcccccatg ccaagaatat taagttttct ttaaagtcta ctttacccat cggtgctggg  12360
ttgggctcaa gcgcctctat ttctgtatca ctggccttag ctatggccta cttggggggg  12420
ttaataggat ctaatgactt ggaaaagctg tcagaaaacg ataagcatat agtgaatcaa  12480
tgggccttca taggtgaaaa gtgtattcac ggtacccctt caggaataga taacgctgtg  12540
gccacttatg gtaatgccct gctatttgaa aaagactcac ataatggaac aataaacaca  12600
```

-continued

```
aacaatttta agttcttaga tgatttccca gccattccaa tgatcctaac ctatactaga  12660

attccaaggt ctacaaaaga tcttgttgct cgcgttcgtg tgttggtcac cgagaaattt  12720

cctgaagtta tgaagccaat tctagatgcc atgggtgaat gtgccctaca aggcttagag  12780

atcatgacta agttaagtaa atgtaaaggc accgatgacg aggctgtaga aactaataat  12840

gaactgtatg aacaactatt ggaattgata agaataaatc atggactgct tgtctcaatc  12900

ggtgtttctc atcctggatt agaacttatt aaaaatctga gcgatgattt gagaattggc  12960

tccacaaaac ttaccggtgc tggtggcggc ggttgctctt tgactttgtt acgaagagac  13020

attactcaag agcaaattga cagtttcaaa aagaaattgc aagatgattt tagttacgag  13080

acatttgaaa cagacttggg tgggactggc tgctgtttgt taagcgcaaa aaatttgaat  13140

aaagatctta aaatcaaatc cctagtattc caattatttg aaaataaaac taccacaaag  13200

caacaaattg acgatctatt attgccagga aacacgaatt taccatggac ttcataagct  13260

aatttgcgat aggcattatt tattagttgt ttttaatctt aactgtgtat gaagttttat  13320

gtaataaaga tagaaagaga aacaaaaaaa aatttttcgt agtatcaatt cagctttcga  13380

agacagaatg aaatttaagc agaccatagt atccttgata cattgactca ggtccgccgg  13440

cgttggacga gcgaagcatc ttgccctgtg cttggccccc agtgcagcga acgttataaa  13500

aacgaatact gagtatatat ctatgtaaaa caaccatatc atttcttgtt ctgaactttg  13560

tttacctaac tagttttaaa tttccctttt tcgtgcatgc gggtgttctt atttattagc  13620

atactacatt tgaaatatca aatttcctta gtagaaaagt gagagaaggt gcactgacac  13680

aaaaaataaa atgctacgta taactgtcaa aactttgcag cagcgggcat ccttccatca  13740

tagcttcaaa catattagcg ttcctgatct tcatacccgt gctcaaaatg atcaaacaaa  13800

ctgttattgc caagaaataa acgcaaggct gccttcaaaa actgatccat tagatcctca  13860

tatcaagctt cctcatagaa cgcccaatta caataagcat gttttgctgt tatcaccggg  13920

tgataggttt gctcaggcgg tttaaacgcg tggccgtgcc gtc                    13963
```